(12) United States Patent
Grimm et al.

(10) Patent No.: US 10,450,365 B2
(45) Date of Patent: Oct. 22, 2019

(54) RECOMBINANT HUMAN ANTIBODIES FOR THERAPY AND PREVENTION OF POLYOMAVIRUS-RELATED DISEASES

(71) Applicants: Neurimmune Holding AG, Schlieren (CH); University of Zurich, Zurich (CH)

(72) Inventors: Jan Grimm, Dübendorf (CH); Roland Martin, Zurich (CH); Benoit Combaluzier, Urdorf (CH); Ivan Jelcic, Zurich (CH)

(73) Assignees: Neurimmune Holding AG, Schlieren (CH); University of Zurich, Zurich (CH)

( * ) Notice: Subject to any disclaimer, the term of this patent is extended or adjusted under 35 U.S.C. 154(b) by 0 days.

(21) Appl. No.: 15/678,965

(22) Filed: Aug. 16, 2017

(65) Prior Publication Data

US 2018/0037635 A1    Feb. 8, 2018

Related U.S. Application Data

(63) Continuation of application No. 14/758,615, filed as application No. PCT/EP2014/050024 on Jan. 2, 2014, now Pat. No. 9,771,413.

(60) Provisional application No. 61/747,541, filed on Dec. 31, 2012.

(30) Foreign Application Priority Data

Dec. 31, 2012 (EP) ..................... 12199837

(51) Int. Cl.
| | | |
|---|---|---|
| A61K 39/42 | (2006.01) | |
| A61K 45/06 | (2006.01) | |
| C07K 14/005 | (2006.01) | |
| C12N 7/00 | (2006.01) | |
| C07K 16/08 | (2006.01) | |
| G01N 33/569 | (2006.01) | |
| G01N 33/68 | (2006.01) | |

(52) U.S. Cl.
CPC ............ *C07K 16/084* (2013.01); *A61K 39/42* (2013.01); *A61K 45/06* (2013.01); *C07K 14/005* (2013.01); *C07K 16/081* (2013.01); *C12N 7/00* (2013.01); *G01N 33/56983* (2013.01); *G01N 33/6893* (2013.01); *C07K 2317/21* (2013.01); *C07K 2317/34* (2013.01); *C07K 2317/76* (2013.01); *C12N 2710/22022* (2013.01); *G01N 2333/025* (2013.01)

(58) Field of Classification Search
None
See application file for complete search history.

(56) References Cited

U.S. PATENT DOCUMENTS

| | | |
|---|---|---|
| 2009/0062237 A1 | 3/2009 | Abraham et al. |
| 2015/0191530 A1 | 7/2015 | Burioni et al. |

FOREIGN PATENT DOCUMENTS

| | | |
|---|---|---|
| CN | 104520318 A | 4/2015 |
| WO | WO-2009/079481 A2 | 6/2009 |
| WO | WO-2010/059543 A1 | 5/2010 |
| WO | WO-2010/090757 A1 | 8/2010 |
| WO | WO-2011/030300 A1 | 3/2011 |
| WO | WO-2013/087601 A2 | 6/2013 |
| WO | WO-2013/142300 A2 | 9/2013 |

OTHER PUBLICATIONS

Wang et al. Human anti-JC virus serum reacts with native but not denatured JC virus major capsid protein VP1. Journal of Virological Methods 78 (1999) 171-176.*
Gorelik et al. Anti-JC Virus Antibodies: Implications for PML Risk Stratification. Ann Neurol 2010;68:295-303.*
"Characterization of monoclonal antibodies specific for the Merkel cell polyomavirus capsid," available in PMC Sep. 15, 2011, published in final edited form as: Virology. 405(1):20-25 (2010) (13 pages).
Atwood, "A combination of low-dose chlorpromazine and neutralizing antibodies inhibits the spread of JC virus (JCV) in a tissue culture model: implications for prophylactic and therapeutic treatment of progressive multifocal leukencephalopathy," J Neurovirol. 7(4):307-10 (2001).
Database UniProt, accession No. C5J3L9, "VP1-fragment; JC polyomavirus (JCPyV) (JCV)," <http://www.uniprot.org/uniprot/C5J3L9>, last modified Mar. 6, 2013, (2009) (3 pages).
Database UniProt, accession No. P03088, "Major capsid protein VP1; BK polyomavirus (BKPyV)," <http://www.uniprot.org/uniprot/P03088>, last modified Apr. 3, 2013, (1986) (7 pages).
Database UniProt, accession No. P03089, "Major capsid protein VP1; JC polyomavirus (JCPyV) (JCV)," <http://www.uniprot.org/uniprot/P03089>, last modified Apr. 3, 2013, (1986) (9 pages).
Kjaerheim et al., "Absence of SV40 antibodies or DNA fragments in prediagnostic mesothelioma serum samples," Int J Cancer. 120(11):2459-65 (2007).

(Continued)

*Primary Examiner* — Nianxiang Zou
(74) *Attorney, Agent, or Firm* — McDermott Will & Emery LLP; Kristina Bieker-Brady

(57) ABSTRACT

Provided are novel human-derived antibodies specifically recognizing polyomavirus polypeptides, preferably capable of binding to polyomaviruses of the type of JC virus (JCV) and/or BK virus (BKV) as well as methods related thereto. Furthermore, assays and kits related to antibodies specific for polyomaviruses, polyomavirus VP1 and or polyomavirus VP1 Virus-Like Particles (VLPs), preferably of the type of JCV and/or BKV, are disclosed. The human-derived antibodies as well as binding fragments, derivatives and variants thereof can be used in pharmaceutical and diagnostic compositions for polyomavirus targeted immunotherapy and diagnostics.

21 Claims, 26 Drawing Sheets

Specification includes a Sequence Listing.

(56) References Cited

OTHER PUBLICATIONS

Marriott et al., "Production and characterization of monoclonal antibodies to polyomavirus major capsid protein VP1," J Virol. 56(2):365-72 (1985).

Nelson et al., "Development trends for human monoclonal antibody therapeutics," Nat Rev Drug Discov. 9(10):767-74 (2010).

Pastrana et al., "Characterization of monoclonal antibodies specific for the Merkel cell polyomavirus capsid," Virology. 405(1):20-5 (2010).

Randhawa et al., "Identification of species-specific and cross-reactive epitopes in human polyomavirus capsids using monoclonal antibodies," J Gen Virol. 90(Pt 3):634-9 (2009).

Randhawa et al., "Polyomavirus BK neutralizing activity in human immunoglobulin preparations," Transplantation. 89(12):1462-5 (2010) (8 pages).

Vajdos et al., "Comprehensive functional maps of the antigen-binding site of an anti-ErbB2 antibody obtained with shotgun scanning mutagenesis," J Mol Biol. 320(2):415-28 (2002).

Vaughan et al., "Human antibodies by design," Nat Biotechnol. 16(6):535-9 (1998).

Youssef et al., "Anti-JCV neutralizing antibodies as a potential therapy for the treatment of PML," J Neurovirol. 18(Suppl 1):S125, Abstract P256 (2012).

Zheng et al., "Characterization of the VP1 loop mutations widespread among JC polyomavirus isolates associated with progressive multifocal leukoencephalopathy," Biochem Biophys Res Commun. 333(3):996-1002 (2005).

International Preliminary Report on Patentability for International Application No. PCT/EP2014/050024, dated Jun. 30, 2015 (12 pages).

International Search Report for International Application No. PCT/EP2014/050024, dated Feb. 13, 2014 (7 pages).

\* cited by examiner

Fig. 1
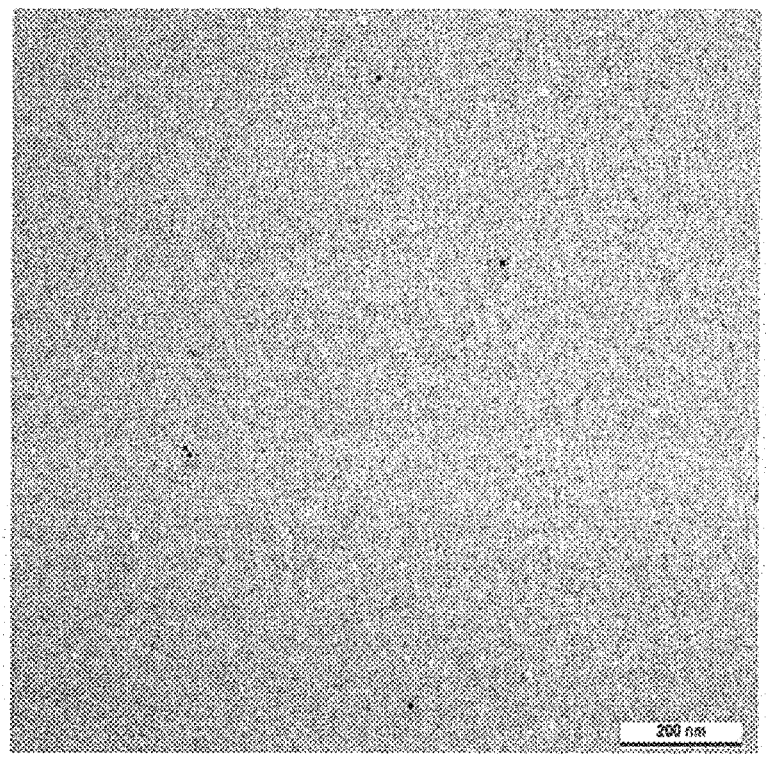
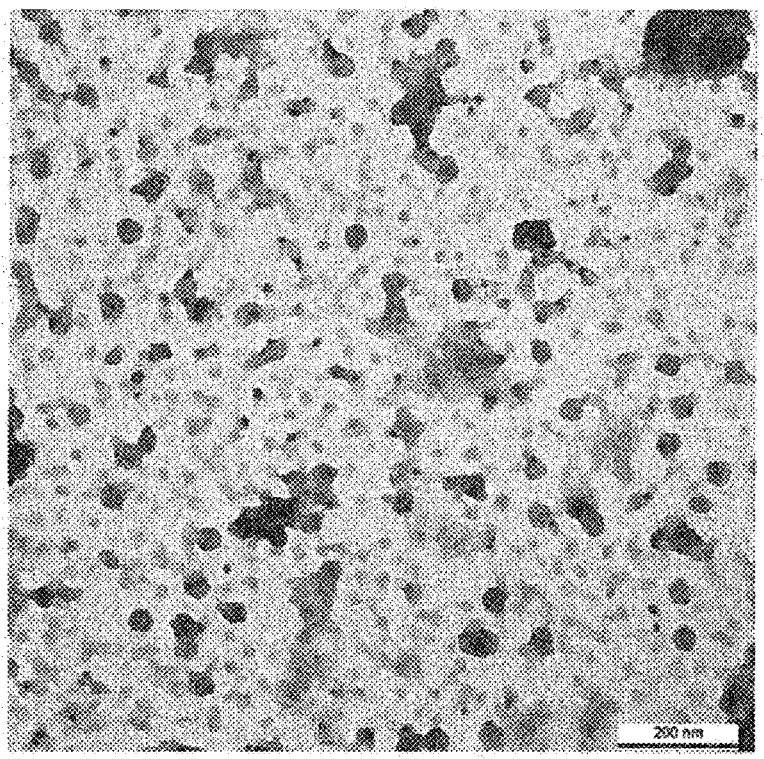

B

| Antibody | JCV VP1 EC$_{50}$ (nM) | JCV VP1 VLP EC$_{50}$ (nM) | BKV VP1 EC$_{50}$ (nM) | BKV VP1 VLP EC$_{50}$ (nM) |
|---|---|---|---|---|
| NI-307.3G4 | 71.0 | 28.2 | 27.4 | 16.4 |
| NI-307.6A2 | 1.59 | 1.39 | 1.79 | 1.17 |
| NI-307.11G6 | 0.0116 | 0.0118 | 0.0188 | 0.0387 |
| NI-307.19F10 | 10.1 | 3.41 | 2.41 | 1.10 |
| NI-307.24F3 | 0.281 | 6.95 | 1.04 | 28.8 |
| NI-307.25G10 | 0.605 | 0.509 | 0.514 | 0.172 |
| NI-307.43A11 | 8.07 | 6.15 | 9.70 | 10.0 |
| NI-307.44F6B | 0.101 | 0.083 | 0.60 | 0.2 |
| NI-307.57D5 | 38.6 | 57 | 37.5 | 104 |
| NI-307.78C3 | 0.859 | 0.932 | 1.96 | 0.939 |

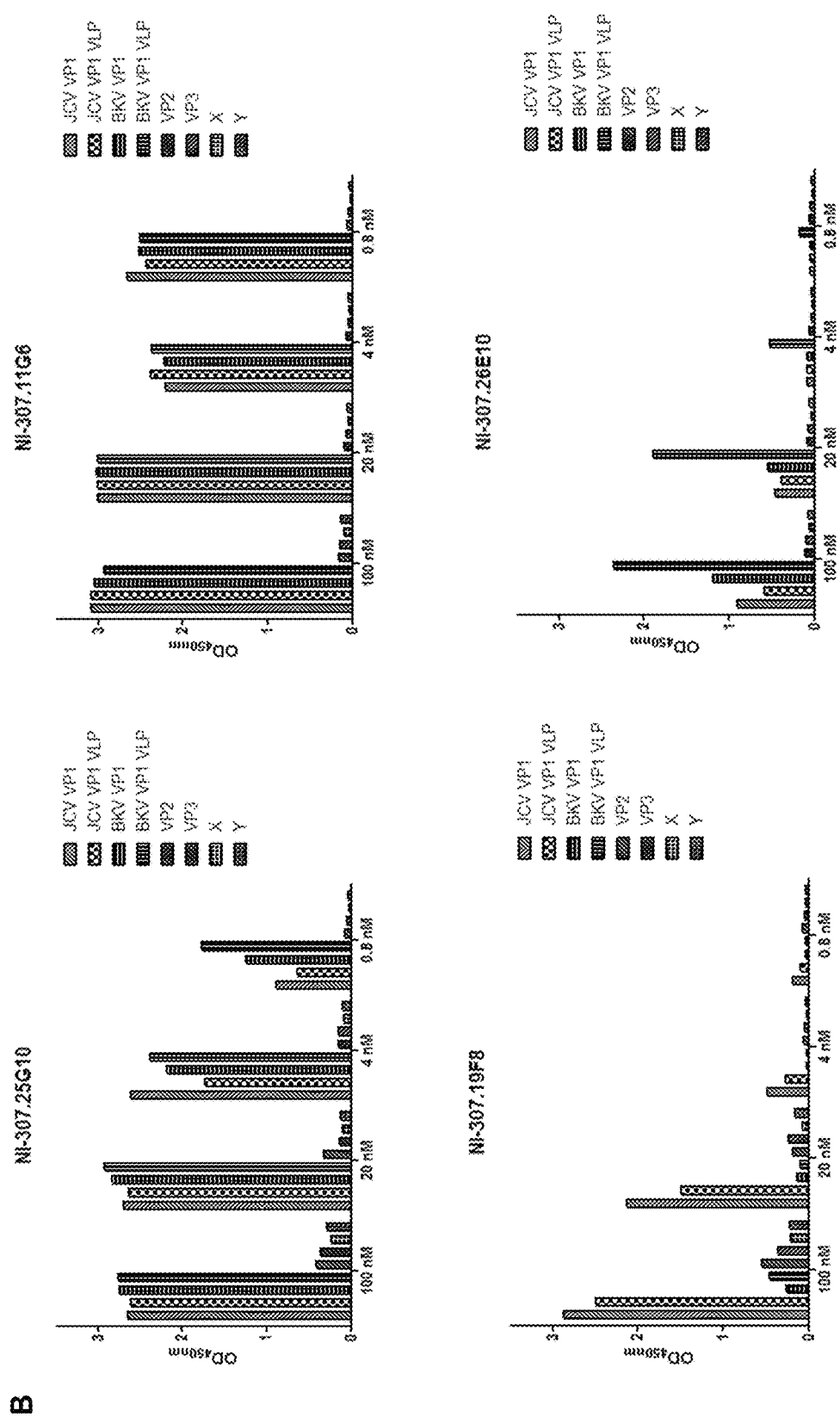

Fig. 7
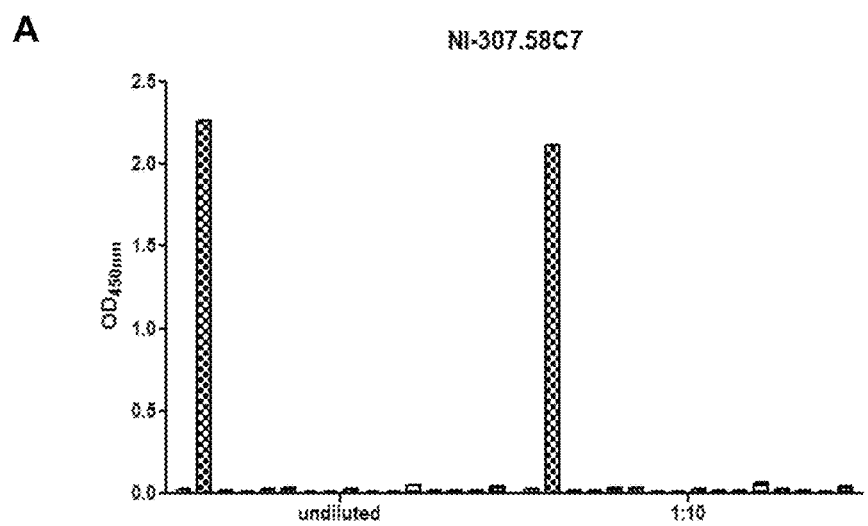
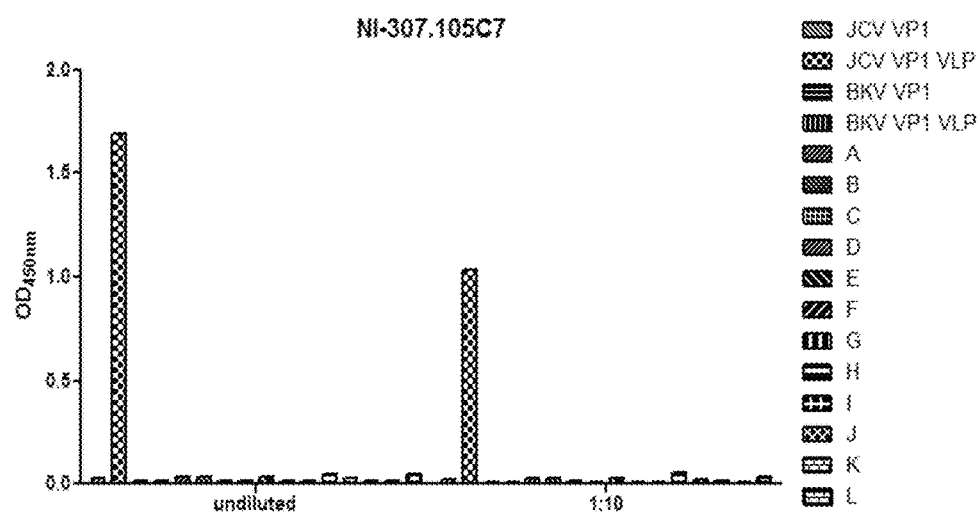

| Antibody | JCV VP1 EC$_{50}$ (nM) | JCV VP1 VLP EC$_{50}$ (nM) | BKV VP1 EC$_{50}$ (nM) | BKV VP1 VLP EC$_{50}$ (nM) |
|---|---|---|---|---|
| NI-307.7J3 | 3.97 | 0.065 | N/A | N/A |
| NI-307.26A3 | 0.263 | 0.049 | N/A | N/A |
| NI-307.27C2 | 0.074 | 0.052 | N/A | N/A |
| NI-307.27C11 | 0.090 | 0.042 | N/A | N/A |
| NI-307.29B1 | 16 | 0.076 | 0.34 | 0.191 |
| NI-307.43E8 | 1.84 | 0.64 | 0.34 | 0.38 |
| NI-307.45E10 | 0.022 | 0.024 | N/A | N/A |
| NI-307.47B11 | 0.2 | 0.048 | N/A | N/A |
| NI-307.50H4 | 0.067 | 0.055 | N/A | N/A |
| NI-307.53B11 | 0.369 | 0.064 | N/A | N/A |
| NI-307.56A8 | 0.067 | 0.041 | N/A | N/A |
| NI-307.57D4 | 0.151 | 0.053 | N/A | N/A |
| NI-307.58C7 | 0.076 | 0.059 | N/A | N/A |
| NI-307.59A7 | 0.021 | 0.066 | N/A | N/A |
| NI-307.72F7 | 0.015 | 0.019 | 0.027 | 0.021 |
| NI-307.72F10 | 0.048 | 0.031 | N/A | N/A |
| NI-307.98D3 | 0.115 | 0.00057 | N/A | N/A |
| NI-307.98H1 | 0.29 | 0.086 | N/A | N/A |
| NI-307.105A6 | 0.077 | 0.069 | N/A | N/A |
| NI-307.105C7 | 9.9 | 0.04 | N/A | N/A |

A    NI-307.13G4-VH    (variable heavy chain sequence VH)(SEQ ID NO: 2)
```
FR1---------------------CDR1------FR2-----------CDR2-------------FR3---
EVQLVESGGGLVQPGGSLRLSCTASGFTFTSYALSWVRQAPGKGLEWVSAISSGRGYTYYADSVKGRFTISR
-------------------------------CDR3------------FR4---------
DNSKNTLYLQMNSLRAEDTAVYYCAKDGTLRGYNYGYIDDIWGQGTLVTVSS
```

NI-307.13G4-VK    (variable light chain sequence VK)(SEQ ID NO: 4)
```
FR1---------------------CDR1--------FR2-------------CDR2-----FR3------------
DIQMTQSPSSLSASVGDRVTITCRASQGISNYLAWLQQKPGKAPKPLIYAVSILQSGVPSKFSGSGSGTDFT
-----------------CDR3-------FR4--------
LTISSLQPEDFATYYCQQYKSYPYTFGQGTKLEIK
```

B    NI-307.19F10-VH    (variable heavy chain sequence VH) (SEQ ID NO: 6)
```
FR1-----------------------CDR1-------FR2------------CDR2---------------FR3----
EVQLVESGGGLVQPGGSVSLSCAASGFTFPVYWMHWVRQAPEKGLMWVSRISPDGTIVDYAGSVKGRFTVSR
-------------------------------CDR3------FR4-----------
DNAKNILYLQIQRLTAEDTAVYFCTKDFDVASGFWGQGTLVTVSS
```

NI-307.19F10-VL    (variable light chain sequence VL) (SEQ ID NO: 8)
```
FR1------------------CDR1----------FR2---------------CDR2---FR3-----------
QSALTQPPSASGSPGQSVTISCTGSKSDVGTCHFVSWYQQHPGKVPKLVIYEGNKRPSGVPDRFSASKSGNT
--------------------CDR3-------FR4--------
ASLTISGLQPGDEADYYCSTCAGPNNYVFGTGTKVTVL
```

C    NI-307.19F8-VH    (variable heavy chain sequence VH) (SEQ ID NO: 10)
```
FR1-------------------------CDR1-------FR2-------------CDR2----------------FR3----
EVQLVESGGGLVKPGGSLRLSCAASGFTFSSYYMNWVRQAPGKGLEWVSSISSSSSYIYYADSVKGRFTISR
---------------------------CDR3---------FR4---------
DNAKNSLYLQMNSLTAEDTAVYYCARDPRLQLWFMFDYWGQGTLVTVSS
```

NI-307.19F8-VL    (variable light chain sequence VL) (SEQ ID NO: 12)
```
FR1---------------------CDR1----------FR2--------------CDR2----FR3---------------
QPVLTQPPSASASLGASVTLTCLSSGYSNYKVDWYQQRPGEGPRFVMRVGTGGIVGSKGDGIPDRFSVLGS
----------------------CDR3---------FR4--------
GLNRYLTIKDIQEEDESDYHCGADHGSGSNFVYVFGTGTKVTVL
```

Fig. 8

D    NI-307.11G6-VH   (variable heavy chain sequence VH) (SEQ ID NO: 14)
```
FR1-----------------------CDR1-------FR2-----------CDR2-----------------FR3----
QVQLVESGGDLVKPGGSLRLSCAASGFTFSDHYMSWIRQAPGKGLEWVSYISTRSTYTNYADSVKGRFTISR
-------------------------------CDR3--------FR4---------
DNAKNSLYLHMNSLRTEDTAVYYCARDYSDTSGPPDYWGQGTLVTVSS
```

NI-307.11G6-VL   (variable light chain sequence VL) (SEQ ID NO: 16)
```
FR1--------------------CDR1-----------FR2---------------CDR2----FR3------------
QSVLTQPPSASGTPGQRVTISCSGSNSNIGSNYVYWYQQLPGTAPKLVIYRNTQRPSGVPDRFSGSKSGTSA
-------------------CDR3--------FR4--------
SLAISGLRSEDEADYYCAAWDDSLSGLVFGGGTKLTVL
```

E    NI-307.17F12-VH   (variable heavy chain sequence VH) (SEQ ID NO: 18)
```
FR1----------------------CDR1---------FR2-----------------CDR2----------------FR3----
QLQLQESGPGLVKPSGTLSLTCAVSGDSITNTNWWCWVRQPPGKGLEWIGEIFHSGGTNYNPSLKSRVTMSV
-----------------------------CDR3-------FR4---------
DKAKNQFSLKVNSVTAADTAVYFCTTNPGGGDGYSYWGQGTLVTVSS
```

NI-307.17F12-VL   (variable light chain sequence VK) (SEQ ID NO: 20)
```
FR1----------------------CDR1-----------FR2-------------CDR2----FR3------------
QSALTQPRSVSGSPGQSVTISCTGTSSDVGGYNYVSWYQQHPGKAPNLMISEVSKRPSGVPDRFSGSKSGNT
-------------------CDR3-------FR4-------
ASLTISGLQAEDEADYFCCSYAGSYRVFGTGTKVTVL
```

F    NI-307.6A2-VH   (variable heavy chain sequence VH) (SEQ ID NO: 22)
```
FR1-------------------------CDR1--------FR2--------------CDR2---------------FR3-----
QVQLQESGPGLVKPSETLSLTCAVSGGSVSSSYWYSWVRQLPGKGLEWIGEIFHTGDTNYNPSLESRVTISI
---------------------------CDR3-----------FR4---------
DTSKNQLSLDVTSATAADTAVYYCARDYCTDSGCDSDALDVWGHGTMVTVSS
```

NI-307.6A2-VL   (variable light chain sequence VL) (SEQ ID NO: 24)
```
FR1--------------------CDR1-----------FR2---------------CDR2---FR3------------
QSALTQPASVSGSPGQSITISCTGTTKDVGNYNLVSWYQQHPGKAPRLVIYEVSERPSGVSNRFSGSKSGNT
-------------------CDR3-------FR4-------
ASLTISGLQAEDEADYHCCSYAGSGTSVFGGGTKVTVL
```

Fig. 8 continued

G    NI-307.5H3-VH    (variable heavy chain sequence VH)  (SEQ ID NO: 26)
FR1-----------------------CDR1--------FR2-------------CDR2---------------FR3----
QVQLQESGPGLLKPLGTLSLICDVS<u>GDSISSSNWWS</u>WVRQSPRKGLEWIGE<u>IYHSGRTNYNPSLTNR</u>VTISV
------------------------CDR3--------------FR4---------
DKSKNQFSLNLNSVTAADTGVYYCAR<u>WDYYYNNDYYIRGFDI</u>WGQGTMVTVSS

NI-307.5H3-VK    (variable light chain sequence VK)  (SEQ ID NO: 28)
FR1-----------------------CDR1--------FR2-------------CDR2----FR3-------------
EIVLTQSPGILSLSPGERATLSC<u>RASQSVDSNYLA</u>WYQQKPGQAPRLLIY<u>STSTRAA</u>GVPDRFSGSGSGTDF
-------------------CDR3-------FR4--------
ALTISGLEPEDFAVYYC<u>QQWGGSPPIT</u>FGQGTRLEIK

H    NI-307.25G10-VH    (variable heavy chain sequence VH)  (SEQ ID NO: 30)
FR1----------------------CDR1------FR2------------CDR2-------------FR3----
EVQLVESGGGLVQPGGSLRLSCVASG<u>IIFKDYDFH</u>WVRQVKEKGLEWVS<u>AIGTAGDPYYAASVKG</u>RFTVSRE
-----------------------------CDR3------------FR4---------
NGKNSVYLRMNNVGAGDTALYYCT<u>SGNYFDRGSFRPSAFDM</u>WGQGTMVTVSS

NI-307.25G10-VK    (variable light chain sequence VK)  (SEQ ID NO: 32)
FR1-----------------------CDR1---------FR2---------------CDR2----FR3--------------
EIVLTQSPGTLSLSPGERATLSC<u>WASQSVSSNYLA</u>WYQHKPGQAPRLLIF<u>RASRRAT</u>DIPERFSAGGSGTDF
-------------------CDR3---------FR4--------
TLTISRLEAEDSAVYYC<u>QEYGSAPPASIT</u>FGQGTRLEIK

I    NI-307.26E10-VH    (variable heavy chain sequence VH)  (SEQ ID NO: 34)
FR1----------------------CDR1------FR2------------CDR2-------------FR3----
EVQLVESGGGLVLPGGSLRLSCAVSG<u>FTVRNEYMR</u>WARQAPGRGLEWVS<u>VIYRDGQTHHADTVKG</u>RFDVSKD
-------------------------------CDR3-FR4---------
TSKNTMYLQMHNLRVDDTAIYYCAR<u>GHYGP</u>WGQGTLVTVSS

NI-307.26E10-VL    (variable light chain sequence VL)  (SEQ ID NO: 36)
FR1------------------------CDR1---------FR2----------------CDR2----FR3---------------
DIQMTQSPSTLPASVGDRVTITC<u>RASQSINNWLA</u>WYQQKPGKAPNLLIY<u>DASNLET</u>GVPSRFSGSGSGTEFT
-------------------CDR3---------FR4---------
LTISSLQPDDFATYYC<u>QQYNSHSHTWT</u>FGQGTKVEIK

Fig. 8 continued

J   NI-307.1E1-VH   (variable heavy chain sequence VH) (SEQ ID NO: 38)
```
FR1-----------------------CDR1--------FR2------------CDR2---------------FR3--
EVQLVESGGGLVKPGGSLRLSCAASGFIFSDAWMNWVRQAPGKGLEWVGHIKSRPAGGTTEYAAPVKGRFTI
---------------------CDR3-FR4--------
SRDDSTDTLYLQMNNLKAEDTAVYYCSTGHYGVYGLGTLVTVSS
```

NI-307.1E1-VK   (variable light chain sequence VK) (SEQ ID NO: 40)
```
FR1---------------------CDR1-------FR2-----------CDR2---FR3------------
DIQMTQSPSTLSASVGDRVTITCRASQSIRDYLAWYQQKPGKAPKLLIYDGSILEGGVPSRFSGSVSGTDFT
-------------------CDR3-------FR4--------
LTISSLQSDDFATYYCQQYTSYSSWTFGQGTKVEIK
```

K   NI-307.24C6-VH   (variable heavy chain sequence VH) (SEQ ID NO: 42)
```
FR1---------------------------CDR1---------FR2-----------CDR2--------------FR3----
QLQLQESGPGLVKPSGTLSLICVVSGSSIRSNIWWWNWVRQSPGKGLEWIGEIYHSGSTNYSPSLKSRVTMS
-------------------------------CDR3-------------FR4---------
VDNSKNQFSLKMSSVTAADTAVYFCAINTRTSISGVLYDTFDVWGQGTMVTVSS
```

NI-307.24C6-VK   (variable light chain sequence VK) (SEQ ID NO: 44)
```
FR1-----------------------CDR1--------FR2------------CDR2---FR3---------------
EIVLTQSPATLSLSSGERATLSCRASQSVSGYLAWYQQKPGQAPRLLIYDGSNRATGIPARFSGSGSGTDFT
-----------------CDR3-------FR4--------
LTISSLEPEDFAVYYCQHRSNWPMYTFGQGTKLEIK
```

L   NI-307.78C3-VH   (variable heavy chain sequence VH) (SEQ ID NO: 46)
```
FR1-----------------------CDR1-------FR2-----------CDR2-------------FR3---
QVQLQESGPGLVKPSGTLSLTCTVSGGSISGRIWWSWVRQPPGKGLEWIGEIYHSGSTNYSPSLRGRVTISV
----------------------------CDR3-----FR4---------
DTSKQHFSLKMTSVTAADTAMYYCVRGELALGFDSWGQGTLVTVSS
```

NI-307.78C3-VL   (variable light chain sequence VL) (SEQ ID NO: 48)
```
FR1---------------------CDR1----------FR2-------------CDR2---FR3--------------
QSALTQPPSASGSPGQSVTISCTGTSSDVGGYNSVSWYQQHPRRAPKLMIYEVSKRPSGVPDRFSGSKSGNT
----------------------CDR3--------FR4---------
ASLTVSGLQADDEAHYYCSSYAGSNNLVFGGGTMLTVL
```

Fig. 8 continued

M      NI-307.57D5-VH   (variable heavy chain sequence VH) (SEQ ID NO: 50)
```
FR1----------------------CDR1------FR2-----------CDR2--------------FR3---
EVQLVESGGGLAQPGGSLRLSCAGSGFTLSDFAMSWVRRAPGKGLEWVSSLTPSGRNSFYSDSVKGRFTISR
------------------------CDR3-----------------FR4----------
DNWKNTLYLEMNLLRPEDTAVYYCARPGAPKNSDSKYSYVRVDFQHWGQGTLVTVSS
```

NI-307.57D51-VL   (variable light chain sequence VL) (SEQ ID NO: 52)
```
FR1---------------------CDR1---------FR2-------------CDR2---FR3------------
NFMLTQPHSVSESPGRTVTISCTRSSGSIANNFVQWYQHRPGSAPTTLIYEDDQRPSGVPDRFSGSVDSFSN
----------------CDR3-------FR4---------
SASLTISGLKTEDEADYFCQSYDNHNWVFGGGTTLTVL
```

N      NI-307.43A11-VH   (variable heavy chain sequence VH) (SEQ ID NO: 54)
```
FR1-----------------------CDR1--------FR2-----------CDR2-------------FR3---
QVQLQESGPGLVKPSGTLSLTCAVTGGSISSSNWWSWVRQSPGKGLEWIGEIHHDGNLNYNPLLKSRVSMSL
----------------------------CDR3-------------FR4---------
DRSKNQFSLKLTSVTAADTAVYYCARWDFFFDSSYYIRGFDLWGQGTMVTVSS
```

NI-307.43A11-VK   (variable light chain sequence VK) (SEQ ID NO: 56)
```
FR1---------------------CDR1---------FR2-------------CDR2---FR3-------------
ETTLTQSPGTLSLSPGERVTLSCRASQSVDRNYLAWYQQKPGQSPRLLIYSASRRATGIPDRFSGSGSGTDF
-------------------CDR3-------FR4--------
TLTISRLEPEDFVVYYCQQYGGSPPITFGQGTRLEIK
```

O      NI-307.3G4-VH   (variable heavy chain sequence VH) (SEQ ID NO: 58)
```
FR1-----------------------CDR1-------FR2-----------CDR2---------------FR3---
QVQLVQSGAELKKPGAAVKVSCQASGYNFLSYGINWVRQIPGQGLQWLGWISTYDGTMNYDQKPDNRVTVTT
--------------------------CDR3----------FR4---------
DTSSSTVYLELRGLRSDDTGVYYCVRDRCAGAGCSHSLGYWGQGTLVTVSS
```

NI-307.78C3-VL   (variable light chain sequence VL) (SEQ ID NO: 60)
```
FR1---------------------CDR1--------FR2-------------CDR2---FR3--------------
DIQMTQSPSALSASVGDRVTISCRASQNINTQLNWYQEKPGKAPELLIYGAFNLQSGAPSTFSGSGSGTDFT
-------------------CDR3------FR4---------
LTITSLQPEDFASYYCQQGFHAPYTFGRGTKVDIK
```

Fig. 8 continued

P  NI-307.61D11-VH (variable heavy chain sequence VH) (SEQ ID NO: 62)
```
FR1-------------------------CDR1-------FR2------------CDR2---------------FR3----
EVQLVQSGAEVKKPGASVKVSCKTSGYTFIGHYMQWVRQVPGQGFEWMGWINPNTGTTKYALKFKDRVTVTR
-----------------------------CDR3--------FR4---------
DTSTATVYMEFHGLTSDDTAVYYCARASAYQLANYDYWGQGTLVTVSS
```

NI-307.61D11-VL (variable light chain sequence VL) (SEQ ID NO: 64)
```
FR1--------------------CDR1----------FR2-------------CDR2---FR3------------
QSALTQPASVSGSPGQSITISCAGTSNDVGDDDFVSWYQHQPGKAPRLMIYEVTNRPSGVSTRFSGSKSGNT
--------------------CDR3---------FR4-------
ASLTISGLQAEDEGDYYCMSYTKNSALGYVFGGGTKVTVL
```

Q  NI-307.24F3-VH (variable heavy chain sequence VH) (SEQ ID NO: 66)
```
FR1------------------------CDR1-------FR2-----------CDR2---------------FR3----
QVQLQESGGGVVQPGRSLRLSCAASGFSFNRYGMHWVRQAPGKGLEWLAVISNDGVNTHYADSVKGRFTISR
---------------------------CDR3---------FR4---------
DNSKSTLYLQASSLRVEDTAVYYCAGYYYGSGTSLFFYWGQGTLVTVSS
```

NI-307.24F3-VK (variable light chain sequence VK) (SEQ ID NO: 68)
```
FR1-------------------CDR1------------FR2-------------CDR2----FR3----------
EIVLTQSPDSLAVSLGERATINCKSSQTVLYSSNNQNYLAWYQQKPGQPPKLLLYWASTRESGVPDRFSGSG
------------------CDR3-------FR4--------
SGTDFTLTISSLQPEDVAVYYCQQYYTAPYTFGQGTKVEIK
```

R  NI-307.18E12-VH (variable heavy chain sequence VH) (SEQ ID NO: 70)
```
FR1---------------------------CDR1-----FR2----------------CDR2---------------FR3-----
QVQLQQWGAGLLKPSETLSLTCAVYGDSFSGFFWAWIRQTPGTGLEWIGEIQHGGSPTYNPSFESRLTISTD
-----------------------CDR3----------FR4---------
ASKSQVSLKMTSVTVTDTAIYYCARCIRGKYGSGSLQLWSQGTLVTVSS
```

NI-307.18E12-VK (variable light chain sequence VK) (SEQ ID NO: 72)
```
FR1-------------------CDR1--------FR2-------------CDR2---FR3-------------
DIQLTQSPSFLSASVGDRVTITCRASQDINYHLAWYRQKPGKAPDLLIHSAHTLHIGVSSRFSGSGSGTEFT
------------------CDR3------FR4--------
LTIHTLQPEDFATYYCHQPKTFPPTFGGGTKVDIK
```

Fig. 8 continued

S    NI-307.20F5-VH   (variable heavy chain sequence VH) (SEQ ID NO: 74)
```
FR1-----------------------CDR1------FR2-----------CDR2--------------FR3---
EVQLVESGGGVVQPGTSLRLSCAASGFSFNKYGVHWVRQAPGKGLEWVANIWYDGTNPFYADFVKGRFVISR
-----------------------------CDR3-------------FR4---------
DTSKNTIYLQMNRLRAEDTAVYYCARDAFCGGDCYGGLLHGLDVWGQGTTVTVSS
```

NI-307.20F5-VK   (variable light chain sequence VK) (SEQ ID NO: 76)
```
FR1--------------------CDR1-----------FR2-----------CDR2---FR3---------
DVVMTQSPLSLPVTPGEPASISCRSSQSLLHSNGLNYLDWYLQKPGQSPQLLIYLGSNRAPGVPDRFSGSGS
-----------------------CDR3----FR4-------
GTDFTLKISRVEAEDVGVYYCLQALQTPAFGQGTKVEIK
```

T    NI-307.58C7-VH   (variable heavy chain sequence VH) (SEQ ID NO: 78)
```
FR1-----------------------CDR1------FR2-----------CDR2--------------FR3---
EVQLVESGGGLVKPGGSLRLSCAASGFTFSDYYVNWIRQAPGKGLEWVACISSSGRTIHYADSVKGRFTISR
----------------------------CDR3-----------FR4---------
DNAKNSLYLQMNSLRAEDTAFYYCARDLDKAATGRPYFDYWGQGTLVTVSS
```

NI-307.58C7-VL  (variable light chain sequence VL) (SEQ ID NO: 80)
```
FR1-------------------CDR1---------FR2-----------CDR2---FR3-------------
QSVLTQPPSASGTPGQRVTISCSGSSSNIGGNAVNWFQQLPGTAPKLLIYGNTQRPSGVPDRFSGSKSGTSA
-------------------CDR3--------FR4--------
SLAISGLQSEDETNYYCAAWDDSLNGVVFGGGTKLTVL
```

U    NI-307.105C7-VH  (variable heavy chain sequence VH) (SEQ ID NO: 82)
```
FR1-----------------------CDR1------FR2-----------CDR2--------------FR3---
EVQLVESGGGLVQPGGSLRLSCAASGFSFGFYAMNWVRQAPGKGLEYVSGVSGGGGSTYYADSVKGRFTISR
---------------------CDR3-------------FR4---------
DNSKNTLYLQMKSLRAEDTAIYYCAKDQSYCSGGSCHPYYLDYWGQGTLVTVSS
```

NI-307.105C7-VL  (variable light chain sequence VL) (SEQ ID NO: 84)
```
FR1-------------------CDR1--------FR2-------------CDR2----FR3---------------
SYVLTQPPSVSVAPGQTARITCGGNNIGSKSVHWYQQKPGQAPVVVVYDDSGRPSGIPERFSGSNSGNTATL
-----------------CDR3---------FR4--------
TISRVEAGDEADYYCQVWDSSSDHPYVFGTGTKVTVL
```

Fig. 8 continued

V    NI-307.98D3 VH    (variable heavy chain sequence VH) (SEQ ID NO: 90)
```
FR1--------------------CDR1------FR2------------CDR2--------------FR3---
EVQLVESGGGVVQPGRSLRLSCAASGFTFSSSAMHWVRQAPGKGLEWVAVISYDGNNQLYADSVKGRLTISR
--------------------------CDR3---------FR4--------
DNSKNALYLQLNSLRTEDTAVYFCARDGGGYSFGTYFFDFWGQGTLVTVSS
```

NI-307.98D3 VK    (variable light chain sequence VK) (SEQ ID NO: 92)
```
FR1--------------------CDR1------------FR2-------CDR2---FR3-------------
DIQMTQSPSSLSASVGERVTITCRASQRISNYLNWYQQKPGKAPKLLIYAASTLQSGVPSRFSGSGSGTDFT
---------------CDR3------FR4---------
LTISSLQPEDFATYYCQQSYSSPPTFGPGTKVDIK
```

W    NI-307.72F7 VH    (variable heavy chain sequence VH) (SEQ ID NO: 94)
```
FR1--------------------CDR1------FR2------------CDR2--------------FR3---
EVQLVESGGGLVQPGGSLRLSCAASGFTFSSYEMNWVRQAPGKGLEWISYISSRGSTIHYADSVKGRFTISR
------------------------CDR3--------------FR4---------
DDAKNSLYLQMNSLRAEDTAIYYCARDRYDFWSGCIKGCYYGMDVWGQGSTVTVSS
```

NI-307.72F7 VK (variable light chain sequence VK) (SEQ ID NO: 96)
```
FR1---------------------CDR1----------FR2--------------CDR2----FR3-------------
EIVLTQSPGTLSLSPGQRATLSCRASQSISSSYLAWYQQRRGQAPRLLIYGASSRATGIPDRFSGSGSGTDF
------------------CDR3-----FR4--------
TLTISRLEPEDFAVYYCQHYGTTLTFGQGTKVDIK
```

X    NI-307.45E10 VH (variable heavy chain sequence VH) (SEQ ID NO: 98)
```
FR1---------------------CDR1------FR2------------CDR2--------------FR3---
EVQLVESGGGLVQPGGSLRLSCAASGFSFRFYAMNWVRQAPGKGLEYVSGISGGGGTTYYADSVKGRFTISR
--------------------------CDR3-------------FR4---------
DNSKNTLYLQMKSLRAEDTAIYYCAKDQSYCSGAGCHPYYLDYWGQGTLVTVSS
```

NI-307.45E10 VL    (variable light chain sequence VL) (SEQ ID NO: 100)
```
FR1--------------------CDR1-------FR2------------CDR2---FR3--------------
SYVLTQPPSVSVAPGQTARITCGGNNIGSKSVHWYQQKPGQAPVVVVYDDSGRPSGMPERFSGSNSGNTATL
------------------CDR3---------FR4--------
TISRVEAGDEADYYCQVWDSSSDHLYVFGTGTKVTVL
```

Fig. 8 continued

Y   NI-307.72F10 VH   (variable heavy chain sequence VH) (SEQ ID NO: 102)
```
FR1-------------------------CDR1---------FR2-------------CDR2---------------FR3----
EVQLVESGGGVVQPGRSLRLSCATSGFTFDDYAMHWVRQAPGKGLEWVSGLTWSSSGVGYADSVKGRFTISR
---------------------------CDR3---------FR4---------
DNAKNSLYLQMNSLRAEDTALYYCAKGSGEWLRLGQDYWGQGTLVTVSS
```

NI-307.72F10 VL   (variable light chain sequence VL) (SEQ ID NO: 104)
```
FR1---------------------CDR1----------FR2--------------CDR2----FR3-----------
QSVLTQPPSVSGTPGQRVTISCTGSSSNIGAGYDVHWYQQLPGTAPKLLIYDNSNRPSGVPDRFSGSKSGTS
----------------------CDR3---------FR4--------
ASLAITGLQAEDEAHYYCQSFDSSLSGSVFGGGTKLAVL
```

Z   NI-307.56A8 VH   (variable heavy chain sequence VH) (SEQ ID NO: 106)
```
FR1----------------------------CDR1-------FR2------------CDR2---------------FR3----
EVQLVESGGGLVKPGGSLRLSCAASGFTFSSYRMNWVRQAPGKGLEWVSSISSSSSYIYYGDSVKGRFTISR
----------------------------CDR3------FR4---------
DNAKNSLYLQMSSLRAEDTAVYYCARYAHDWNIDYWGQGTLVTVSS
```

NI-307.56A8 VL   (variable light chain sequence VL) (SEQ ID NO: 108)
```
FR1---------------------CDR1---------FR2--------------CDR2----FR3---------------
QSVLTQPPSASGTPGQRVTISCSGSSSNIGSNTVNWYQQLPGTAPKLLIYSNSQRPSGVPDRFSGSKSGTSA
----------------------CDR3---------FR4--------
SLAISGLQSEDEADYYCAAWDDSLNGWVFGGGTKLTVL
```

A2   NI-307.27C11 VH   (variable heavy chain sequence VH) (SEQ ID NO: 110)
```
FR1-------------------------CDR1--------FR2--------------CDR2----------------FR3-----
QVQLQESGPGLVKPSGTLSLTCAVSGDSISSSNWWSWVRQPPGKGLEWIGEIYHSGGTKYNPSLKSRVTISV
------------------------CDR3--------------FR4---------
DKSKNHFSLKLRSVTAADTAVYYCARNRWFDNNRGGYYYYGMDVWGQGTTVTVSS
```

NI-307.27C11 VK   (variable light chain sequence VK) (SEQ ID NO: 112)
```
FR1----------------------CDR1---------FR2--------------CDR2---FR3---------------
DIQMTQSPSSLSASVGDRVTITCRASQGISSYLNWYQQKPGKAPKLLISATSDLQSGVPSRFSGSGSGTDFT
--------------------CDR3------FR4--------
LTISSLQPEDFATYYCQQSYSTPYTFGQGTKLEIK
```

Fig. 8 continued

B2  NI-307.47B11 VH  (variable heavy chain sequence VH) (SEQ ID NO: 114)
```
FR1---------------------CDR1------FR2-----------CDR2--------------FR3---
EVQLVESGGGLVKPGGSLRLSCAASGFTFSDYYMNWIRQAPGKGLEWLSCISSSGNTIYYADSVKGRFTISR
---------------------------CDR3-----------FR4---------
DNAKNSLYLQMNSLRAEDTAVYYCARDLDKAATGRPYFDYWGQGTLVTVSS
```

NI-307.47B11 VL  (variable light chain sequence VL) (SEQ ID NO: 116)
```
FR1--------------------CDR1---------FR2-------------CDR2---FR3-----------
QSVLTQPPSASGTPGQRVTISCSGSSSNIGSNTVNWYQQLPGTAPKLLIYSNNQRPSGVPDRFSGSRSGTSA
--------------------CDR3--------FR4--------
SLAISGLQSEDEADYYCAAWDDSLNGVVFGGGTKLTVL
```

C2  NI-307.26A3 VH  (variable heavy chain sequence VH) (SEQ ID NO: 118)
```
FR1-----------------------CDR1------FR2-----------CDR2---------------FR3----
EVQLVESGGVLVQPGGSLRLSCAASGFTFSSYAMTWVRQAPEKGLEWVSTIIGNGAYTYYADSVKGRFTISR
--------------------------CDR3-----------FR4---------
DNSKNTLILQMNSLRADDAAVYYCAKGTELAPYYYYFALDVWGQGTTVTVSS
```

NI-307.26A3 VK  (variable light chain sequence VK) (SEQ ID NO: 120)
```
FR1-----------------------CDR1---------FR2-------------CDR2---FR3------------
EIVLTQSPGTLSLSPGERATLSCRASQSISSSHLAWYQQKPGQAPRLLIYGASSRATGIPDRFSGGGSGTDF
--------------------CDR3------FR4--------
TLTITRLEPEDFAVYYCQQYGSSPYTFGQGTKLEIK
```

D2  NI-307.27C2 VH  (variable heavy chain sequence VH) (SEQ ID NO: 122)
```
FR1-----------------------CDR1------FR2-----------CDR2--------------FR3----
EVQLVESGGGLVKPGGSLRLSCAASGFTFSSYIMNWVRQAPGKGLQWVSSISSSSTYMYYGDSVKGRFTISR
--------------------------CDR3------FR4---------
DNARNSLYLQMNSLRVEDTAVYYCARYAHDWNVDYWGQGTLVTVSS
```

NI-307.27C2 VL  variable light chain sequence VL) (SEQ ID NO: 124)
```
FR1------------------CDR1-----------FR2--------------CDR2----FR3-----------
QSVLTQPPSASGTPGQRVTISCSGGSSNIGSNPVNWFQQFPGTAPKLLIYANTQRPSGVPDRFSGSKSGTSV
-------------------CDR3--------FR4--------
SLAISGLQSEDEGDYHCAAWDDSLKGWVFGGGTKLTVL
```

Fig. 8 continued

E2    NI-307.57D4 VH (variable heavy chain sequence VH) (SEQ ID NO: 126)
```
FR1----------------------CDR1------FR2-----------CDR2--------------FR3---
EVQLVESGGGLVQPGRSLRLSCAASGFTFDHYAMHWVRQVPGRGLEWVSGVTWNSGIIGYADSVKGRFTISR
--------------------------CDR3---------FR4--------
DNAKNSLYLQMTSLRAEDTALYYCAKGTNDFVSYGLDVWGQGTTVTVSS
```

NI-307.57D4 VL (variable light chain sequence VL) (SEQ ID NO: 128)
```
FR1-------------------------CDR1-----------FR2--------------CDR2----FR3-----------------
QSVLTQPPSVSGAPGQRVSISCTGTSSNLGAGFDVHWYQQIPRKAPELLIYGNSIRPSGVPDRFSGSKSGTS
-----------------------------CDR3---------FR4--------
ASLAITGLQAEDEADYYCQSYDSRLSGSVFGGGTKLTVL
```

F2    NI-307.50H4 VH (variable heavy chain sequence VH) (SEQ ID NO: 130)
```
FR1-----------------------CDR1--------FR2------------CDR2-------------FR3---
QVQLQESGPGLVKPSGTLSLTCAVSGDSISSSNWWSWVRQPPGKRLEWIGEIYHSGGTKYNPSLKSRVTISV
-------------------------------CDR3--------------FR4--------
DKSKNHFSLKLRSVTAADTAVYYCARNRWFDNNRGGYYYYGMDVWGQGTMVTVSS
```

NI-307.50H4 VK (variable light chain sequence VK) (SEQ ID NO: 132)
```
FR1---------------------CDR1--------FR2-------------CDR2---FR3--------------
DIQMTQSPSSLSASVGDRVTITCRAGQGISTYLNWYQQKPGKAPNLLIYATSDLQSGVPSRFSGSGSGTDFT
----------------CDR3------FR4--------
LTISSLQPEDFATYYCQQSYNNPYTFGQGTKVEIK
```

G2    NI-307.53B11 VH (variable heavy chain sequence VH) (SEQ ID NO: 134)
```
FR1----------------------CDR1-------FR2------------CDR2--------------FR3---
EVQLVQSGAEVKKPGESLKISCKGSGYSFTSYWIGWVRQMPGKGLEWMGIIYPGDSDTRYSPSFQGQVTISA
--------------------------CDR3--------FR4---------
DKSITTAYLQWSSLKASDTALYYCARRGSGSFSNYDFWGQGTLVTVSS
```

NI-307.53B11 VK  (variable light chain sequence VK) (SEQ ID NO: 136)
```
FR1------------------CDR1-----------FR2-------------CDR2---FR3------------
QSALTQPRSVSGSPGQSVTISCTGTSSDVGAYNYVSWYQQHPVKAPKLMIYDVSKRPSGVPDRFSGSRSGNT
-------------------CDR3-------FR4--------
ASLTISGLQADDEADYYCCSYAGTYTVLFGGGTKLTVL
```

Fig. 8 continued

H2    NI-307.7J3 VH  (variable heavy chain sequence VH)  (SEQ ID NO: 138)
```
FR1----------------------CDR1---------FR2-----------CDR2--------------FR3--
QVQLQESGPGLVKPSQTLSLTCTVSGGSISSGDYYWSWIRQPPGKGLEWIGYIYYSGTTYYNPSLKSRVTIS
-----------------------CDR3-------------FR4---------
VDTSKNQFSLKLSFVTVADTAVYYCARDGRFTMVRGGYYYYGMDVWGQGTTVTVSS
```

NI-307.7J3 VK   (variable light chain sequence VK)  (SEQ ID NO: 140)
```
FR1----------------------CDR1--------FR2-------------CDR2---FR3-------------
DIQMTQSPSSLSVSVGDRVTITCRASQSISSYLNWYQQKLGKAPKLLIYDASSLQSGVPSRFSGSGSGTDFT
-------------------CDR3------FR4--------
LTISSLQPEDFATYYCQQSYTTPRTFGQGTKVEIK
```

I2    NI-307.59A7 VH   (variable heavy chain sequence VH)  (SEQ ID NO: 142)
```
FR1------------------------CDR1--------FR2-----------CDR2-------------------FR3----
EVQLVESGGGLVQPGGSLRLSCAASGFTFSSYEMNWVRQAPGKGLEWVSYISSSGTNIYHADSVKGRFTISR
------------------------CDR3-----------FR4---------
DNAKNSLYLQMNSLRAEDTAVYYCARDGPSPRGHNYGHDYWGQGTLVTVSS
```

NI-307.59A7 VL  (variable light chain sequence VL)  (SEQ ID NO: 144)
```
FR1----------------------CDR1----------FR2----------------CDR2----FR3------------
QSVLTQPPSASGTPGQRVTISCSGSSSNIGSNAVNWYQQVPGTAPKLLIYTNNQRPSGVPDRFSGSKSGTSA
-------------------CDR3--------FR4--------
SLAISGLQSEDETDYYCAAWDDSLGGPVFGGGTKLTVL
```

J2    NI-307.105A6 VH  (variable heavy chain sequence VH)  (SEQ ID NO: 146)
```
FR1------------------------CDR1-------FR2------------CDR2-------------FR3-----
EVQLVESGGGLVQPGRSLRLSCAASGFTFDDYAMHWVRQAPGKGLEWVSGITWNSGSIGYADSVKGRFTISR
------------------------CDR3--------FR4---------
DNAKNSLYLQMNSLSAEDTALYYCAKGARDYLSYGMDVWGQGTTVTVSS
```

NI-307.105A6 VL  (variable light chain sequence VL)  (SEQ ID NO: 148)
```
FR1----------------------CDR1----------FR2--------------CDR2----FR3-------------
QSVVTQPPSVSGAPGQRVTISCTGSSSNIGAGYDVHWYQQLPGTAPKLLIFSNTIRPSGVPDRFSGSKSGTS
----------------------CDR3--------FR4--------
ASLAITGLQAEDEANYYCQSYDSSLSGSVFGGGTKLTVL
```

Fig. 8 continued

K2    NI-307.29B1 VH (variable heavy chain sequence VH) (SEQ ID NO: 150)
```
FR1------------------------CDR1---------FR2-----------CDR2-------------------FR3---
EVQLVESGGGLVKPGGSLRLSCAASGITFQYYAMNWVRQAPGKGLEWVSSIGGRGDTTYYTDSVKGRFTISR
-------------------------CDR3--------------FR4--------
DNSKSTLYLQMNSLRAEDTAVYYCAKEPFDSSGDHRGVFDYWGQGTLVTVSS
```

NI-307.29B1 VL (variable light chain sequence VL) (SEQ ID NO: 152)
```
FR1-------------------CDR1----------FR2------------CDR2---FR3----------
QSVVTQPPSVSGAPGQRVTISCAGSRSNIGAGYDVNWYQQLPRTAPKLLIYDNTRRPSGVPARFSGSKSGSS
--------------------CDR3-------FR4--------
ASLTITGLQAEDEADYYCQSYDSKLNKVFGGGTKLTVL
```

L2    NI-307.44F6B VH   (variable heavy chain sequence VH) (SEQ ID NO: 154)
```
FR1------------------------CDR1------FR2-----------CDR2-------------FR3---
EVQLVESGGSVVRPGGSLRLACEVSGLRFDDFAMSWVRQVPGKGLEWIAGIFWNSGGTLYADSVKGRFTISR
-------------------------CDR3---------FR4---------
DNAENSLYLQMNSLRAEDTALYRCVRGRSHAAYYGMDVWGKGTTVTVSS
```

NI-307.44F6B VK (variable light chain sequence VK) (SEQ ID NO: 156)
```
FR1---------------------CDR1------------FR2-------------CDR2---FR3---------
EIVLTQSPLSLPVTPGEPASISCRSSQSLLHSNGYNYLDWYLQKPGQSPQLLIYLGSNRASGVPDRFSGSGS
----------------------CDR3------FR4--------
GTDFTLTISRVEAEDVGIYYCMQALQNALAFGGGTKLEIK
```

M2    NI-307.98H1 VH (variable heavy chain sequence VH) (SEQ ID NO: 158)
```
FR1-------------------------CDR1---------FR2------------CDR2--------------FR3---
QLQLQESGPGLVKPSQTLSLTCAVSGASISSGTYYWGWIRQHPGKGLEWIGYIYPSGSTYYNPSLKSRVIIS
----------------------------CDR3--------------FR4----------
LDTSKSQFSLNLSSVTAADTAVYYCARDYYDSSGHMGGYYHYAMDVWGQGTTVTVSS
```

NI-307.98H1 VK (variable light chain sequence VK) (SEQ ID NO: 160)
```
FR1---------------------CDR1--------FR2-------------CDR2---FR3-------------
DIQLTQSPSSLSASVGDRVTITCRASQSISSHLNWYQQKPGKVPKLLIYAASTLQSGVPSRFSGSGSGTDFT
-------------------CDR3------FR4--------
LAISSLQPADFATYYCQQSYSTPRTFGQGTKVDIK
```

Fig. 8 continued

N2  NI-307.43E8 VH (variable heavy chain sequence VH) (SEQ ID NO: 162)
```
FR1-----------------------CDR1-------FR2------------CDR2-----------------FR3----
EVQLVESGGDVVQPGRSLRLSCAASGFAFSIYAMNWVRQAPGKGLEWVALISTSGTEHYADSVKGRFTISRD
------------------------CDR3------------FR4---------
NSKNTLFLQINSLRVEDTAVYYCARDLDSTGYYENNYWGQGTLVTVSS
```

NI-307.43E8 VK (variable light chain sequence VK) (SEQ ID NO: 164)
```
FR1---------------------CDR1-------------FR2-------------CDR2----FR3----------
DVVMTQSPLSSPVSLGQPASISCRSSHSLVHSNGDTYLSWLQQRPGQPPRLLIYKISNRFSGVPDRFSGSGA
-------------------------CDR3------FR4----------
GTDFTLKISRVEAEDVGVYFCMQATSFPRTFGQGTKVEIK
```

O2  NI-307.18F4A VH (variable heavy chain sequence VH) (SEQ ID NO: 166)
```
FR1----------------------CDR1-------FR2------------CDR2-----------------FR3----
EVQLVESGGGLVKPGGSLRLSCAASGFTFTNYYMTWVRQAPGKGLEWVSYITGGGSTTYYADSVTGRFTISR
---------------------------CDR3----------FR4----------
DNAKNSLYLQMSSLRVEDTAVYYCARGRGYPDNWFDPWGQGTLVTVSS
```

NI-307.18F4A VK (variable light chain sequence VK) (SEQ ID NO: 168)
```
FR1---------------------CDR1-------FR2-------------CDR2---FR3---------------
SYVLTQPPSVSVSPGQTARITCSGDALPKQYVYWYQQKPGQAPVLMIYKDAERPSGIPDRFSGSSSGTTVTL
------------------CDR3--------FR4--------
TISGVQAEDEADYYCQSTDISGAAVVFGGGTKLTVL
```

Fig. 8 continued

Fig. 10
A
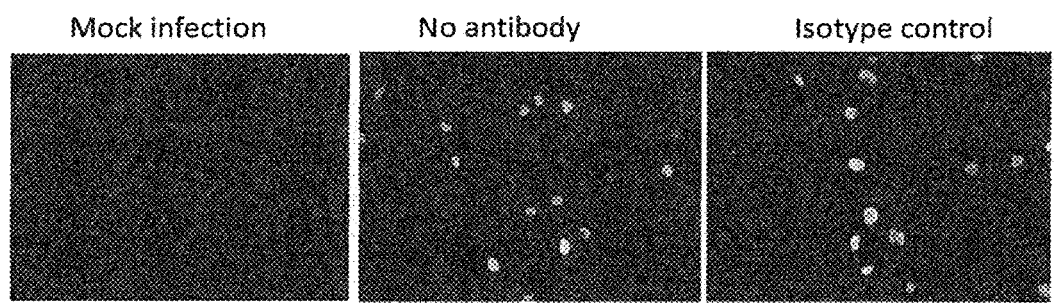
B
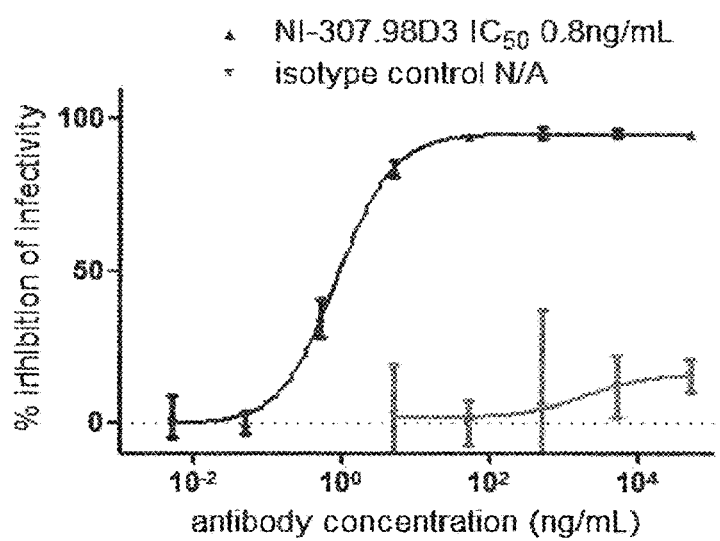

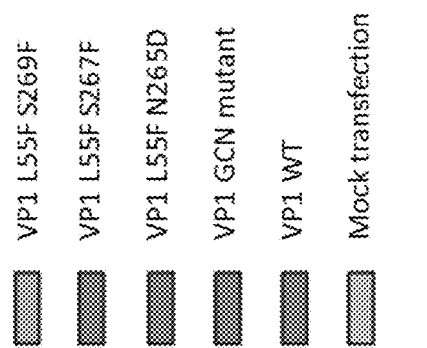
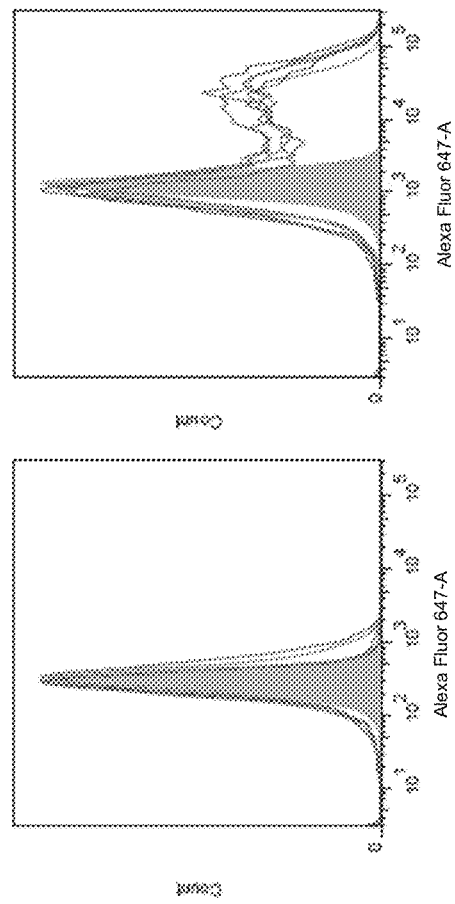
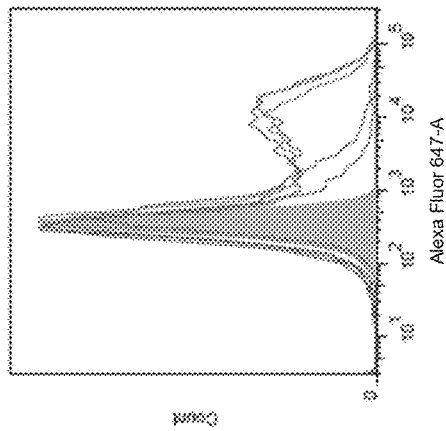
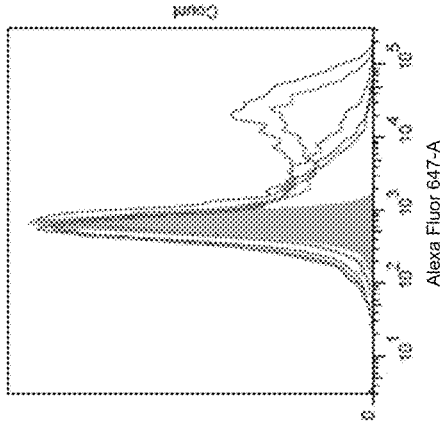
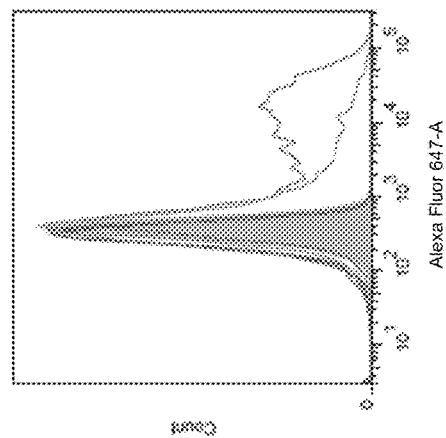
Fig. 11

RECOMBINANT HUMAN ANTIBODIES FOR THERAPY AND PREVENTION OF POLYOMAVIRUS-RELATED DISEASES

RELATED APPLICATIONS

This application is a continuation of U.S. application Ser. No. 14/758,615 (now patented as U.S. Pat. No. 9,771,413), which is a United States National Phase under 35 U.S.C. § 371 of International Application No. PCT/EP2014/050024, filed on Jan. 2, 2014, which claims priority to EP 12199837.1, filed on Dec. 31, 2012 and U.S. 61/747,541, filed on Dec. 31, 2012, the contents of each of which are hereby incorporated by reference in their entirety for all purposes.

SEQUENCE LISTING

This application contains a Sequence Listing which has been submitted electronically in ASCII format via EFS-Web and is incorporated by reference in its entirety. Said ASCII copy is named 105375_0015_revised_sequence_listing.txt, is 265 kilobytes in size, and was created on Feb. 2, 2019.

FIELD OF THE INVENTION

The present invention generally relates to novel molecules specifically binding to human polyomavirus and/or antigens thereof, particularly human antibodies as well as fragments, derivatives and variants thereof that recognize the JC virus (JCV) or BK virus (BKV), JCV VP1 protein and/or BKV VP1 protein or a fragment thereof.

In addition, the present invention relates to pharmaceutical and diagnostic compositions comprising such binding molecules, antibodies and mimics thereof valuable both as a diagnostic tool to identify polyomaviruses and/or polyomavirus VP1 proteins, preferably JC virus (JCV) and/or BK virus (BKV), JCV VP1 protein and/or BKV VP1 protein or a fragment thereof and also a passive vaccination strategy for treating disorders related to polyomavirus infection such as Progressive Multifocal Leukoencephalopathy (PML), infection of granule neurons, hyperchromatic nuclei, granule cell neuronopathy, cerebral autothrophy, encephalopathy, meningitis, Polyoma-induced tumors, immune reconstitution inflammatory syndrome (IRIS), hemorrhagic cystitis, pneumonia, retinitis, colitis, vasculitis, interstitial kidney disease, infections of respiratory tract.

BACKGROUND OF THE INVENTION

Polyomaviruses are small non-enveloped double-stranded DNA viruses which display restricted species and cell-type specificity. Up to ten different polyomaviruses have been found in humans that have oncogenic potential and can cause chronic infections. JC virus, or John Cunningham virus (JCV), is a member of the Polyomaviridae family and the causative agent of Progressive Multifocal Leukoencephalopathy (PML), a life-threatening viral infection of the brain. BK virus (BKV) is also a human specific polyomavirus which is responsible for BK nephropathy and loss of graft in renal transplant patients. JCV and BKV are both opportunistic pathogens which infect the human population during early childhood, while the infection is mostly asymptotic. The seroprevalescence in adults is about 70-80% (Knowls, ADV. Exp. Med. Biol. 577 (2006), 19-45). The viruses remain latent mostly in the kidney cells of the host until reactivation which occurs in immunosuppressed individuals.

The viral capsid is about 40 nm in diameter and is formed by 72 pentamers of the VP1 protein. Each pentamer is associated with one molecule of either VP2 or VP3, the 2 minor capsid proteins. Only VP1 is exposed on the surface of the virus and it is therefore the protein responsible for the receptor binding. The virus genome is divided into early coding regions (small and large T antigens) and late coding regions (VP1, VP2, VP3 and agnoprotein).

Up to 90% of the global population has been exposed to JCV without developing any clinical syndrome. The virus can stay in a dormant state in patients for a long period of time and is kept under control by the immune system. However, JCV can be reactivated and can cause a demyelinating disease of the central nervous system (CNS), namely Progressive Multifocal Leukoencephalopathy (PML). PML is an opportunistic and often fatal infection that occurs in states of immunocompromise such as human immunodeficiency virus (HIV) infection, cancer, organ transplantation, haematological malignancies or rarely during autoimmune diseases. In Acquired immunodeficiency syndrome (AIDS) patients, PML was one of the most serious complications, although its incidence decreased after introduction of anti-retroviral therapy.

Furthermore, immunomodulatory therapies that target immune cells or therapies for conditions such as Multiples Sclerosis (MS) as well as patients with liver or renal impairment, and patients with psoriasis, systemic lupus erythematosus, chronic lymphocytic leukemia (CLL), Hodgkin's lymphoma, and Crohn's disease have an increased risk of incident of PML. JCV infects cerebelar granual cells, oligodendrocytes, astocytes, and pyramidal cells. So far its primary infection is restricted to kidney, epithelial cells, tonsillar stromal cells, bone marrow, oligodendrocytes, and astrocytes (Frenchy et al., Clin. Microbiol. Rev. 425 (2012), 471-506).

The pathogenesis of PML is characterized by a lytic infection of myelin-forming oligodendrocytes and abortive infection of astrocytes in the absence of a notable immune reaction. However, other central nervous system (CNS) cells such as cerebellar granule neurons can also be infected by JCV. The most frequent symptoms of PML include cognitive impairments, motor dysfunctions, visual deficits, seizures, impaired speech and headaches.

There is no specific antiviral drug against JCV to treat PML so the reconstitution or restoration of the immune system is the best solution. On the other hand, the increased immune system activity can lead to an important influx of lymphocytes into the brain and to the immune reconstitution inflammatory syndrome (IRIS).

Many broad-spectrum nucleotide analog chemotherapeutics that interrupt RNA and DNA synthesis including for example cytosine arabinoside, acyclovir, and cidofovir have been used to inhibit JC virus (JCV) replication in PML patients, but without much success (Frenchy et al., Clin. Microbiol. Rev. 25 (2012), 471-506).

In addition, further treatment strategies include inhibition of the virus entry into the host cell by for example $5HT_{2a}$ antagonists, an increase in T cell amount by for example IL-2, plasma exchange in patients who develop PML as a consequence of for example natalizumab.

Identifying a therapy for the prevention of onset or treatment of PML addresses an urgent unmet medical need in several fields of medicine including acquired and hereditary immunodeficiencies, oncology, transplant medicine and autoimmune diseases. This often fatal viral disease represents a severe opportunistic infection associated with immunodeficiencies such as HIV infection, allotransplantation, and cancer chemotherapy. Over the past decades, the incidence of PML has significantly increased related to the AIDS pandemic and, more recently, to the growing use of immunosuppressive drugs. Reports of PML-related deaths of patients receiving natalizumab (Tysabri; Biogen/Elan) for Multiple Sclerosis (MS), efalizumab (Raptiva; Genentech/Merck Serono) for psoriasis, rituximab (Rituxan; Genentech/Biogen) for systemic lupus erythematosus, and infliximab (Remicade; Centocor) for rheumatoid arthritis and Morbus Crohn, highlight the tremendous negative impact of PML for the future use of these otherwise safe and efficacious life-saving treatments. After several cases of PML with fatal outcome efalizumab had to be withdrawn from the market. Similarly, recent estimates assume an incidence of PML in 1:500 MS patients, who are treated with natalizumab, with a strong increase beyond 2 years of treatment thus jeopardizing the further use of this currently most effective treatment for MS. Increased risk of PML is also evident for several novel drug candidates that are in late stage development for MS such as rituximab/ocrelizumab (anti-CD20; Roche) and alemtuzumab (anti-CD52; Sanofi-Aventis/Genzyme).

BK virus (BKV) is also widespread in the global population and the infection can stay asymptomatic. However, immune-compromised patients cannot repress anymore the viral replication and BKV reactivation can lead to several diseases. BKV became mainly an issue in cases of severe immune depression, for example in patients who received a transplant and who therefore had to take immunosuppressive drugs. In those patients, the virus can multiply inside the graft cells and cause a disease named BK nephropathy which can finally lead to graft loss. BKV is also an issue for patients who received a bone marrow transplant and who can develop a hemorrhagic cystitis. (Bogdanovic et al., Anticancer Res. 26 (2006), 1311-1318; Hirsch, Am. J. Transplant. 2 (2002), 25-30). However, in transplant recipients BKV reactivation is common and leads to distinctive pathological entries in different patient groups (Van Alderen et al., Neth. J. Med. 70 (2012), 172-183). Furthermore, the BKV can be reactivated in HIV infected patients leading to for example meningitis.

There is no available treatment to clear BKV infection. Some small molecules have been reported to limit the viral spread but their mechanisms of action are not entirely understood. The most efficient way to control the viral replication is to restore the immune system or to decrease the doses of immunosuppressive drugs. However, this could also lead to graft rejection.

Thus, there is a need for therapeutic means capable of preventing an infection or spreading of polyomavirus in the human body and the onset and progression of diseases related to polyomavirus infection including those, where common medical treatment activates polyomavirus replication such as the use of immunosuppressive drugs.

This technical problem has been solved by the embodiments characterized in the claims and described further below as illustrated in the Examples and Figures.

SUMMARY OF THE INVENTION

Targeted therapy with monoclonal antibodies provides a novel therapeutic approach to block the spreading of the JCV and/or BKV by passive immunization addressing the large unmet medical needs associated with JCV and BKV related diseases. The first in class recombinant human antibodies subject to the present invention that were generated based on B-cell analysis of selected human donor populations including donors recovered from PML and PML-IRIS represent highly promising novel drug candidates for these indications.

The present invention makes the use of the human polyomavirus specific immune response of healthy human subjects for the generation of recombinant anti-human polyomavirus specific human monoclonal antibodies. Experiments performed in accordance with the present invention were successful in the generation of recombinant monoclonal human antibodies targeting human polyomaviruses, i.e. JC virus (JCV) and BK virus (BKV) from pools of healthy human subjects and from pools of patients that have successfully recovered from PML and PML-IRIS, respectively, and other patient groups with polyomavirus-associated diseases; see also the description in the background of the invention, supra.

In particular, immune repertoires obtained from cohorts of healthy donors (HLA-DRB1*04:01+ or unknown haplotype) or patients recovered from PML and PML-IRIS were screened for memory B cells against VP1. Positive hits were counter-screened to exclude clones cross-reacting with unrelated targets and selective VP1-reactive B-cells were subjected to cDNA cloning of IgG heavy and light chains and sub-cloned in expression constructs by using Ig-framework specific primers for human variable heavy and light chain families in combination with human J-H segment-specific primers. The amino acid and DNA sequences of the resulting antibodies are provided in Table II. Those antibodies were tested for their binding specificity and binding efficiency on JCV VP1, JCV VP1 VLP, BKV VP1 and BKV VP1 VLP. To test the binding of antibody hits to the Virus-Like Particles (VLPs), the refolding of VP1 proteins were set up (see Example 2). Human VP1-specific antibodies showed high affinity to their targets, within the picomolar range. They were either JCV specific (see Example 4) or also crossreactive towards VP1 protein from BKV (see Example 5). Some of the antibodies were binding VP1 protein from both viruses but with a preference for BKV (see Example 6). The binding epitope of VP1 antibodies was next assessed by binding analyses of linear overlapping peptides spanning the full-length VP1 sequence (see Example 8).

To test the potency of antibody hits to block the virus infection and spreading, virus neutralization assays can be performed (see Example 9).

Since safety of antibody-based therapy is highly dependent on target specificity, the cross-reactivity of VP1 antibodies towards a panel of unrelated proteins was evaluated by direct ELISA. VP1 antibodies demonstrated minimal cross-reactivity to unrelated targets (FIG. 6). The antibody hits obtained from healthy donors and from a post-PML-IRIS patient that developed in response to immunotherapy of multiple sclerosis were compared. Elevated numbers of VP1 specific high affine antibodies produced by the memory B cells of such patient that are likely protective and responsible for the recovery could be identified. Interestingly, most of those antibodies were only recognizing JCV VP1 VLP (see Example 10).

To test the potency of the exemplary antibodies to recognize and block the JCV in vivo, the ability of the exemplary antibodies to bind in solution to the VP1 VLPs and JCV has been assessed (see Example 11).

During the infection and the course of the PML/PML-IRIS disease, the VP1 protein from the JC virus could acquire mutations to escape the immune system or to gain an advantage compared to the WT virus. Therefore the ability of the exemplary antibodies to bind to the most common PML-associated VP1 mutants has been tested (see Example 12).

Although the mechanisms of controlling JCV infection are as yet incompletely understood, latency of JCV infection is probably controlled by effective humoral and/or cellular immune responses in healthy individuals. Accordingly, the presence of JCV-specific CD8+ cytotoxic T cells has been linked to the recovery from PML, while these cells were absent in PML cases with fatal outcome. Also, PML occurs preferentially in situations of decreased CD4+ T cell numbers or compromised CD4+ cell functions such as AIDS and idiopathic CD4+ lymphopenia. Comparable to the role of CD8+ JCV-specific T cells, the resolution of PML follows the restoration of CD4+ number and function, indicating that both CD4+ and CD8+ virus-specific T cells are crucial for host protection. Finally, there is evidence that the intrathecal antibody response plays an important role in PML and in elimination of JCV from the brain during PML-IRIS, where both memory B- and plasma cell infiltration in the brain and prominent high intrathecal JCV VP1-specific antibody responses with a predominance of IgG1 and IgG3 subclasses were found. It is probably the interplay between all major players of adaptive immune responses, i.e. JCV-specific CD4+ T cells, -CD8+ T cells and antibodies, that assures that JCV infection is controlled in the healthy individuals and PML does not develop.

The present invention is thus directed to human and human-derived antibodies, antigen-binding fragments, and similar antigen-binding molecules which are capable of specifically recognizing polyomavirus, and/or polyomavirus VP1 protein or a fragment thereof. If not indicated otherwise, by "specifically recognizing "polyomavirus and/or polyomavirus VP1 protein", "antibodies specific to/for polyomavirus", and "anti-polyomavirus antibody" is meant specifically, generally, and collectively, antibodies to the native form of polyomaviruses and/or antibodies binding specifically to either forms of polyomavirus and/or antibodies binding to polyomavirus specific VP1 proteins. Provided herein are human antibodies specific for polyomavirus, polyomavirus VP1 protein, and/or polyomavirus VP1 virus-like particles (VLPs).

In a preferred embodiment of the present invention, the human antibody or antigen-binding fragment thereof demonstrates the immunological binding characteristics of an antibody characterized by the variable region $V_H$ and/or $V_L$ as set forth in FIG. 8.

Furthermore, the present invention relates to compositions comprising the antibody of the present invention or active fragments thereof and to immunotherapeutic and immunodiagnostic methods using such compositions in the prevention, diagnosis or treatment of disorders related to polyomaviruses, such as PML, wherein an effective amount of the composition is administered to a patient in need thereof.

Naturally, the present invention extends to human B memory lymphocytes and B cells, respectively, that produce the antibody or antigen-binding fragment thereof having the distinct and unique characteristics as defined below.

The present invention also relates to polynucleotides encoding at least a variable region of an immunoglobulin chain of the antibody of the invention. Preferably, said variable region comprises at least one complementarity determining region (CDR) of the variable region as set forth in FIG. 8.

Accordingly, the present invention also encompasses vectors comprising said polynucleotides and host cells transformed therewith as well as their use for the production of an antibody and equivalent binding molecules which are specific for polyomavirus and/or polyomavirus VP1 protein. Means and method for the recombinant production of antibodies and mimics thereof as well as methods of screening for competing binding molecules, which may or may not be antibodies, are known in the art. However, as described herein, in particular with respect to therapeutic applications in humans, the antibody of the present invention is a human antibody in the sense that application of said antibody is substantially free of an immune response directed against such antibody otherwise observed for chimeric and humanized antibodies.

Furthermore, disclosed herein are compositions and methods that can be used to identify polyomavirus and/or polyomavirus VP1 protein in samples and/or in vivo. The anti-polyomavirus and/or anti-polyomavirus VP1 protein antibodies and/or binding fragments thereof can be used to screen human samples for the presence of polyomavirus, preferably JCV and/or BKV in samples, for example by using ELISA based on surface adapted assays.

In one embodiment of the present invention the polyomavirus-binding molecule and/or binding fragment thereof comprising at least one CDR of an antibody of the present invention are for use in in vivo detection of or targeting a therapeutic and/or diagnostic agent to polyomaviruses in the human. The methods and compositions disclosed herein can add in disorders-related to polyomaviruses and can be used to monitor disease progression and therapeutic efficacy of the therapy provided to the subject, for example in in vivo imaging related diagnostic methods. Therefore, in one embodiment the polyomavirus-binding molecule of the present invention is provided, wherein said in vivo imaging comprises positron emission tomography (PET), single photon emission tomography (SPECT), near infrared (NIR), optical imaging or magnetic resonance imaging (MRI).

Hence, it is a particular object of the present invention to provide methods for treating, diagnosing and/or preventing diseases related to polyomaviruses such as PML. The methods comprise administering an effective amount of a human antibody or antibody derivative to the subject where the antibody targets polyomaviruses and/or fragments thereof.

In a further aspect, the present invention provides a peptide having an epitope of a polyomavirus, polyomavirus VP1 protein and/or an antigen-binding fragment thereof, preferably of JCV and/or BKV specifically recognizing an antibody of the present invention. Said peptide comprises or consists of an amino acid sequence as indicated below in the detailed description and in the Examples or a modified sequence thereof in which one or more amino acids are substituted, deleted, and/or added.

Additionally, the present invention provides a method for diagnosing disorder associated with a polyomavirus, comprising a step of determining the presence of an antibody that binds to said peptide in a biological sample of said subject.

In detail the present invention is directed to (1) A human monoclonal antibody or an antigen-binding fragment thereof which is capable of binding to a polyomavirus and/or antigen thereof.

(2) The antibody or antigen binding fragment of (1), wherein the polyomavirus is JC virus (JCV) or BK virus (BKV).

(3) The antibody or an antigen binding fragment of (1) or (2), which is capable of binding VP1 protein or a fragment thereof, preferably wherein the antibody or antigen binding fragment thereof is capable of binding at least one, two, three, etc., or more of the VP1 mutants described in Example 12 and FIG. 11.

(4) The antibody or an antigen binding fragment of any one of (1) to (3), which is capable of recognizing an epitope exposed on the surface of the virus.

(5) The antibody or an antigen binding fragment of any one of (1) to (4), which does not substantially recognize serum albumin, preferably bovine serum albumin (BSA).

(6) The antibody or an antigen binding fragment of any one of (1) to (5), which is capable of binding preferentially to JCV over BKV or preferentially to BKV over JCV.

(7) The antibody or an antigen binding fragment of any one of (1) to (6), which is capable of specifically binding at least one VP1 epitope which comprises or essentially consists of the amino acid sequence LPGDPDM (SEQ ID NO: 85), GQATHDN (SEQ ID NO: 86), MRYVD-KYGQLQT (SEQ ID NO: 87) or RVFEGTEELPG (SEQ ID NO: 88). In one embodiment, the antibody or fragment thereof recognizes two of the mentioned epitopes.

(8) The antibody or an antigen binding fragment thereof of any one of claims (1) to (7), comprising in its variable region
 (a) at least one complementarity determining region (CDR) of the $V_H$ and/or $V_L$ variable region amino acid sequence depicted in FIG. 8
  (i) $V_H$ sequence (SEQ ID NOs: 1, 5, 9, 13, 17, 21, 25, 29, 33, 37, 41, 45, 49, 53, 57, 61, 65, 69, 73, 77, 81, 89, 93, 97, 101, 105, 109, 113, 117, 121, 125, 129, 133, 137, 141, 145, 149, 153, 157, 161, 165); and
  (ii) $V_L$ or $V_k$ sequence (SEQ ID NOs: 3, 7, 11, 15, 19, 23, 27, 31, 35, 39, 43, 47, 51, 55, 59, 63, 67, 71, 75, 79, 83, 91, 95, 99, 103, 107, 111, 115, 119, 123, 127, 131, 135, 139, 143, 147, 151, 155, 159, 163, 167);
 (b) an amino acid sequence of the $V_H$ and/or $V_L$ region as depicted in FIG. 8;
 (c) at least one CDR consisting of an amino acid sequence resulted from a partial alteration of any one of the amino acid sequences of (a); and/or
 (d) a heavy chain and/or a light variable region comprising an amino acid sequence resulted from a partial alteration of any one of the amino acid sequences of (b);
 the antibody or antigen binding fragment thereof optionally further comprising a polypeptide sequence which is heterologous to the $V_H$ and/or $V_L$ region or the least one CDR, preferably wherein polypeptide sequence comprises a human constant domain, preferably of the IgG type, most preferably of the IgG1 class or isotype.

(9) A polynucleotide encoding at least a binding domain of a variable region of an immunoglobulin chain of the antibody or an antigen binding fragment thereof of any one of (1) to (8).

(10) A vector comprising the polynucleotide of (9), optionally in combination with a polynucleotide of (9) that encodes the variable region of the other immunoglobulin chain of the antibody or an antigen binding fragment thereof.

(11) A host cell comprising a polynucleotide of (9) or a vector of (10).

(12) A method for preparing an antibody which binds to polyomavirus and/or an antigen binding fragment/domain thereof, or immunoglobulin chain(s) thereof, said method comprising
 (a) culturing the cell of (11); and
 (b) isolating said antibody or immunoglobulin chain(s) thereof from the culture.

(13) An antibody encoded by a polynucleotide of (9) or obtainable by the method of (12).

(14) The antibody of any one of (1) to (8) or (13), which is detectably labelled.

(15) The antibody of (14), wherein the detectable label is selected from the group consisting of an enzyme, a radioisotope, a flurophore, a peptide and a heavy metal.

(16) The antibody of any one of (1) to (8) or (13) to (15), which is attached to a drug.

(17) A composition comprising the antibody of any one of (1) to (8) or (13) to (16), the polynucleotide of (10), the vector of (11) or the cell of (12), preferably wherein the composition
 (a) is a pharmaceutical composition and further comprises a pharmaceutical acceptable carrier, or
 (b) a diagnostic composition, and further comprises reagents conventionally used in immune- or nucleic acid based diagnostic methods.

(18) The composition of (17), which is vaccine.

(19) The composition of (17) or (18) further comprising an immunomodulatory agent.

(20) An antibody of any one of (1) to (8) or (13) to (16), or a polyomavirus VP1 binding molecule having substantially the same binding specificities of any one thereof, the polynucleotide of (9), the vector of (10) or the cell of (11) for use in the preparation of a pharmaceutical or diagnostic composition for prophylactic and therapeutic treatment monitoring the progression or respond to treatment of Progressive Multifocal Leukoencephalopathy (PML), infection of granule neurons, hyperchromatic nuclei, granule cell neuronopathy, cerebral autothrophy, encephalopathy, meningitis, Polyoma-induced tumors, immune reconstitution inflammatory syndrome (IRIS), hemorrhagic cystitis, pneumonia, retinitis, colitis, vasculitis, interstitial kidney disease, infections of respiratory tract, JCV nephropathy, BKV nephropathy, meningitis, Merkel cell carcinoma, trichodysplasia spinulosa or malignant pleural mesothelioma.

(21) A polyomavirus binding molecule comprising at least one CDR of an antibody of any one of (1) to (8) or (13) to (16) for use in in vivo detection of or targeting a therapeutic and/or diagnostic agent to polyomaviruses in the human or animal body.

(22) The polyomavirus binding molecule of (21), wherein said in vivo imaging comprises positron emission tomography (PET), single photon emission tomography (SPECT), near infrared (NIR), optical imaging or magnetic resonance imaging (MRI).

(23) A peptide having an epitope of polyomavirus specifically recognized by an antibody of any one of claims (1) to (8) or (13) to (16).

(24) The peptide of (23), wherein the peptide comprises an amino acid sequence as defined in (7) or a modified sequence thereof in which one or more amino acids are substituted, deleted and/or added, wherein the peptide is recognized by the antibody of (7) or (8).

(25) A method for diagnosing JC virus (JCV) or BK virus (BKV) infection and disorders associated with polyomavirus in a subject such as Progressive Multifocal Leukoencephalopathy (PML) or BK (nephropathy), comprising steps of determining the presence of an antibody that binds to a peptide of (23) or (24) in a biological sample of said subject.

(26) A kit useful in the diagnosis or monitoring of the progression of Progressive Multifocal Leukoencephalopathy (PML) and/or transplant rejection following clinical bone marrow, kidney, and other solid organs transplantations, said kit comprising at least one antibody of any one of (1) to (8) or (13) to (16) or a polyomavirus binding molecule having substantially the same binding specificities of any one thereof, the polynucleotide of (9), the vector of (10) or the cell of (11) and/or the peptide of (23) or (24), optionally with reagents and/or instructions for use.

(27) At least one antibody of any one of (1) to (8) or (13) to (16) for use in combination, concomitantly or sequentially with an immunomodulatory agent in the treatment of a disease associated with the (re)activation of polyomaviruses.

(28) The composition of (19) or antibody of (27), wherein the disease is Progressive Multifocal Leukoencephalopathy (PML), infection of granule neurons, hyperchromatic nuclei, granule cell neuronopathy, cerebral autothrophy, encephalopathy, meningitis, Polyoma-induced tumors, immune reconstitution inflammatory syndrome (IRIS), hemorrhagic cystitis, pneumonia, retinitis, colitis, vasculitis, interstitial kidney disease, infections of respiratory tract, JCV nephropathy, BKV nephropathy, meningitis, Merkel cell carcinoma, trichodysplasia spinulosa or malignant pleural mesothelioma and/or the agent is natalizumab, efalizumab, rituximab, infliximab, ocrelizumab, alemtuzumab, bentuximab or vedotin.

Further embodiments of the present invention will be apparent from the description and Examples that follow.

BRIEF DESCRIPTION OF THE DRAWINGS

FIG. 1: Characterization of VP1 preparations by transmission electron microscopy. Electron microscopy images of the VP1 proteins used for ELISA plates coating diluted to 200 μg/ml either in carbonate coating buffer (A) or reassociation buffer (B). The VP1 proteins were stained with anti-VP1 antibody (Ab34756) and then with a goat anti-mouse IgG, 10 nm gold. Scale bar represents 200 nm.

The underlined amino acids differ between JCV VP1 and BKV VP1 protein.

Figure 6:
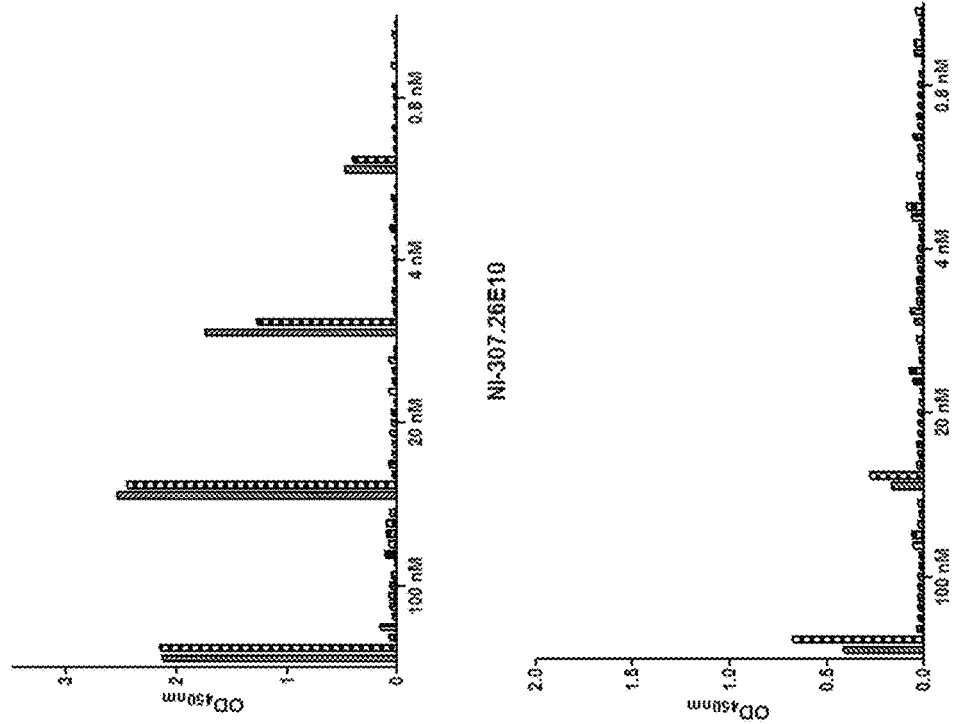

FIG. 6: Cross-reactivity testing of VP1 antibodies towards monomeric or aggregated proteins by direct ELISA.
- (A) ELISA plates were coated with the indicated antigens at different concentrations and then incubated with recombinant NI-307.11G6, NI-307.25G10, NI-307.19F8 and NI-307.26E10 antibodies. The antibodies showed a specific binding to the VP1 preparations and no binding to the unrelated proteins. Data are expressed as OD values at 450 nm.
- (B) ELISA plates were coated with the indicated antigens at a concentration of 1 μg/mL and then incubated with recombinant NI-307.11G6, NI-307.25G10, NI-307.19F8 and NI-307.26E10 antibodies. The antibodies showed a specific binding to different VP1 preparations and no binding to JCV VP2 and VP3 proteins (Bioclone Inc) and other unrelated proteins. Data are expressed as OD values at 450 nm.

FIG. 7: Isolation of VP1 specific antibodies from a post-PML-IRIS patient.
- (A) ELISA plates were coated with the indicated antigens at different concentrations and then incubated with recombinant NI-307.58C7 and NI-307.105C7 antibodies cloned from a patient that had successfully recovered from PML and PML-IRIS. The antibodies showed a specific binding to the JCV VP1 VLP and no binding to disrupted particles (JCV VP1), BKV VP1 preparations or unrelated monomeric or aggregated proteins. Data are expressed as OD values at 450 nm.

(B) The EC50 values for the antibodies NI-307.7J3, NI-307.26A3, NI-307.27C2, NI-307.27C11, NI-307.29B1, NI-307.43E8, NI-307.45E10, NI-307.47B11, NI-307.50H4, NI-307.53B11, NI-307.56A8, NI-307.57D4, NI-307.58C7, NI-307.59A7, NI-307.72F7, NI-307.72F10, NI-307.98D3, NI-307.98H1, NI-307.105A6 and NI-307.105C7 were estimated by a non-linear regression using GraphPad Prism software. N/A: not applicable.

FIG. 8: Amino acid and nucleotide sequences of the variable region, i.e. heavy chain and kappa/lambda light chain of human JCV and/or BKV antibodies.

(A) NI-307.13G4, (B) NI-307.19F10, (C) NI-307.19F8, (D) NI-307.11G6, (E) NI-307.17F12, (F) NI-307.6A2, (G) NI-307.5H3, (H) NI-307.25G10, (I) NI-307.26E10, (J) NI-307.1E1, (K) NI-307.24C6, (L) NI-307.78C3, (M) NI-307.57D5, (N) NI-307.43A11, (O) NI-307.3G4, (P) NI-307.61D11, (Q) NI-307.24F3, (R) NI-307.18E12, (S) NI-307.20F5, (T) NI-307.58C7, (U) NI-307.105C7, (V) NI-307.98D3, (W) NI-307.72F7, (X) NI-307.45E10, (Y) NI-307.72F10, (Z) NI-307.56A8, (A2) NI-307.27C11, (B2) NI-307.47B11, (C2) NI-307.26A3, (D2) NI-307.27C2, (E2) NI-307.57D4, (F2) NI-307.50H4, (G2) NI-307.53B11, (H2) NI-307.7J3, (I2) NI-307.59A7, (J2) NI-307.105A6, (K2) NI-307.29B1, (L2) NI-307.44F6B, (M2) NI-307.98H1, (N2) NI-307.43E8 and (O2) NI-307.18F4A. Framework (FR) and complementarity determining regions (CDRs) are indicated with the CDRs being underlined. Due to the cloning strategy the amino acid sequence at the N-terminus of the heavy and light chain may potentially contain primer-induced alterations in F1, which however do not substantially affect the biological activity of the antibody. In order to provide a consensus human antibody, the nucleotide and amino acid sequences of the original clone were aligned and tuned in accordance with the pertinent human germ line variable region sequences in the data base; see, e.g., V base (http://vbase.mrc-cpe.cam.ac.uk/) hosted by the MRC Center for protein engineering (Cambridge, UK).

Figure 9:
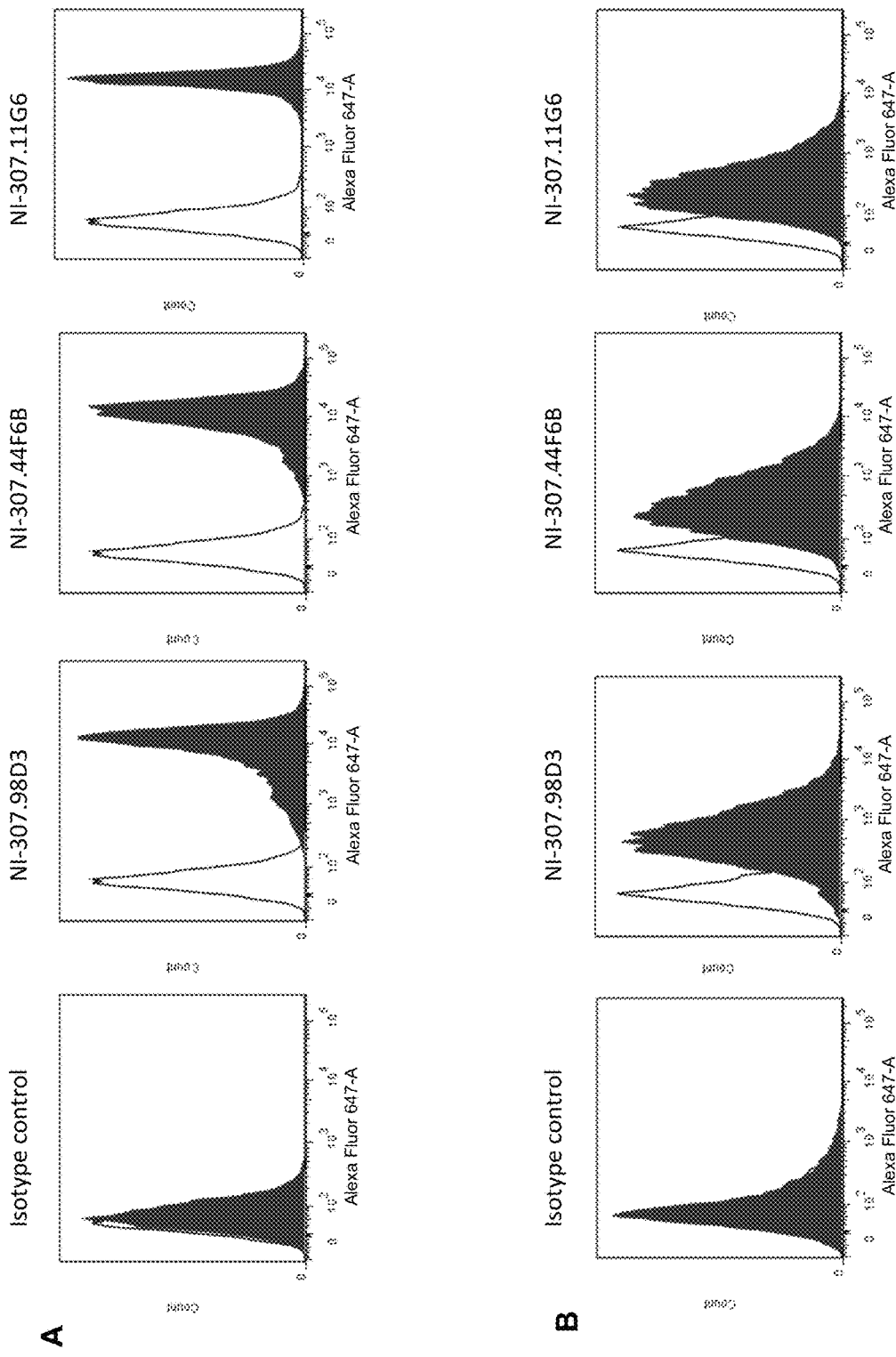

FIG. 9: Binding in solution to VP1 VLPs and JCV of the recombinant human-derived antibodies assessed by flow cytometry.

(A) Assembled VP1 VLPs were incubated with latex beads to allow them to attach. The beads were afterwards washed, stained with NI-307.98D3, NI-307.44F6B and NI-307.11G6 and then analyzed by flow cytometry to assess the binding of the exemplary antibodies to the VP1 VLPs.

(B) JCV produced by infected SVG-A cells were incubated with latex beads to allow them to attach. The beads were afterwards washed, stained with NI-307.98D3, NI-307.44F6B and NI-307.11G6 and then analyzed by flow cytometry to assess the binding of the exemplary antibodies to JCV.

FIG. 10: Neutralization of the JCV infection of the SVG-A cells by the recombinant human-derived antibodies.

(A) JCV was incubated with either the exemplary antibodies or an isotype control. The viruses were afterwards added to SVG-A cells which were then fixed 3-day post-infection, permeabilized and stained with DAPI (blue color) and anti-VP1 antibodies (green color, bright). The stained cells were then visualized with a fluorescent microscope.

(B) JCV was incubated with either the exemplary NI-307.98D3 antibody or an isotype control at different concentrations. The viruses were afterwards added to SVG-A cells which were then fixed 3-day post-infection, permeabilized and stained with DAPI and anti-VP1 antibodies. The stained cells were then visualized with a fluorescent microscope and the number of infected cells was quantified for each condition that was done in triplicate. The maximum number of infected cells was determined by counting the number of cells infected when the viruses were pre-incubated in medium containing no antibody. The IC50 corresponds to the antibody concentration necessary to neutralize the infection of 50% of the possibly infected cells and is estimated by a non-linear regression using GraphPad Prism software.

FIG. 11: Binding to PML-associated VP1 mutants of the recombinant human-derived antibodies assessed by flow cytometry.

293TT cells were transiently transfected to express VP1 L55F S269F, VP1 L55F S267F, VP1 L55F N265D, VP1 GCN mutant and wild type VP1 or mock transfected. They were then fixed, permeabilized and stained with the exemplary NI-307.11G6, NI-307.98D3, NI-307.27C11 and NI-307.53B11 antibodies and the isotype control. The antibody binding to the VP1 mutants was then measured by flow cytometry.

DETAILED DESCRIPTION OF THE INVENTION

The present invention relates to human and recombinant human-derived monoclonal antibodies and antigen binding fragments thereof, which have been generated based on sequence information obtained from selected human donor populations and are capable of binding to polyomavirus and/or antigen thereof, in particular to JCV or BKV and/or the VP1 protein thereof. The antibody of the present invention is advantageously characterized by specifically binding to the virus and/or isolated viral proteins which make it suitable for both targeting the virus as well as diagnosing viral proteins which are released into body fluids such as blood. Furthermore, the antibody of the present invention typically does not show any cross-activities with unrelated proteins such as serum albumin, in particular bovine serum albumin, i.e. proteins which are commonly used in the formulation of pharmaceuticals or laboratory use. Accordingly, the antibody of the present invention, also due to its human origin and affinity maturation can be reasonably expected to be safe as therapeutic agent and specific as a laboratory reagent for the detection of polyomavirus without giving false positives.

In addition, due to its polyomavirus neutralizing activity, the antibody of the present invention as well as the derivatives thereof can be used for combination therapy of patients suffering from a disease to be treated with for example immunosuppressive drugs and bearing the risk of opportunistic polyomavirus infection and activation of polyomavirus replication such as those described in the background section herein before. Thus, as a particular advantageous embodiment, the present invention relates to the human monoclonal antibody and any derivatives thereof described herein for use in the treatment of immune-compromised patients, for example receiving an organ transplant either alone or in the treatment of patients receiving immunosuppressive drugs such as those described in the background section, wherein the antibody of the present invention and any of its derivatives is designed to be administered concomitantly with the immunosuppressive drug or sequentially before or after administration of the same. In one embodiment of the present invention, pharmaceutical compositions are provided comprising both a human monoclonal antibody of the present invention or any derivatives thereof and one or more immunosuppressive drugs.

I. Definitions

Unless otherwise stated, a term as used herein is given the definition as provided in the Oxford Dictionary of Biochemistry and Molecular Biology, Oxford University Press, 1997, revised 2000 and reprinted 2003, ISBN 0 19 850673 2.

It is to be noted that the term "a" or "an" entity refers to one or more of that entity; for example, "an antibody", is understood to represent one or more antibodies. As such, the terms "a" (or "an"), "one or more," and "at least one" can be used interchangeably herein.

If not specifically indicated other the term "polyomavirus", "JCV", and "BKV" is used interchangeably to specifically refer to native monomeric, dimeric and oligomeric forms of polyomavirus peptides, JCV peptides, and BKV peptides. The terms are also used to generally identify other forms of the peptide, for example oligomers and/or aggregates, VP1, VP2, VP3 proteins and are also used to refer collectively to all types and forms.

The human anti-polyomavirus, preferably anti-JCV, and anti-BKV antibodies disclosed herein specifically bind polyomaviruses, preferably JCV and/or BKV, polyomavirus VP1 proteins, preferably JCV VP1 and/or BKV VP1 and epitopes thereof and to various variants of polyomaviruses, preferably JCV and/or BKV and epitopes thereof, see Ferenczy et al., Clinical Microbiology Reviews 25 (3) (2012), 471-506 and Gorelik et al., The Journal of Infectious Diseases 204 (2011), 103-114. As used herein, reference to an antibody that "specifically binds", "selectively binds", or "preferably binds" polyomavirus, JCV and/or BKV, polyomavirus VP1 proteins, preferably JCV VP1 and/or BKV VP1 refers to an antibody that does not bind other unrelated proteins. In one embodiment, a polyomavirus, JCV and/or BKV antibody disclosed herein can bind a polyomavirus, preferably JCV and/or BKV, polyomavirus VP1 protein, preferably JCV VP1 and/or BKV VP1 protein, and polyomavirus VP1 Virus Like Particles (VLP), preferably JCV VP1 VLP and/or BKV VP1 VLP or an epitope thereof and shows no binding to BSA and other proteins. Since the human polyomavirus, JCV and/or BKV antibodies of the present invention have been generated from a pool of healthy human subjects or from pools of PML-IRIS patients exhibiting a polyomavirus, preferably JCV and/or BKV specific immune response the polyomavirus, preferably JCV and/or BKV antibodies of the present invention may also be called "human-derived antibodies" in order to emphasize that those antibodies were indeed derived from antibodies expressed by the subject and have not been isolated from, for example a human immunoglobulin expressing phage library, which represents a common method for trying to provide human-like antibodies.

Peptide:

The term "peptide" as used herein is understood to include the terms "polypeptide" and "protein" (which, at times, may be used interchangeably herein) within its meaning. Similarly, fragments of proteins and polypeptides are also contemplated and may be referred to herein as "peptides". Nevertheless, the term "peptide" preferably denotes an amino acid polymer including at least 5 contiguous amino acids, preferably at least 10 contiguous amino acids, more preferably at least 15 contiguous amino acids, still more preferably at least 20 contiguous amino acids, and particularly preferred at least 25 contiguous amino acids. In addition, the peptide in accordance with present invention typically has no more than 100 contiguous amino acids, preferably less than 80 contiguous amino acids and more preferably less than 50 contiguous amino acids.

Polypeptides:

As used herein, the term "polypeptide" is intended to encompass a singular "polypeptide" as well as plural "polypeptides", and refers to a molecule composed of monomers (amino acids) linearly linked by amide bonds (also known as peptide bonds). The term "polypeptide" refers to any chain or chains of two or more amino acids, and does not refer to a specific length of the product. Thus, "peptides," "dipeptides", "tripeptides, "oligopeptides", "proteins," "amino acid chains", or any other term used to refer to a chain or chains of two or more amino acids, are included within the definition of "polypeptide", and the term "polypeptide" may be used instead of, or interchangeably with any of these terms.

The term "polypeptide" is also intended to refer to the products of post-expression modifications of the polypeptide, including without limitation glycosylation, acetylation, phosphorylation, amidation and derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

"Recombinant peptides, polypeptides or proteins" refer to peptides, polypeptides or proteins produced by recombinant DNA techniques, i.e. produced from cells, microbial or mammalian, transformed by an exogenous recombinant DNA expression construct encoding the fusion protein including the desired peptide. Proteins or peptides expressed in most bacterial cultures will typically be free of glycan.

Proteins or polypeptides expressed in yeast may have a glycosylation pattern different from that expressed in mammalian cells.

Included as polypeptides of the present invention are fragments, derivatives, analogs or variants of the foregoing polypeptides and any combinations thereof as well. The terms "fragment", "variant", "derivative" and "analog" include peptides and polypeptides having an amino acid sequence sufficiently similar to the amino acid sequence of the natural peptide. The term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that comprise a common structural domain that is at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100%, identical are defined herein as sufficiently similar. Preferably, variants will be sufficiently similar to the amino acid sequence of the preferred peptides of the present invention, in particular to polyomaviruses, preferably JCV and/or BKV, polyomavirus VP1 proteins, preferably JCV VP1 and/or BKV VP1 proteins, polyomavirus VP1 Virus Like Particles (VLPs), preferably JCV VP1 VLPs and/or BKV VP1 VLPs or fragments, variants, derivatives or analogs of either of them. Such variants generally retain the functional activity of the peptides of the present invention. Variants include peptides that differ in amino acid sequence from the native and wild-type (wt) peptide, respectively, by way of one or more amino acid deletion(s), addition(s), and/or substitution(s). These may be naturally occurring variants as well as artificially designed ones.

Furthermore, the terms "fragment", "variant" "derivative" and "analog" when referring to antibodies or antibody polypeptides of the present invention include any polypeptides which retain at least some of the antigen-binding properties of the corresponding native binding molecule, antibody, or polypeptide. Fragments of polypeptides of the present invention include proteolytic fragments, as well as deletion fragments, in addition to specific antibody fragments discussed elsewhere herein. Variants of antibodies and antibody polypeptides of the present invention include fragments as described above, and also polypeptides with altered amino acid sequences due to amino acid substitutions, deletions, or insertions. Variants may occur naturally or be non naturally occurring. Non-naturally occurring variants may be produced using art-known mutagenesis techniques. Variant polypeptides may comprise conservative or non-conservative amino acid substitutions, deletions or additions. Derivatives of polyomavirus, preferably JCV and/or BKV specific binding molecules, e.g., antibodies and antibody polypeptides of the present invention, are polypeptides which have been altered so as to exhibit additional features not found on the native polypeptide. Examples include fusion proteins. Variant polypeptides may also be referred to herein as "polypeptide analogs". As used herein a "derivative" of a binding molecule or fragment thereof, an antibody, or an antibody polypeptide refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

Determination of Similarity and/or Identity of Molecules:

"Similarity" between two peptides is determined by comparing the amino acid sequence of one peptide to the sequence of a second peptide. An amino acid of one peptide is similar to the corresponding amino acid of a second peptide if it is identical or a conservative amino acid substitution. Conservative substitutions include those described in Dayhoff, M. O., ed., The Atlas of Protein Sequence and Structure 5, National Biomedical Research Foundation, Washington, D.C. (1978), and in Argos, EMBO J. 8 (1989), 779-785. For example, amino acids belonging to one of the following groups represent conservative changes or substitutions: -Ala, Pro, Gly, Gln, Asn, Ser, Thr; -Cys, Ser, Tyr, Thr; -Val, Ile, Leu, Met, Ala, Phe; -Lys, Arg, His; -Phe, Tyr, Trp, His; and -Asp, Glu.

"Similarity" between two polynucleotides is determined by comparing the nucleic acid sequence of one polynucleotide to the sequence of a polynucleotide. A nucleic acid of one polynucleotide is similar to the corresponding nucleic acid of a second polynucleotide if it is identical or, if the nucleic acid is part of a coding sequence, the respective triplet comprising the nucleic acid encodes for the same amino acid or for a conservative amino acid substitution.

The determination of percent identity or similarity between two sequences is preferably accomplished using the mathematical algorithm of Karlin and Altschul (1993) Proc. Natl. Acad. Sci. USA 90: 5873-5877. Such an algorithm is incorporated into the BLASTn and BLASTp programs of Altschul et al. (1990) J. Mol. Biol. 215: 403-410 available at NCBI (http://www.ncbi.nlm nih.gov/blast/Blast.cge).

The determination of percent identity or similarity is performed with the standard parameters of the BLASTn and BLASTp programs, as recommended on the NCBI webpage and in the "BLAST Program Selection Guide" in respect of sequences of a specific length and composition.

BLAST polynucleotide searches are performed with the BLASTn program.

For the general parameters, the "Max Target Sequences" box may be set to 100, the "Short queries" box may be ticked, the "Expect threshold" box may be set to 1000 and the "Word Size" box may be set to 7 as recommended for short sequences (less than 20 bases) on the NCBI webpage. For longer sequences the "Expect threshold" box may be set to 10 and the "Word Size" box may be set to 11. For the scoring parameters the "Match/mismatch Scores" may be set to 1,−2 and the "Gap Costs" box may be set to linear. For the Filters and Masking parameters, the "Low complexity regions" box may not be ticked, the "Species-specific repeats" box may not be ticked, the "Mask for lookup table only" box may be ticked, the "DUST Filter Settings" may be ticked and the "Mask lower case letters" box may not be ticked. In general the "Search for short nearly exact matches" may be used in this respect, which provides most of the above indicated settings. Further information in this respect may be found in the "BLAST Program Selection Guide" published on the NCBI webpage.

BLAST protein searches are performed with the BLASTp program. For the general parameters, the "Max Target Sequences" box may be set to 100, the "Short queries" box may be ticked, the "Expect threshold" box may be set to 10 and the "Word Size" box may be set to "3". For the scoring parameters the "Matrix" box may be set to "BLOSUM62", the "Gap Costs" Box may be set to "Existence: 11 Extension: 1", the "Compositional adjustments" box may be set to "Conditional compositional score matrix adjustment". For the Filters and Masking parameters the "Low complexity regions" box may not be ticked, the "Mask for lookup table only" box may not be ticked and the "Mask lower case letters" box may not be ticked.

Modifications of both programs, e.g., in respect of the length of the searched sequences, are performed according to the recommendations in the "BLAST Program Selection Guide" published in a HTML and a PDF version on the NCBI webpage.

Polynucleotides:

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding an antibody contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, polynucleotide or a nucleic acid may be or may include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid of the invention may encode heterologous coding regions, either fused or unfused to a nucleic acid encoding a binding molecule, an antibody, or fragment, variant, or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally may include a promoter and/or other transcription or translation control elements operable associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operable associated" or "operable linked" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operable associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operable associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA).

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full-length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operable associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

A "binding molecule" as used in the context of the present invention relates primarily to antibodies, and fragments thereof, but may also refer to other non-antibody molecules that bind to polyomaviruses, polyomavirus VP1 proteins as well as polyomavirus VP1 Virus-Like Particles (VLPs), preferably of the type of JCV and/or BKV including but not limited to hormones, receptors, ligands, major histocompatibility complex (MHC) molecules, chaperones such as heat shock proteins (HSPs) as well as cell-cell adhesion molecules such as members of the cadherin, integrin, C-type lectin and immunoglobulin (Ig) superfamilies Thus, for the sake of clarity only and without restricting the scope of the present invention most of the following embodiments are discussed with respect to antibodies and antibody-like molecules which represent the preferred binding molecules for the development of therapeutic and diagnostic agents.

Antibodies:

The terms "antibody" and "immunoglobulin" are used interchangeably herein. An antibody or immunoglobulin as used herein is a polyomavirus-, polyomavirus VP1 protein-, and/or polyomavirus VP1 VLPs-binding molecule, preferably of the type of JCV and/or BKV which comprises at least the variable domain of a heavy chain, and normally comprises at least the variable domains of a heavy chain and a light chain. Basic immunoglobulin structures in vertebrate systems are relatively well understood; see, e.g., Harlow et al., Antibodies: A Laboratory Manual, (Cold Spring Harbor Laboratory Press, 2nd ed. 1988).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernible to the skilled artisan in view of the instant disclosure and, accordingly, are within the scope of the instant invention. All immunoglobulin classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light ($V_L$) and heavy ($V_H$) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the $V_L$ domain and $V_H$ domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the $V_H$ and $V_L$ chains. Any antibody or immunoglobulin fragment which contains sufficient structure to specifically bind to polyomavirus, polyomavirus VP1 protein, and/or polyomavirus VP1 Virus-Like Particles (VLP), preferably of the type of JCV and/or BKV is denoted herein interchangeably as a "binding fragment" or an "immunospecific fragment".

An antibody comprises six hypervariable regions, sometimes called "complementarity determining regions" or "CDRs" present in each antigen-binding domain, which are short, non-contiguous sequences of amino acids that are specifically positioned to form the antigen-binding domain as the antibody assumes its three dimensional configuration in an aqueous environment. The "CDRs" are flanked by four relatively conserved "framework" regions or "FRs" which show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined; see, "Sequences of Proteins of Immunological Interest" Kabat et al., U.S. Department of Health and Human Services, (1983); and Chothia and Lesk, J. Mol. Biol., 196 (1987), 901-917, which are incorporated herein by reference in their entireties.

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia and Lesk, J. Mol. Biol., 196 (1987), 901-917, which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table I as a comparison. The exact residue numbers which encompass a particular CDR will vary depending on the sequence and size of the CDR. Those skilled in the art can routinely determine which residues comprise a particular hypervariable region or CDR of the human IgG subtype of antibody given the variable region amino acid sequence of the antibody.

TABLE I

CDR Definitions[1]

| | Kabat | Chothia |
|---|---|---|
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table I is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody or antigen-binding fragment, variant, or derivative thereof of the present invention are according to the Kabat numbering system, which however is theoretical and may not equally apply to every antibody of the present invention. For example, depending on the position of the first CDR the following CDRs might be shifted in either direction.

Antibodies or antigen-binding fragments, immunospecific fragments, variants, or derivatives thereof of the invention include, but are not limited to, polyclonal, monoclonal, multispecific, human, humanized, primatized, murinized or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a $V_L$ or $V_H$ domain, fragments produced by a Fab expression library, and anti-idiotypic (anti-Id) antibodies (including, e.g., anti-Id antibodies to antibodies disclosed herein). ScFv molecules are known in the art and are described, e.g., in U.S. Pat. No. 5,892,019 Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule.

In one embodiment, the human anti-polyomavirus antibody and antigen-binding molecules of the present invention described herein are characterized by comprising a constant domain or part thereof, which is heterologous to the variable region, for example as shown in FIG. 8 or at least one CDR thereof. For example, while the native antibody as originally produced by the human B cell may be of the IgA type such as antibody NI-307.13G4 (see Table IV), the subject human antibody is preferably of the IgG type. Thus, the variable region of antibody NI-307.13G4 is fused to a constant domain of human immunoglobulin gamma 1. Likewise, if the native antibody as originally produced by the human B cell belongs to the IgG3 class such as antibody NI-307.45E10 (see Table IV), the subject human antibody is preferably of the IgG1 class. Here, the IgG3 constant domain or part thereof is preferably substituted with an IgG1 constant domain or part thereof. Alternatively, if the native antibody is already of the IgG1 type and subclass the variable region is preferably cloned into a generic backbone, e.g. native IgG1 are re-cloned into a generic IgG1 backbone. In a preferred embodiment, antibody of the present invention is cloned and expressed as a human IgG1 for biochemical characterization and/or as a murine IgG2 for in vivo experiments in animal models, see e.g. Example 1.

In one embodiment, the antibody of the present invention is not IgM or a derivative thereof with a pentavalent structure. Particular, in specific applications of the present invention, especially therapeutic use, IgMs are less useful than IgG and other bivalent antibodies or corresponding binding molecules since IgMs due to their pentavalent structure and lack of affinity maturation often show unspecific cross-reactivities and very low affinity.

In a particularly preferred embodiment, the antibody of the present invention is not a polyclonal antibody, i.e. it substantially consists of one particular antibody species rather than being a mixture obtained from a plasma immunoglobulin sample.

Antibody fragments, including single-chain antibodies, may comprise the variable region(s) alone or in combination with the entirety or a portion of the following: hinge region, CH1, CH2, and CH3 domains. Also included in the invention are antibodies and antibody-like binding molecules recognizing polyomavirus, polyomavirus VP1 protein-, and/or polyomavirus VP1 Virus-Like Particles (VLP), preferably of the type of JCV and/or BKV, which comprise any combination of variable region(s) with a hinge region, CH1, CH2, and CH3 domains. Antibodies or immunospecific fragments thereof of the present invention may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

In one aspect, the antibody of the present invention is a human monoclonal antibody isolated from a human. Optionally, the framework region of the human antibody is aligned and adapted in accordance with the pertinent human germ line variable region sequences in the database; see, e.g., Vbase (http://vbase.mrc-cpe.cam.ac.uk/) hosted by the MRC Centre for Protein Engineering (Cambridge, UK). For example, amino acids considered to potentially deviate from the true germ line sequence could be due to the PCR primer sequences incorporated during the cloning process. Compared to artificially generated human-like antibodies such as single chain antibody fragments (scFvs) from a phage displayed antibody library or xenogeneic mice, the human monoclonal antibody of the present invention is characterized by (i) being obtained using the human immune response rather than that of animal surrogates, i.e. the antibody has been generated in response to polyomavirus, polyomavirus VP1, and/or polyomavirus VP1 VLP, preferably of the type of JCV and/or BKV in its relevant conformation in the human body, (ii) is at least significant for the presence of polyomavirus, polyomavirus VP1, and/or polyomavirus VP1 VLP, preferably of the type of JCV and/or BKV and (iii) since the antibody is of human origin the risks of cross-reactivity against self-antigens is minimized Thus, in accordance with the present invention the terms "human monoclonal antibody", "human monoclonal autoantibody", "human antibody" and the like are used to denote an polyomavirus, polyomavirus VP1, and/or polyomavirus VP1 VLP-binding molecule, preferably of the type of JCV and/or BKV which is of human origin, i.e. which has been isolated from a human cell such as a B cell or hybridoma thereof or the cDNA of which has been directly cloned from mRNA of a human cell, for example a human memory B cell. A human antibody is still "human" even if amino acid substitutions are made in the antibody, e.g., to improve binding characteristics.

Antibodies derived from human immunoglobulin libraries or from animals transgenic for one or more human immunoglobulins and that do not express endogenous immunoglobulins, as described infra and, for example in, U.S. Pat. No. 5,939,598 by Kucherlapati et al., are denoted human-like antibodies in order distinguish them from truly human antibodies of the present invention.

For example, the paring of heavy and light chains of human-like antibodies such as synthetic and semi-synthetic antibodies typically isolated from phage display do not necessarily reflect the original paring as it occurred in the original human B cell. Accordingly Fab and scFv fragments obtained from recombinant expression libraries as commonly used in the prior art can be considered as being artificial with all possible associated effects on immunogenicity and stability.

In contrast, the present invention provides isolated affinity-matured antibodies from selected human subjects, which are characterized by their therapeutic utility and their tolerance in man.

As used herein, the term "rodentized antibody" or "rodentized immunoglobulin" refers to an antibody comprising one or more CDRs from a human antibody of the present invention; and a human framework region that contains amino acid substitutions and/or deletions and/or insertions that are based on a rodent antibody sequence. When referred to rodents, preferably sequences originating in mice and rats are used, wherein the antibodies comprising such sequences are referred to as "murinized" or "ratinized" respectively. The human immunoglobulin providing the CDRs is called the "parent" or "acceptor" and the rodent antibody providing the framework changes is called the "donor". Constant regions need not be present, but if they are, they are usually substantially identical to the rodent antibody constant regions, i.e. at least about 85-90%, preferably about 95% or more identical. Hence, in some embodiments, a full-length murinized human heavy or light chain immunoglobulin contains a mouse constant region, human CDRs, and a substantially human framework that has a number of "murinizing" amino acid substitutions. Typically, a "murinized antibody" is an antibody comprising a murinized variable light chain and/or a murinized variable heavy chain. For example, a murinized antibody would not encompass a typical chimeric antibody, e.g., because the entire variable region of a chimeric antibody is non-mouse. A modified antibody that has been "murinized" by the process of "murinization" binds to the same antigen as the parent antibody that provides the CDRs and is usually less immunogenic in mice, as compared to the parent antibody. The above explanations in respect of "murinized" antibodies apply analogously for other "rodentized" antibodies, such as "ratinized antibodies", wherein rat sequences are used instead of the murine.

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. For example, a binding polypeptide for use in the invention may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention may lack at least a portion of a CH2 domain (e.g., all or part of a CH2 domain). As set forth above, it will be understood by one of ordinary skill in the art that these domains (e.g., the heavy chain portions) may be modified such that they vary in amino acid sequence from the naturally occurring immunoglobulin molecule.

In certain antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the invention are not identical. For example, each monomer may comprise a different target binding site, forming, for example, a bispecific antibody or diabody.

In another embodiment, the antibodies, or antigen-binding fragments, variants, or derivatives thereof disclosed herein are composed of a single polypeptide chain such as scFvs and are to be expressed intracellularly (intrabodies) for potential in vivo therapeutic and diagnostic applications.

The heavy chain portions of a binding polypeptide for use in the diagnostic and treatment methods disclosed herein may be derived from different immunoglobulin molecules. For example, a heavy chain portion of a polypeptide may comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain. Preferably, the light chain portion comprises at least one of a $V_L$ or CL domain.

The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. In the present invention, a peptide or polypeptide epitope recognized by antibodies of the present invention contains a sequence of at least 4, at least 5, at least 6, at least 7, more preferably at least 8, at least 9, at least 10, at least 15, at least 20, at least 25, or between about 15 to about 30 contiguous or non-contiguous amino acids of the polyomavirus, polyomavirus VP1, and/or polyomavirus VP1 VLP, preferably of the type of JCV and/or BKV.

By "specifically binding", or "specifically recognizing", used interchangeably herein, it is generally meant that a binding molecule, e.g., an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D".

Where present, the term "immunological binding characteristics", or other binding characteristics of an antibody with an antigen, in all of its grammatical forms, refers to the specificity, affinity, cross-reactivity, and other binding characteristics of an antibody.

By "preferentially binding", it is meant that the binding molecule, e.g., antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

By way of non-limiting example, a binding molecule, e.g., an antibody may be considered to bind a first epitope preferentially if it binds said first epitope with a dissociation constant ($K_D$) that is less than the antibody's $K_D$ for the second epitope. In another non-limiting example, an antibody may be considered to bind a first antigen preferentially if it binds the first epitope with an affinity that is at least one order of magnitude less than the antibody's $K_D$ for the second epitope. In another non-limiting example, an antibody may be considered to bind a first epitope preferentially if it binds the first epitope with an affinity that is at least two orders of magnitude less than the antibody's $K_D$ for the second epitope.

In another non-limiting example, a binding molecule, e.g., an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope.

A binding molecule, e.g., an antibody or antigen-binding fragment, variant, or derivative disclosed herein may be said to bind to polyomavirus, polyomavirus VP1 protein, and/or polyomavirus VP1 VLP, or a fragment or variant thereof, preferably of the type of JCV and/or BKV with an off rate (k(off)) of less than or equal to $5\times10^{-2}$ sec$^{-1}$, $10^{-2}$ sec$^{-1}$, $5\times10^{-3}$ sec$^{-1}$ or $10^{-3}$ sec$^{-1}$. More preferably, an antibody of the invention may be said to bind to polyomavirus, polyomavirus VP1 protein, and/or polyomavirus VP1 VLP or a fragment or variant thereof, preferably of the type of JCV and/or BKV with an off rate (k(off)) less than or equal to $5\times10^{-4}$ sec$^{-1}$, $10^{-4}$ sec$^{-1}$, $5\times10^{-5}$ sec$^{-1}$, or $10^{-5}$ sec$^{-1}$ $5\times10^{-6}$ sec$^{-1}$, $10^{-6}$ sec$^{-1}$, $5\times10^{-7}$ sec$^{-1}$ or $10^{-7}$ sec$^{-1}$.

A binding molecule, e.g., an antibody or antigen-binding fragment, variant, or derivative disclosed herein may be said to bind to polyomavirus, polyomavirus VP1 protein, and/or polyomavirus VP1 VLP or a fragment or variant thereof, preferably of the type of JC JCV and/or BKV with an on rate (k(on)) of greater than or equal to $10^3$ M$^{-1}$ sec$^{-1}$, $5\times10^3$ M$^{-1}$ sec$^{-1}$, $10^4$ M$^{-1}$ sec$^{-1}$ or $5\times10^4$ M$^{-1}$ sec$^{-1}$. More preferably, an antibody of the invention may be said to bind to polyomavirus, polyomavirus VP1 protein, and/or polyomavirus VP1 VLP or a fragment or variant thereof, preferably of the type of JCV and/or BKV with an on rate (k(on)) greater than or equal to $10^5$ M$^{-1}$ sec$^{-1}$, $5\times10^5$ M$^{-1}$ sec$^{-1}$, $10^6$ M$^{-1}$ sec$^{-1}$, or $5\times10^6$ M$^{-1}$ sec$^{-1}$ or $10^7$ M$^{-1}$ sec$^{-1}$.

A binding molecule, e.g., an antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of a binding molecule, e.g., an immunoglobulin molecule; see, e.g., Harlow et al., Antibodies: A Laboratory Manual, Cold Spring Harbor Laboratory Press, 2nd ed. (1988) at pages 27-28. As used herein, the term "avidity" refers to the overall stability of the complex between a population of immunoglobulins and an antigen, that is, the functional combining strength of an immunoglobulin mixture with the antigen; see, e.g., Harlow at pages 29-34. Avidity is related to both the affinity of individual immunoglobulin molecules in the population with specific epitopes, and also the valences of the immunoglobulins and the antigen. For example, the interaction between a bivalent monoclonal antibody and an antigen with a highly repeating epitope structure, such as a polymer, would be one of high avidity. The affinity or avidity of an antibody for an antigen can be determined experimentally using any suitable method; see, for example, Berzofsky et al., "Antibody-Antigen Interactions" In Fundamental Immunology, Paul, W. E., Ed., Raven Press New York, N Y (1984), Kuby, Janis Immunology, W. H. Freeman and Company New York, N Y (1992), and methods described herein. General techniques for measuring the affinity of an antibody for an antigen include ELISA, RIA, and surface plasmon resonance. The measured affinity of a particular antibody-antigen interaction can vary if measured under different conditions, e.g., salt concentration, pH. Thus, measurements of affinity and other antigen-binding parameters, e.g., $K_D$, $IC_{50}$, are preferably made with standardized solutions of antibody and antigen, and a standardized buffer.

Binding molecules, e.g., antibodies or antigen-binding fragments, variants or derivatives thereof of the invention may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

Binding molecules, e.g., antibodies or antigen-binding fragments, variants or derivatives thereof of the invention may also be described or specified in terms of their binding affinity to polyomavirus, polyomavirus VP1, and/or polyomavirus VP1 VLP, preferably of the type of JCV and/or BKV. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

As previously indicated, the subunit structures and three dimensional configuration of the constant regions of the various immunoglobulin classes are well known. As used herein, the term "VI" domain" includes the amino terminal variable domain of an immunoglobulin heavy chain and the term "CH1 domain" includes the first (most amino terminal) constant region domain of an immunoglobulin heavy chain. The CH1 domain is adjacent to the $V_H$ domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al. op. cit). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains; see Roux et al., J. Immunol. 161 (1998), 4083-4090.

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the terms "linked", "fused" or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature). Although the reading frame is thus made continuous throughout the fused segments, the segments may be physically or spatially separated by, for example, in-frame linker sequence. For example, polynucleotides encoding the CDRs of an immunoglobulin variable region may be fused, in-frame, but be separated by a polynucleotide encoding at least one immunoglobulin framework region or additional CDR regions, as long as the "fused" CDRs are co-translated as part of a continuous polypeptide.

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product, and the translation of mRNA into polypeptide(s). If the final desired product is a biochemical, expression includes the creation of that biochemical and any precursors. Expression of a gene produces a "gene product". As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, the term "sample" refers to any biological material obtained from a subject or patient. In one aspect, a sample can comprise blood, peritoneal fluid, CSF, saliva or urine. In other aspects, a sample can comprise whole blood, blood plasma, blood serum, B cells enriched from blood samples, and cultured cells (e.g., B cells from a subject). A sample can also include a biopsy or tissue sample including neural tissue. In still other aspects, a sample can comprise whole cells and/or a lysate of the cells. Blood samples can be collected by methods known in the art. In one aspect, the pellet can be resuspended by vortexing at 4° C. in 200 μl buffer (20 mM Tris, pH. 7.5, 0.5% Nonidet, 1 mM EDTA, 1 mM PMSF, 0.1M NaCl, IX Sigma Protease Inhibitor, and IX Sigma Phosphatase Inhibitors 1 and 2). The suspension can be kept on ice for 20 minutes with intermittent vortexing. After spinning at 15,000×g for 5 minutes at about 4° C., aliquots of supernatant can be stored at about −70° C.

Diseases:

Unless stated otherwise, the terms "disorder" and "disease" are used interchangeably herein and comprise any undesired physiological change in a subject, an animal, an isolated organ, tissue or cell/cell culture.

Polyomavirus infections lead to the development of several diseases after reactivation of the polyomavirus in immunodepressed patients. The mode of transmission is broad and occurs mostly through direct inter-human contamination. Nevertheless, soiled waters are also one of the most important reservoirs for polyomaviruses. The primary infection with polyomaviruses of the type of JCV and/or BKV occurs mostly in early childhood while the polyomavirus remain in a phase of latency until it become reactivated during specific pathological and/or physiological states as e.g. an immunosuppressed state is developed. The diseases associated with polyomaviruses like JCV or BKV are broad. The most common disease of the JCV is the induced demyelination disease of the human brain, Progressive Multifocal Leukoencephalopathy (PML), causing a defect in the immune function. The development of PML as a side effect of immunomodulatory therapy is a growing concern with reports of fatal PML cases in patients treated for multiple sclerosis (MS) and Crohn's disease, Hodgkin's lymphoma, rheumatoid arthritis, autoimmune hematatological disorders, myasthenia gravis, systemic lupus erythematosus, B cell lymphoma, plaque soreasis, ankylosing spondylitis, psoriatic arthritis, ulcerative colitis, and suppression of organ transplant rejections (Frenchy et al., Clin. Micro Biol. Rev. 25 (2012), 471-506). Furthermore, JCV was also associated with other neurological disorders and human cancers. Besides JCV, the BKV also targets the respiratory tree leading to upper respiratory tract infections and pneumonia as well as hemorrhagic cystitis by the infection of the urinary ladder or infections of kidney, central nervous system (CNS), eye, digestive tract, and endothelium leading to diseases like interstitial kidney disease related to polyomavirus, ureter stenosis, loss of graft, meningitis, encephalitis, retinitis, colitis, and vasulitis. The present invention provides several human derived antibodies from pools of healthy donors or PML-IRIS patients for the treatment or vaccination against polyomavirus infections, which were cloned and produced recombinantly as described herein below in more detail.

In one embodiment of the present invention the antibodies of the present invention, binding molecules having substantially the same binding specificities of any one thereof, the polynucleotides, the vectors or the cells of the present invention are used for the preparation of a pharmaceutical or diagnostic composition for prophylactic and/or therapeutic treatment, monitoring the progression or a response to treatment and/or diagnosis of diseases from the group of PML, infection of granule neurons, hyperchromatic nuclei, granule cell neuronopathy, cerebral autothrophy, encephalopathy, meningitis, polyomavirus-induced tumors, immune reconstitution inflammatory syndrome (IRIS), hemorrhagic cystitis, pneumonia, retinitis, colitis, vasulitis, interstitial kidney disease, infections of respiratory tract.

Furthermore, the antibodies of the present invention, binding molecules having substantially the same binding specificities of any one thereof, the polynucleotides, the vectors or the cells of the present invention are used for the preparation of a composition for detection of a polyomavirus infection, e.g. JCV and/or BKV infection.

Disorders such as PML are observed often as a symptom of JCV infections in immunodepressed patients which lead to demyelinisation of the central nervous system (CNS) and can lead in severe cases to death.

Many disorders are known to be associated with polyomavirus infection. Therefore, in one embodiment the antibodies of the present invention, binding molecules having substantially the same binding specificities of any one thereof, the polynucleotides, the vectors or the cells of the present invention are used for the preparation of a pharmaceutical or diagnostic composition for prophylactic and/or therapeutic treatment, amelioration, monitoring the progression or a response to treatment and/or for diagnosis of a group of disorders following to polyomavirus infection.

Treatment:

As used herein, the terms "treat" or "treatment" refer to both therapeutic treatment and prophylactic or preventative measures, wherein the object is to prevent or slow down (lessen) an undesired physiological change or disorder. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the manifestation of the condition or disorder is to be prevented.

If not stated otherwise the term "drug", "medicine", or "medicament" are used interchangeably herein and shall include but are not limited to all (A) articles, medicines and preparations for internal or external use, and any substance or mixture of substances intended to be used for diagnosis, cure, mitigation, treatment, or prevention of disease of either man or other animals; and (B) articles, medicines and preparations (other than food) intended to affect the structure or any function of the body of man or other animals; and (C) articles intended for use as a component of any article specified in clause (A) and (B). The term "drug," "medicine," or "medicament" shall include the complete formula of the preparation intended for use in either man or other animals containing one or more "agents", "compounds", "substances" or "(chemical) compositions" as and in some other context also other pharmaceutically inactive excipients as fillers, disintegrants, lubricants, glidants, binders or ensuring easy transport, disintegration, disaggregation, dissolution and biological availability of the "drug", "medicine", or "medicament" at an intended target location within the body of man or other animals, e.g., at the skin, in the stomach or the intestine. The terms "agent", "compound", or "substance" are used interchangeably herein and shall include, in a more particular context, but are not limited to all pharmacologically active agents, i.e. agents that induce a desired biological or pharmacological effect or are investigated or tested for the capability of inducing such a possible pharmacological effect by the methods of the present invention.

By "subject" or "individual" or "animal" or "patient" or "mammal", is meant any subject, particularly a mammalian subject, e.g., a human patient, for whom diagnosis, prognosis, prevention, or therapy is desired.

Pharmaceutical Carriers:

Pharmaceutically acceptable carriers and administration routes can be taken from corresponding literature known to the person skilled in the art. The pharmaceutical compositions of the present invention can be formulated according to methods well known in the art; see for example Remington:

The Science and Practice of Pharmacy (2000) by the University of Sciences in Philadelphia, ISBN 0-683-306472, Vaccine Protocols, 2nd Edition by Robinson et al., Humana Press, Totowa, N.J., USA, 2003; Banga, Therapeutic Peptides and Proteins: Formulation, Processing, and Delivery Systems. 2nd Edition by Taylor and Francis. (2006), ISBN: 0-8493-1630-8. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well-known conventional methods. These pharmaceutical compositions can be administered to the subject at a suitable dose. Administration of the suitable compositions may be effected by different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods. Aerosol formulations such as nasal spray formulations include purified aqueous or other solutions of the active agent with preservative agents and isotonic agents. Such formulations are preferably adjusted to a pH and isotonic state compatible with the nasal mucous membranes. Pharmaceutical compositions for oral administration, such as single domain antibody molecules (e.g., "Nanobodies™") etc. are also envisaged in the present invention. Such oral formulations may be in tablet, capsule, powder, liquid or semi-solid form. A tablet may comprise a solid carrier, such as gelatin or an adjuvant. Formulations for rectal or vaginal administration may be presented as a suppository with a suitable carrier; see also O'Hagan et al., Nature Reviews, Drug Discovery 2(9) (2003), 727-735. Further guidance regarding formulations that are suitable for various types of administration can be found in Remington's Pharmaceutical Sciences, Mace Publishing Company, Philadelphia, Pa., 17th ed. (1985) and corresponding updates. For a brief review of methods for drug delivery see Langer, Science 249 (1990), 1527-1533.

II. Antibodies of the Present Invention

The present invention generally relates to human anti-polyomavirus antibodies, anti-polyomavirus VP1 antibodies, and anti-polyomavirus VP1 VLP antibodies and antigen-binding fragments thereof, which preferably demonstrate the immunological binding characteristics and/or biological properties as outlined for the antibodies illustrated in the Examples. In accordance with the present invention human monoclonal antibodies specific for polyomaviruses, preferably of the type of JCV and/or BKV, were cloned from a pool of healthy elderly human subjects with unknown HLA typing and anti-JCV titers, HLA-DRB1*04:01+ healthy donors who presented a robust JCV-specific antibody production, and of patients who received monoclonal antibody therapy to treat multiple sclerosis (MS) and who developed symptoms of PML and PML-IRIS.

In the course of the experiments performed in accordance with the present invention antibodies of human memory B cell repertoire were screened by high-throughput analysis for polyomavirus VP protein-specific binding. Only B-cell cultures positive for polyomavirus VP1 protein but not for BSA were subjected to antibody cloning.

Due to this measure, several antibodies could be isolated. Selected antibodies were further analyzed for class and light chain subclass determination. Selected relevant antibody messages from memory B cell cultures could then be transcribed by RT-PCR, cloned and combined into expression vectors for recombinant production. Recombinant expression of the human antibodies in HEK 293 or CHO cells and the subsequent characterization of their binding specificities towards polyomavirus VP1 proteins, preferably human JCV VP1 and/or BKV VP1 protein (FIGS. 2 to 4 and 7; Examples 2 to 4 and 10), confirmed that for the first time human antibodies have been cloned that are highly specific for JCV and/or BKV and JCV VP1 and/or BKV VP1 protein.

Furthermore, those antibodies were tested for their binding specificity and binding efficiency on different polyomavirus VP1 proteins and binding to Virus-Like Particles (VLPs). Thus, the present invention generally relates to a human-derived monoclonal anti-polyomavirus, anti-polyomavirus VP1 protein, and/or anti-polyomavirus VP1 VLP antibody and binding fragments, derivatives and variants thereof, preferably of the type of JCV and/or BKV.

In one embodiment of the invention, the antibody is capable of binding human polyomavirus and/or antigen thereof, preferably JCV and/or BKV.

In a preferred embodiment, the antibody of the present invention is capable of binding to mutated human polyomavirus and/or antigen thereof, polyomavirus VP1 protein, and/or polyomavirus VP1 VLP, preferably of the JCV and/or BKV type. Put in other words, preferably the binding affinity of the human-derived anti-polyomavirus antibody of the present invention is not substantially affected by mutations in the viral proteins; see Example 12 and FIG. 11. This may be particularly true for those antibodies recognizing discontinuous or conformational epitopes that may not be influenced by individual amino acid substitutions in the amino acid sequence of the viral antigen, in particular when presented in the virus particle or VLPs.

In one embodiment, the present invention is directed to an polyomavirus antibody, or antigen-binding fragment, variant or derivatives thereof, where the antibody specifically binds to the same epitope of polyomavirus as a reference antibody selected from the group consisting of (A) NI-307.13G4, (B) NI-307.18E12, (C) NI-307.19F8, (D) NI-307.20F5, (E) NI-307.61D11, (F) NI-307.3G4 (G) NI-307.6A2, (H) NI-307.11G6, (I) NI-307.19F10, (J) NI-307.24F3, (K) NI-307.25G10, (L) NI-307.43A11, (M) NI-307.57D5, (N) NI-307.78C3, (O) NI-307.1E1, (P) NI-307.5H3, (Q) NI-307.24C6, (R) NI-307.26E10, (S) NI-307.11G6, (T) NI-307.13G4, (U) NI-307.61D11, (V) NI-307.98D3, (W) NI-307.72F7, (X) NI-307.45E10, (Y) NI-307.72F10, (Z) NI-307.56A8, (A2) NI-307.27C11, (B2) NI-307.47B11, (C2) NI-307.26A3, (D2) NI-307.27C2, (E2) NI-307.57D4, (F2) NI-307.50H4, (G2) NI-307.53B11, (H2) NI-307.7J3, (I2) NI-307.59A7, (J2) NI-307.105A6, (K2) NI-307.29B1, (L2) NI-307.44F6B, (M2) NI-307.98H1, (N2) NI-307.43E8, (O2) NI-307.18F4A. Epitope mapping identified a sequence within the human polyomavirus including aa 333-LPGD-PDM-339 as the unique linear epitope recognized by antibody NI-307.11G6 of this invention and a sequence within the human polyomavirus JCV including aa 124-SQATHDN-130 as the unique linear epitope recognized by antibody NI-307.13G4 of this invention (see FIG. 8 and Example 7). Therefore, in one embodiment the antibody of the present invention is provided, wherein the antibody specifically binds an polyomavirus epitope which comprises or consist of the amino acid sequences LPGDPDM (SEQ ID NO: 85), GQATHDN (SEQ ID NO: 86), MRYVDKYGQLQT (SEQ ID NO: 87) or RVFEGTEELPG (SEQ ID NO: 88). In a preferred embodiment the antibody of the present invention binds an epitope comprising GQATHDN (SEQ ID NO: 86), MRYVDKYGQLQT (SEQ ID NO: 87).

Furthermore, without intending to be bound by initial experimental observations as demonstrated in the Examples 4 to 7 and shown in FIGS. 2 to 4 and 7, the human monoclonal (A) NI-307.13G4, (B) NI-307.19F10, (C) NI-307.19F8, (D) NI-307.11G6, (E) NI-307.17F12, (F) NI-307.6A2, (G) NI-307.5H3, (H) NI-307.25G10, (I) NI-307.26E10, (J) NI-307.1E1, (K) NI-307.24C6, (L) NI-307.78C3, (M) NI-307.57D5, (N) NI-307.43A11, (O) NI-307.3G4, (P) NI-307.61D11, (Q) NI-307.24F3, (R) NI-307.18E12, (S) NI-307.20F5, (T) NI-307.58C7 (U) NI-307.105C7, (V) NI-307.98D3, (W) NI-307.72F7, (X) NI-307.45E10, (Y) NI-307.72F10, (Z) NI-307.56A8, (A2) NI-307.27C11, (B2) NI-307.47B11, (C2) NI-307.26A3, (D2) NI-307.27C2, (E2) NI-307.57D4, (F2) NI-307.50H4, (G2) NI-307.53B11, (H2) NI-307.7J3, (I2) NI-307.59A7, (J2) NI-307.105A6, (K2) NI-307.29B1, (L2) NI-307.44F6B, (M2) NI-307.98H1, (N2) NI-307.43E8 and (O2) NI-307.18F4A antibodies of the present invention are preferably characterized in specifically binding to polyomavirus VP1 proteins and VP1 VLP proteins and not substantially recognizing BSA; see Examples 4 to 6 and 10. Hence, the present invention provides a set of human anti-polyomavirus, anti-JCV and/or anti-BKV antibodies with binding specificities, which are thus particularly useful for diagnostic and therapeutic purposes.

In one embodiment, the antibody of the present invention exhibits the binding properties of the exemplary recombinant human NI-307.13G4, NI-307.18E12, NI-307.19F8, NI-307.20F5, and NI-307.61D11 antibodies specifically binding to JCV VP1 and not or weakly to BKV VP1 as described in Example 2. In this context, the binding specificities may be in the range as shown for the exemplary NI-307.13G4, NI-307.18E12, NI-307.18F4A, NI-307.19F8, NI-307.20F5, and NI-307.61D11 antibodies in FIG. 2, i.e. having half maximal effective concentrations (EC50) of about 1 pM to 100 nM, preferably an EC50 of about 10 pM to 50 nM, most preferably an EC50 of about 100 pM to 5 nM for JCV VP1 as shown for NI-307.13G4, NI-307.18E12, NI-307.18F4A, NI-307.19F8, NI-307.20F5, and NI-307.61D11.

In addition, or alternatively, the anti-polyomavirus antibody of the present invention binds specifically to JCV VP1 and BKV VP1. In this context, the binding specificities may range as shown for the exemplary NI-307.3G4, NI-307.6A2, NI-307.11G6, NI-307.19F10, NI-307.24F3, NI-307.25G10, NI-307.43A11, NI-307.44F6B, NI-307.57D5, and NI-307.78C3 in Example 5 and FIG. 3, having half maximal effective concentration (EC50) of about 1 pM to 500 nM, preferably an EC50 of about 10 pM to 100 nM most preferably an EC50 of about 500 pM to 80 nM for JCV VP1 and an EC50 of about 1 pM to 500 nM, preferably an EC50 of about 5 pM to 100 nM, most preferably an EC50 of about 10 pM to 30 nM for VP1 VLP. Respectively, recombinant human derived antibodies NI-307.3 G4, NI-307.6A2, NI-307.11G6, NI-307.19F10, NI-307.24F3, NI-307.25G10, NI-307.43A11, NI-307.44F6B, NI-307.57D5, and NI-307.78C3 with the high affinity to BKV VP1 with an EC50 of about 1 pM to 500 nM, preferably an EC50 of about 5 pM to 100 nM, most preferably an EC50 of about 10 pM to 50 nM for BKV VP1 and an EC50 of about 1 pM to 500 nM, preferably an EC50 of about 10 pM to 200 nM, most preferably an EC50 of about 30 pM to 120 nM for BKV VP1 VLP. In addition, or alternatively, the anti-polyomavirus antibody of the present invention binds specifically to BKV VP1 as described in Example 6 and FIG. 4. In one embodiment, the antibody of the present invention exhibits the binding properties of the exemplary recombinant human NI-307.1E1, NI-307.5H3, NI-307.24C6, and NI-307.26E10 which strongly bind to VP1 from the BKV and weakly to JCV VP1. In this context, the binding specificities may be in the range as shown for the exemplary NI-307.1E1, NI-307.5H3, NI-307.24C6, and NI-307.26E10 in Example 6 and respective FIG. 4, i.e. having half maximal effective concentrations (EC50) of about 1 pM to 500 nM, preferably an EC50 of about 10 pM to 100 nM, and most preferably an EC50 of about 800 pM to 5 nM for BKV VP1 and an EC50 of about 1 pM to 500 nM, preferably an EC50 of about 10 pM to 100 nM, most preferably an EC50 of about 200 pM to 20 nm for BKV VP1 VLP and an EC50 of about 1 pM to 500 nM, preferably an EC50 of about 10 pM to 300 nM, most preferably an EC50 of about 1 pM to 200 nM for JCV VP1 and an EC50 of about 1 pM to 500 nM, preferably an EC50 of about 100 pM to 300 nM, most preferably 1 pM to 300 nM for JCV VP1 VLP.

In a preferred embodiment, the antibody of the present invention exhibits the binding properties of the exemplary recombinant human NI-307.7J3, NI-307.26A3, NI-307.27C2, NI-307.27C11, NI-307.29B1, NI-307.43E8, NI-307.45E10, NI-307.47B11, NI-307.50H4, NI-307.53B11, NI-307.56A8, NI-307.57D4, NI-307.58C7, NI-307.59A7, NI-307.72F7, NI-307.72F10, NI-307.98D3, NI-307.98H1, NI-307.105A6 and NI-307.105C7 antibodies strongly binding to JCV VP1 VLPs as described in Example 10. In this context, the binding specificities may be in the range as shown for the exemplary NI-307.7J3, NI-307.26A3, NI-307.27C2, NI-307.27C11, NI-307.29B 1, NI-307.43E8, NI-307.45E10, NI-307.47B11, NI-307.50H4, NI-307.53B11, NI-307.56A8, NI-307.57D4, NI-307.58C7, NI-307.59A7, NI-307.72F7, NI-307.72F10, NI-307.98D3, NI-307.98H1, NI-307.105A6 and NI-307.105C7 antibodies in FIG. 7, i.e. having half maximal effective concentrations (EC50) of about 0.1 pM to 1 nM, preferably an EC50 of less than 1 nM for JCV VP1 VLPs as shown for NI-307.7J3, NI-307.26A3, NI-307.27C2, NI-307.27C11, NI-307.29B1, NI-307.43E8, NI-307.45E10, NI-307.47B11, NI-307.50H4, NI-307.53B11, NI-307.56A8, NI-307.57D4, NI-307.58C7, NI-307.59A7, NI-307.72F7, NI-307.72F10, NI-307.98D3, NI-307.98H1, NI-307.105A6 and NI-307.105C7.

In one embodiment the anti-polyomavirus antibody of the present invention preferably exhibits the binding properties of exemplary antibodies NI-307.13G4, NI-307.18E12, NI-307.18F4A, NI-307.19F8, NI-307.20F5 and NI-307.61D11, preferentially binding JCV VP1 over BKV VP1.

In addition or alternatively, the antibody of the present invention preferably exhibits the binding properties of exemplary antibodies NI-307.3G4, NI-307.6A2, NI-307.11G6, NI-307.19F10, NI-307.24F3, NI-307.25G10, NI-307.43A11, NI-307.44F6B, NI-307.57D5 and NI-307.78C3 binding both JCV and BKV VP1 proteins.

In another embodiment, the antibody of the present invention in addition or alternatively exhibits the binding properties of exemplary antibodies NI-307.1E1, NI-307.5H3, NI-307.24C6 and NI-307.26E10, preferentially binding BKV VP1 over JCV VP1.

In a still further embodiment, the antibody of the present invention preferably exhibits the binding properties of exemplary antibodies NI-307.7J3, NI-307.26A3, NI-307.27C2, NI-307.27C11, NI-307.29B1, NI-307.43E8, NI-307.45E10, NI-307.47B11, NI-307.50H4, NI-307.53B11, NI-307.56A8, NI-307.57D4, NI-307.58C7, NI-307.59A7, NI-307.72F7, NI-307.72F10, NI-307.98D3, NI-307.98H1, NI-307.105A6 and NI-307.105C7 binding with a high affinity to JCV VP1 VLPs.

The present invention is also drawn to an antibody, or antigen-binding fragment, variant or derivatives thereof, where the antibody comprises an antigen-binding domain identical to that of an antibody selected from the group consisting of (A) NI-307.13G4, (B) NI-307.18E12, (C) NI-307.19F8, (D) NI-307.20F5, (E) NI-307.61D11, (F) NI-307.3G4 (G) NI-307.6A2, (H) NI-307.11G6, (I) NI-307.19F10, (J) NI-307.24F3, (K) NI-307.25G10, (L) NI-307.43A11, (M) NI-307.57D5, (N) NI-307.78C3, (O) NI-307.1E1, (P) NI-307.5H3, (Q) NI-307.24C6, (R) NI-307.26E10, (S) NI-307.11G6, (T) NI-307.13G4, (U) NI-307.61D11(V) NI-307.98D3, (W) NI-307.72F7, (X) NI-307.45E10, (Y) NI-307.72F10, (Z) NI-307.56A8, (A2) NI-307.27C11, (B2) NI-307.47B11, (C2) NI-307.26A3, (D2) NI-307.27C2, (E2) NI-307.57D4, (F2) NI-307.50H4, (G2) NI-307.53B11, (H2) NI-307.7J3, (I2) NI-307.59A7, (J2) NI-307.105A6, (K2) NI-307.29B1, (L2) NI-307.44F6B, (M2) NI-307.98H1, (N2) NI-307.43E8 and (O2) NI-307.18F4A.

The present invention further exemplifies several such binding molecules, e.g., antibodies and binding fragments thereof, which may be characterized by comprising in their variable region, e.g., binding domain at least one complementarity determining region (CDR) of the $V_H$ and/or $V_L$ variable region comprising any one of the amino acid sequences depicted in FIG. 8. The corresponding nucleotide sequences encoding the above-identified variable regions are set forth in Table II respective Table III below. Exemplary sets of CDRs of the above amino acid sequences of the $V_H$ and/or $V_L$ region are depicted in FIG. 8. However, as discussed in the following the person skilled in the art is well aware of the fact that in addition or alternatively CDRs may be used, which differ in their amino acid sequence from those set forth in FIG. 8 by one, two, three or even more amino acids in case of CDR2 and CDR3. Therefore, in one embodiment the antibody of the present invention or a polyomavirus and/or polyomavirus VP1 binding fragment thereof is provided comprising in its variable region at least one CDR as depicted in FIG. 8 and/or one or more CDRs thereof comprising one or more amino acid substitutions.

In one embodiment, the antibody of the present invention is any one of the antibodies comprising an amino acid sequence of the $V_H$ and/or $V_L$ region as depicted in FIG. 8 or a $V_H$ and/or $V_L$ region thereof comprising one or more amino acid substitutions. Preferably, the antibody of the present invention is characterized by the preservation of the cognate pairing of the heavy and light chain as was present in the human B-cell.

Alternatively, the antibody of the present invention is an antibody or antigen-binding fragment, derivative or variant thereof, which competes for binding to polyomavirus and/or polyomavirus VP1 protein with at least one of the antibodies having the $V_H$ and/or $V_L$ region as depicted in FIG. 8.

As already indicated before, some of the antibodies of the present invention have been shown to be capable of binding both, polyomaviruses JCV and BKV.

Therefore, alternatively or in addition to the above, in one embodiment the antibody of the present invention or a polyomavirus VP1, an JCV VP1 and/or BKV VP1 binding fragment thereof is provided comprising in its variable region at least one CDR as depicted in FIG. 8 and/or one or more CDRs thereof comprising one or more amino acid substitutions.

Alternatively, the antibody of the present invention is an antibody or antigen-binding fragment, derivative or variant thereof, which competes for binding to polyomavirus VP1 and/or polyomavirus VP1 VLP, preferably to JCV VP1, JCV VP1 VLP and/or BKV VP1, BKV VP1 VLP with at least one of the antibodies having the $V_H$ and/or $V_L$ region as depicted in FIG. 8.

The antibody of the present invention may be human, in particular for therapeutic applications.

Alternatively, the antibody of the present invention is a rodent, rodentized or chimeric rodent-human antibody, preferably a murine, murinized or chimeric murine-human antibody or a rat, ratinized or chimeric rat-human antibody which are particularly useful for diagnostic methods and studies in animals. In one embodiment the antibody of the present invention is a chimeric rodent-human or a rodentized antibody.

As mentioned above, due to its generation upon a human immune response the human monoclonal antibody of the present invention will recognize epitopes which are of particular pathological relevance and which might not be accessible or less immunogenic in case of immunization processes for the generation of, for example, mouse monoclonal antibodies and in vitro screening of phage display libraries, respectively. Accordingly, it is prudent to stipulate that the epitope of the human anti-polyomavirus, anti-polyomavirus VP1 and/or polyomavirus VP1 VLP antibody of the present invention is unique and no other antibody which is capable of binding to the epitope recognized by the human monoclonal antibody of the present invention exists.

In another embodiment, the present invention provides an isolated polypeptide comprising, consisting essentially of, or consisting of an immunoglobulin heavy chain variable region ($V_H$), where at least one of $V_H$-CDRs of the heavy chain variable region or at least two of the $V_H$-CDRs of the heavy chain variable region are at least 80%, 85%, 90% or 95% identical to reference heavy chain $V_H$-CDR1, $V_H$-CDR2 or $V_H$-CDR3 amino acid sequences from the antibodies disclosed herein. Alternatively, the $V_H$-CDR1, $V_H$-CDR2 and $V_H$-CDR3 regions of the $V_H$ are at least 80%, 85%, 90% or 95% identical to reference heavy chain $V_H$-CDR1, $V_H$-CDR2 and $V_H$-CDR3 amino acid sequences from the antibodies disclosed herein. Thus, according to this embodiment a heavy chain variable region of the invention has $V_H$-CDR1, $V_H$-CDR2 and $V_H$-CDR3 polypeptide sequences related to the groups shown in FIG. 8. While FIG. 8 shows $V_H$-CDRs defined by the Kabat system, other CDR definitions, e.g., $V_H$-CDRs defined by the Chothia system, are also included in the present invention, and can be easily identified by a person of ordinary skill in the art using the data presented in FIG. 8.

In a further embodiment, the present invention provides an isolated polypeptide comprising, consisting essentially of, or consisting of an immunoglobulin heavy chain variable region ($V_H$) in which the $V_H$-CDR1, $V_H$-CDR2 and $V_H$-CDR3 regions have polypeptide sequences which are identical to the $V_H$-CDR1, $V_H$-CDR2 and $V_H$-CDR3 groups shown in FIG. 8.

In another embodiment, the present invention provides an isolated polypeptide comprising, consisting essentially of, or consisting of an immunoglobulin heavy chain variable region ($V_H$) in which the $V_H$-CDR1, $V_H$-CDR2 and $V_H$-CDR3 regions have polypeptide sequences which are identical to the $V_H$-CDR1, $V_H$-CDR2 and $V_H$-CDR3 groups shown in FIG. 8, except for one, two, three, four, five, or six amino acid substitutions in any one $V_H$-CDR. In certain embodiments the amino acid substitutions are conservative.

In a further embodiment, the present invention provides an isolated polypeptide comprising, consisting essentially of, or consisting of an immunoglobulin light chain variable region ($V_L$), where at least one of the $V_L$-CDRs of the light chain variable region or at least two of the $V_L$-CDRs of the light chain variable region are at least 80%, 85%, 90% or 95% identical to reference light chain $V_L$-CDR1, $V_L$-CDR2 or $V_L$-CDR3 amino acid sequences from antibodies disclosed herein. Alternatively, the $V_L$-CDR1, $V_L$-CDR2 and $V_L$-CDR3 regions of the $V_L$ are at least 80%, 85%, 90% or 95% identical to reference light chain $V_L$-CDR1, $V_L$-CDR2 and $V_L$-CDR3 amino acid sequences from antibodies disclosed herein. Thus, according to this embodiment a light chain variable region of the invention has $V_L$-CDR1, $V_L$-CDR2 and $V_L$-CDR3 polypeptide sequences related to the polypeptides shown in FIG. 8. While FIG. 8 shows $V_L$-CDRs defined by the Kabat system, other CDR definitions, e.g., $V_L$-CDRs defined by the Chothia system, are also included in the present invention.

In another embodiment, the present invention provides an isolated polypeptide comprising, consisting essentially of, or consisting of an immunoglobulin light chain variable region ($V_L$) in which the $V_L$-CDR1, $V_L$-CDR2 and $V_L$-CDR3 regions have polypeptide sequences which are identical to the $V_L$-CDR1, $V_L$-CDR2 and $V_L$-CDR3 groups shown in FIG. 8.

In a further embodiment, the present invention provides an isolated polypeptide comprising, consisting essentially of, or consisting of an immunoglobulin heavy chain variable region ($V_L$) in which the $V_L$-CDR1, $V_L$-CDR2 and $V_L$-CDR3 regions have polypeptide sequences which are identical to the $V_L$-CDR1, $V_L$-CDR2 and $V_L$-CDR3 groups shown in FIG. 8, except for one, two, three, four, five, or six amino acid substitutions in any one $V_L$-CDR. In certain embodiments the amino acid substitutions are conservative.

An immunoglobulin or its encoding cDNA may be further modified. Thus, in a further embodiment the method of the present invention comprises any one of the step(s) of producing a chimeric antibody, murinized antibody, single-chain antibody, Fab-fragment, bi-specific antibody, fusion antibody, labeled antibody or an analog of any one of those. Corresponding methods are known to the person skilled in the art and are described, e.g., in Harlow and Lane "Antibodies, A Laboratory Manual", CSH Press, Cold Spring Harbor (1988). When derivatives of said antibodies are obtained by the phage display technique, surface plasmon resonance as employed in the BIAcore system can be used to increase the efficiency of phage antibodies which bind to the same epitope as that of any one of the antibodies described herein (Schier, Human Antibodies Hybridomas 7 (1996), 97-105; Malmborg, J. Immunol. Methods 183 (1995), 7-13). The production of chimeric antibodies is described, for example, in international application WO 89/09622. Methods for the production of humanized antibodies are described in, e.g., European application EP-A1 0 239 400 and international application WO 90/07861. Further sources of antibodies to be utilized in accordance with the present invention are so-called xenogeneic antibodies. The general principle for the production of xenogeneic antibodies such as human-like antibodies in mice is described in, e.g., international applications WO 91/10741, WO 94/02602, WO 96/34096 and WO 96/33735. As discussed above, the antibody of the invention may exist in a variety of forms besides complete antibodies; including, for example, Fv, Fab and F(ab)2, as well as in single chains; see e.g. international application WO 88/09344. In one embodiment therefore, the antibody of the present invention is provided, which is selected from the group consisting of a single chain Fv fragment (scFv), an F(ab') fragment, an F(ab) fragment, and an F(ab')$_2$ fragment.

The antibodies of the present invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, *Molecular Cloning A Laboratory Manual*, Cold Spring Harbor Laboratory (1989) N.Y. and Ausubel, *Current Protocols in Molecular Biology*, Green Publishing Associates and Wiley Interscience, N.Y. (1994). Modifications of the antibody of the invention include chemical and/or enzymatic derivatizations at one or more constituent amino acids, including side chain modifications, backbone modifications, and N- and C-terminal modifications including acetylation, hydroxylation, methylation, amidation, and the attachment of carbohydrate or lipid moieties, cofactors, and the like. Likewise, the present invention encompasses the production of chimeric proteins which comprise the described antibody or some fragment thereof at the amino terminus fused to heterologous molecule such as an immunostimulatory ligand at the carboxyl terminus; see, e.g., international application WO 00/30680 for corresponding technical details.

Additionally, the present invention encompasses peptides including those containing a binding molecule as described above, for example containing the CDR3 region of the variable region of any one of the mentioned antibodies, in particular CDR3 of the heavy chain since it has frequently been observed that heavy chain CDR3 (HCDR3) is the region having a greater degree of variability and a predominant participation in antigen-antibody interaction. Such peptides may easily be synthesized or produced by recombinant means to produce a binding agent useful according to the invention. Such methods are well known to those of ordinary skill in the art. Peptides can be synthesized for example, using automated peptide synthesizers which are commercially available. The peptides can also be produced by recombinant techniques by incorporating the DNA expressing the peptide into an expression vector and transforming cells with the expression vector to produce the peptide.

Hence, the present invention relates to any binding molecule, e.g., an antibody or binding fragment thereof which is oriented towards the human anti-polyomavirus, anti-polyomavirus VP1 and/or anti-polyomavirus VP1 VLP antibodies of the present invention and displays the mentioned properties, i.e. which specifically recognizes polyomavirus, polyomavirus VP1 and/or polyomavirus VP1 VLP. Such antibodies and binding molecules can be tested for their binding specificity and affinity by ELISA and immunohistochemistry as described herein, see, e.g., Examples 2 to 4 and 10. These characteristics of the antibodies and binding molecules can be tested by Western Blot as well.

As an alternative to obtaining immunoglobulins directly from the culture of B cells or B memory cells, the cells can be used as a source of rearranged heavy chain and light chain loci for subsequent expression and/or genetic manipulation. Rearranged antibody genes can be reverse transcribed from appropriate mRNAs to produce cDNA. If desired, the heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Once the genetic material is available, design of analogs as described above which retain both their ability to bind the desired target is straightforward. Methods for the cloning of antibody variable regions and generation of recombinant antibodies are known to the person skilled in the art and are described, for example, Gilliland et al., Tissue Antigens 47 (1996), 1-20; Doenecke et al., Leukemia 11 (1997), 1787-1792.

Once the appropriate genetic material is obtained and, if desired, modified to encode an analog, the coding sequences, including those that encode, at a minimum, the variable regions of the heavy and light chain, can be inserted into expression systems contained on vectors which can be transfected into standard recombinant host cells. A variety of such host cells may be used; for efficient processing, however, mammalian cells are preferred. Typical mammalian cell lines useful for this purpose include, but are not limited to, CHO cells, HEK 293 cells, or NSO cells.

The production of the antibody or analog is then undertaken by culturing the modified recombinant host under culture conditions appropriate for the growth of the host cells and the expression of the coding sequences. The antibodies are then recovered by isolating them from the culture. The expression systems are preferably designed to include signal peptides so that the resulting antibodies are secreted into the medium; however, intracellular production is also possible.

In accordance with the above, the present invention also relates to a polynucleotide encoding the antibody or equivalent binding molecule of the present invention, in case of the antibody preferably at least a variable region of an immunoglobulin chain of the antibody described above. Typically, said variable region encoded by the polynucleotide comprises at least one complementarity determining region (CDR) of the $V_H$ and/or $V_L$ of the variable region of the said antibody.

The person skilled in the art will readily appreciate that the variable domain of the antibody having the above-described variable domain can be used for the construction of other polypeptides or antibodies of desired specificity and biological function. Thus, the present invention also encompasses polypeptides and antibodies comprising at least one CDR of the above-described variable domain and which advantageously have substantially the same or similar binding properties as the antibody described in the appended examples. The person skilled in the art knows that binding affinity may be enhanced by making amino acid substitutions within the CDRs or within the hypervariable loops (Chothia and Lesk, J. Mol. Biol. 196 (1987), 901-917) which partially overlap with the CDRs as defined by Kabat; see, e.g., Riechmann, et al, Nature 332 (1988), 323-327. Thus, the present invention also relates to antibodies wherein one or more of the mentioned CDRs comprise one or more, preferably not more than two amino acid substitutions. Preferably, the antibody of the invention comprises in one or both of its immunoglobulin chains two or all three CDRs of the variable regions as set forth in FIG. 8.

Binding molecules, e.g., antibodies, or antigen-binding fragments, variants, or derivatives thereof of the invention, as known by those of ordinary skill in the art, can comprise a constant region which mediates one or more effector functions. For example, binding of the C1 component of complement to an antibody constant region may activate the complement system. Activation of complement is important in the opsonization and lysis of cell pathogens. The activation of complement also stimulates the inflammatory response and may also be involved in autoimmune hypersensitivity. Further, antibodies bind to receptors on various cells via the Fc region, with a Fc receptor binding site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

Accordingly, certain embodiments of the present invention include an antibody, or antigen-binding fragment, variant, or derivative thereof, in which at least a fraction of one or more of the constant region domains has been deleted or otherwise altered so as to provide desired biochemical characteristics For example, certain antibodies for use in the diagnostic and treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted. In other embodiments, certain antibodies for use in the diagnostic and treatment methods described herein have a constant region, e.g., an IgG heavy chain constant region, which is altered to eliminate glycosylation, referred to elsewhere herein as aglycosylated or "agly" antibodies. Such "agly" antibodies may be prepared enzymatically as well as by engineering the consensus glycosylation site(s) in the constant region. While not being bound by theory, it is believed that "agly" antibodies may have an improved safety and stability profile in vivo. Methods of producing aglycosylated antibodies, having desired effector function are found for example in international application WO 2005/018572, which is incorporated by reference in its entirety.

In certain antibodies, or antigen-binding fragments, variants, or derivatives thereof described herein, the Fc portion may be mutated to decrease effector function using techniques known in the art. In other cases it may be that constant region modifications consistent with the instant invention moderate complement binding and thus reduce the serum half-life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, biodistribution and serum half-life, may easily be measured and quantified using well know immunological techniques without undue experimentation.

In certain antibodies, or antigen-binding fragments, variants, or derivatives thereof described herein, the Fc portion may be mutated or exchanged for alternative protein sequences to increase the cellular uptake of antibodies by way of example by enhancing receptor-mediated endocytosis of antibodies via Fcγ receptors, LRP, or Thy1 receptors or by 'SuperAntibody Technology', which is said to enable antibodies to be shuttled into living cells without harming them (Expert Opin. Biol. Ther. (2005), 237-241). For example, the generation of fusion proteins of the antibody binding region and the cognate protein ligands of cell surface receptors or bi- or multi-specific antibodies with a specific sequences binding to polyomavirus, polyomavirus VP1 and/or polyomavirus VP1 VLP as well as a cell surface receptor may be engineered using techniques known in the art.

In certain antibodies, or antigen-binding fragments, variants, or derivatives thereof described herein, the Fc portion may be mutated or exchanged for alternative protein sequences or the antibody may be chemically modified to increase its blood brain barrier penetration.

Modified forms of antibodies, or antigen-binding fragments, variants, or derivatives thereof of the invention can be made from whole precursor or parent antibodies using techniques known in the art. Exemplary techniques are discussed in more detail herein. Antibodies, or antigen-binding fragments, variants, or derivatives thereof of the invention can be made or manufactured using techniques that are known in the art. In certain embodiments, antibody molecules or fragments thereof are "recombinantly produced", i.e., are produced using recombinant DNA technology. Exemplary techniques for making antibody molecules or fragments thereof are discussed in more detail elsewhere herein.

Antibodies, or antigen-binding fragments, variants, or derivatives thereof of the invention also include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

In another embodiment, antibodies, or antigen-binding fragments, variants, or derivatives thereof of the invention will not elicit a deleterious immune response in the animal to be treated, e.g., in a human. In certain embodiments, binding molecules, e.g., antibodies, or antigen-binding fragments thereof of the invention are derived from a patient, e.g., a human patient, and are subsequently used in the same species from which they are derived, e.g., human, alleviating or minimizing the occurrence of deleterious immune responses.

De-immunization can also be used to decrease the immunogenicity of an antibody. As used herein, the term "de-immunization" includes alteration of an antibody to modify T cell epitopes; see, e.g., international applications WO 98/52976 and WO 00/34317. For example, $V_H$ and $V_L$ sequences from the starting antibody are analyzed and a human T cell epitope "map" from each V region showing the location of epitopes in relation to CDRs and other key residues within the sequence. Individual T cell epitopes from the T cell epitope map are analyzed in order to identify alternative amino acid substitutions with a low risk of altering activity of the final antibody. A range of alternative $V_H$ and $V_L$ sequences are designed comprising combinations of amino acid substitutions and these sequences are subsequently incorporated into a range of binding polypeptides, e.g., polyomavirus, polyomavirus VP1 and/or polyomavirus VP1 VLP-specific antibodies or immunospecific fragments thereof for use in the diagnostic and treatment methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, Cold Spring Harbor Laboratory Press, 2nd ed. (1988); Hammerling et al., in: *Monoclonal Antibodies and T-Cell Hybridomas* Elsevier, N.Y., 563-681 (1981), said references incorporated by reference in their entireties. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology. In certain embodiments, antibodies of the present invention are derived from human B cells which have been immortalized via transformation with Epstein-Barr virus.

In the well-known hybridoma process (Kohler et al., Nature 256 (1975), 495) the relatively short-lived, or mortal, lymphocytes from a mammal, e.g., B cells derived from a human subject as described herein, are fused with an immortal tumor cell line (e.g., a myeloma cell line), thus, producing hybrid cells or "hybridomas" which are both immortal and capable of producing the genetically coded antibody of the B cell. The resulting hybrids are segregated into single genetic strains by selection, dilution, and re-growth with each individual strain comprising specific genes for the formation of a single antibody. They produce antibodies, which are homogeneous against a desired antigen and, in reference to their pure genetic parentage, are termed "monoclonal".

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. The binding specificity of the monoclonal antibodies produced by hybridoma cells is determined by in vitro assays such as immunoprecipitation, radioimmunoassay (RIA) or enzyme-linked immunoabsorbent assay (ELISA) as described herein. After hybridoma cells are identified that produce antibodies of the desired specificity, affinity and/or activity, the clones may be subcloned by limiting dilution procedures and grown by standard methods; see, e.g., Goding, *Monoclonal Antibodies: Principles and Practice*, Academic Press, pp. 59-103 (1986). It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

In another embodiment, lymphocytes can be selected by micromanipulation and the variable genes isolated. For example, peripheral blood mononuclear cells can be isolated from an immunized or naturally immune mammal, e.g., a human, and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the $V_H$ and $V_L$ genes can be amplified using, e.g., RT-PCR. The $V_H$ and $V_L$ genes can be cloned into an antibody expression vector and transfected into cells (e.g., eukaryotic or prokaryotic cells) for expression.

Alternatively, antibody-producing cell lines may be selected and cultured using techniques well known to the skilled artisan. Such techniques are described in a variety of laboratory manuals and primary publications. In this respect, techniques suitable for use in the invention as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

Antibody fragments that recognize specific epitopes may be generated by known techniques. For example, Fab and F(ab')$_2$ fragments may be produced recombinantly or by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CH1 domain of the heavy chain. Such fragments are sufficient for use, for example, in immunodiagnostic procedures involving coupling the immunospecific portions of immunoglobulins to detecting reagents such as radioisotopes.

Human antibodies, such as described herein, are particularly desirable for therapeutic use in human patients. Human antibodies of the present invention are isolated, e.g., from healthy elderly human subjects with unknown HLA typing and anti-JCV titers, HLA-DRB1*04:01+ healthy donors who present a robust JCV-specific antibody production, and patients who received monoclonal antibody therapy to treat MS and who developed symptoms of PML and PML-IRIS.

In one embodiment, an antibody of the invention comprises at least one heavy or light chain CDR of an antibody molecule. In another embodiment, an antibody of the invention comprises at least two CDRs from one or more antibody molecules. In another embodiment, an antibody of the invention comprises at least three CDRs from one or more antibody molecules. In another embodiment, an antibody of the invention comprises at least four CDRs from one or more antibody molecules. In another embodiment, an antibody of the invention comprises at least five CDRs from one or more antibody molecules. In another embodiment, an antibody of the invention comprises at least six CDRs from one or more antibody molecules. Exemplary antibody molecules comprising at least one CDR that can be included in the subject antibodies are described herein.

Antibodies of the present invention can be produced by any method known in the art for the synthesis of antibodies, in particular, by chemical synthesis or preferably by recombinant expression techniques as described herein.

In one embodiment, an antibody, or antigen-binding fragment, variant, or derivative thereof of the invention comprises a synthetic constant region wherein one or more domains are partially or entirely deleted ("domain-deleted antibodies"). In certain embodiments compatible modified antibodies will comprise domain deleted constructs or variants wherein the entire CH2 domain has been removed (ΔCH2 constructs). For other embodiments a short connecting peptide may be substituted for the deleted domain to provide flexibility and freedom of movement for the variable region. Those skilled in the art will appreciate that such constructs are particularly preferred due to the regulatory properties of the CH2 domain on the catabolic rate of the antibody. Domain deleted constructs can be derived using a vector encoding an IgG$_1$ human constant domain, see, e.g., international applications WO 02/060955 and WO 02/096948A2. This vector is engineered to delete the CH2 domain and provide a synthetic vector expressing a domain deleted IgG$_1$ constant region.

In certain embodiments, antibodies, or antigen-binding fragments, variants, or derivatives thereof of the present invention are minibodies. Minibodies can be made using methods described in the art, see, e.g., U.S. Pat. No. 5,837,821 or international application WO 94/09817.

In one embodiment, an antibody, or antigen-binding fragment, variant, or derivative thereof of the invention comprises an immunoglobulin heavy chain having a deletion or substitution of a few or even a single amino acid as long as it permits association between the monomeric subunits. For example, the mutation of a single amino acid in selected areas of the CH2 domain may be enough to substantially reduce Fc binding. Similarly, it may be desirable to simply delete that part of one or more constant region domains that control the effector function (e.g. complement binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be synthetic through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. Yet other embodiments comprise the addition of one or more amino acids to the constant region to enhance desirable characteristics such as an effector function or provide for more cytotoxin or carbohydrate attachment. In such embodiments it may be desirable to insert or replicate specific sequences derived from selected constant region domains.

The present invention also provides antibodies that comprise, consist essentially of, or consist of, variants (including derivatives) of antibody molecules (e.g., the $V_H$ regions and/or $V_L$ regions) described herein, which antibodies or fragments thereof immunospecifically bind to polyomavirus, polyomavirus VP1 and/or polyomavirus VP1 VLP. Standard techniques known to those of skill in the art can be used to introduce mutations in the nucleotide sequence encoding an antibody, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference $V_H$ region, $V_H$-CDR1, $V_H$-CDR2, $V_H$-CDR3, $V_L$ region, $V_L$-CDR1, $V_L$-CDR2, or $V_L$-CDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity.

For example, it is possible to introduce mutations only in framework regions or only in CDR regions of an antibody molecule. Introduced mutations may be silent or neutral missense mutations, e.g., have no, or little, effect on an antibody's ability to bind antigen, indeed some such mutations do not alter the amino acid sequence whatsoever. These types of mutations may be useful to optimize codon usage, or improve a hybridoma's antibody production. Codon-optimized coding regions encoding antibodies of the present invention are disclosed elsewhere herein. Alternatively, non-neutral mis sense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen-binding activity or alteration in binding activity (e.g., improvements in antigen-binding activity or change in antibody specificity). Following mutagenesis, the encoded protein may routinely be expressed and the functional and/or biological activity of the encoded protein can be determined using techniques described herein or by routinely modifying techniques known in the art.

III. Polynucleotides Encoding Antibodies

A polynucleotide encoding an antibody, or antigen-binding fragment, variant, or derivative thereof can be composed of any polyribonucleotide or polydeoxribonucleotide, which may be unmodified RNA or DNA or modified RNA or DNA. For example, a polynucleotide encoding an antibody, or antigen-binding fragment, variant, or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, a polynucleotide encoding an antibody, or antigen-binding fragment, variant, or derivative thereof can be composed of triple-stranded regions comprising RNA or DNA or both RNA and DNA. A polynucleotide encoding an antibody, or antigen-binding fragment, variant, or derivative thereof may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

An isolated polynucleotide encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. Preferably, conservative amino acid substitutions are made at one or more non-essential amino acid residues.

As is well known, RNA may be isolated from the original B cells, hybridoma cells or from other transformed cells by standard techniques, such as a guanidinium isothiocyanate extraction and precipitation followed by centrifugation or chromatography. Where desirable, mRNA may be isolated from total RNA by standard techniques such as chromatography on oligo dT cellulose. Suitable techniques are familiar in the art. In one embodiment, cDNAs that encode the light and the heavy chains of the antibody may be made, either simultaneously or separately, using reverse transcriptase and DNA polymerase in accordance with well-known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as human constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis.

In this context, the present invention also relates to a polynucleotide encoding at least the binding domain or variable region of an immunoglobulin chain of the antibody of the present invention. In one embodiment, the present invention provides an isolated polynucleotide comprising, consisting essentially of, or consisting of a nucleic acid encoding an immunoglobulin heavy chain variable region ($V_H$), where at least one of the CDRs of the heavy chain variable region or at least two of the $V_H$-CDRs of the heavy chain variable region are at least 80%, 85%, 90% or 95% identical to reference heavy chain $V_H$-CDR1, $V_H$-CDR2, or $V_H$-CDR3 amino acid sequences from the antibodies disclosed herein. Alternatively, the $V_H$-CDR1, $V_H$-CDR2, or $V_H$-CDR3 regions of the $V_H$ are at least 80%, 85%, 90% or 95% identical to reference heavy chain $V_H$-CDR1, $V_H$-CDR2, and $V_H$-CDR3 amino acid sequences from the antibodies disclosed herein. Thus, according to this embodiment a heavy chain variable region of the invention has $V_H$-CDR1, $V_H$-CDR2, or $V_H$-CDR3 polypeptide sequences related to the polypeptide sequences shown in FIG. 8 has $V_H$-CDR1, $V_H$-CDR2, or $V_H$-CDR3 polypeptide sequences related to the polypeptide sequences shown in FIG. 8.

In another embodiment, the present invention provides an isolated polynucleotide comprising, consisting essentially of, or consisting of a nucleic acid encoding an immunoglobulin light chain variable region ($V_L$), where at least one of the $V_L$-CDRs of the light chain variable region or at least two of the $V_L$-CDRs of the light chain variable region are at least 80%, 85%, 90% or 95% identical to reference light chain $V_L$-CDR1, $V_L$-CDR2, or $V_L$-CDR3 amino acid sequences from the antibodies disclosed herein. Alternatively, the $V_L$-CDR1, $V_L$-CDR2, or $V_L$-CDR3 regions of the $V_L$ are at least 80%, 85%, 90% or 95% identical to reference light chain $V_L$-CDR1, $V_L$-CDR2, and $V_L$-CDR3 amino acid sequences from the antibodies disclosed herein. Thus, according to this embodiment a light chain variable region of the invention has $V_L$-CDR1, $V_L$-CDR2, or $V_L$-CDR3 polypeptide sequences related to the polypeptide sequences shown in FIG. 8, or respectively has $V_L$-CDR1, $V_L$-CDR2, or $V_L$-CDR3 polypeptide sequences related to the polypeptide sequences shown in FIG. 8.

In another embodiment, the present invention provides an isolated polynucleotide comprising, consisting essentially of, or consisting of a nucleic acid encoding an immunoglobulin heavy chain variable region ($V_H$) in which the $V_H$-CDR1, $V_H$-CDR2, and $V_H$-CDR3 regions have polypeptide sequences which are identical to the $V_H$-CDR1, $V_H$-CDR2, and $V_H$-CDR3 groups shown in FIG. 8 respectively are identical to the $V_H$-CDR1, $V_H$-CDR2, and $V_H$-CDR3 groups as shown in FIG. 8.

As known in the art, "sequence identity" between two polypeptides or two polynucleotides is determined by comparing the amino acid or nucleic acid sequence of one polypeptide or polynucleotide to the sequence of a second polypeptide or polynucleotide. When discussed herein, whether any particular polypeptide is at least about 40%, 45%, 50%, 55%, 60%, 65%, 70%, 75%, 80%, 85%, 90% or 95% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2 (1981), 482-489, to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

In a preferred embodiment of the present invention, the polynucleotide comprises, consists essentially of, or consists of a nucleic acid having a polynucleotide sequence of the $V_H$ or $V_L$ region of an anti-polyomavirus, anti-polyomavirus VP1 and/or anti-polyomavirus VP1 VLP antibody as depicted in Table II. In this respect, the person skilled in the art will readily appreciate that the polynucleotides encoding at least the variable domain of the light and/or heavy chain may encode the variable domain of both immunoglobulin chains or only one. In one embodiment therefore, the polynucleotide comprises, consists essentially of, or consists of a nucleic acid having a polynucleotide sequence of the $V_H$ and the $V_L$ region of an anti-polyomavirus, anti-polyomavirus VP1, and/or anti-polyomavirus VP1 VLP, preferably of an anti-JCV VP1 or VLP or anti-BKV VP1 or VLP antibody as depicted in Table II or in Table III.

TABLE II

Nucleotide sequences of the $V_H$ and $V_L$ region of exemplary polyomavirus, polyomavirus VP1, and polyomavirus VP1 VLP antibodies.

| Antibody | Nucleotide sequences of variable heavy (VH) and variable light (VL) chains |
|---|---|
| NI-307.13G4-$V_H$ | GAGGTGCAGCTGGTGGAGTCTGGGGGAGGCTTGGTACAGCCT<br>GGGGGGTCCCTGAGACTCTCCTGTACAGCCTCTGGATTCACCT<br>TTACCTCCTATGCCCTGAGCTGGGTCCGCCAGGCTCCAGGGA<br>AGGGGCTGGAGTGGGTCTCAGCAATTAGTAGTGGTCGTGGTT<br>ACACATACTACGCAGACTCCGTGAAGGGCCGGTTCACCATCT<br>CCAGAGACAATTCCAAGAACACGCTGTATCTGCAAATGAACA<br>GTCTGAGAGCCGAGGACACGGCCGTATATTACTGTGCGAAAG<br>ATGGCACCCTACGTGGATACAACTATGGTTACATAGATGATA<br>TCTGGGGCCAAGGCACCCTGGTCACCGTCTCCTCG<br>SEQ ID NO: 1 |
| NI-307.13G4-$V_L$ | GACATCCAGATGACCCAGTCTCCATCGTCACTGTCTGCATCTG<br>TAGGAGACAGAGTCACCATCACTTGTCGGGCGAGTCAGGGCA<br>TCAGCAATTATTTAGCCTGGCTTCAGCAGAAACCAGGGAAAG<br>CCCCTAAGCCCCTGATCTATGCCGTATCCATTTTGCAAAGTGG<br>GGTCCCATCAAAGTTCAGCGGCAGTGGATCTGGGACAGATTT<br>CACTCTCACCATCAGCAGCCTGCAGCCTGAGGATTTTGCAAC<br>TTATTACTGCCAACAGTATAAGAGTTACCCTTACACCTTTGGC<br>CAGGGGACCAAGCTGGAGATCAAA<br>SEQ ID NO: 3 |
| NI-307.19F10-$V_H$ | GAGGTGCAGCTGGTGGAGTCTGGGGGAGGCTTAGTTCAGCCG<br>GGGGGGTCCGTGAGCCTCTCCTGTGCAGCCTCTGGATTCACCT<br>TCCCTGTCTACTGGATGCACTGGGTCCGCCAAGCTCCAGAGA<br>AGGGCCTGATGTGGGTCTCACGGATTAGTCCTGATGGGACCA<br>TAGTAGACTACGCGGGCTCCGTGAAGGGCCGATTCACCGTCT<br>CCAGAGACAACGCCAAGAACATTCTTTATCTGCAAATTCAAC<br>GTCTGACTGCCGAGGACACGGCTGTGTATTTCTGTACAAAGG<br>ACTTCGATGTTGCCGAGTGGATTCTGGGGCCAGGGAACCCTGG<br>TCACCGTCTCCTCG<br>SEQ ID NO: 5 |

TABLE II-continued

Nucleotide sequences of the V_H and V_L region of exemplary polyomavirus, polyomavirus VP1, and polyomavirus VP1 VLP antibodies.

| Antibody | Nucleotide sequences of variable heavy (VH) and variable light (VL) chains |
| --- | --- |
| NI-307.19F10-V_L | CAGTCTGCCCTGACTCAGCCTCCCTCCGCGTCCGGGTCTCCTG<br>GACAGTCAGTCACCATCTCCTGCACTGGATCCAAAAGTGACG<br>TTGGTACTTGTCACTTTGTCTCCTGGTACCAGCAGCACCCAGG<br>CAAAGTCCCCAAACTCGTCATTTATGAGGGCAATAAGCGGCC<br>CTCAGGGGTCCCTGATCGCTTCTCTGCCTCCAAGTCTGGCAAC<br>ACGGCCTCCCTCACCATCTCTGGGCTGCAGCCTGGCGACGAG<br>GCGGACTATTATTGCAGCACATGTGCAGGCCCCAACAACTAT<br>GTCTTCGGAACTGGGACCAAGGTCACCGTCCTT<br>SEQ ID NO: 7 |
| NI-307.19F8-V_H | GAGGTGCAGCTGGTGGAGTCTGGGGGAGGCCTGGTCAAGCCT<br>GGGGGGTCCCTGAGACTCTCCTGTGCAGCCTCTGGATTCACCT<br>TCAGTAGCTATTACATGAACTGGGTCCGCCAGGCTCCAGGGA<br>AGGGGCTGGAGTGGGTCTCATCCATTAGTAGTAGTAGTAGTT<br>ACATATACTACGCAGACTCAGTGAAGGGCCGATTCACCATCT<br>CCAGAGACAACGCCAAGAACTCACTGTATCTGCAAATGAACA<br>GCCTGACAGCCGAGGACACGGCTGTGTATTACTGTGCGAGAG<br>ATCCCCGCCTACAACTATGGTTCATGTTTGACTACTGGGGCCA<br>GGGAACCCTGGTCACCGTCTCCTCG<br>SEQ ID NO: 9 |
| NI-307.19F8-V_L | CAGCCTGTGCTGACTCAGCCACCTTCTGCATCAGCCTCCCTGG<br>GAGCCTCGGTCACACTCACCTGCACCCTGAGCAGCGGCTACA<br>GTAATTATAAAGTGGACTGGTACCAGCAGAGACCAGGGGAG<br>GGCCCCCGCTTTGTGATGCGAGTGGGCACTGGTGGGATTGTG<br>GGATCCAAGGGGGATGGCATCCCTGATCGCTTCTCAGTCTTG<br>GGCTCAGGCCTGAATCGGTACCTGACCATCAAGGACATCCAG<br>GAAGAGGATGAGAGTGACTACCACTGTGGGGCAGACCATGG<br>CAGTGGGAGCAACTTCGTGTATGTCTTCGGAACTGGGACCAA<br>GGTCACCGTCCTA<br>SEQ ID NO: 11 |
| NI-307.11G6-V_H | CAGGTGCAGCTGGTGGAGTCTGGGGGAGACTTGGTCAAGCCT<br>GGAGGGTCCCTGAGACTCTCCTGTGCAGCCTCTGGATTCACCT<br>TCAGTGACCACTACATGAGCTGGATCCGCCAGGCTCCAGGGA<br>AGGGGCTGGAATGGGTTTCATACATTAGTACTAGAAGTACTT<br>ACACAAACTACGCAGACTCTGTGAAGGGCCGATTCACCATCT<br>CCAGAGACAACGCCAAGAACTCACTATATCTGCACATGAACA<br>GCCTGAGAACCGAGGACACGGCTGTTTATTACTGTGCGAGAG<br>ATTACTCTGATACTAGTGGACCCCCTGACTACTGGGGCCAGG<br>GCACCCTGGTCACCGTCTCCTCG<br>SEQ ID NO: 13 |
| NI-307.11G6-V_L | CAGTCTGTGCTGACTCAGCCACCCTCAGCGTCTGGGACCCCC<br>GGGCAGAGGGTCACCATCTCTTGTTCTGGGAGCAACTCCAAC<br>ATCGGAAGTAATTATGTATACTGGTACCAGCAGCTCCCAGGA<br>ACGGCCCCCAAACTCGTCATCTATAGGAATACTCAGCGGCCC<br>TCAGGGGTCCCTGACCGATTCTCTGGCTCCAAGTCTGGCACCT<br>CAGCCTCCCTGGCCATCAGTGGGCTCCGGTCCGAAGATGAGG<br>CTGATTATTACTGTGCAGCATGGGATGACAGCCTGAGTGGTC<br>TGGTGTTCGGCGGAGGGACCAAGCTGACCGTCCTG<br>SEQ ID NO: 15 |
| NI-307.17F12-V_H | CAGCTGCAGCTGCAGGAGTCGGGCCCAGGACTGGTGAAGCCT<br>TCGGGGACCCTGTCCCTCACCTGCGCTGTCTCTGGTGACTCCA<br>TCACCAATACTAACTGGTGGTGTTGGGTCCGCCAGCCCCCAG<br>GGAAGGGGCTGGAGTGGATTGGGGAAATCTTTCATAGTGGGG<br>GCACCAACTACAACCCGTCCCTCAAGAGTCGAGTCACCATGT<br>CAGTAGACAAGGCCAAGAACCAGTTCTCCCTGAAGGTGAACT<br>CTGTGACCGCCGCGGACACGGCCGTGTACTTCTGTACGACCA<br>ACCCCGGGGGGGAGATGGCTACAGTTACTGGGGCCAGGGC<br>ACCCTGGTCACCGTCTCCTCG<br>SEQ ID NO: 17 |
| NI-307.17F12-V_L | CAGTCTGCCCTGACTCAGCCTCGCTCAGTGTCCGGGTCTCCTG<br>GACAGTCAGTCACCATCTCCTGCACTGGAACCAGCAGTGATG<br>TTGGTGGTTATAACTATGTCTCCTGGTACCAACAACACCCAG<br>GCAAAGCCCCCAATCTCATGATTTCTGAGGTCAGTAAGCGGC<br>CCTCAGGGGTCCCTGATCGCTTCTCTGGCTCCAAGTCTGGCAA<br>CACGGCCTCCCTGACCATCTCTGGGCTCCAGGCTGAGGATGA<br>GGCTGATTATTTCTGCTGCTCATATGCAGGCAGTTACAGGGTC<br>TTCGGAACTGGGACCAAGGTCACCGTCCTA<br>SEQ ID NO: 19 |

TABLE II-continued

Nucleotide sequences of the V$_H$ and V$_L$ region of exemplary polyomavirus, polyomavirus VP1, and polyomavirus VP1 VLP antibodies.

| Antibody | Nucleotide sequences of variable heavy (VH) and variable light (VL) chains |
|---|---|
| NI-307.6A2-V$_H$ | CAGGTGCAGCTGCAGGAGTCGGGCCCAGGACTGGTGAAGCCT<br>TCGGAGACCCTGTCCCTCACCTGCGCTGTCTCTGGAGGCTCCG<br>TCAGCAGTAGTTACTGGTACAGTTGGGTCCGCCAGCTCCCAG<br>GAAAGGGGCTGGAATGGATCGGAGAAATCTTTCATACTGGGG<br>ACACCAACTACAACCCGTCCCTCGAGAGTCGAGTCACCATTT<br>CAATAGACACGTCCAAGAACCAGTTGTCCCTGGATGTGACCT<br>CTGCGACCGCCGCGGACACGGCCGTATACTACTGCGCGAGAG<br>ATTATTGTACTGATAGCGGTTGCGACTCTGATGCTCTTGATGT<br>CTGGGGCCACGGGACAATGGTCACCGTCTCTTCG<br>SEQ ID NO: 21 |
| NI-307.6A2-V$_L$ | CAGTCTGCCCTGACTCAGCCTGCCTCCGTGTCTGGGTCTCCTG<br>GACAGTCGATCACCATCTCCTGCACTGGAACCACCAAAGATG<br>TTGGAAATTATAACCTTGTCTCCTGGTACCAACAGCACCCGG<br>GCAAAGCCCCCAGACTCGTGATTTATGAGGTCAGTGAGCGGC<br>CCTCAGGGGTTTCTAATCGCTTCTCTGGCTCCAAGTCTGGCAA<br>CACGGCCTCCCTGACAATCTCTGGGCTCCAGGCTGAGGACGA<br>GGCTGATTATCACTGCTGCTCATATGCAGGTAGTGGCACATC<br>GGTATTCGGCGGAGGGACCAAGGTGACCGTCCTA<br>SEQ ID NO: 23 |
| NI-307.5H3-V$_H$ | CAGGTGCAGCTGCAGGAGTCCGGCCCAGGACTGCTGAAGCCT<br>TTGGGAACCCTGTCCCTCATCTGCGATGTCTCTGGTGACTCCA<br>TCAGTAGTAGTAACTGGTGGAGTTGGGTCCGCCAGTCCCCCC<br>GGAAGGGGCTGGAGTGGATTGGCGAAATCTATCATAGTGGG<br>AGGACCAACTACAATCCGTCACTCACGAATCGAGTTACCATT<br>TCAGTGGACAAGTCCAAGAACCAGTTCTCCCTGAATCTGAAC<br>TCTGTGACCGCCGCGGACACGGGCGTATATTATTGTGCGAGA<br>TGGGATTATTATTATAATAATGATTATTATATCCGCGGTTTTG<br>ATATATGGGGCCAAGGGACAATGGTCACCGTCTCTTCG<br>SEQ ID NO: 25 |
| NI-307.5H3-V$_L$ | GAAATTGTGTTGACGCAGTCTCCAGGCATCCTGTCTTTGTCTC<br>CAGGGGAAAGAGCCACCCTCTCCTGCAGGGCCAGTCAGAGTG<br>TTGACAGCAACTACCTAGCCTGGTACCAGCAGAAACCTGGCC<br>AGGCTCCCAGGCTCCTCATCTATAGTACATCCACCAGGGCCG<br>CTGGCGTCCCAGACAGGTTCAGTGGCAGTGGGTCTGGGACAG<br>ACTTCGCTCTCACCATCAGCGGACTGGAGCCTGAAGATTTTG<br>CAGTGTATTACTGTCAGCAGTGGGTGGCTCACCTCCGATCA<br>CCTTCGGCCAAGGGACACGACTGGAGATTAAA<br>SEQ ID NO: 27 |
| NI-307.25G10-V$_H$ | GAGGTGCAGCTGGTGGAGTCTGGGGGAGGCTTAGTACAGCCG<br>GGGGGGTCCCTGAGACTCTCCTGTGTGGCCTCTGGAATCATCT<br>TCAAAGACTACGACTTCCACTGGGTCCGACAAGTTAAAGAAA<br>AAGGTCTGGAGTGGGTCTCAGCTATTGGTACTGCTGGTGACC<br>CATATTATGCAGCTTCCGTGAAGGGCCGCTTCACCGTCTCCAG<br>GGAAAATGGCAAGAACTCCGTGTATCTTCGAATGAACAACGT<br>GGGAGCCGGTGACACGGCTCTGTATTATTGTACGAGCGGCAA<br>TTACTTCGATAGAGGTTCTTTCAGGCCGAGTGCTTTTGATATG<br>TGGGGCCAAGGGACAATGGTCACCGTCTCTTCG<br>SEQ ID NO: 29 |
| NI-307.25G10-V$_L$ | GAAATTGTGCTGACTCAGTCTCCAGGCACCCTGTCTTTGTCTC<br>CAGGGGAAAGAGCCACCCTCTCCTGCTGGGCCAGTCAGAGTG<br>TTTCTAGCAACTACTTAGCCTGGTATCAGCACAAACCTGGCC<br>AGGCTCCCAGACTCCTCATCTTTCGCGCATCTCGTAGGGCCAC<br>TGACATCCCAGAGAGGTTCAGTGCCGAGGGTCTGGGACAGA<br>CTTCACTCTCACCATCAGCAGACTGGAAGCTGAAGACTCTGC<br>AGTCTATTACTGTCAGGAGTATGGTAGTGCACCTCCGGCGTC<br>GATCACGTTCGGCCAAGGGACACGACTGGAGATTAAA<br>SEQ ID NO: 31 |
| NI-307.26E10-V$_H$ | GAGGTGCAGCTGGTGGAGTCTGGGGGAGGCCTGGTCCTGCCG<br>GGGGGGTCCCTGAGACTCTCCTGTGCAGTCTCTGGATTCACTG<br>TCAGAAATGAGTACATGAGGTGGGCCCGCCAGGCTCCAGGG<br>AGGGGGCTGGAGTGGGTCTCAGTGATTTACAGAGATGGCCAG<br>ACACACCACGCAGACACCGTGAAGGGCAGATTCGACGTCTCC<br>AAAGACACTTCCAAGAACACGATGTACCTTCAGATGCACAAT |

TABLE II-continued

Nucleotide sequences of the V$_H$ and V$_L$ region of exemplary polyomavirus, polyomavirus VP1, and polyomavirus VP1 VLP antibodies.

| Antibody | Nucleotide sequences of variable heavy (VH) and variable light (VL) chains |
| --- | --- |
| | CTGAGAGTCGACGACACGGCCATCTATTACTGTGCGAGGGGG<br>CATTACGGTCCTTGGGGCCAGGGCACCCTGGTCACCGTCTCCT<br>CG<br>SEQ ID NO: 33 |
| NI-307.26E10-V$_L$ | GACATCCAGATGACCCAGTCTCCTTCCACCCTGCCTGCATCTG<br>TAGGAGACAGAGTCACCATCACTTGCCGGGCCAGTCAGAGTA<br>TTAATAATTGGTTGGCCTGGTATCAGCAGAAGCCAGGGAAAG<br>CCCCTAACCTCCTGATTTATGATGCCTCCAATTTGGAAACTGG<br>GGTCCCATCAAGGTTCAGCGGCAGTGGATCTGGGACAGAATT<br>CACTCTCACCATCAGCAGCCTGCAGCCTGATGATTTTGCAACT<br>TATTACTGTCAGCAGTATAATAGTCATTCTCACACGTGGACGT<br>TCGGCCAAGGGACCAAGGTGGAAATCAAA<br>SEQ ID NO: 35 |
| NI-307.1E1-V$_H$ | GAGGTGCAGCTGGTGGAGTCTGGGGGAGGCTTGGTAAAGCC<br>GGGGGGGTCCCTTAGACTCTCCTGTGCAGCCTCTGGATTCATA<br>TTTAGTGACGCCTGGATGAACTGGGTCCGCCAGGCTCCAGGG<br>AAGGGACTGGAGTGGGTTGGCCATATTAAAAGCAGACCTGCT<br>GGTGGGACAACTGAGTACGCTGCACCCGTGAAAGGCAGATTC<br>ACCATCTCAAGAGATGATTCTACAGACACACTATATCTCCAA<br>ATGAACAACCTGAAAGCCGAGGACACAGCCGTCTATTACTGT<br>TCCACAGGGCACTATGGTGTCTATGGGCTGGGAACCCTGGTC<br>ACCGTCTCCTCG<br>SEQ ID NO: 37 |
| NI-307.1E1-V$_L$ | GACATCCAGATGACCCAGTCTCCTTCCACCCTGTCTGCATCTG<br>TAGGAGACAGAGTCACCATCACTTGCCGGGCCAGTCAGAGTA<br>TTAGAGACTACTTGGCCTGGTATCAGCAGAAACCAGGGAAAG<br>CCCCTAAACTTCTAATCTATGATGGCTCCATTTTGGAAGGTGG<br>GGTCCCATCAAGGTTCAGCGGCAGTGTATCTGGGACAGATTT<br>CACTCTCACCATCAGCAGTCTGCAGTCTGATGATTTTGCAACT<br>TATTACTGCCAACAGTATACTAGTTATTCTTCGTGGACGTTCG<br>GCCAAGGGACCAAGGTGGAAATCAAA<br>SEQ ID NO: 39 |
| NI-307.24C6-V$_H$ | CAGCTGCAGCTGCAGGAGTCGGGCCCAGGACTGGTGAAGCCC<br>TCGGGGACCCTGTCCCTCATTTGTGTTGTCTCTGGTTCCTCCA<br>TCAGAAGTAATATTTGGTGGTGGAATTGGGTCCGCCAGTCCC<br>CAGGGAAGGGGCTTGAGTGGATTGGGGAAATCTATCATAGTG<br>GGAGTACCAATTACAGCCCGTCCCTCAAGAGTCGAGTCACCA<br>TGTCAGTAGACAACTCCAAGAACCAGTTCTCCCTGAAAATGA<br>GCTCTGTGACCGCCGCGGACACGGCCGTATATTTCTGTGCGA<br>TAAACACCAGGACTTCGATCTCTGGAGTGCTCTATGATACTTT<br>TGATGTCTGGGGCCAAGGGACAATGGTCACCGTCTCTTCG<br>SEQ ID NO: 41 |
| NI-307.24C6-V$_L$ | GAAATTGTGCTGACTCAGTCTCCAGCCACCCTGTCTTTGTCTT<br>CAGGGGAAAGAGCCACCCTCTCCTGCAGGGCCAGTCAGAGTG<br>TTAGCGGCTACTTAGCCTGGTACCAACAGAAACCTGGCCAGG<br>CTCCCAGGCTCCTCATCTATGATGGGTCCAACAGGGCCACTG<br>GCATCCCAGCCAGGTTTAGTGGCAGTGGGTCTGGGACAGACT<br>TCACTCTCACCATCAGCAGCCTGGAACCTGAAGATTTTGCAG<br>TTTATTACTGTCAGCATCGTAGCAACTGGCCCATGTACACTTT<br>TGGCCAGGGGACCAAGCTGGAGATCAAA<br>SEQ ID NO: 43 |
| NI-307.78C3-V$_H$ | CAGGTGCAGCTGCAGGAGTCGGGCCCAGGACTGGTGAAGCCT<br>TCGGGGACCCTGTCCCTCACCTGCACTGTCTCTGGTGGCTCCA<br>TCAGCCGGTCGTATCTGGTGGAGCTGGGTCCGCCAGCCCCAG<br>GGAAGGGGCTGGAGTGGATTGGGAAATCTATCATAGTGGG<br>AGCACCAACTACAGCCCGTCCCTCAGGGGTCGAGTCACCATA<br>TCAGTGGACACGTCCAAGCAGCACTTCTCCCTGAAGATGACC<br>TCTGTGACCGCCGCGGACACGGCCATGTATTACTGTGTGAGA<br>GGCGAACTAGCACTCGGCTTCGACTCCTGGGGCCAGGGAACC<br>CTGGTCACCGTCTCCTCG<br>SEQ ID NO: 45 |
| NI-307.78C3-V$_L$ | CAGTCTGCCCTGACTCAGCCTCCCTCCGCGTCCGGGTCTCCTG<br>GACAGTCAGTCACCATCTCCTGCACTGGAACCAGCAGTGACG<br>TTGGTGGTTATAACTCTGTCTCCTGGTACCAACAGCACCCACG<br>CAGAGCCCCCAAACTCATGATTTATGAGGTCAGTAAGCGGCC<br>CTCAGGGGTCCCTGATCGCTTCTCTGGCTCCAAGTCTGGCAAC |

TABLE II-continued

Nucleotide sequences of the V<sub>H</sub> and V<sub>L</sub> region of exemplary polyomavirus, polyomavirus VP1, and polyomavirus VP1 VLP antibodies.

| Antibody | Nucleotide sequences of variable heavy (VH) and variable light (VL) chains |
| --- | --- |
| | ACGGCCTCCCTGACCGTCTCTGGCCTCCAGGCTGACGATGAG<br>GCTCATTATTACTGCAGCTCATATGCAGGCAGCAACAATTTG<br>GTGTTCGGCGGAGGGACCATGCTGACCGTCCTA<br>SEQ ID NO: 47 |
| NI-307.57D5-V<sub>H</sub> | GAGGTGCAGCTGGTGGAGTCTGGGGGAGGCTTGGCACAGCC<br>GGGGGGGTCCCTGAGACTCTCCTGTGCAGGCTCTGGATTCAC<br>ACTCAGTGATTTTGCCATGAGTTGGGTCCGCCGGGCTCCAGG<br>GAAGGGGCTGGAATGGGTCTCGTCGCTTACTCCTTCCGGTCG<br>AAATTCATTTTATTCAGACTCCGTGAAGGGCCGGTTCACCATC<br>TCCAGAGACAATTGGAAGAACACACTGTATTTAGAAATGAAT<br>CTCCTGAGACCCGAGGACACGGCCGTCTATTACTGTGCGAGA<br>CCCGGCGCCCCTAAGAATTCTGACAGTAAATATTCCTATGTG<br>AGAGTGGACTTCCAGCACTGGGGCCAGGGCACCCTGGTCACC<br>GTCTCCTCG<br>SEQ ID NO: 49 |
| NI-307.57D5-V<sub>L</sub> | AATTTTATGCTGACTCAGCCCCACTCTGTGTCGGAGTCTCCGG<br>GGAGGACGGTTACCATTTCGTGCACCCGCAGCAGCGGCAGCA<br>TTGCCAACAACTTTGTGCAGTGGTACCAGCACCGCCCGGGCA<br>GTGCCCCCACCACTTTGATCTATGAGGATGATCAGAGACCCT<br>CTGGGGTCCCTGATCGATTCTCTGGCTCCGTCGACAGTTTTTC<br>CAACTCTGCCTCCCTCACCATCTCTGGGCTGAAGACTGAGGA<br>CGAGGCTGACTACTTCTGTCAGTCTTATGATAACCACAATTGG<br>GTTTTCGGCGGTGGGACCACGCTGACCGTCCTA<br>SEQ ID NO: 51 |
| NI-307.43A11-V<sub>H</sub> | CAGGTGCAGCTGCAGGAGTCGGGCCCAGGACTGGTGAAGCCT<br>TCGGGGACCCTGTCCCTCACCTGCGCTGTTACTGGTGGCTCCA<br>TCAGTAGTAGTAATTGGTGGAGTTGGGTCCGCCAGTCCCCAG<br>GAAAGGGGCTGGAGTGGATTGGAGAAATTCATCATGATGGA<br>AATCTCAACTACAATCCACTCCTCAAGAGTCGAGTCAGCATG<br>TCACTAGACAGATCCAAGAACCAATTTTCTCTGAAGCTGACC<br>TCTGTGACAGCCGCGGACACGGCCGTATATTATTGTGCGAGA<br>TGGGATTTCTTTTTTGATAGTTCTTATTATATTCGTGGTTTTGA<br>TCTCTGGGGCCAGGGGACAATGGTCACCGTCTCTTCG<br>SEQ ID NO: 53 |
| NI-307.43A11-V<sub>L</sub> | GAAACGACACTCACGCAGTCTCCAGGCACCCTGTCTTTGTCTC<br>CAGGGGAAAGAGTCACCCTCTCTTGCAGGGCCAGTCAGAGTG<br>TTGACAGGAACTATTTAGCCTGGTACCAGCAGAAACCTGGCC<br>AGTCTCCCAGGCTCCTCATCTATAGTGCATCCAGAAGGGCCA<br>CTGGCATCCCAGACAGGTTCAGTGGCAGTGGGTCTGGGACAG<br>ACTTCACTCTCACCATCAGCAGACTGGAGCCTGAAGATTTTGT<br>AGTGTATTATTGTCAGCAGTATGGTGGCTCACCGCCGATCAC<br>CTTCGGCCAGGGGACACGACTGGAGATTAAA<br>SEQ ID NO: 55 |
| NI-307.3G4-V<sub>H</sub> | CAGGTGCAGCTGGTGCAGTCTGGAGCTGAATTGAAGAAGCCT<br>GGGGCCGCAGTGAAGGTCTCCTGCCAGGCTTCTGGGTACAAC<br>TTCCTTAGTTATGGTATTAATTGGGTGCGACAGATCCCTGGAC<br>AAGGGCTTCAGTGGTTGGGATGGATCAGCACTTATGATGGGA<br>CCATGAACTATGACCAGAAGCCCGACAACAGAGTCACCGTGA<br>CCACAGACACATCCTCGAGTACAGTCTATTTGGAACTGAGGG<br>GCCTGAGATCTGACGACACGGGCGTTTATTACTGTGTGAGGG<br>ATCGTTGTGCTGGTGCTGGCTGCTCCCACTCCCTCGGCTATTG<br>GGGCCAGGGAACCCTGGTCACCGTCTCCTCG<br>SEQ ID NO: 57 |
| NI-307.3G4-VL | GACATCCAGATGACCCAGTCTCCATCCGCCCTGTCTGCATCTG<br>TAGGAGACAGAGTCACCATCTCTTGCCGGGCAAGTCAGAACA<br>TTAATACCCAGTTAAATTGGTATCAGGAGAAACCAGGGAAAG<br>CCCCAGAGTTATTGATCTATGGTGCATTCAATTTGCAAAGTGG<br>GGCCCCATCAACGTTCAGTGGCAGTGGTTCTGGGACAGATTT<br>CACTCTCACCATCACCAGTCTGCAACCTGAAGATTTTGCAAGT<br>TACTACTGTCAACAGGGTTTCCATGCCCCGTACACTTTTGGCC<br>GGGGGACCAAAGTGGATATCAAA<br>SEQ ID NO: 59 |
| NI-307.61D11-V<sub>H</sub> | GAGGTGCAGCTGGTGCAGTCTGGGGCTGAGGTGAAGAAACCT<br>GGGGCCTCAGTGAAGGTCTCCTGCAAGACTTCTGGATACACC<br>TTCATCGGCCACTACATGCAGTGGGTGCGACAGGTCCCTGGA<br>CAAGGGCTTTGAGTGGATGGGATGGATCAACCCTAACACCGGT |

TABLE II-continued

Nucleotide sequences of the V<sub>H</sub> and V<sub>L</sub> region of exemplary polyomavirus, polyomavirus VP1, and polyomavirus VP1 VLP antibodies.

| Antibody | Nucleotide sequences of variable heavy (VH) and variable light (VL) chains |
|---|---|
| | ACTACAAAGTATGCACTGAAGTTTAAGGACCGGGTCACCGTG<br>ACCAGGGACACGTCCACAGCAACAGTGTACATGGAGTTTCAT<br>GGACTGACATCTGACGACACGGCCGTGTATTACTGCGCGAGA<br>GCCAGTGCCTATCAACTGGCAAACTATGACTACTGGGGCCAG<br>GGAACCCTGGTCACCGTCTCCTCG<br>SEQ ID NO: 61 |
| NI-307.61D11-V<sub>L</sub> | CAGTCTGCCCTGACTCAGCCTGCCTCCGTGTCTGGGTCTCCTG<br>GACAGTCGATCACCATCTCCTGCGCTGGAACCAGCAATGACG<br>TTGGTGATGATGACTTTGTCTCCTGGTACCAACACCAACCAG<br>GGAAAGCCCCCAGACTCATGATTTATGAGGTCACTAATCGGC<br>CCTCAGGGGTTTCTACTCGCTTCTCTGGCTCCAAGTCTGGCAA<br>CACGGCCTCCCTGACCATCTCTGGACTCCAGGCTGAAGACGA<br>GGGTGATTATTACTGTATGTCATATACAAAGAACAGCGCTCT<br>CGGTTATGTCTTCGGAGGTGGGACCAAGGTCACCGTCCTA<br>SEQ ID NO: 63 |
| NI-307.24F3-V<sub>H</sub> | CAGGTGCAGCTGCAGGAGTCGGGGGGAGGCGTGGTCCAGCC<br>TGGGAGGTCCCTAAGACTCTCCTGTGCAGCGTCAGGATTCAG<br>CTTCAATAGGTATGGCATGCACTGGGTCCGCCAGGCTCCAGG<br>CAAGGGGCTGGAGTGGTTGGCAGTCATCTCAAATGATGGAGT<br>CAATACACACTACGCAGACTCCGTGAAGGGCCGATTCACCAT<br>CTCCAGAGACAATTCCAAGAGCACGCTGTATTTGCAAGCGAG<br>CAGCCTGAGAGTTGAGGACACGGCTGTGTATTACTGTGCGGG<br>GTATTACTATGGTTCGGGGACTTCACTTTTCTTCTACTGGGGC<br>CAGGGAACCCTGGTCACCGTCTCCTCG<br>SEQ ID NO: 65 |
| NI-307.24F3-V<sub>L</sub> | GAAATTGTGCTGACTCAGTCTCCAGACTCCCTGGCTGTGTCTC<br>TGGGCGAGAGGGCCACCATCAACTGCAAGTCCAGCCAGACTG<br>TTTTATACAGCTCCAACAATCAGAACTACTTAGCTTGGTACCA<br>GCAGAAACCAGGACAGCCTCCTAAGCTGCTCCTTTACTGGGC<br>ATCTACCCGGGAATCCGGGGTCCCTGACCGGTTCAGTGGCAG<br>CGGGTCTGGGACAGATTTCACTCTCACCATCAGCAGCCTGCA<br>GCCTGAAGATGTGGCAGTTTATTACTGTCAGCAATATTATACT<br>GCTCCGTACACTTTTGGCCAGGGGACCAAGGTGGAGATCAAA<br>SEQ ID NO: 67 |
| NI-307.18E12-VH | CAGGTGCAGCTACAGCAGTGGGGCGCAGGGCTGTTGAAGCCT<br>TCGGAGACCCTGTCCCTCACGTGCGCTGTATATGGTGACTCCT<br>TCAGTGGTTTCTTCTGGGCCTGGATCCGCCAGACTCCAGGGA<br>CGGGGCTGGAGTGGATTGGGGAAATCCAACATGGTGGAAGC<br>CCCACGTACAATCCGTCGTTCGAGAGTCGACTCACCATATCG<br>ACTGACGCGTCTAAGAGTCAAGTCTCTCTTAAAATGACATCT<br>GTGACCGTCACGGACACGGCTATATATTATTGTGCGAGGTGT<br>ATCCGGGGTAAATATGGTTCGGGCAGTTTGCAGTTGTGGAGT<br>CAGGGCACCCTGGTCACCGTCTCCTCG<br>SEQ ID NO: 69 |
| NI-307.18E12-V<sub>L</sub> | GACATCCAGTTGACCCAGTCTCCATCCTTCCTGTCTGCATCTG<br>TGGGAGACAGAGTCACCATCACTTGCCGGGCCAGTCAGGACA<br>TTAATTATCATTTAGCCTGGTATCGGCAGAAGCCAGGAAAAG<br>CCCCTGACCTCCTGATCCATAGTGCGCACACTTTGCACATTGG<br>GGTCTCATCGAGGTTCAGCGGCAGTGGATCTGGGACAGAATT<br>CACTCTCACAATCCACACCTTGCAGCCTGAAGATTTTGCAACC<br>TATTATTGTCACCAGCCTAAAACTTTTCCTCCCACTTTCGGCG<br>GCGGGACCAAAGTGGATATCAAA<br>SEQ ID NO: 71 |
| NI-307.20F5-V<sub>H</sub> | GAGGTGCAGCTGGTGGAGTCTGGGGGAGGCGTGGTCCAGCCT<br>GGGACGTCCCTGAGACTCTCCTGTGCAGCGTCTGGGTTTAGTT<br>TCAATAAATATGGCGTACACTGGGTCCGCCAGGCTCCTGGCA<br>AGGGGCTGGAGTGGGTGGCAGAATATTGGTATGATGGAACTA<br>ATCCTTTTTATGCAGACTTCGTGAAGGGCCGGTTCGTCATCTC<br>CAGAGACACTTCCAAGAACACGATTTATCTGCAAATGAACAG<br>ACTGAGGGCCGAGGACACGGCTGTGTATTATTGTGCGAGAGA<br>TGCATTTTGTGGTGGAGACTGTTATGGTGGCCTATTACACGGT<br>TTGGACGTCTGGGGCCAAGGGACCACGGTCACCGTCTCCTCG<br>SEQ ID NO: 73 |
| NI-307.20F5-V<sub>L</sub> | GATGTTGTGATGACTCAGTCTCCACTCTCCCTGCCCGTCACTC<br>CTGGAGAGCCGGCCTCCATCTCCTGCAGGTCTAGTCAGAGCC<br>TCCTGCATAGTAATGGGCTCAATTATTTAGATTGGTACCTGCA |

TABLE II-continued

Nucleotide sequences of the V_H and V_L region of exemplary polyomavirus, polyomavirus VP1, and polyomavirus VP1 VLP antibodies.

| Antibody | Nucleotide sequences of variable heavy (VH) and variable light (VL) chains |
|---|---|
| | GAAGCCAGGACAGTCTCCACAGCTCCTGATCTATTTGGGTTCT<br>AATCGGGCCCCCGGGGTCCCTGACAGGTTCAGTGGCAGTGGA<br>TCAGGCACAGATTTTACACTGAAAATCAGCAGAGTGGAGGCT<br>GAGGATGTTGGGGTTTATTACTGCTTGCAAGCTCTACAAACTC<br>CGGCGTTCGGCCAGGGGACCAAGGTGGAAATCAAA<br>SEQ ID NO: 75 |
| NI-307.58C7-V_H | GAGGTGCAGCTGGTGGAGTCCGGGGGAGGCTTGGTCAAGCCT<br>GGAGGGTCCCTGAGACTCTCCTGTGCAGCCTCTGGATTCACCT<br>TCAGTGACTACTACGTCAACTGGATCCGCCAGGCTCCAGGGA<br>AGGGGCTGGAGTGGGTTGCATGCATTAGTAGTAGTGGTCGTA<br>CCATACACTACGCAGACTCCGTGAAGGGCCGATTCACCATCT<br>CCAGGGACAACGCCAAGAACTCACTGTATCTGCAAATGAACA<br>GCCTGAGAGCCGAGGACACGGCCTTTTATTACTGTGCGAGAG<br>ACCTGGACAAAGCAGCAACTGGCAGACCCTACTTTGACTACT<br>GGGGCCAGGGAACCCTGGTCACCGTCTCCTCG<br>SEQ ID NO: 77 |
| NI-307.58C7-V_L | CAGTCTGTGCTGACTCAGCCACCCTCAGCGTCTGGGACCCCC<br>GGGCAGAGGGTCACCATCTCTTGTTCTGGAAGCAGCTCCAAC<br>ATCGGAGGTAATGCTGTGAACTGGTTCCAACAGCTCCCAGGA<br>ACGGCCCCCAAACTCCTCATCTATGGTAATACTCAGCGGCCC<br>TCAGGGGTCCCTGACCGATTCTCTGGCTCCAAGTCTGGCACCT<br>CAGCCTCCCTGGCCATCAGTGGGCTCCAGTCTGAAGATGAGA<br>CTAATTATTACTGTGCAGCATGGGATGACAGCCTGAATGGTG<br>TGGTATTCGGCGGAGGGACCAAGCTGACCGTCCTA<br>SEQ ID NO: 79 |
| NI-307.105C7-V_H | GAGGTGCAGCTGGTGGAGTCTGGGGGAGGCTTGGTACAGCCT<br>GGGGGGTCCCTGAGACTCTCCTGTGCAGCCTCTGGATTCTCCT<br>TTGGATTCTATGCCATGAACTGGGTCCGCCAGGCTCCAGGGA<br>AGGGGCTGGAGTACGTCTCAGGTGTCAGTGGTGGTGGTGGTA<br>GCACATACTACGCAGACTCCGTGAAGGGCCGGTTCACCATCT<br>CCAGAGACAATTCCAAGAACACGCTGTATCTGCAAATGAAGA<br>GCCTGAGAGCCGAGGACACGGCCATATATTACTGTGCGAAAG<br>ATCAGTCTTACTGTAGTGGTGGTAGCTGCCACCCCTACTACTT<br>AGACTACTGGGGCCAGGGAACCCTGGTCACCGTCTCCTCG<br>SEQ ID NO: 81 |
| NI-307.105C7-V_L | TCCTATGTGCTGACTCAGCCACCCTCGGTGTCCGTGGCCCCAG<br>GACAGACGGCCAGGATTACCTGTGGGGGAAATAACATTGGA<br>AGTAAAAGTGTGCACTGGTACCAGCAGAAGCCAGGCCAGGC<br>CCCTGTGGTGGTCGTCTATGATGATAGCGGCCGGCCCTCAGG<br>TATCCCTGAGCGATTCTCTGGCTCCAATTCTGGGAACACGGCC<br>ACCCTGACCATCAGCAGGGTCGAAGCCGGGGATGAGGCCGA<br>CTATTACTGTCAGGTGTGGGATAGTAGTAGTGATCATCCTTAT<br>GTCTTCGGAACTGGGACCAAGGTCACCGTCCTA<br>SEQ ID NO: 83 |
| NI-307.98D3-V_H | GAGGTGCAGCTGGTGGAGTCTGGGGGAGGCGTGGTCCAGCCT<br>GGGAGGTCCCTGAGACTCTCCTGTGCAGCCTCTGGATTCACCT<br>TCAGCAGCTCCGCTATGCACTGGGTCCGCCAGGCTCCAGGCA<br>AGGGGCTGGAGTGGGTGGCAGTTATATCATATGATGGGAATA<br>ATCAATTATACGCAGACTCCGTGAAGGGCCGATTAACCATCT<br>CCAGAGACAATTCCAAGAATGCACTGTATCTTCAACTGAACA<br>GCCTGAGAACTGAGGACACGGCTGTTTATTTCTGTGCGAGAG<br>ATGGGGGTGGATACAGCTTTGGCACTTACTTCTTTGACTTCTG<br>GGGCCAGGGAACCCTGGTCACCGTCTCCTCG<br>SEQ ID NO: 89 |
| NI-307.98D3-V_K | GACATCCAGATGACCCAGTCTCCATCCTCCCTGTCTGCATCTG<br>TAGGAGAGAGAGTCACCATCACTTGTCGGGCAAGTCAGAGG<br>ATTAGCAACTATTTAAATTGGTATCAGCAGAAACCAGGGAAA<br>GCCCCTAAGCTCCTGATCTATGCTGCATCCACTTTGCAAAGTG<br>GGGTCCCATCAAGGTTCAGTGGCAGTGGATCTGGGACAGATT<br>TCACTCTCACCATCAGCAGTCTGCAACCTGAAGATTTTGCAAC<br>TTACTACTGTCAACAGAGTTACAGTAGTCCCCCCACTTTCGGC<br>CCTGGGACCAAAGTGGATATCAAA<br>SEQ ID NO: 91 |
| NI-307.72F7-V_H | GAGGTGCAGCTGGTGGAGTCTGGGGGAGGCTTGGTACAGCCT<br>GGAGGGTCCCTGAGACTCTCCTGTGCAGCCTCTGGATTCACCT<br>TCAGTAGTTATGAAATGAACTGGGTCCGCCAGGCTCCAGGGA |

TABLE II-continued

Nucleotide sequences of the $V_H$ and $V_L$ region of exemplary polyomavirus, polyomavirus VP1, and polyomavirus VP1 VLP antibodies.

| Antibody | Nucleotide sequences of variable heavy (VH) and variable light (VL) chains |
|---|---|
| | AGGGGCTGGAGTGGATTTCATACATTAGTAGTCGTGGGAGTA<br>CCATACACTACGCAGACTCTGTGAAGGGCCGATTCACCATCT<br>CCAGAGACGACGCCAAGAACTCACTGTATCTGCAAATGAACA<br>GCCTGAGAGCCGAGGACACGGCTATTTATTACTGTGCGAGAG<br>ATCGGTACGATTTCTGGAGTGGTTGCATCAAGGGGTGCTACT<br>ACGGCATGGACGTCTGGGGCCAAGGGTCCACGGTCACCGTCT<br>CCTCG<br>SEQ ID NO: 93 |
| NI-307.72F7-$V_K$ | GAAATTGTGTTGACGCAGTCTCCAGGCACCCTGTCTTTGTCTC<br>CAGGGCAAAGAGCCACCCTCTCCTGCAGGGCCAGTCAGAGCA<br>TTAGCAGCAGCTACTTGGCCTGGTACCAGCAGAGACGTGGCC<br>AGGCTCCCAGGCTCCTCATCTATGGTGCATCCAGCAGGGCCA<br>CTGGCATCCCAGACAGGTTCAGTGGCAGTGGGTCTGGGACAG<br>ACTTCACTCTCACCATCAGCAGACTGGAGCCTGAAGATTTTG<br>CAGTGTATTACTGTCAGCACTATGGTACCACACTGACGTTCG<br>GCCAAGGGACCAAAGTGGATATCAAA<br>SEQ ID NO: 95 |
| NI-307.45E10-$V_H$ | GAGGTGCAGCTGGTGGAGTCTGGGGGAGGCTTGGTGCAGCCT<br>GGGGGGTCCCTGAGACTCTCCTGTGCAGCCTCTGGATTCTCCT<br>TTAGATTCTATGCCATGAACTGGGTCCGCCAGGCTCCAGGGA<br>AGGGGCTGGAGTACGTCTCAGGTATCAGTGGTGGTGGTGGTA<br>CTACATACTACGCAGACTCCGTGAAGGGCCGGTTCACCATCT<br>CCAGAGACAATTCCAAGAACACCCTGTATCTGCAAATGAAGA<br>GCCTGAGAGCCGAGGACACGGCCATATATTACTGTGCGAAAG<br>ATCAGTCTTACTGTAGTGGTGCTGGCTGCCACCCCTACTACTT<br>AGACTACTGGGGCCAGGGAACCCTGGTCACCGTCTCCTCG<br>SEQ ID NO: 97 |
| NI-307.45E10-$V_L$ | TCCTATGTGCTGACTCAGCCACCCTCGGTGTCCGTGGCCCCAG<br>GACAGACGGCCAGGATTACCTGTGGGGGAAATAACATTGGA<br>AGTAAAAGTGTGCACTGGTACCAGCAGAAGCCAGGCCAGGC<br>CCCTGTGGTGGTCGTCTATGATGATAGTGGCCGGCCCTCAGG<br>GATGCCTGAGCGATTCTCTGGCTCCAACTCTGGGAACACGGC<br>CACCCTGACCATCAGCAGGGTCGAAGCCGGGGATGAGGCCG<br>ACTATTACTGTCAGGTGTGGGATAGTAGTAGTGATCATCTTTA<br>TGTCTTCGGAACTGGGACCAAGGTCACCGTCCTA<br>SEQ ID NO: 99 |
| NI-307.72F10-$V_H$ | GAGGTGCAGCTGGTGGAGTCTGGGGGAGGCGTGGTACAGCCT<br>GGCAGGTCCCTGAGACTCTCCTGTGCAACCTCTGGATTCACCT<br>TTGATGATTATGCCATGCACTGGGTCCGGCAAGCTCCAGGGA<br>AGGGCCTGGAGTGGGTCTCAGGTCTGACTTGGAGTAGTAGTG<br>GCGTTGGCTATGCCGACTCTGTGAAGGGCCGATTCACCATCT<br>CCAGAGACAACGCCAAGAACTCCCTGTATCTGCAAATGAACA<br>GTCTGAGAGCTGAGGACACGGCCTTGTATTACTGTGCAAAAG<br>GTTCCGGGGAGTGGCTACGATTAGGACAAGACTACTGGGGCC<br>AGGGAACCCTGGTCACCGTCTCCTCG<br>SEQ ID NO: 101 |
| NI-307.72F10-$V_L$ | CAGTCTGTGCTGACTCAGCCACCCTCAGTCTCTGGGACCCCA<br>GGGCAGAGGGTCACCATCTCCTGCACTGGGAGCAGCTCCAAC<br>ATCGGGGCAGGTTATGATGTACACTGGTACCAGCAGCTTCCA<br>GGAACAGCCCCCAAACTCCTCATCTATGATAACAGTAATCGG<br>CCCTCAGGGGTCCCTGACCGATTCTCTGGCTCCAAGTCTGGCA<br>CCTCAGCCTCCCTGGCCATCACTGGGCTCCAGGCTGAGGATG<br>AGGCTCATTATTACTGCCAGTCCTTTGACAGCAGCCTGAGTG<br>GTTCGGTTTTCGGCGGAGGGACCAAGCTGGCCGTCCTA<br>SEQ ID NO: 103 |
| NI-307.56A8-$V_H$ | GAGGTGCAGCTGGTGGAGTCTGGGGGAGGCCTGGTCAAGCCT<br>GGGGGGTCCCTGAGACTCTCCTGTGCAGCCTCTGGATTCACCT<br>TCAGTAGCTATAGAATGAACTGGGTCCGCCAGGCTCCAGGGA<br>AGGGGCTGGAGTGGGTCTCATCCATTAGTAGTAGCAGTAGTT<br>ACATATACTATGGAGACTCAGTGAAGGGCCGATTCACCATCT<br>CCAGAGACAACGCCAAGAACTCACTGTATCTGCAAATGAGCA<br>GCCTGAGAGCCGAGGACACGGCTGTGTATTACTGTGCGAGAT<br>ACGCGCACGACTGGAACATTGACTACTGGGGCCAGGGAACCC<br>TGGTCACCGTCTCCTCG<br>SEQ ID NO: 105 |

TABLE II-continued

Nucleotide sequences of the $V_H$ and $V_L$ region of exemplary polyomavirus, polyomavirus VP1, and polyomavirus VP1 VLP antibodies.

| Antibody | Nucleotide sequences of variable heavy (VH) and variable light (VL) chains |
|---|---|
| NI-307.56A8-$V_L$ | CAGTCTGTGCTGACTCAGCCACCCTCAGCGTCTGGGACCCCC<br>GGGCAGAGGGTCACCATCTCTTGTTCTGGAAGCAGCTCCAAC<br>ATCGGAAGTAATACTGTAAACTGGTACCAGCAGCTCCCAGGA<br>ACGGCCCCCAAACTCCTCATCTATAGTAATAGTCAGCGGCCC<br>TCAGGGGTCCCTGACCGATTCTCTGGCTCCAAGTCTGGCACCT<br>CAGCCTCCCTGGCCATCAGTGGGCTCCAGTCTGAGGATGAGG<br>CTGATTATTACTGTGCAGCATGGGATGACAGCCTGAATGGTT<br>GGGTGTTCGGCGGAGGGACCAAGCTGACCGTCCTA<br>SEQ ID NO: 107 |
| NI-307.27C11-$V_H$ | CAGGTGCAGCTGCAGGAGTCGGGCCCAGGACTGGTGAAGCCT<br>TCGGGGACCCTGTCCCTCACCTGCGCTGTCTCTGGTGACTCTA<br>TCAGCAGTAGTAACTGGTGGAGTTGGGTCCGCCAGCCCCAG<br>GGAAGGGGCTGGAGTGGATTGGGAGATCTATCATAGTGGG<br>GGCACCAAGTACAACCCGTCCCTCAAGAGTCGAGTCACCATT<br>TCAGTAGACAAGTCCAAGAATCACTTCTCCCTGAAGCTGAGG<br>TCTGTGACCGCCGCGGACACGGCCGTGTATTATTGTGCGAGA<br>AATAGGTGGTTCGACAATAACCGGGGGGGCTACTACTACTAC<br>GGCATGGACGTCTGGGGCCAAGGGACCACGGTCACCGTCTCC<br>TCG<br>SEQ ID NO: 109 |
| NI-307.27C11-$V_K$ | GACATCCAGATGACCCAGTCTCCATCCTCCCTGTCTGCATCTG<br>TGGGAGACAGAGTCACCATCACTTGCCGGGCAAGTCAGGGCA<br>TCAGTAGTTATTTAAATTGGTATCAGCAGAAACCAGGGAAAG<br>CCCCTAAACTCCTGATCTCTGCTACATCCGATTTGCAAAGTGG<br>GGTCCCATCAAGGTTCAGTGGCAGTGGATCTGGGACAGATTT<br>CACTCTCACCATCAGCAGTCTGCAACCTGAAGATTTTGCTACT<br>TACTACTGTCAACAGAGTTACAGTACCCCGTACACTTTTGGCC<br>AGGGGACCAAGCTGGAGATCAAA<br>SEQ ID NO: 111 |
| NI-307.47B11-$V_H$ | GAGGTGCAGCTGGTGGAGTCTGGGGGAGGCTTGGTCAAGCCT<br>GGAGGGTCCCTGAGACTCTCCTGTGCAGCCTCTGGATTCACCT<br>TCAGTGACTACTACATGAACTGGATCCGCCAGGCTCCAGGGA<br>AGGGGCTGGAGTGGCTTTCATGCATTAGTAGTAGTGGTAATA<br>CCATTTACTACGCAGACTCTGTGAAGGGCCGATTCACCATCTC<br>CAGGGACAACGCCAAGAACTCACTGTATCTGCAAATGAACAG<br>CCTGAGAGCCGAGGACACGGCCGTATATTACTGTGCGAGAGA<br>TTTGGACAAAGCAGCAACTGGCAGACCCTACTTTGACTACTG<br>GGGCCAGGGAACCCTGGTCACCGTCTCCTCG<br>SEQ ID NO: 113 |
| NI-307.47B11-$V_L$ | CAGTCTGTGCTGACTCAGCCACCCTCAGCGTCTGGGACCCCC<br>GGGCAGAGGGTCACCATCTCTTGTTCTGGAAGCAGCTCCAAC<br>ATCGGAAGTAATACTGTAAACTGGTACCAGCAGCTCCCAGGA<br>ACGGCCCCCAAACTCCTCATCTATAGTAATAATCAGCGGCCC<br>TCAGGGGTCCCTGACCGATTCTCTGGCTCCAGGTCTGGCACCT<br>CAGCCTCCCTGGCCATCAGTGGGACTCCAGTCTGAGGATGAGG<br>CTGATTATTACTGTGCAGCATGGGATGACAGCCTGAATGGTG<br>TGGTATTCGGCGGAGGGACCAAGCTGACCGTCCTA<br>SEQ ID NO: 115 |
| NI-307.26A3-$V_H$ | GAGGTGCAGCTGGTGGAGTCTGGGGGAGTCTTGGTACAGCCT<br>GGGGGGTCCCTGAGACTCTCCTGTGCAGCCTCTGGATTCACCT<br>TTAGCAGCTATGCCATGACCTGGGTCCGCCAGGCTCCAGAGA<br>AGGGGCTGGAGTGGGTCTCAACTATTATTGGTAATGGTGCTT<br>ACACATACTACGCAGACTCCGTGAAGGGCCGGTTCACCATCT<br>CCAGAGACAATTCCAAGAACACGCTGATTCTGCAAATGAACA<br>GCCTGAGAGCCGACGACGCGGCCGTATATTACTGTGCGAAAG<br>GCACAGAATTAGCCCCCTACTACTACTACTTCGCTTTGGACGT<br>CTGGGGCCAAGGGACCACGGTCACCGTCTCCTCG<br>SEQ ID NO: 117 |
| NI-307.26A3-$V_K$ | GAAATTGTGTTGACGCAGTCTCCAGGCACCCTGTCTTTGTCTC<br>CAGGGGAAAGAGCCACCCTCTCCTGCAGGGCCAGTCAGAGTA<br>TTAGCAGCAGCCACTTAGCCTGGTACCAGCAGAAACCTGGCC<br>AGGCTCCCAGGCTCCTCATCTATGGTGCATCCAGCAGGGCCA<br>CTGGCATCCCAGACAGGTTCAGTGGCGGTGGGTCTGGGACAG |

TABLE II-continued

Nucleotide sequences of the V_H and V_L region of exemplary polyomavirus, polyomavirus VP1, and polyomavirus VP1 VLP antibodies.

| Antibody | Nucleotide sequences of variable heavy (VH) and variable light (VL) chains |
|---|---|
|  | ACTTCACTCTCACCATCACCAGACTGGAGCCTGAAGATTTTGC<br>AGTGTATTACTGTCAGCAGTATGGTAGCTCTCCGTACACTTTT<br>GGCCAGGGGACCAAGCTGGAGATCAAA<br>SEQ ID NO: 119 |
| NI-307.27C2-V_H | GAGGTGCAGCTGGTGGAGTCTGGGGGAGGCCTGGTCAAGCCT<br>GGGGGGTCCCTGAGACTCTCCTGTGCAGCCTCTGGATTCACCT<br>TCAGTAGCTATACCATGAACTGGGTCCGCCAGGCTCCAGGGA<br>AGGGGCTGCAGTGGGTCTCATCCATCAGTAGTAGTAGTACCT<br>ACATGTACTACGGAGACTCAGTGAAGGGCCGATTCACCATCT<br>CCAGAGACAACGCCAGGAACTCACTCTATCTGCAAATGAACA<br>GCCTGAGAGTCGAGGACACGGCTGTATATTACTGTGCGAGAT<br>ACGCGCACGACTGGAACGTTGACTACTGGGGCCAGGGAACCC<br>TGGTCACCGTCTCCTCG<br>SEQ ID NO: 121 |
| NI-307.27C2-V_L | CAGTCTGTGCTGACTCAGCCACCCTCAGCGTCTGGGACCCCC<br>GGGCAGAGGGTCACCATCTCTTGTTCTGGAGGCAGCTCCAAC<br>ATCGGAAGTAATCCTGTGAACTGGTTCCAACAATTCCCAGGA<br>ACGGCCCCCAAACTCCTCATCTATGCTAATACTCAGCGGCCCT<br>CAGGGGTCCCTGACCGATTCTCTGGCTCCAAGTCTGGCACCTC<br>AGTTTCCTGGCCATCAGTGGGCTCCAGTCTGAGGATGAGGG<br>TGATTATCACTGTGCAGCATGGGATGACAGCCTGAAGGGTTG<br>GGTGTTCGGCGGAGGGACCAAGCTGACCGTCCTA<br>SEQ ID NO: 123 |
| NI-307.57D4-V_H | GAGGTGCAGCTGGTGGAGTCTGGGGGAGGCCTGGTACAGCCT<br>GGCAGGTCCCTGAGACTCTCCTGTGCAGCCTCTGGATTCACCT<br>TTGATCATTATGCCATGCACTGGGTCCGGCAAGTTCCAGGGA<br>GGGGCCTGGAGTGGGTCTCAGGTGTTACTTGGAATAGTGGTA<br>TCATAGGCTATGCGGACTCTGTGAAGGGCCGATTCACCATCT<br>CCAGAGACAATGCCAAGAATTCCCTCTATCTGCAAATGACCA<br>GTCTGAGAGCTGAGGACACGGCCTTGTATTACTGTGCAAAAG<br>GGACAAATGACTTCGTAAGCTACGGTTTGGACGTCTGGGGCC<br>AAGGGACCACGGTCACCGTCTCCTCG<br>SEQ ID NO: 125 |
| NI-307.57D4-V_L | CAGTCTGTGTTGACGCAGCCGCCCTCAGTGTCTGGGGCCCCA<br>GGGCAGAGGGTCTCCATCTCCTGCACTGGGACCAGCTCCAAC<br>CTCGGGGCAGGTTTTGATGTACACTGGTACCAGCAGATTCCA<br>AGAAAAGCCCCCGAACTCCTCATCTATGGTAACAGCATTCGG<br>CCCTCAGGGGTCCCTGACCGATTCTCTGGCTCCAAGTCTGGCA<br>CCTCAGCCTCCCTGGCCATCACTGGGCTCCAGGCTGAGGATG<br>AGGCTGATTATTACTGCCAGTCCTATGACAGCAGGTTGAGTG<br>GCTCGGTGTTCGGCGGGGGACCAAGCTGACCGTCCTA<br>SEQ ID NO: 127 |
| NI-307.50H4-V_H | CAGGTGCAGCTGCAGGAGTCGGGCCCAGGACTGGTGAAGCCT<br>TCGGGGACCCTGTCCCTCACCTGCGCTGTCTCTGGTGACTCCA<br>TCAGCAGTAGTAACTGGTGGAGTTGGGTCCGCCAGCCCCCAG<br>GGAAGAGGCTGGAGTGGATTGGGGAGATCTATCATAGTGGG<br>GGCACCAAGTACAACCCGTCCCTCAAGAGTCGAGTCACCATT<br>TCAGTGGACAAGTCCAAGAACCACTTCTCCCTGAAGCTGAGG<br>TCTGTGACCGCCGCGGACACGGCCGTGTATTATTGTGCGAGA<br>AATAGGTGGTTCGACAATAACCGGGGGGGCTACTACTATTAC<br>GGCATGGACGTCTGGGGCCAAGGGACAATGGTCACCGTCTCT<br>TCG<br>SEQ ID NO: 129 |
| NI-307.50H4-V_K | GACATCCAGATGACCCAGTCTCCATCCTCCCTGTCTGCATCTG<br>TGGGAGACAGAGTCACCATCACTTGCCGGGCAGGTCAGGGCA<br>TTAGCACCTATTTAAATTGGTATCAGCAGAAACCAGGGAAAG<br>CCCCTAACCTCCTGATCTATGCTACATCCGATTTGCAAAGTGG<br>GGTCCCATCAAGGTTCAGTGGCAGTGGATCTGGGACAGATTT<br>CACTCTCACCATCAGCAGTCTGCAACCTGAAGATTTTGCTACT<br>TACTACTGTCAACAGAGTTACAATAACCCGTACACTTTTGGCC<br>AGGGGACCAAGGTGGAGATCAAA<br>SEQ ID NO: 131 |
| NI-307.53B11-V_H | GAGGTGCAGCTGGTGCAGTCTGGAGCAGAGGTGAAAAAGCC<br>CGGGGAATCTCTGAAGATCCTGTAAGGGTTCTGGATACAG<br>CTTTTACCAGCTACTGGATCGGCTGGGTGCGCCAGATGCCCGG<br>GAAAGGCCTGGAGTGGATGGGGATCATCTATCCTGGTGACTC |

TABLE II-continued

Nucleotide sequences of the $V_H$ and $V_L$ region of exemplary polyomavirus, polyomavirus VP1, and polyomavirus VP1 VLP antibodies.

| Antibody | Nucleotide sequences of variable heavy (VH) and variable light (VL) chains |
|---|---|
|  | TGATACCAGATACAGCCCGTCCTTCCAAGGCCAGGTCACCAT<br>CTCAGCCGACAAGTCCATCACCACCGCCTACCTGCAGTGGAG<br>CAGCCTGAAGGCCTCGGACACCGCCTTATATTACTGTGCGAG<br>ACGGGGTAGTGGGAGCTTCTCCAACTATGACTTCTGGGGCCA<br>GGGCACCCTGGTCACCGTCTCCTCG<br>SEQ ID NO: 133 |
| NI-307.53B11-$V_K$ | CAGTCTGCCCTGACTCAGCCTCGCTCAGTGTCCGGGTCTCCTG<br>GGCAGTCAGTCACCATCTCCTGCACTGGAACCAGCAGTGATG<br>TTGGTGCTTATAACTATGTCTCCTGGTACCAACAGCACCCAGT<br>CAAAGCCCCCAAACTCATGATTTATGATGTCAGTAAGCGGCC<br>CTCAGGGGTCCCTGATCGCTTCTCTGGCTCCAGGTCTGGCAAC<br>ACGGCCTCCCTGACCATCTCTGGGCTCCAGGCTGACGATGAG<br>GCTGATTATTACTGCTGCTCATATGCAGGCACCTACACTGTGC<br>TTTTCGGCGGAGGGACCAAGCTGACCGTCCTA<br>SEQ ID NO: 135 |
| NI-307.7J3-$V_H$ | CAGGTGCAGCTGCAGGAGTCGGGCCCAGGACTGGTGAAGCCT<br>TCACAGACCCTGTCCCTCACCTGCACTGTCTCTGGTGGCTCCA<br>TCAGCAGTGGTGATTACTACTGGAGTTGGATCCGCCAGCCCC<br>CAGGGAAGGGCCTGGAGTGGATTGGGTACATCTATTACAGTG<br>GGACCACCTACTACAACCCGTCCCTCAAGAGTCGAGTTACCA<br>TATCAGTAGACACGTCCAAGAACCAGTTCTCCCTGAAGCTGA<br>GTTTTGTGACTGTCGCAGACACGGCCGTGTATTACTGTGCCAG<br>AGATGGCCGTTTTACTATGGTTCGGGGAGGCTACTACTACTA<br>CGGTATGGACGTCTGGGGCCAAGGGACCACGGTCACCGTCTC<br>CTCG<br>SEQ ID NO: 137 |
| NI-307.7J3-$V_K$ | GACATCCAGATGACCCAGTCTCCATCCTCCCTGTCTGTATCTG<br>TAGGAGACAGAGTCACCATCACTTGCCGGGCAAGTCAGAGCA<br>TTAGCAGCTATTTAAATTGGTATCAGCAGAAATTAGGGAAAG<br>CCCCTAAGCTCCTGATTTATGATGCATCCAGTTTGCAAAGTGG<br>GGTCCCATCAAGGTTCAGTGGCAGTGGATCTGGGACAGATTT<br>CACTCTCACCATCAGCAGTCTGCAACCTGAAGATTTTGCAACT<br>TACTACTGTCAACAGAGTTACACTACCCCTCGAACGTTCGGC<br>CAAGGGACCAAGGTGGAGATCAAA<br>SEQ ID NO: 139 |
| NI-307.59A7-$V_H$ | GAGGTGCAGCTGGTGGAGTCTGGGGGAGGCTTGGTACAGCCT<br>GGAGGGTCCCTGAGACTCTCCTGTGCAGCCTCTGGATTCACCT<br>TCAGTAGTTATGAAATGAACTGGGTCCGCCAGGCTCCAGGGA<br>AGGGGCTGGAGTGGGTTTCATACATTAGTAGTAGTGGTACCA<br>ACATATACCACGCAGACTCTGTGAAGGGCCGATTCACCATCT<br>CCAGAGACAACGCCAAGAACTCACTGTATCTGCAAATGAACA<br>GCCTGAGAGCCGAGGACACGGCTGTTTATTACTGTGCGAGAG<br>ATGGTCCTTCACCACGCGGACACAACTATGGTCATGACTACT<br>GGGGCCAAGGCACCCTGGTCACCGTCTCCTCG<br>SEQ ID NO: 141 |
| NI-307.59A7-$V_L$ | CAGTCTGTGCTGACTCAGCCACCCTCAGCGTCTGGGACCCCC<br>GGGCAGAGGGTCACCATCTCTTGTTCTGGAAGCAGCTCCAAC<br>ATCGGAAGTAATGCTGTAAACTGGTACCAGCAGGTCCCAGGA<br>ACGGCCCCCAAACTCCTCATCTATACTAATAATCAGCGGCCC<br>TCAGGGGTCCCTGACCGATTCTCTGGCTCCAAGTCTGGCACCT<br>CAGCCTCCCTGGCCATCAGTGGGCTCCAGTCTGAGGATGAGA<br>CTGATTATTACTGTGCAGCATGGGATGACAGCCTGGGTGGTC<br>CGGTTTTCGGCGGAGGGACCAAGCTGACCGTCCTA<br>SEQ ID NO: 143 |
| NI-307.105A6-$V_H$ | GAAGTGCAGCTGGTGGAGTCTGGGGGAGGCTTGGTACAGCCT<br>GGCAGGTCCCTGAGACTCTCCTGTGCAGCCTCTGGATTCACCT<br>TTGATGATTATGCCATGCACTGGGTCCGGCAAGCTCCAGGGA<br>AGGGCTTGGAGTGGGTCTCAGGTATTACTTGGAATAGTGGTA<br>GTATAGGCTATGCGGACTCTGTGAAGGGCCGATTCACCATCT<br>CCAGAGACAACGCCAAGAACTCCCTATATCTGCAAATGAACA<br>GTCTGAGCGCTGAGGACACGGCCTTGTATTACTGTGCAAAAG<br>GGGCGCGTGACTACTTAAGCTATGGTATGGACGTCTGGGGCC<br>AAGGGACCACGGTCACCGTCTCCTCG<br>SEQ ID NO: 145 |
| NI-307.105A6-$V_L$ | CAGTCTGTCGTGACGCAGCCGCCCTCAGTGTCTGGGGCCCCA<br>GGGCAGAGGGTCACCATCTCCTGCACTGGGAGCAGTTCCAAC |

TABLE II-continued

Nucleotide sequences of the $V_H$ and $V_L$ region of exemplary polyomavirus, polyomavirus VP1, and polyomavirus VP1 VLP antibodies.

| Antibody | Nucleotide sequences of variable heavy (VH) and variable light (VL) chains |
|---|---|
|  | ATCGGGGCAGGTTATGATGTACACTGGTACCAGCAGCTTCCA<br>GGAACAGCCCCCAAACTCCTCATCTTTAGTAACACCATTCGG<br>CCCTCAGGGGTCCCTGACCGATTCTCTGGCTCCAAGTCTGGCA<br>CCTCAGCCTCCCTGGCCATCACTGGGCTCCAGGCTGAGGATG<br>AGGCTAATTATTACTGCCAGTCTTATGACAGCAGCCTGAGTG<br>GTTCGGTGTTCGGCGGAGGGACCAAGCTGACCGTCCTA<br>SEQ ID NO: 147 |
| NI-307.29B1-$V_H$ | GAGGTGCAGCTGGTGGAGTCTGGGGGAGGCTTGGTAAAGCCT<br>GGGGGGTCCCTGAGACTCTCCTGTGCAGCCTCTGGAATCACC<br>TTTCAATACTATGCCATGAATTGGGTCCGCCAGGCTCCAGGG<br>AAGGGGCTGGAGTGGGTCTCTTCTATTGGCGGTCGTGGTGAT<br>ACCACATACTACACAGACTCCGTGAAGGGCCGCTTCACCATC<br>TCCAGAGACAATTCCAAGAGCACACTATATCTGCAAATGAAC<br>AGCCTGAGAGCCGAGGACACGGCCGTCTATTACTGTGCGAAA<br>GAGCCATTTGACAGTAGTGGTGATCACCGAGGCGTCTTTGAC<br>TACTGGGGCCAGGGAACCCTGGTCACCGTCTCCTCG<br>SEQ ID NO: 149 |
| NI-307.29B1-$V_L$ | CAGTCTGTCGTGACGCAGCCGCCCTCAGTGTCTGGGGCCCCA<br>GGGCAGAGGGTCACCATCTCCTGCGCTGGGAGCAGGTCCAAC<br>ATCGGGGCAGGTTATGATGTAAATTGGTACCAGCAACTTCCA<br>AGAACTGCCCCCAAACTGCTCATCTATGATAACACCAGGCGG<br>CCGTCAGGTGTCCCTGCCCGATTCTCTGGTTCCAAGTCTGGCT<br>CCTCAGCCTCCCTGACCATCACTGGGCTCCAGGCTGAAGATG<br>AGGCTGATTATTACTGCCAGTCCTATGACAGCAAACTGAATA<br>AGTGTTCGGCGGAGGGACCAAGGTTGACCGTCCTA<br>SEQ ID NO: 151 |
| NI-307.44F6B-$V_H$ | GAGGTGCAGCTGGTGGAGTCTGGGGGAAGTGTGGTTCGGCCT<br>GGGGGGGTCCCTGAGACTTGCCTGTGAAGTGTCTGGACTCAGG<br>TTTGATGATTTCGCCATGAGTTGGGTCCGCCAAGTTCCAGGG<br>AAGGGGCTGGAGTGGATCGCTGGCATTTTTTGGAACAGTGGT<br>GGCACACTTTATGCGGATTCTGTGAAGGGCCGATTCACCATC<br>TCCAGAGACAACGCCGAAAATTCCCTGTATTTGCAAATGAAC<br>AGTCTGAGAGCCGAGGACACGGCCTTATATCGATGTGTGAGA<br>GGAAGGTCACACGCCGCCTACTACGGCATGGACGTCTGGGGC<br>AAAGGGACCACGGTCACCGTCTCCTCG<br>SEQ ID NO: 153 |
| NI-307.44F6B-$V_K$ | GAAATTGTGCTGACTCAGTCTCCACTCTCCCTGCCCGTCACCC<br>CTGGAGAGCCGGCCTCCATCTCCTGCAGGTCTAGTCAGAGCC<br>TCCTCCACAGTAATGGATACAACTATTTGGACTGGTACCTGC<br>AGAAGCCAGGGCAGTCTCCACAGCTCCTGATCTATTTGGGTT<br>CTAATCGGGCCTCCGGGGTCCCTGACAGGTTCAGTGGCAGTG<br>GATCAGGCACAGATTTCACACTGACAATCAGCAGAGTGGAGG<br>CTGAGGATGTTGGGATTTATTACTGCATGCAAGCACTACAGA<br>ACGCGCTCGCTTTCGGCGGAGGGACCAAGCTGGAGATCAAA<br>SEQ ID NO: 155 |
| NI-307.98H1-$V_H$ | CAGCTGCAGCTGCAGGAGTCGGGCCCAGGACTGGTGAAGCCT<br>TCACAGACCCTGTCCCTCACCTGCGCTGTCTCTGGTGCCTCCA<br>TCAGCAGTGGTACTTACTACTGGGGCTGGATCCGACAGCACC<br>CAGGGAAGGGCCTGGAGTGGATTGGGTACATCTATCCCAGTG<br>GGAGCACCTACTACAACCCGTCCCTCAAGAGTCGAGTTATCA<br>TATCATTAGACACGTCTAAGAGCCAGTTCTCCCTGAACCTGA<br>GCTCTGTGACTGCCGCGGACACGGCCGTGTATTACTGTGCGA<br>GAGATTACTACGATAGTAGTGGCCATATGGGGGGCTACTACC<br>ACTACGCTATGGACGTCTGGGGCCAAGGGACCACGGTCACCG<br>TCTCCTCG<br>SEQ ID NO: 157 |
| NI-307.98H1-$V_K$ | GACATCCAGTTGACCCAGTCTCCATCCTCCCTGTCTGCATCTG<br>TAGGAGACAGAGTCACCATCACTTGCCGGGCAAGTCAGAGCA<br>TTAGTAGCCATTTAAATTGGTATCAGCAGAAACCAGGGAAAG<br>TCCCTAAGCTCCTGATCTATGCTGCATCCACCTTGCAAAGTGG<br>GGTCCCATCAAGGTTCAGTGGCAGTGGATCTGGGACAGATTT<br>CACTCTCGCCATCAGCAGTCTGCAACCTGCAGATTTTGCAACT<br>TATTACTGTCAACAGAGTTACAGTACCCCTCGGACGTTCGGC<br>CAAGGGACCAAAGTGGATATCAAA<br>SEQ ID NO: 159 |

TABLE II-continued

Nucleotide sequences of the V_H and V_L region of exemplary polyomavirus, polyomavirus VP1, and polyomavirus VP1 VLP antibodies.

| Antibody | Nucleotide sequences of variable heavy (VH) and variable light (VL) chains |
|---|---|
| NI-307.43E8-V$_H$ | GAGGTGCAGCTGGTGGAGTCTGGGGGAGACGTGGTCCAGCCT<br>GGGAGGTCCCTGAGACTCTCCTGTGCAGCCTCTGGATTCGCCT<br>TCAGTATTTATGCTATGAACTGGGTCCGCCAGGCTCCAGGCA<br>AGGGGCTGGAGTGGGTGGCACTTATATCAACTTCTGGAACTG<br>AACACTACGCAGACTCCGTGAAGGGCCGATTCACCATCTCCA<br>GAGACAATTCCAAGAACACGTTGTTTCTGCAAATTAATAGTC<br>TGAGAGTTGAGGACACGGCTGTGTATTACTGTGCGAGAGATC<br>TTGACAGTACTGGTTATTACGAGAATAACTACTGGGGCCAGG<br>GCACCCTGGTCACCGTCTCCTCG<br>SEQ ID NO: 161 |
| NI-307.43E8-V$_K$ | GATGTTGTGATGACTCAGTCTCCACTCTCCTCACCTGTCAGTC<br>TTGGACAGCCGGCCTCCATCTCCTGCAGGTCTAGTCACAGCCT<br>CGTACACAGTAATGGAGATACCTACTTGAGTTGGCTTCAGCA<br>GAGGCCAGGCCAGCCTCCAAGACTGCTAATCTATAAGATTTC<br>TAACCGATTCTCTGGGGTCCCAGACAGATTCAGTGGCAGTGG<br>GGCAGGGACAGATTTCACACTGAAAATCAGCAGGGTGGAAG<br>CTGAGGATGTCGGGGTCTATTTCTGCATGCAAGCTACGTCTTT<br>TCCTCGAACATTCGGCCAAGGGACCAAGGTGGAAATCAAA<br>SEQ ID NO: 163 |
| NI-307.18F4A-V$_H$ | GAGGTGCAGCTGGTGGAGTCTGGGGGAGGCTTGGTCAAGCCT<br>GGAGGGTCCCTGAGACTCTCCTGTGCAGCCTCTGGATTCACCT<br>TCACTAACTACTACATGACCTGGGTCCGTCAGGCTCCAGGAA<br>AGGGGCTGGAGTGGGTTTCATACATTACTGGTGGTGGGAGTA<br>CTACATACTACGCAGACTCTGTGACGGGCCGATTCACCATCT<br>CCAGGGACAACGCCAAGAACTCACTGTATCTGCAAATGAGCA<br>GCCTGAGAGTCGAGGACACGGCCGTCTATTATTGTGCGAGAG<br>GGAGAGGCTACCCCGACAACTGGTTCGACCCCTGGGGCCAGG<br>GAACCCTGGTCACCGTCTCCTCG<br>SEQ ID NO: 165 |
| NI-307.18F4A-V$_K$ | TCCTATGTGCTGACTCAGCCACCCTCGGTGTCAGTGTCCCCAG<br>GACAGACGGCCAGGATCACCTGCTCTGGAGATGCATTGCCAA<br>AACAATATGTTTATTGGTACCAGCAGAAGCCAGGCCAGGCCC<br>CTGTGTTGATGATATATAAAGACGCTGAGAGGCCCTCAGGGA<br>TCCCTGACCGATTCTCTGGCTCCAGCTCAGGGACAACAGTCA<br>CTTTGACCATCAGTGGAGTCCAGGCAGAAGACGAGGCTGACT<br>ATTACTGTCAGTCTACAGACATCAGTGGTGCTGCTGTGGTTTT<br>CGGCGGAGGGACCAAGCTGACCGTCCTA<br>SEQ ID NO: 167 |

TABLE III

Amino acid sequences of the VH and VL region of exemplary polyomavirus, polyomavirus VP1 and polyomavirus VP1 VLP antibodies with CDRs underlined.

| Antibody | Protein sequences of variable heavy (VH) and variable light (VL) chains |
|---|---|
| NI-307.13G4-V$_H$ | EVQLVESGGGLVQPGGSLRLSCTAS<u>GFTFTSYALS</u>WVRQAPGKG<br>LEWVS<u>AISSGRGYTYYADSVKG</u>RFTISRDNSKNTLYLQMNSLRA<br>EDTAVYYCAK<u>DGTLRGYNYGYIDDI</u>WGQGTLVTVSS<br>SEQ ID NO: 2 |
| NI-307.13G4-V$_K$ | DIQMTQSPSSLSASVGDRVTITC<u>RASQGISNYLA</u>WLQQKPGKAP<br>KPLIY<u>AVSILQSG</u>VPSKFSGSGSGTDFTLTISSLQPEDFATYYC<u>QQ</u><br><u>YKSYPYT</u>FGQGTKLEIK<br>SEQ ID NO: 4 |
| NI-307.19F10-V$_H$ | EVQLVESGGGLVQPGGSVSLSCAAS<u>GFTFPVYWMH</u>WVRQAPEK<br>GLMWVS<u>RISPDGTIVDYAGSVKG</u>RFTVSRDNAKNILYLQIQRLT<br>AEDTAVYFCTK<u>DFDVASGF</u>WGQGTLVTVSS<br>SEQ ID NO: 6 |

TABLE III-continued

Amino acid sequences of the VH and VL region of exemplary polyomavirus, polyomavirus VP1 and polyomavirus VP1 VLP antibodies with CDRs underlined.

| Antibody | Protein sequences of variable heavy (VH) and variable light (VL) chains |
|---|---|
| NI-307.19F10-V$_L$ | QSALTQPPSASGSPGQSVTISC<u>TGSKSDVGTCHFVS</u>WYQQHPGK<br>VPKLVIY<u>EGNKRPS</u>GVPDRFSASKSGNTASLTISGLQPGDEADYY<br>C<u>STCAGPNNYV</u>FGTGTKVTVL<br>SEQ ID NO: 8 |
| NI-307.19F8-V$_H$ | EVQLVESGGGLVKPGGSLRLSCAAS<u>GFTFSSYYMN</u>WVRQAPGK<br>GLEWVS<u>SISSSSSYIYYADSVKG</u>RFTISRDNAKNSLYLQMNSLTA<br>EDTAVYYCARD<u>PRLQLWFMFDY</u>WGQGTLVTVSS<br>SEQ ID NO: 10 |
| NI-307.19F8-V$_L$ | QPVLTQPPSASASLGASVTLTC<u>TLSSGYSNYKVD</u>WYQQRPGEGP<br>RFVMR<u>VGTGGIV</u>GSKDGIPDRFSVLGSGLNRYLTIKDIQEEDES<br>DYHC<u>GADHGSGSNFVYV</u>FGTGTKVTVL<br>SEQ ID NO: 12 |
| NI-307.11G6-V$_H$ | QVQLVESGGDLVKPGGSLRLSCAAS<u>GFTFSDHYMS</u>WIRQAPGK<br>GLEWVS<u>YISTRSTYTNYADSVKG</u>RFTISRDNAKNSLYLHMNSLR<br>TEDTAVYYCARD<u>YSDTSGPPDY</u>WGQGTLVTVSS<br>SEQ ID NO: 14 |
| NI-307.11G6-V$_L$ | QSVLTQPPSASGTPGQRVTISCS<u>GSNSNIGSNYVY</u>WYQQLPGTAP<br>KLVIY<u>RNTQRPS</u>GVPDRFSGSKSGTSASLAISGLRSEDEADYYC<u>A<br>AWDDSLSGLV</u>FGGGTKLTVL<br>SEQ ID NO: 16 |
| NI-307.17F12-V$_H$ | QLQLQESGPGLVKPSGTLSLTCAVS<u>GDSITNTNWWC</u>WVRQPPG<br>KGLEWIG<u>EIFHSGGTNYNPSLKS</u>RVTMSVDKAKNQFSLKVNSVT<br>AADTAVYFCTT<u>NPGGGDGYSY</u>WGQGTLVTVSS<br>SEQ ID NO: 18 |
| NI-307.17F12-V$_L$ | QSALTQPRSVSGSPGQSVTISC<u>TGTSSDVGGYNYVS</u>WYQQHPGK<br>APNLMIS<u>EVSKRPS</u>GVPDRFSGSKSGNTASLTISGLQAEDEADYF<br>CC<u>SYAGSYRV</u>FGTGTKVTVL<br>SEQ ID NO: 20 |
| NI-307.6A2-V$_H$ | QVQLQESGPGLVKPSETLSLTCAVS<u>GGSVSSSYWYS</u>WVRQLPGK<br>GLEWIG<u>EIFHTGDTNYNPSLES</u>RVTISIDTSKNQLSLDVTSATAAD<br>TAVYYCARD<u>YCTDSGCDSDALDV</u>WGHGTMVTVSS<br>SEQ ID NO: 22 |
| NI-307.6A2-V$_L$ | QSALTQPASVSGSPGQSITISC<u>TGTTKDVGNYNLVS</u>WYQQHPGK<br>APRLVIY<u>EVSERPS</u>GVSNRFSGSKSGNTASLTISGLQAEDEADYH<br>CC<u>SYAGSGTSV</u>FGGGTKVTVL<br>SEQ ID NO: 24 |
| NI-307.5H3-V$_H$ | QVQLQESGPGLLKPLGTLSLICDVS<u>GDSISSSNWWS</u>WVRQSPRK<br>GLEWIG<u>EIYHSGRTNYNPSLTN</u>RVTISVDKSKNQFSLNLNSVTAA<br>DTGVYYCARW<u>DYYYNNDYYIRGFDI</u>WGQGTMVTVSS<br>SEQ ID NO: 26 |
| NI-307.5H3-V$_K$ | EIVLTQSPGILSLSPGERATLSC<u>RASQSVDSNYLA</u>WYQQKPGQAP<br>RLLIY<u>STSTRAA</u>GVPDRFSGSGSGTDFALTISGLEPEDFAVYYC<u>Q<br>QWGGSPPIT</u>FGQGTRLEIK<br>SEQ ID NO: 28 |
| NI-307.25G10-V$_H$ | EVQLVESGGGLVQPGGSLRLSCVAS<u>GIIFKDYDFH</u>WVRQVKEKG<br>LEWVS<u>AIGTAGDPYYAASVKG</u>RFTVSRENGKNSVYLRMNNVG<br>AGDTALYYCTS<u>GNYFDRGSFRPSAFDM</u>WGQGTMVTVSS<br>SEQ ID NO: 30 |
| NI-307.25G10-V$_K$ | EIVLTQSPGTLSLSPGERATLSC<u>WASQSVSSNYLA</u>WYQHKPGQA<br>PRLLIF<u>RASRRAT</u>DIPERFSAGGSGTDFTLTISRLEAEDSAVYYC<u>Q<br>EYGSAPPASIT</u>FGQGTRLEIK<br>SEQ ID NO: 32 |
| NI-307.26E10-V$_H$ | EVQLVESGGGLVLPGGSLRLSCAVS<u>GFTVRNEYMRW</u>ARQAPGR<br>GLEWVS<u>VIYRDGQTHHADTVKG</u>RFDVSKDTSKNTMYLQMHNL<br>RVDDTAIYYCAR<u>GHYGPW</u>GQGTLVTVSS<br>SEQ ID NO: 34 |

TABLE III-continued

Amino acid sequences of the VH and VL region of exemplary polyomavirus, polyomavirus VP1 and polyomavirus VP1 VLP antibodies with CDRs underlined.

| Antibody | Protein sequences of variable heavy (VH) and variable light (VL) chains |
|---|---|
| NI-307.26E10-$V_K$ | DIQMTQSPSTLPASVGDRVTITC<u>RASQSINNWLA</u>WYQQKPGKAP<br>NLLIY<u>DASNLET</u>GVPSRFSGSGSGTEFTLTISSLQPDDFATYYC<u>QQ</u><br><u>YNSHSHTWT</u>FGQGTKVEIK<br>SEQ ID NO: 36 |
| NI-307.1E1-$V_H$ | EVQLVESGGGLVKPGGSLRLSCAAS<u>GFIFSDAWMN</u>WVRQAPGK<br>GLEWVG<u>HIKSRPAGGTTEYAAPVKG</u>RFTISRDDSTDTLYLQMNN<br>LKAEDTAVYYCST<u>GHYGV</u>YGLGTLVTSS<br>SEQ ID NO: 38 |
| NI-307.1E1-$V_K$ | DIQMTQSPSTLSASVGDRVTITC<u>RASQSIRDYLA</u>WYQQKPGKAP<br>KLLIY<u>DGSILEG</u>GVPSRFSGSVSGTDFTLTISSLQSDDFATYYC<u>QQ</u><br><u>YTSYSSWT</u>FGQGTKVEIK<br>SEQ ID NO: 40 |
| NI-307.24C6-$V_H$ | QLQLQESGPGLVKPSGTLSLICVVS<u>GSSIRSNIWWWNW</u>VRQSPG<br>KGLEWIG<u>EIYHSGSTNYSPSLKS</u>RVTMSVDNSKNQFSLKMSSVT<br>AADTAVYFCA<u>INTRTSISGVLYDTFDV</u>WGQGTMVTVSS<br>SEQ ID NO: 42 |
| NI-307.24C6-$V_K$ | EIVLTQSPATLSLSSGERATLSC<u>RASQSVSGYLA</u>WYQQKPGQAPR<br>LLIY<u>DGSNRAT</u>GIPARFSGSGSGTDFTLTISSLEPEDFAVYYC<u>QHR</u><br><u>SNWPMYT</u>FGQGTKLEIK<br>SEQ ID NO: 44 |
| NI-307.78C3-$V_H$ | QVQLQESGPGLVKPSGTLSLTCTVS<u>GGSISGRIWWS</u>WVRQPPGK<br>GLEWIG<u>EIYHSGSTNYSPSLRG</u>RVTISVDTSKQHFSLKMTSVTAA<br>DTAMYYCVR<u>GELALGFDS</u>WGQGTLVTVSS<br>SEQ ID NO: 46 |
| NI-307.78C3-$V_L$ | QSALTQPPSASGSPGQSVTISC<u>TGTSSDVGGYNSVS</u>WYQQHPRR<br>APKLMIY<u>EVSKRPS</u>GVPDRFSGSKSGNTASLTVSGLQADDEAHY<br>YC<u>SSYAGSNNLV</u>FGGGTMLTVL<br>SEQ ID NO: 48 |
| NI-307.57D5-$V_H$ | EVQLVESGGGLAQPGGSLRLSCAGS<u>GFTLSDFAMS</u>WVRRAPGK<br>GLEWVS<u>SLTPSGRNSFYSDSVKG</u>RFTISRDNWKNTLYLEMNLLR<br>PEDTAVYYCAR<u>PGAPKNSDSKYSYVRVDFQH</u>WGQGTLVTVSS<br>SEQ ID NO: 50 |
| NI-307.57D5-$V_L$ | NFMLTQPHSVSESPGRTVTISC<u>TRSSGSIANNFVQ</u>WYQHRPGSAP<br>TTLIY<u>EDDQRPS</u>GVPDRFSGSVDSFSNSASLTISGLKTEDEADYFC<br><u>QSYDNHNWV</u>FGGGTTLTVL<br>SEQ ID NO: 52 |
| NI-307.43A11-$V_H$ | QVQLQESGPGLVKPSGTLSLTCAVT<u>GGSISSSNWWS</u>WVRQSPGK<br>GLEWIG<u>EIHHDGNLNYNPLLKS</u>RVSMSLDRSKNQFSLKLTSVTA<br>ADTAVYYCAR<u>WDFFFDSSYYIRGFDL</u>WGQGTMVTVSS<br>SEQ ID NO: 54 |
| NI-307.43A11-$V_K$ | ETTLTQSPGTLSLSPGERVTLSC<u>RASQSVDRNYLA</u>WYQQKPGQS<br>PRLLIY<u>SASRRAT</u>GIPDRFSGSGSGTDFTLTISRLEPEDFVVYYC<u>Q</u><br><u>QYGGSPPIT</u>FGQGTRLEIK<br>SEQ ID NO: 56 |
| NI-307.3G4-$V_H$ | QVQLVQSGAELKKPGAAVKVSCQAS<u>GYNFLSYGIN</u>WVRQIPGQ<br>GLQWLG<u>WISTYDGTMNYDQKPDN</u>RVTVTTDTSSSTVYLELRGL<br>RSDDTGVYYCVR<u>DRCAGAGCSHSLGY</u>WGQGTLVTVSS<br>SEQ ID NO: 58 |
| NI-307.3G4-$V_K$ | DIQMTQSPSALSASVGDRVTISC<u>RASQNINTQLNW</u>YQEKPGKAP<br>ELLIY<u>GAFNLQS</u>GAPSTFSGSGSGTDFTLTITSLQPEDFASYYC<u>QQ</u><br><u>GFHAPYT</u>FGRGTKVDIK<br>SEQ ID NO: 60 |
| NI-307.61D11-$V_H$ | EVQLVQSGAEVKKPGASVKVSCKTS<u>GYTFIGHYMQ</u>WVRQVPG<br>QGFEWMG<u>WINPNTGTTKYALKFKD</u>RVTVTRDTSTATVYMEFH<br>GLTSDDTAVYYCAR<u>ASAYQLANYDY</u>WGQGTLVTVSS<br>SEQ ID NO: 62 |

TABLE III-continued

Amino acid sequences of the VH and VL region of exemplary polyomavirus, polyomavirus VP1 and polyomavirus VP1 VLP antibodies with CDRs underlined.

| Antibody | Protein sequences of variable heavy (VH) and variable light (VL) chains |
|---|---|
| NI-307.61D11-$V_L$ | QSALTQPASVSGSPGQSITISC<u>AGTSNDVGDDDFVS</u>WYQHQPGK APRLMIY<u>EVTNRPS</u>GVSTRFSGSKSGNTASLTISGLQAEDEGDYY C<u>MSYTKNSALGYV</u>FGGGTKVTVL<br>SEQ ID NO: 64 |
| NI-307.24F3-$V_H$ | QVQLQESGGGVVQPGRSLRLSCAAS<u>GFSFNRYGMH</u>WVRQAPG KGLEWLA<u>VISNDGVNTHYADSVKG</u>RFTISRDNSKSTLYLQASSL RVEDTAVYYCAG<u>YYYGSGTSLFFY</u>WGQGTLVTVSS<br>SEQ ID NO: 66 |
| NI-307.24F3-$V_K$ | EIVLTQSPDSLAVSLGERATINC<u>KSSQTVLYSSNNQNYLA</u>WYQQ KPGQPPKLLLY<u>WASTRES</u>GVPDRFSGSGSGTDFTLTISSLQPEDV AVYYC<u>QQYYTAPYT</u>FGQGTKVEIK<br>SEQ ID NO: 68 |
| NI-307.18E12-$V_H$ | QVQLQQWGAGLLKPSETLSLTCAVY<u>GDSFSGFF</u>WAWIRQTPGT GLEWIG<u>EIQHGGSPTYNPSFES</u>RLTISTDASKSQVSLKMTSVTVT DTAIYYCAR<u>CIRGKYGSGSLQL</u>WSQGTLVTVSS<br>SEQ ID NO: 70 |
| NI-307.18E12-$V_K$ | DIQLTQSPSFLSASVGDRVTITC<u>RASQDINYHLA</u>WYRQKPGKAPD LLIH<u>SAHTLHI</u>GVSSRFSGSGSGTEFTLTIHTLQPEDFATYYC<u>HQP KTFPPT</u>FGGGTKVDIK<br>SEQ ID NO: 72 |
| NI-307.20F5-$V_H$ | EVQLVESGGGVVQPGTSLRLSCAAS<u>GFSFNKYGVH</u>WVRQAPGK GLEWVA<u>NIWYDGTNPFYADFVKG</u>RFVISRDTSKNTIYLQMNRL RAEDTAVYYCARD<u>AFCGGDCYGGLLHGLDV</u>WGQGTTVTVSS<br>SEQ ID NO: 74 |
| NI-307.20F5-$V_K$ | DVVMTQSPLSLPVTPGEPASISC<u>RSSQSLLHSNGLNYLD</u>WYLQKP GQSPQLLIY<u>LGSNRAP</u>GVPDRFSGSGSGTDFTLKISRVEAEDVGV YYC<u>LQALQTPAF</u>GQGTKVEIK<br>SEQ ID NO: 76 |
| NI-307.58C7-$V_H$ | EVQLVESGGGLVKPGGSLRLSCAAS<u>GFTFSDYYVN</u>WIRQAPGKG LEWVA<u>CISSSGRTIHYADSVKG</u>RFTISRDNAKNSLYLQMNSLRA EDTAFYYCARD<u>LDKAATGRPYFDY</u>WGQGTLVTVSS<br>SEQ ID NO: 78 |
| NI-307.58C7-$V_L$ | QSVLTQPPSASGTPGQRVTISC<u>SGSSSNIGGNAVN</u>WFQQLPGTAP KLLIY<u>GNTQRPS</u>GVPDRFSGSKSGTSASLAISGLQSEDETNYYC<u>A AWDDSLNGVV</u>FGGGTKLTVL<br>SEQ ID NO: 80 |
| NI-307.105C7-$V_H$ | EVQLVESGGGLVQPGGSLRLSCAAS<u>GFSFGFYAMN</u>WVRQAPGK GLEYVS<u>GVSGGGGSTYYADSVKG</u>RFTISRDNSKNTLYLQMKSLR AEDTAIYYCAK<u>DQSYCSGGSCHPYYLDY</u>WGQGTLVTVSS<br>SEQ ID NO: 82 |
| NI-307.105C7-$V_L$ | SYVLTQPPSVSVAPGQTARITC<u>GGNNIGSKSVH</u>WYQQKPGQAPV VVVY<u>DDSGRPS</u>GIPERFSGSNSGNTATLTISRVEAGDEADYYC<u>Q VWDSSSDHPYV</u>FGTGTKVTVL<br>SEQ ID NO: 84 |
| NI-307.98D3-$V_H$ | EVQLVESGGGVVQPGRSLRLSCAAS<u>GFTFSSSAMH</u>WVRQAPGK GLEWVA<u>VISYDGNNQLYADSVKG</u>RLTISRDNSKNALYLQLNSL RTEDTAVYFCARD<u>GGGYSFGTYFFDF</u>WGQGTLVTVSS<br>SEQ ID NO: 90 |
| NI-307.98D3-$V_K$ | DIQMTQSPSSLSASVGERVTITC<u>RASQRISNYLN</u>WYQQKPGKAPK LLIY<u>AASTLQS</u>GVPSRFSGSGSGTDFTLTISSLQPEDFATYYC<u>QQS YSSPPT</u>FGPGTKVDIK<br>SEQ ID NO: 92 |
| NI-307.72F7-$V_H$ | EVQLVESGGGLVQPGGSLRLSCAAS<u>GFTFSSYEMN</u>WVRQAPGK GLEWIS<u>YISSRGSTIHYADSVKG</u>RFTISRDDAKNSLYLQMNSLRA EDTAIYYCARD<u>RYDFWSGCIKGCYYGMDV</u>WGQGSTVTVSS<br>SEQ ID NO: 94 |

TABLE III-continued

Amino acid sequences of the VH and VL region of exemplary polyomavirus, polyomavirus VP1 and polyomavirus VP1 VLP antibodies with CDRs underlined.

| Antibody | Protein sequences of variable heavy (VH) and variable light (VL) chains |
|---|---|
| NI-307.72F7-V$_K$ | EIVLTQSPGTLSLSPGQRATLSC<u>RASQSISSSYLA</u>WYQQRRGQAP<br>RLLIY<u>GASSRAT</u>GIPDRFSGSGSGTDFTLTISRLEPEDFAVYYC<u>QH<br>YGTTLT</u>FGQGTKVDIK<br>SEQ ID NO: 96 |
| NI-307.45E10-V$_H$ | EVQLVESGGGLVQPGGSLRLSCAAS<u>GFSFRFYAMN</u>WVRQAPGK<br>GLEYVS<u>GISGGGGTTYYADSVKG</u>RFTISRDNSKNTLYLQMKSLR<br>AEDTAIYYCAK<u>DQSYCSGAGCHPYYLDY</u>WGQGTLVTVSS<br>SEQ ID NO: 98 |
| NI-307.45E10-V$_L$ | SYVLTQPPSVSVAPGQTARITC<u>GGNNIGSKSVH</u>WYQQKPGQAPV<br>VVVY<u>DDSGRPS</u>GMPERFSGSNSGNTATLTISRVEAGDEADYYC<u>Q<br>VWDSSSDHLYV</u>FGTGTKVTVL<br>SEQ ID NO: 100 |
| NI-307.72F10-V$_H$ | EVQLVESGGGVVQPGRSLRLSCATS<u>GFTFDDYAMH</u>WVRQAPGK<br>GLEWVS<u>GLTWSSSGVGYADSVKG</u>RFTISRDNAKNSLYLQMNSL<br>RAEDTALYYCAK<u>GSGEWLRLGQDY</u>WGQGTLVTVSS<br>SEQ ID NO: 102 |
| NI-307.72F10-V$_L$ | QSVLTQPPSVSGTPGQRVTISC<u>TGSSSNIGAGYDVH</u>WYQQLPGT<br>APKLLIY<u>DNSNRPS</u>GVPDRFSGSKSGTSASLAITGLQAEDEAHYY<br>C<u>QSFDSSLSGSV</u>FGGGTKLAVL<br>SEQ ID NO: 104 |
| NI-307.56A8-V$_H$ | EVQLVESGGGLVKPGGSLRLSCAAS<u>GFTFSSYRMN</u>WVRQAPGK<br>GLEWVS<u>SISSSSSYIYYGDSVKG</u>RFTISRDNAKNSLYLQMSSLRA<br>EDTAVYYCAR<u>YAHDWNIDY</u>WGQGTLVTVSS<br>SEQ ID NO: 106 |
| NI-307.56A8-V$_L$ | QSVLTQPPSASGTPGQRVTISC<u>SGSSSNIGSNTVN</u>WYQQLPGTAP<br>KLLIY<u>SNSQRPS</u>GVPDRFSGSKSGTSASLAISGLQSEDEADYYC<u>A<br>AWDDSLNGWV</u>FGGGTKLTVL<br>SEQ ID NO: 108 |
| NI-307.27C11-V$_H$ | QVQLQESGPGLVKPSGTLSLTCAVS<u>GDSISSSNWWS</u>WVRQPPGK<br>GLEWIG<u>EIYHSGGTKYNPSLKS</u>RVTISVDKSKNHFSLKLRSVTAA<br>DTAVYYCAR<u>NRWFDNNRGGYYYYGMDV</u>WGQGTTVTVSS<br>SEQ ID NO: 110 |
| NI-307.27C11-V$_K$ | DIQMTQSPSSLSASVGDRVTITC<u>RASQGISSYLN</u>WYQQKPGKAPK<br>LLIS<u>ATSDLQS</u>GVPSRFSGSGSGTDFTLTISSLQPEDFATYYC<u>QQS<br>YSTPYT</u>FGQGTKLEIK<br>SEQ ID NO: 112 |
| NI-307.47B11-V$_H$ | EVQLVESGGGLVKPGGSLRLSCAAS<u>GFTFSDYYMN</u>WIRQAPGK<br>GLEWLS<u>CISSSGNTIYYADSVKG</u>RFTISRDNAKNSLYLQMNSLRA<br>EDTAVYYCAR<u>DLDKAATGRPYFDY</u>WGQGTLVTVSS<br>SEQ ID NO: 114 |
| NI-307.47B11-V$_L$ | QSVLTQPPSASGTPGQRVTISC<u>SGSSSNIGSNTVN</u>WYQQLPGTAP<br>KLLIY<u>SNNQRPS</u>GVPDRFSGSRSGTSASLAISGLQSEDEADYYC<u>A<br>AWDDSLNGVV</u>FGGGTKLTVL<br>SEQ ID NO: 116 |
| NI-307.26A3-V$_H$ | EVQLVESGGVLVQPGGSLRLSCAAS<u>GFTFSSYAMT</u>WVRQAPEK<br>GLEWVS<u>TIIGNGAYTYYADSVKG</u>RFTISRDNSKNTLILQMNSLRA<br>DDAAVYYCAK<u>GTELAPYYYYFALDV</u>WGQGTTVTVSS<br>SEQ ID NO: 118 |
| NI-307.26A3-V$_K$ | EIVLTQSPGTLSLSPGERATLSC<u>RASQSISSSHLA</u>WYQQKPGQAPR<br>LLIY<u>GASSRAT</u>GIPDRFSGGGSGTDFTLTITRLEPEDFAVYYC<u>QQY<br>GSSPYT</u>FGQGTKLEIK<br>SEQ ID NO: 120 |
| NI-307.27C2-V$_H$ | EVQLVESGGGLVKPGGSLRLSCAAS<u>GFTFSSYTMN</u>WVRQAPGK<br>GLQWVS<u>SISSSSTYMYYGDSVKG</u>RFTISRDNARNSLYLQMNSLR<br>VEDTAVYYCAR<u>YAHDWNVDY</u>WGQGTLVTVSS<br>SEQ ID NO: 122 |

TABLE III-continued

Amino acid sequences of the VH and VL region of exemplary polyomavirus, polyomavirus VP1 and polyomavirus VP1 VLP antibodies with CDRs underlined.

| Antibody | Protein sequences of variable heavy (VH) and variable light (VL) chains |
|---|---|
| NI-307.27C2-V$_L$ | QSVLTQPPSASGTPGQRVTISC<u>SGGSSNIGSNPVN</u>WFQQFPGTAP<br>KLLIY<u>ANTQRPS</u>GVPDRFSGSKSGTSVSLAISGLQSEDEGDYHC<u>A</u><br><u>AWDDSLKGWV</u>FGGGTKLTVL<br>SEQ ID NO: 124 |
| NI-307.57D4-V$_H$ | EVQLVESGGGLVQPGRSLRLSCAAS<u>GFTFDHYAMH</u>WVRQVPGR<br>GLEWVS<u>GVTWNSGIIGYADSVK</u>GRFTISRDNAKNSLYLQMTSLR<br>AEDTALYYCAK<u>GTNDFVSYGLDV</u>WGQGTTVTVSS<br>SEQ ID NO: 126 |
| NI-307.57D4-V$_L$ | QSVLTQPPSVSGAPGQRVSISC<u>TGTSSNLGAGFDVH</u>WYQQIPRK<br>APELLIY<u>GNSIRPS</u>GVPDRFSGSKSGTSASLAITGLQAEDEADYYC<br><u>QSYDSRLSGSV</u>FGGGTKLTVL<br>SEQ ID NO: 128 |
| NI-307.50H4-V$_H$ | QVQLQESGPGLVKPSGTLSLTCAVS<u>GDSISSSNWWS</u>WVRQPPGK<br>RLEWIG<u>EIYHSGGTKYNPSLKS</u>RVTISVDKSKNHFSLKLRSVTAA<br>DTAVYYCAR<u>NRWFDNNRGGYYYYGMDV</u>WGQGTMVTVSS<br>SEQ ID NO: 130 |
| NI-307.50H4-V$_K$ | DIQMTQSPSSLSASVGDRVTITC<u>RAGQGISTYLN</u>WYQQKPGKAP<br>NLLIY<u>ATSDLQS</u>GVPSRFSGSGSGTDFTLTISSLQPEDFATYYC<u>QQ</u><br><u>SYNNPYT</u>FGQGTKVEIK<br>SEQ ID NO: 132 |
| NI-307.53B11-V$_H$ | EVQLVQSGAEVKKPGESLKISCKGS<u>GYSFTSYWIG</u>WVRQMPGK<br>GLEWMG<u>IIYPGDSDTRYSPSFQG</u>QVTISADKSITTAYLQWSSLKA<br>SDTALYYCAR<u>RGSGSFSNYDF</u>WGQGTLVTVSS<br>SEQ ID NO: 134 |
| NI-307.53B11-V$_K$ | QSALTQPRSVSGSPGQSVTISC<u>TGTSSDVGAYNYVS</u>WYQQHPVK<br>APKLMIY<u>DVSKRPS</u>GVPDRFSGSRSGNTASLTISGLQADDEADY<br>YCC<u>SYAGTYTVL</u>FGGGTKLTVL<br>SEQ ID NO: 136 |
| NI-307.7J3-V$_H$ | QVQLQESGPGLVKPSQTLSLTCTVS<u>GGSISSGDYYWS</u>WIRQPPGK<br>GLEWIG<u>YIYYSGTTYYNPSLKS</u>RVTISVDTSKNQFSLKLSFVTVA<br>DTAVYYCARD<u>GRFTMVRGGYYYYGMDV</u>WGQGTTVTVSS<br>SEQ ID NO: 138 |
| NI-307.7J3-V$_K$ | DIQMTQSPSSLSVSVGDRVTITC<u>RASQSISSYLN</u>WYQQKLGKAPK<br>LLIY<u>DASSLQS</u>GVPSRFSGSGSGTDFTLTISSLQPEDFATYYC<u>QQS</u><br><u>YTTPRT</u>FGQGTKVEIK<br>SEQ ID NO: 140 |
| NI-307.59A7-V$_H$ | EVQLVESGGGLVQPGGSLRLSCAAS<u>GFTFSSYEMN</u>WVRQAPGK<br>GLEWVS<u>YISSSGTNIYHADSVK</u>GRFTISRDNAKNSLYLQMNSLR<br>AEDTAVYYCAR<u>DGPSPRGHNYGHDY</u>WGQGTLVTVSS<br>SEQ ID NO: 142 |
| NI-307.59A7-V$_L$ | QSVLTQPPSASGTPGQRVTISC<u>SGSSSNIGSNAVN</u>WYQQVPGTAP<br>KLLIY<u>TNNQRPS</u>GVPDRFSGSKSGTSASLAISGLQSEDETDYYC<u>A</u><br><u>AWDDSLGGPV</u>FGGGTKLTVL<br>SEQ ID NO: 144 |
| NI-307.105A6-V$_H$ | EVQLVESGGGLVQPGRSLRLSCAAS<u>GFTFDDYAMH</u>WVRQAPGK<br>GLEWVS<u>GITWNSGSIGYADSVK</u>GRFTISRDNAKNSLYLQMNSLS<br>AEDTALYYCAK<u>GARDYLSYGMDV</u>WGQGTTVTVSS<br>SEQ ID NO: 146 |
| NI-307.105A6-V$_L$ | QSVVTQPPSVSGAPGQRVTISC<u>TGSSSNIGAGYDVH</u>WYQQLPGT<br>APKLLIF<u>SNTIRPS</u>GVPDRFSGSKSGTSASLAITGLQAEDEANYYC<br><u>QSYDSSLSGSV</u>FGGGTKLTVL<br>SEQ ID NO: 148 |
| NI-307.29B1-V$_H$ | EVQLVESGGGLVKPGGSLRLSCAAS<u>GITFQYYAMN</u>WVRQAPGK<br>GLEWVS<u>SIGGRGDTTYYTDSVK</u>GRFTISRDNSKSTLYLQMNSLR<br>AEDTAVYYCAK<u>EPFDSSGDHRGVFDY</u>WGQGTLVTVSS<br>SEQ ID NO: 150 |

TABLE III-continued

Amino acid sequences of the VH and VL region of exemplary polyomavirus, polyomavirus VP1 and polyomavirus VP1 VLP antibodies with CDRs underlined.

| Antibody | Protein sequences of variable heavy (VH) and variable light (VL) chains |
|---|---|
| NI-307.29B1-$V_L$ | QSVVTQPPSVSGAPGQRVTISC<u>AGSRSNIGAGYDVN</u>WYQQLPRT APKLLIY<u>DNTRRPS</u>GVPARFSGSKSGSSASLTITGLQAEDEADYY C<u>QSYDSKLNKV</u>FGGGTKLTVL<br>SEQ ID NO: 152 |
| NI-307.44F6B-$V_H$ | EVQLVESGGSVVRPGGSLRLACEVS<u>GLRFDDFAMS</u>WVRQVPGK GLEWIA<u>GIFWNSGGTLYADSVK</u>GRFTISRDNAENSLYLQMNSLR AEDTALYRCVR<u>GRSHAAYYGMDV</u>WGKGTTVTVSS<br>SEQ ID NO: 154 |
| NI-307.44F6B-$V_K$ | EIVLTQSPLSLPVTPGEPASISC<u>RSSQSLLHSNGYNYLD</u>WYLQKPG QSPQLLIY<u>LGSNRAS</u>GVPDRFSGSGSGTDFTLTISRVEAEDVGIYY C<u>MQALQNALA</u>FGGGTKLEIK<br>SEQ ID NO: 156 |
| NI-307.98H1-$V_H$ | QLQLQESGPGLVKPSQTLSLTCAVS<u>GASISSGTYYWG</u>WIRQHPG KGLEWIG<u>YIYPSGSTYYNPSLKS</u>RVIISLDTSKSQFSLNLSSVTAA DTAVYYCAR<u>DYYDSSGHMGGYYHYAMDV</u>WGQGTTVTVSS<br>SEQ ID NO: 158 |
| NI-307.98H1-$V_K$ | DIQLTQSPSSLSASVGDRVTITC<u>RASQSISSHLN</u>WYQQKPGKVPK LLIY<u>AASTLQS</u>GVPSRFSGSGSGTDFTLAISSLQPADFATYYC<u>QQS YSTPRT</u>FGQGTKVDIK<br>SEQ ID NO: 160 |
| NI-307.43E8-$V_H$ | EVQLVESGGDVVQPGRSLRLSCAAS<u>GFAFSIYAMN</u>WVRQAPGK GLEWVA<u>LISTSGTEHYADSVK</u>GRFTISRDNSKNTLFLQINSLRVE DTAVYYCARD<u>LDSTGYYENNY</u>WGQGTLVTVSS<br>SEQ ID NO: 162 |
| NI-307.43E8-$V_K$ | DVVMTQSPLSSPVSLGQPASISC<u>RSSHSLVHSNGDTYLS</u>WLQQRP GQPPRLLIY<u>KISNRFS</u>GVPDRFSGSGAGTDFTLKISRVEAEDVGV YFC<u>MQATSFPRT</u>FGQGTKVEIK<br>SEQ ID NO: 164 |
| NI-307.18F4A-$V_H$ | EVQLVESGGGLVKPGGSLRLSCAAS<u>GFTFTNYYMT</u>WVRQAPGK GLEWVS<u>YITGGGSTTYYADSVT</u>GRFTISRDNAKNSLYLQMSSLR VEDTAVYYCAR<u>GRGYPDNWFDP</u>WGQGTLVTVSS<br>SEQ ID NO: 166 |
| NI-307.18F4A-$V_K$ | SYVLTQPPSVSVSPGQTARITC<u>SGDALPKQYVY</u>WYQQKPGQAPV LMIY<u>KDAERPS</u>GIPDRFSGSSSGTTVTLTISGVQAEDEADYYC<u>QS TDISGAAVV</u>FGGGTKLTVL<br>SEQ ID NO: 168 |

The present invention also includes fragments of the polynucleotides of the invention, as described elsewhere. Additionally polynucleotides which encode fusion polynucleotides, Fab fragments, and other derivatives, as described herein, are also contemplated by the invention.

The polynucleotides may be produced or manufactured by any method known in the art. For example, if the nucleotide sequence of the antibody is known, a polynucleotide encoding the antibody may be assembled from chemically synthesized oligonucleotides, e.g., as described in Kutmeier et al., BioTechniques 17 (1994), 242, which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody, or antigen-binding fragment, variant, or derivative thereof may be generated from nucleic acid from a suitable source. If a clone containing a nucleic acid encoding a particular antibody is not available, but the sequence of the antibody molecule is known, a nucleic acid encoding the antibody may be chemically synthesized or obtained from a suitable source (e.g., an antibody cDNA library, or a cDNA library generated from, or nucleic acid, preferably polyA+ RNA, isolated from, any tissue or cells expressing polyomavirus, the polyomavirus VP1 and/or polyomavirus VP1 VLP-specific antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody Amplified nucleic acids generated by PCR may then be cloned into replicable cloning vectors using any method well known in the art.

Once the nucleotide sequence and corresponding amino acid sequence of the antibody, or antigen-binding fragment, variant, or derivative thereof is determined, its nucleotide sequence may be manipulated using methods well known in the art for the manipulation of nucleotide sequences, e.g., recombinant DNA techniques, site directed mutagenesis, PCR, etc. (see, for example, the techniques described in Sambrook et al., *Molecular Cloning, A Laboratory Manual*, 2d Ed., Cold Spring Harbor Laboratory, Cold Spring Harbor, N.Y. (1990) and Ausubel et al., eds., *Current Protocols in Molecular Biology*, John Wiley & Sons, NY (1998), which are both incorporated by reference herein in their entireties), to generate antibodies having a different amino acid sequence, for example to create amino acid substitutions, deletions, and/or insertions.

IV. Expression of Antibody Polypeptides

Following manipulation of the isolated genetic material to provide antibodies, or antigen-binding fragments, variants, or derivatives thereof of the invention, the polynucleotides encoding the antibodies are typically inserted in an expression vector for introduction into host cells that may be used to produce the desired quantity of antibody. Recombinant expression of an antibody, or fragment, derivative or analog thereof, e.g., a heavy or light chain of an antibody which binds to a target molecule is described herein. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operable linked to a promoter. Such vectors may include the nucleotide sequence encoding the constant region of the antibody molecule (see, e.g., international applications WO 86/05807 and WO 89/01036; and U.S. Pat. No. 5,122,464) and the variable domain of the antibody may be cloned into such a vector for expression of the entire heavy or light chain.

The term "vector" or "expression vector" is used herein to mean vectors used in accordance with the present invention as a vehicle for introducing into and expressing a desired gene in a host cell. As known to those skilled in the art, such vectors may easily be selected from the group consisting of plasmids, phages, viruses and retroviruses. In general, vectors compatible with the present invention will comprise a selection marker, appropriate restriction sites to facilitate cloning of the desired gene and the ability to enter and/or replicate in eukaryotic or prokaryotic cells. For the purposes of this invention, numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by co-transformation. Additional elements may also be needed for optimal synthesis of mRNA. These elements may include signal sequences, splice signals, as well as transcriptional promoters, enhancers, and termination signals.

In particularly preferred embodiments the cloned variable region genes are inserted into an expression vector along with the heavy and light chain constant region genes (preferably human) as discussed above. In one embodiment, this is accomplished using a proprietary expression vector of Biogen IDEC, Inc., referred to as NEOSPLA, and disclosed in U.S. Pat. No. 6,159,730. This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high level expression of antibodies upon incorporation of variable and constant region genes, transfection in CHO cells, followed by selection in G418 containing medium and methotrexate amplification. Of course, any expression vector which is capable of eliciting expression in eukaryotic cells may be used in the present invention. Examples of suitable vectors include, but are not limited to plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). In general, screening large numbers of transformed cells for those which express suitably high levels if immunoglobulin heavy and light chains is routine experimentation which can be carried out, for example, by robotic systems. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other preferred embodiments the antibodies, or antigen-binding fragments, variants, or derivatives thereof of the invention may be expressed using polycistronic constructs such as those disclosed in US patent application publication no. 2003-0157641 A1 and incorporated herein in its entirety. In these expression systems, multiple gene products of interest such as heavy and light chains of antibodies may be produced from a single polycistronic construct. These systems advantageously use an internal ribosome entry site (IRES) to provide relatively high levels of antibodies. Compatible IRES sequences are disclosed in U.S. Pat. No. 6,193,980 which is also incorporated herein. Those skilled in the art will appreciate that such expression systems may be used to effectively produce the full range of antibodies disclosed in the instant application. Therefore, in one embodiment the present invention provides a vector comprising the polynucleotide encoding at least the binding domain or variable region of an immunoglobulin chain of the antibody, optionally in combination with a polynucleotide that encodes the variable region of the other immunoglobulin chain of said binding molecule.

More generally, once the vector or DNA sequence encoding a monomeric subunit of the antibody has been prepared, the expression vector may be introduced into an appropriate host cell. Introduction of the plasmid into the host cell can be accomplished by various techniques well known to those of skill in the art. These include, but are not limited to, transfection including lipotransfection using, e.g., Fugene® or lipofectamine, protoplast fusion, calcium phosphate precipitation, cell fusion with enveloped DNA, microinjection, and infection with intact virus. Typically, plasmid introduction into the host is via standard calcium phosphate co-precipitation method. The host cells harboring the expression construct are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

The expression vector is transferred to a host cell by conventional techniques and the transfected cells are then cultured by conventional techniques to produce an antibody for use in the methods described herein. Thus, the invention includes host cells comprising a polynucleotide encoding an antibody of the invention, or a heavy or light chain thereof, or at least the binding domain or variable region of an immunoglobulin thereof, which preferably are operable linked to a heterologous promoter. In addition or alternatively the invention also includes host cells comprising a vector, as defined hereinabove, comprising a polynucleotide encoding at least the binding domain or variable region of an immunoglobulin chain of the antibody, optionally in combination with a polynucleotide that encodes the variable region of the other immunoglobulin chain of said binding molecule. In preferred embodiments for the expression of double-chained antibodies, a single vector or vectors encoding both the heavy and light chains may be co-expressed in the host cell for expression of the entire immunoglobulin molecule, as detailed below.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain is advantageously placed before the heavy chain to avoid an excess of toxic free heavy chain; see Proudfoot, Nature 322 (1986), 52; Kohler, Proc. Natl. Acad. Sci. USA 77 (1980), 2197. The coding sequences for the heavy and light chains may comprise cDNA or genomic DNA.

As used herein, "host cells" refers to cells which harbor vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

A variety of host-expression vector systems may be utilized to express antibody molecules for use in the methods described herein. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *Escherichia coli*, *Bacillus subtilis*) transformed with recombinant bacteriophage DNA, plasmid DNA or cosmid DNA expression vectors containing antibody coding sequences; yeast (e.g., *Saccharomyces*, *Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, NSO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5 K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese Hamster Ovary (CHO) cells, in conjunction with a vector such as the major intermediate early gene promoter element from human cytomegalovirus is an effective expression system for antibodies; see, e.g., Foecking et al., Gene 45 (1986), 101; Cockett et al., Bio/Technology 8 (1990), 2.

The host cell line used for protein expression is often of mammalian origin; those skilled in the art are credited with ability to preferentially determine particular host cell lines which are best suited for the desired gene product to be expressed therein. Exemplary host cell lines include, but are not limited to, CHO (Chinese Hamster Ovary), DG44 and DUXB11 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, WI38, R1610 (Chinese hamster fibroblast) BALBC/3T3 (mouse fibroblast), HAK (hamster kidney line), SP2/O (mouse myeloma), P3×63-Ag3.653 (mouse myeloma), BFA-1c1BPT (bovine endothelial cells), RAH (human lymphocyte) and 293 (human kidney). CHO and 293 cells are particularly preferred. Host cell lines are typically available from commercial services, the American Tissue Culture Collection or from published literature.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media.

The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antibody molecule.

A number of selection systems may be used, including but not limited to the herpes simplex virus thymidine kinase (Wigler et al., Cell 11 (1977), 223), hypoxanthine-guanine phosphoribosyltransferase (Szybalska & Szybalski, Proc. Natl. Acad. Sci. USA 48 (1992), 202), and adenine phosphoribosyltransferase (Lowy et al., Cell 22 (1980), 817) genes can be employed in tk-, hgprt- or aprt-cells, respectively. Also, anti-metabolite resistance can be used as the basis of selection for the following genes: dhfr, which confers resistance to methotrexate (Wigler et al., Natl. Acad. Sci. USA 77 (1980), 357; O'Hare et al., Proc. Natl. Acad. Sci. USA 78 (1981), 1527); gpt, which confers resistance to mycophenolic acid (Mulligan & Berg, Proc. Natl. Acad. Sci. USA 78 (1981), 2072); neo, which confers resistance to the aminoglycoside G-418 Goldspiel et al., Clinical Pharmacy 12 (1993), 488-505; Wu and Wu, Biotherapy 3 (1991), 87-95; Tolstoshev, Ann. Rev. Pharmacol. Toxicol. 32 (1993), 573-596; Mulligan, Science 260 (1993), 926-932; and Morgan and Anderson, Ann. Rev. Biochem. 62 (1993), 191-217; TIB TECH 11 (1993), 155-215; and hygro, which confers resistance to hygromycin (Santerre et al., Gene 30 (1984), 147. Methods commonly known in the art of recombinant DNA technology which can be used are described in Ausubel et al. (eds.), *Current Protocols in Molecular Biology*, John Wiley & Sons, N Y (1993); Kriegler, *Gene Transfer and Expression*, A Laboratory Manual, Stockton Press, N Y (1990); and in Chapters 12 and 13, Dracopoli et al. (eds), *Current Protocols in Human Genetics*, John Wiley & Sons, N Y (1994); Colberre-Garapin et al., J. Mol. Biol. 150:1 (1981), which are incorporated by reference herein in their entireties.

The expression levels of an antibody molecule can be increased by vector amplification, for a review, see Bebbington and Hentschel, *The use of vectors based on gene amplification for the expression of cloned genes in mammalian cells in DNA cloning*, Academic Press, New York, Vol. 3. (1987). When a marker in the vector system expressing antibody is amplifiable, increase in the level of inhibitor present in culture of host cell will increase the number of copies of the marker gene. Since the amplified region is associated with the antibody gene, production of the antibody will also increase; see Crouse et al., Mol. Cell. Biol. 3 (1983), 257.

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-) affinity chromatography, e.g., after preferential biosynthesis of a synthetic hinge region polypeptide or prior to or subsequent to the HIC chromatography step described herein.

Genes encoding antibodies, or antigen-binding fragments, variants or derivatives thereof of the invention can also be expressed in non-mammalian cells such as bacteria or insect or yeast or plant cells. Bacteria which readily take up nucleic acids include members of the enterobacteriaceae, such as strains of *Escherichia coli* or *Salmonella*; Bacillaceae, such as *Bacillus subtilis; Pneumococcus; Streptococcus*, and *Haemophilus influenzae*. It will further be appreciated that, when expressed in bacteria, the heterologous polypeptides typically become part of inclusion bodies. The heterologous polypeptides must be isolated, purified and then assembled into functional molecules. Where tetravalent forms of antibodies are desired, the subunits will then self-assemble into tetravalent antibodies; see, e.g., international application WO 02/096948.

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *Escherichia coli* expression vector pUR278 (Ruther et al., EMBO J. 2 (1983), 1791), in which the antibody coding sequence may be ligated individually into the vector in frame with the lacZ coding region so that a fusion protein is produced; pIN vectors (Inouye & Inouye, Nucleic Acids Res. 13 (1985), 3101-3109; Van Heeke & Schuster, J. Biol. Chem. 24 (1989), 5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix of glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes may also be used. *Saccharomyces cerevisiae*, or common baker's yeast, is the most commonly used among eukaryotic microorganisms although a number of other strains are commonly available, e.g., *Pichia pastoris*. For expression in *Saccharomyces*, the plasmid YRp7, for example, (Stinchcomb et al., Nature 282 (1979), 39; Kingsman et al., Gene 7 (1979), 141; Tschemper et al., Gene 10 (1980), 157) is commonly used. This plasmid already contains the TRP1 gene which provides a selection marker for a mutant strain of yeast lacking the ability to grow in tryptophan, for example ATCC No. 44076 or PEP4-1 (Jones, Genetics 85 (1977), 12). The presence of the trp1 lesion as a characteristic of the yeast host cell genome then provides an effective environment for detecting transformation by growth in the absence of tryptophan.

In an insect system, *Autographa californica* nuclear polyhedrosis virus (AcNPV) is typically used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

Once an antibody molecule of the invention has been recombinantly expressed, the whole antibodies, their dimers, individual light and heavy chains, or other immunoglobulin forms of the present invention, can be purified according to standard procedures of the art, including for example, by chromatography (e.g., ion exchange, affinity, particularly by affinity for the specific antigen after Protein A, and sizing column chromatography), centrifugation, differential solubility, e g ammonium sulfate precipitation, or by any other standard technique for the purification of proteins; see, e.g., Scopes, "Protein Purification", Springer Verlag, N.Y. (1982). Alternatively, a preferred method for increasing the affinity of antibodies of the invention is disclosed in US patent publication 2002-0123057 A1. In one embodiment therefore, the present invention also provides a method for preparing an anti-polyomavirus, an anti-polyomavirus VP1 or an anti-polyomavirus VP1 VLP antibody or immunoglobulin chain(s) thereof, said method comprising:

(a) culturing the host cell as defined hereinabove, which cell comprised a polynucleotide or a vector as defined hereinbefore; and
(b) isolating said antibody or immunoglobulin chain(s) thereof from the culture.

Furthermore, in one embodiment the present invention also relates to an antibody or immunoglobulin chain(s) thereof encoded by a polynucleotide as defined hereinabove or obtainable by said method for preparing an anti-polyomavirus, an anti-polyomavirus VP1 or an anti-polyomavirus VP1 VLP antibody or immunoglobulin chain(s) thereof.

V. Fusion Proteins and Conjugates

In certain embodiments, the antibody polypeptide comprises an amino acid sequence or one or more moieties not normally associated with an antibody. Exemplary modifications are described in more detail below. For example, a single-chain Fv antibody fragment of the invention may comprise a flexible linker sequence, or may be modified to add a functional moiety (e.g., PEG, a drug, a toxin, or a label such as a fluorescent, radioactive, enzyme, nuclear magnetic, heavy metal and the like)

An antibody polypeptide of the invention may comprise, consist essentially of, or consist of a fusion protein. Fusion proteins are chimeric molecules which comprise, for example, an immunoglobulin polyomavirus, polyomavirus VP1 and/or polyomavirus VP1 VLP-binding domain with at least one target binding site, and at least one heterologous portion, i.e., a portion with which it is not naturally linked in nature. The amino acid sequences may normally exist in separate proteins that are brought together in the fusion polypeptide or they may normally exist in the same protein but are placed in a new arrangement in the fusion polypeptide. Fusion proteins may be created, for example, by chemical synthesis, or by creating and translating a polynucleotide in which the peptide regions are encoded in the desired relationship.

The term "heterologous" as applied to a polynucleotide or a polypeptide, means that the polynucleotide or polypeptide is derived from a distinct entity from that of the rest of the entity to which it is being compared. For instance, as used herein, a "heterologous polypeptide" to be fused to an antibody, or an antigen-binding fragment, variant, or analog thereof is derived from a non-immunoglobulin polypeptide of the same species, or an immunoglobulin or non-immunoglobulin polypeptide of a different species.

As discussed in more detail elsewhere herein, antibodies, or antigen-binding fragments, variants, or derivatives thereof of the invention may further be recombinantly fused to a heterologous polypeptide at the N- or C-terminus or chemically conjugated (including covalent and non-covalent conjugations) to polypeptides or other compositions. For example, antibodies may be recombinantly fused or conjugated to molecules useful as labels in detection assays and effector molecules such as heterologous polypeptides, drugs, radionuclides, or toxins; see, e.g., international applications WO 92/08495; WO 91/14438; WO 89/12624; U.S. Pat. No. 5,314,995; and European patent application EP 0 396 387.

Antibodies, or antigen-binding fragments, variants, or derivatives thereof of the invention can be composed of amino acids joined to each other by peptide bonds or modified peptide bonds, i.e., peptide isosteres, and may contain amino acids other than the 20 gene-encoded amino acids. Antibodies may be modified by natural processes, such as posttranslational processing, or by chemical modification techniques which are well known in the art. Such modifications are well described in basic texts and in more detailed monographs, as well as in a voluminous research literature. Modifications can occur anywhere in the antibody, including the peptide backbone, the amino acid side-chains and the amino or carboxyl termini, or on moieties such as carbohydrates. It will be appreciated that the same type of modification may be present in the same or varying degrees at several sites in a given antibody. Also, a given antibody may contain many types of modifications. Antibodies may be branched, for example, as a result of ubiquitination, and they may be cyclic, with or without branching. Cyclic, branched, and branched cyclic antibodies may result from posttranslational natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination; see, e.g., *Proteins—Structure And Molecular Properties*, T. E. Creighton, W. H. Freeman and Company, New York 2nd Ed., (1993); *Posttranslational Covalent Modification Of Proteins*, B. C. Johnson, Ed., Academic Press, New York, pgs. 1-12 (1983); Seifter et al., Meth. Enzymol. 182 (1990), 626-646; Rattan et al., Ann. NY Acad. Sci. 663 (1992), 48-62).

The present invention also provides for fusion proteins comprising an antibody, or antigen-binding fragment, variant, or derivative thereof, and a heterologous polypeptide. In one embodiment, a fusion protein of the invention comprises, consists essentially of, or consists of, a polypeptide having the amino acid sequence of any one or more of the $V_H$ regions of an antibody of the invention or the amino acid sequence of any one or more of the $V_L$ regions of an antibody of the invention or fragments or variants thereof, and a heterologous polypeptide sequence. In another embodiment, a fusion protein for use in the diagnostic and treatment methods disclosed herein comprises, consists essentially of, or consists of a polypeptide having the amino acid sequence of any one, two, three of the $V_H$-CDRs of an antibody, or fragments, variants, or derivatives thereof, or the amino acid sequence of any one, two, three of the $V_L$-CDRs of an antibody, or fragments, variants, or derivatives thereof, and a heterologous polypeptide sequence. In one embodiment, the fusion protein comprises a polypeptide having the amino acid sequence of a $V_H$-CDR3 of an antibody of the present invention, or fragment, derivative, or variant thereof, and a heterologous polypeptide sequence, which fusion protein specifically binds to polyomavirus, polyomavirus VP1 and/or polyomavirus VP1 VLP. In another embodiment, a fusion protein comprises a polypeptide having the amino acid sequence of at least one $V_H$ region of an antibody of the invention and the amino acid sequence of at least one $V_L$ region of an antibody of the invention or fragments, derivatives or variants thereof, and a heterologous polypeptide sequence. Preferably, the $V_H$ and $V_L$ regions of the fusion protein correspond to a single source antibody (or scFv or Fab fragment) which specifically binds polyomavirus, polyomavirus VP1 and/or polyomavirus VP1 VLP. In yet another embodiment, a fusion protein for use in the diagnostic and treatment methods disclosed herein comprises a polypeptide having the amino acid sequence of any one, two, three or more of the $V_H$ CDRs of an antibody and the amino acid sequence of any one, two, three or more of the $V_L$ CDRs of an antibody, or fragments or variants thereof, and a heterologous polypeptide sequence. Preferably, two, three, four, five, six, or more of the $V_H$-CDR(s) or $V_L$-CDR(s) correspond to single source antibody (or scFv or Fab fragment) of the invention. Nucleic acid molecules encoding these fusion proteins are also encompassed by the invention.

Exemplary fusion proteins reported in the literature include fusions of the T cell receptor (Gascoigne et al., Proc. Natl. Acad. Sci. USA 84 (1987), 2936-2940; CD4 (Capon et al., Nature 337 (1989), 525-531; Traunecker et al., Nature 339 (1989), 68-70; Zettmeissl et al., DNA Cell Biol. USA 9 (1990), 347-353; and Byrn et al., Nature 344 (1990), 667-670); L-selectin (homing receptor) (Watson et al., J. Cell. Biol. 110 (1990), 2221-2229; and Watson et al., Nature 349 (1991), 164-167); CD44 (Aruffo et al., Cell 61 (1990), 1303-1313); CD28 and B7 (Linsley et al., J. Exp. Med. 173 (1991), 721-730); CTLA-4 (Lisley et al., J. Exp. Med. 174 (1991), 561-569); CD22 (Stamenkovic et al., Cell 66 (1991), 1133-1144); TNF receptor (Ashkenazi et al., Proc. Natl. Acad. Sci. USA 88 (1991), 10535-10539; Lesslauer et al., Eur. J. Immunol. 27 (1991), 2883-2886; and Peppel et al., J. Exp. Med. 174 (1991), 1483-1489 (1991); and IgE receptor a (Ridgway and Gorman, J. Cell. Biol. 115 (1991), Abstract No. 1448).

As discussed elsewhere herein, antibodies, or antigen-binding fragments, variants, or derivatives thereof of the invention may be fused to heterologous polypeptides to increase the in vivo half-life of the polypeptides or for use in immunoassays using methods known in the art. For example, in one embodiment, PEG can be conjugated to the antibodies of the invention to increase their half-life in vivo; see, e.g., Leong et al., Cytokine 16 (2001), 106-119; Adv. in Drug Deliv. Rev. 54 (2002), 531; or Weir et al., Biochem. Soc. Transactions 30 (2002), 512.

Moreover, antibodies, or antigen-binding fragments, variants, or derivatives thereof of the invention can be fused to marker sequences, such as a peptide to facilitate their purification or detection. In preferred embodiments, the marker amino acid sequence is a hexa-histidine peptide (HIS), such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86 (1989), 821-824, for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37 (1984), 767), GST, c-myc and the "flag" tag; see, e.g., Bill Brizzard, BioTechniques 44 (2008) 693-695 for a review of epitope tagging techniques, and Table 1 on page 694 therein listing the most common epitope tags usable in the present invention, the subject matter of which is hereby expressly incorporated by reference.

Fusion proteins can be prepared using methods that are well known in the art; see for example U.S. Pat. Nos. 5,116,964 and 5,225,538. The precise site at which the fusion is made may be selected empirically to optimize the secretion or binding characteristics of the fusion protein. DNA encoding the fusion protein is then transfected into a host cell for expression, which is performed as described hereinbefore.

Antibodies of the present invention may be used in non-conjugated form or may be conjugated to at least one of a variety of molecules, e.g., to improve the therapeutic properties of the molecule, to facilitate target detection, or for imaging or therapy of the patient. Antibodies, or antigen-binding fragments, variants, or derivatives thereof of the invention can be labeled or conjugated either before or after purification, when purification is performed. In particular, antibodies, or antigen-binding fragments, variants, or derivatives thereof of the invention may be conjugated to therapeutic agents, prodrugs, peptides, proteins, enzymes, viruses, lipids, biological response modifiers, pharmaceutical agents, or PEG.

Conjugates that are immunotoxins including conventional antibodies have been widely described in the art. The toxins may be coupled to the antibodies by conventional coupling techniques or immunotoxins containing protein toxin portions can be produced as fusion proteins. The antibodies of the present invention can be used in a corresponding way to obtain such immunotoxins. Illustrative of such immunotoxins are those described by Byers, Seminars Cell. Biol. 2 (1991), 59-70 and by Fanger, Immunol. Today 12 (1991), 51-54.

Those skilled in the art will appreciate that conjugates may also be assembled using a variety of techniques depending on the selected agent to be conjugated. For example, conjugates with biotin are prepared, e.g., by reacting a polyomavirus, a polyomavirus VP1 and/or polyomavirus VP1 VLP binding polypeptide with an activated ester of biotin such as the biotin N-hydroxysuccinimide ester. Similarly, conjugates with a fluorescent marker may be prepared in the presence of a coupling agent, e.g. those listed herein, or by reaction with an isothiocyanate, preferably fluorescein-isothiocyanate. Conjugates of the antibodies, or antigen-binding fragments, variants or derivatives thereof of the invention are prepared in an analogous manner.

The present invention further encompasses antibodies, or antigen-binding fragments, variants, or derivatives thereof of the invention conjugated to a diagnostic or therapeutic agent. The antibodies can be used diagnostically to, for example, demonstrate presence of a polyomavirus to monitor the development or progression of a disease associated with a polyomavirus, i.e. a disease showing the occurrence of polyomavirus proteins, polyomavirus VP1 and/or polyomavirus VP1 VLP as part of a clinical testing procedure to, e.g., determine the efficacy of a given treatment and/or prevention regimen. In one embodiment thus, the present invention relates to an antibody, which is detectably labeled. Furthermore, in one embodiment, the present invention relates to an antibody, which is attached to a drug. Detection can be facilitated by coupling the antibody, or antigen-binding fragment, variant, or derivative thereof to a detectable substance. The detectable substances or label may be in general an enzyme; a heavy metal, preferably gold; a dye, preferably a fluorescent or luminescent dye; or a radioactive label. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions; see, e.g., U.S. Pat. No. 4,741,900 for metal ions which can be conjugated to antibodies for use as diagnostics according to the present invention. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc. Therefore, in one embodiment the present invention provides a detectably labeled antibody, wherein the detectable label is selected from the group consisting of an enzyme, a radioisotope, a fluorophore, a protein and a heavy metal.

An antibody, or antigen-binding fragment, variant, or derivative thereof also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

One of the ways in which an antibody, or antigen-binding fragment, variant, or derivative thereof can be detectably labeled is by linking the same to an enzyme and using the linked product in an enzyme immunoassay (EIA) (Voller, A., "The Enzyme Linked Immunosorbent Assay (ELISA)" Microbiological Associates Quarterly Publication, Walkersville, Md., Diagnostic Horizons 2 (1978), 1-7); Voller et al., J. Clin. Pathol. 31 (1978), 507-520; Butler, Meth. Enzymol. 73 (1981), 482-523; Maggio, E. (ed.), *Enzyme Immunoassay*, CRC Press, Boca Raton, Fla., (1980); Ishikawa, E. et al., (eds.), *Enzyme Immunoassay*, Kgaku Shoin, Tokyo (1981). The enzyme, which is bound to the antibody, will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibody, or antigen-binding fragment, variant, or derivative thereof, it is possible to detect the antibody through the use of a radioimmunoassay (RIA) (see, for example, Weintraub, B., Principles of Radioimmunoassays, Seventh Training Course on Radioligand Assay Techniques, The Endocrine Society, (March, 1986), which is incorporated by reference herein). The radioactive isotope can be detected by means including, but not limited to, a gamma counter, a scintillation counter, or autoradiography.

An antibody, or antigen-binding fragment, variant, or derivative thereof can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

Techniques for conjugating various moieties to an antibody, or antigen-binding fragment, variant, or derivative thereof are well known, see, e.g., Arnon et al., "Monoclonal Antibodies For Immunotargeting Of Drugs In Cancer Therapy", in *Monoclonal Antibodies And Cancer Therapy*, Reisfeld et al. (eds.), pp. 243-56 (Alan R. Liss, Inc. (1985); Hellstrom et al., "Antibodies For Drug Delivery", in *Controlled Drug Delivery* (2nd Ed.), Robinson et al. (eds.), Marcel Dekker, Inc., pp. 623-53 (1987); Thorpe, "Antibody Carriers Of Cytotoxic Agents In Cancer Therapy: A Review", in *Monoclonal Antibodies '84: Biological And Clinical Applications*, Pinchera et al. (eds.), pp. 475-506 (1985); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), Academic Press pp. 303-16 (1985), and Thorpe et al., "The Preparation And Cytotoxic Properties Of Antibody-Toxin Conjugates", Immunol. Rev. 62 (1982), 119-158.

As mentioned, in certain embodiments, a moiety that enhances the stability or efficacy of a binding molecule, e.g., a binding polypeptide, e.g., an antibody or immunospecific fragment thereof can be conjugated. For example, in one embodiment, PEG can be conjugated to the binding molecules of the invention to increase their half-life in vivo. Leong et al., Cytokine 16 (2001), 106; Adv. in Drug Deliv. Rev. 54 (2002), 531; or Weir et al., Biochem. Soc. Transactions 30 (2002), 512.

VI. Compositions and Methods of Use

The present invention relates to compositions comprising the aforementioned polyomavirus, polyomavirus VP1 and/or polyomavirus VP1 VLP binding molecule, e.g., antibody or antigen-binding fragment thereof of the present invention or derivative or variant thereof, or the polynucleotide, vector or cell of the invention as defined hereinbefore. In one embodiment, the composition of the present invention is a pharmaceutical composition and further comprises a pharmaceutically acceptable carrier. Furthermore, the pharmaceutical composition of the present invention may comprise further agents such as interleukins or interferons depending on the intended use of the pharmaceutical composition. For use in the treatment of diseases associated with polyomavirus showing the occurrence of polyomavirus, polyomavirus VP1 and/or polyomavirus VP1 VLP, the additional agent may be selected from the group consisting of small organic molecules, anti-polyomavirus, anti-polyomavirus VP1 and/or anti-polyomavirus VP1 VLP antibodies, and combinations thereof. Hence, in a particular preferred embodiment the present invention relates to the use of the polyomavirus proteins, polyomavirus VP1 and/or polyomavirus VP1 VLP binding molecule, e.g., antibody or antigen-binding fragment thereof of the present invention or of a binding molecule having substantially the same binding specificities of any one thereof, the polynucleotide, the vector or the cell of the present invention for the preparation of a pharmaceutical or diagnostic composition for prophylactic and/or therapeutic treatment of a metabolic disease, monitoring the progression of a metabolic disease or a response to a metabolic disease treatment in a subject or for determining a subject's risk for developing a metabolic disease.

In one embodiment the present invention relates to a method of treating a disorder associated with polyomavirus, preferably of the type of JCV and/or BKV, which method comprises administering to a subject in need thereof a therapeutically effective amount of any one of the afore-described polyomavirus, polyomavirus VP1 and/or polyomavirus VP1 VLP binding molecules, antibodies, polynucleotides, vectors or cells of the present invention.

A particular advantage of the therapeutic approach of the present invention lies in the fact that the antibodies of the present invention are derived from B cells or memory B cells from healthy elderly human subjects, patients who received monoclonal antibody therapy to treat multiple sclerosis (MS) and who developed symptoms of and recovered from PML and PML-IRIS with a certain probability, capable of preventing a clinically manifest disease related to polyomavirus, polyomavirus VP1 and/or polyomavirus VP1 VLP, or of diminishing the risk of the occurrence of the clinically manifest disease, or of delaying the onset or progression of the clinically manifest disease. Typically, the antibodies of the present invention also have already successfully gone through somatic maturation, i.e. the optimization with respect to selectivity and effectiveness in the high affinity binding to the target polyomavirus, polyomavirus VP1 and/or polyomavirus VP1 VLP molecule by means of somatic variation of the variable regions of the antibody.

The knowledge that such cells in vivo, e.g. in a human, have not been activated by means of related or other physiological proteins or cell structures in the sense of an autoimmunological or allergic reaction is also of great medical importance since this signifies a considerably increased chance of successfully living through the clinical test phases. So to speak, efficiency, acceptability and tolerability have already been demonstrated before the preclinical and clinical development of the prophylactic or therapeutic antibody in at least one human subject. It can thus be expected that the human anti-polyomavirus, anti-polyomavirus VP1 and/or anti-polyomavirus VP1 VLP antibodies of the present invention, both its target structure-specific efficiency as therapeutic agent and its decreased probability of side effects significantly increase its clinical probability of success.

The present invention also provides a pharmaceutical and diagnostic, respectively, pack or kit comprising one or more containers filled with one or more of the above described ingredients, e.g. anti-polyomavirus, anti-polyomavirus VP1 and/or anti-polyomavirus VP1 VLP antibody, binding fragment, derivative or variant thereof, polynucleotide, vector or cell of the present invention. Associated with such container(s) can be a notice in the form prescribed by a governmental agency regulating the manufacture, use or sale of pharmaceuticals or biological products, which notice reflects approval by the agency of manufacture, use or sale for human administration. In addition or alternatively the kit comprises reagents and/or instructions for use in appropriate diagnostic assays. The composition, e.g. kit of the present invention is of course particularly suitable for the risk assessment, diagnosis, prevention, monitoring and treatment of a disorder which is accompanied with the presence of polyomavirus, polyomavirus VP1 and/or polyomavirus VP1 VLP, and in particular applicable for the treatment of disorders generally characterized by polyomavirus infection.

The pharmaceutical compositions of the present invention can be formulated according to methods well known in the art; see for example Remington: The Science and Practice of Pharmacy (2000) by the University of Sciences in Philadelphia, ISBN 0-683-306472. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well-known conventional methods. These pharmaceutical compositions can be administered to the subject at a suitable dose. Administration of the suitable compositions may be effected by different ways, e.g., by intravenous, intraperitoneal, subcutaneous, intramuscular, intranasal, topical or intradermal administration or spinal or brain delivery. Aerosol formulations such as nasal spray formulations include purified aqueous or other solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 μg (or of nucleic acid for expression or for inhibition of expression in this range); however, doses below or above this exemplary range are envisioned, especially considering the aforementioned factors. Generally, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated. Progress can be monitored by periodic assessment. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents such as dopamine or psychopharmacologic drugs, depending on the intended use of the pharmaceutical composition.

Furthermore, in a preferred embodiment of the present invention the pharmaceutical composition may be formulated as a vaccine, for example, if the pharmaceutical composition of the invention comprises an anti-polyomavirus, anti-polyomavirus VP1 and/or anti-polyomavirus VP1 VLP antibody or binding fragment, derivative or variant thereof for passive immunization.

In one embodiment, it may be beneficial to use recombinant bispecific or multispecific constructs of the antibody of the present invention. For a reference see Fischer and Léger, Pathobiology 74 (2007), 3-14. Such bispecific molecule might be designed to target different polyomaviruses or diseases caused by infection of polyomaviruses. A bispecific molecule might also be designed to bind with the second binding arm other entities known in pathogenesis associated with polyomaviruses.

In one embodiment, it may be beneficial to use recombinant Fab (rFab) and single chain fragments (scFvs) of the antibody of the present invention, which might more readily penetrate a cell membrane. The perceived advantages of using small Fab and scFv engineered antibody formats which lack the effector function include more efficient passage across the blood-brain barrier and minimizing the risk of triggering inflammatory side reactions. Furthermore, besides scFv and single-domain antibodies retain the binding specificity of full-length antibodies, they can be expressed as single genes and intracellularly in mammalian cells as intrabodies, with the potential for alteration of the folding, interactions, modifications, or subcellular localization of their targets; see for review, e.g., Miller and Messer, Molecular Therapy 12 (2005), 394-401.

In a different approach Muller et al., Expert Opin. Biol. Ther. (2005), 237-241, describe a technology platform, so-called 'SuperAntibody Technology', which is said to enable antibodies to be shuttled into living cells without harming them. Such cell-penetrating antibodies open new diagnostic and therapeutic windows. The term 'TransMabs' has been coined for these antibodies.

In one embodiment, the antibody, pharmaceutical composition or vaccine of the present invention is used in combination, concomitantly or sequentially with an immunomodulatory agent in the treatment of a disease associated with the (re)activation of polyomaviruses, preferably, for treatment of Progressive Multifocal Leukoencephalopathy (PML), infection of granule neurons, hyperchromatic nuclei, granule cell neuronopathy, cerebral autothrophy, encephalopathy, meningitis, Polyoma-induced tumors, immune reconstitution inflammatory syndrome (IRIS), hemorrhagic cystitis, pneumonia, retinitis, colitis, vasculitis, interstitial kidney disease, infections of respiratory tract, JCV nephropathy, BKV nephropathy, meningitis, Merkel cell carcinoma, trichodysplasia spinulosa or malignant pleural mesothelioma and/or in co-administration with the agent natalizumab, efalizumab, rituximab, infliximab, ocrelizumab, alemtuzumab, bentuximab, or vedotin.

A therapeutically effective dose or amount refers to that amount of the active ingredient sufficient to ameliorate the symptoms or condition. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$. Preferably, the therapeutic agent in the composition is present in an amount sufficient to e.g. prevent transplant rejection, PML and other diseases caused by polyomavirus infection.

From the foregoing, it is evident that the present invention encompasses any use of an polyomavirus, polyomavirus VP1 and/or polyomavirus VP1 VLP binding molecule comprising at least one CDR of the above described antibody, in particular for diagnosing and/or treatment of a disease related to polyomavirus infection. Preferably, said binding molecule is an antibody of the present invention or an immunoglobulin chain thereof. In addition, the present invention relates to anti-idiotypic antibodies of any one of the mentioned antibodies described hereinbefore. These are antibodies or other binding molecules which bind to the unique antigenic peptide sequence located on an antibody's variable region near the antigen-binding site and are useful, e.g., for the detection of anti-polyomavirus, anti-polyomavirus VP1 and/or anti-polyomavirus VP1 VLP antibodies in a sample obtained from a subject. In one embodiment thus, the present invention provides an antibody as defined hereinabove and below or an polyomavirus, polyomavirus VP1 and/or polyomavirus VP1 VLP binding molecule having substantially the same binding specificities of any one thereof, the polynucleotide, the vector or the cell as defined herein or a pharmaceutical or diagnostic composition comprising any one thereof for use in prophylactic treatment, therapeutic treatment and/or monitoring the progression or a response to treatment of a disorder related to polyomavirus infection, preferably wherein the disorder is selected from the group comprising PML, infection of granule neurons, hyperchromatic nuclei, granule cell neuronopathy, cerebral autothrophy, encephalopathy, meningitis, Polyomavirus-induced tumors, immune reconstitution inflammatory syndrome (IRIS), hemorrhagic cystitis, pneumonia, retinitis, colitis, vasculitis, interstitial kidney disease, infections of respiratory tract. The above group of disorders will be referred to as the group of disorders related to polyomavirus, polyomavirus VP1 and/or polyomavirus VP1 VLP.

In another embodiment the present invention relates to a diagnostic composition comprising any one of the above described polyomavirus, polyomavirus VP1 and/or polyomavirus VP1 VLP binding molecules, antibodies, antigen-binding fragments, polynucleotides, vectors or cells of the invention and optionally suitable means for detection such as reagents conventionally used in immuno- or nucleic acid-based diagnostic methods. The antibodies of the invention are, for example, suited for use in immunoassays in which they can be utilized in liquid phase or bound to a solid phase carrier. Examples of immunoassays which can utilize the antibody of the invention are competitive and non-competitive immunoassays in either a direct or indirect format. Examples of such immunoassays are the radioimmunoassay (RIA), the sandwich (immunometric assay), flow cytometry and the Western blot assay. The antigens and antibodies of the invention can be bound to many different carriers and used to isolate cells specifically bound thereto. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds; see also the embodiments discussed hereinabove.

By a further embodiment, the polyomavirus, polyomavirus VP1 and/or polyomavirus VP1 VLP binding molecules, in particular antibodies of the present invention may also be used in a method for the diagnosis of a disorder in an individual by obtaining a body fluid sample from the tested individual which may be a blood sample, a plasma sample, a serum sample, a lymph sample or any other body fluid sample, such as a saliva or a urine sample and contacting the body fluid sample with an antibody of the instant invention under conditions enabling the formation of antibody-antigen complexes. The level of such complexes is then determined by methods known in the art, a level significantly higher than that formed in a control sample indicating the disease in the tested individual. In the same manner, the specific antigen bound by the antibodies of the invention may also be used. Thus, the present invention relates to an in vitro immunoassay comprising the binding molecule, e.g., antibody or antigen-binding fragment thereof of the invention.

In this context, the present invention also relates to means specifically designed for this purpose. For example, an antibody-based array may be used, which is for example loaded with antibodies or equivalent antigen-binding molecules of the present invention which specifically recognize polyomavirus, polyomavirus VP1 and/or polyomavirus VP1 VLP. Design of microarray immunoassays is summarized in Kusnezow et al., Mol. Cell Proteomics 5 (2006), 1681-1696. Accordingly, the present invention also relates to microarrays loaded with polyomavirus, polyomavirus VP1 and/or polyomavirus VP1 VLP binding molecules identified in accordance with the present invention.

In one embodiment, the present invention relates to a method of diagnosing a disease related to polyomavirus infection in a subject, the method comprising determining the presence of polyomavirus, polyomavirus VP1 and/or polyomavirus VP1 VLP in a sample from the subject to be diagnosed with at least one antibody of the present invention, a binding fragment thereof or a binding molecule having substantially the same binding specificities of any one thereof.

The level of polyomavirus, polyomavirus VP1 and/or polyomavirus VP1 VLPs be assessed by any suitable method known in the art comprising, e.g., analyzing polyomavirus, polyomavirus VP1 and/or polyomavirus VP1 VLP by one or more techniques chosen from Western blot, immunoprecipitation, enzyme-linked immunosorbent assay (ELISA), radioimmunoassay (RIA), fluorescent activated cell sorting (FACS), two-dimensional gel electrophoresis, mass spectroscopy (MS), matrix-assisted laser desorption/ionization-time of flight-MS (MALDI-TOF), surface-enhanced laser desorption ionization-time of flight (SELDI-TOF), high performance liquid chromatography (HPLC), fast protein liquid chromatography (FPLC), multidimensional liquid chromatography (LC) followed by tandem mass spectrometry (MS/MS), and laser densitometry. Preferably, said in vivo imaging of VP1 comprises positron emission tomography (PET), single photon emission tomography (SPECT), near infrared (NIR) optical imaging or magnetic resonance imaging (MRI).

In one embodiment thus, an antibody of the present invention or a polyomavirus, polyomavirus VP1 and/or polyomavirus VP1 VLP binding molecule having substantially the same binding specificities of any one thereof, the polynucleotide, the vector or the cell as defined hereinabove or a pharmaceutical or diagnostic composition comprising any one thereof is provided for use in prophylactic treatment, therapeutic treatment and/or monitoring the progression or a response to treatment of a disorder related to a polyomavirus infection. In general thus, the present invention also relates to a method of diagnosing or monitoring the progression of a disorder related to polyomavirus infection.

As indicated above, the antibodies of the present invention, fragments thereof and molecules of the same binding specificity as the antibodies and fragments thereof may be used not only in vitro but in vivo as well, wherein besides diagnostic, therapeutic applications as well may be pursued. In one embodiment thus, the present invention also relates to a polyomavirus, polyomavirus VP1 and/or polyomavirus VP1 VLP binding molecule comprising at least one CDR of an antibody of the present invention for the preparation of a composition for in vivo detection of or targeting a therapeutic and/or diagnostic agent to polyomavirus in the human or animal body. Potential therapeutic and/or diagnostic agents may be chosen from the nonexhaustive enumerations of the therapeutic agents useful in treatment of diseases associated with polyomavirus. In respect of the in vivo imaging, in one preferred embodiment the present invention provides said polyomavirus, polyomavirus VP1 and/or polyomavirus VP1 VLP binding molecule comprising at least one CDR of an antibody of the present invention, wherein said in vivo imaging comprises positron emission tomography (PET), single photon emission tomography (SPECT), near infrared (NIR) optical imaging or magnetic resonance imaging (MRI). In a further embodiment the present invention also provides said polyomavirus, polyomavirus VP1 and/or polyomavirus VP1 VLP binding molecule comprising at least one CDR of an antibody of the present invention, or said molecule for the preparation of a composition for the above specified in vivo imaging methods, for the use in the method of diagnosing or monitoring the progression of a disorder associated with a polyomavirus infection in a subject, as defined hereinabove.

VII. Peptides with Polyomavirus Specific Epitopes

In a further aspect the present invention relates to peptides having an epitope of polyomavirus VP1 specifically recognized by any antibody of the present invention. Preferably, such peptide comprises or consists of an amino acid sequence as indicated in SEQ ID NOs: 85 to 88 as the unique linear epitope recognized by the antibody or a modified sequence thereof in which one or more amino acids are substituted, deleted and/or added, wherein the peptide is recognized by any antibody of the present invention, preferably by antibody (A) NI-307.13G4, (B) NI-307.19F10, (C) NI-307.19F8, (D) NI-307.11G6, (E) NI-307.17F12, (F) NI-307.6A2, (G) NI-307.5H3, (H) NI-307.25G10, (I) NI-307.26E10, (J) NI-307.1E1, (K) NI-307.24C6, (L) NI-307.78C3, (M) NI-307.57D5, (N) NI-307.43A11, (O) NI-307.3G4, (P) NI-307.61D11, (Q) NI-307.24F3, (R) NI-307.18E12, (S) NI-307.20F5, (T) NI-307.58C7, (U) NI-307.105C7, (V) NI-307.98D3, (W) NI-307.72F7, (X) NI-307.45E10, (Y) NI-307.72F10, (Z) NI-307.56A8, (A2) NI-307.27C11, (B2) NI-307.47B11, (C2) NI-307.26A3, (D2) NI-307.27C2, (E2) NI-307.57D4, (F2) NI-307.50H4, (G2) NI-307.53B11, (H2) NI-307.7J3, (I2) NI-307.59A7, (J2) NI-307.105A6, (K2) NI-307.29B1, (L2) NI-307.44F6B, (M2) NI-307.98H1, (N2) NI-307.43E8 and/or (O2) NI-307.18F4A.

In one embodiment of this invention such a peptide may be used for diagnosing and/or monitoring a disease related to polyomavirus infection in a subject comprising a step of determining the presence of an antibody that binds to a peptide in a biological sample of said subject, and being used for diagnosis of such a disease in said subject by measuring the levels of antibodies which recognize the above described peptide of the present invention and comparing the measurements to the levels which are found in healthy subjects of comparable age and gender. Thus in one embodiment the present invention relates to a method for diagnosing PML. The peptide of the present invention may be formulated in an array, a kit and composition, respectively, as described hereinbefore. In this context, the present invention also relates to a kit useful in the diagnosis or monitoring the progression of polyomavirus infections, said kit comprising at least one antibody of the present invention or a polyomavirus, polyomavirus VP1 and/or polyomavirus VP1 VLP binding molecule having substantially the same binding specificities of any one thereof, the polynucleotide, the vector or the cell and/or the peptide as respectively defined hereinbefore, optionally with reagents and/or instructions for use.

These and other embodiments are disclosed and encompassed by the description and examples of the present invention. Further literature concerning any one of the materials, methods, uses and compounds to be employed in accordance with the present invention may be retrieved from public libraries and databases, using for example electronic devices. For example the public database "Medline" may be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL) are known to the person skilled in the art and can also be obtained using internet search engines. An overview of patent information in biotechnology and a survey of relevant sources of patent information useful for retrospective searching and for current awareness is given in Berks, TIBTECH 12 (1994), 352-364.

The above disclosure generally describes the present invention. Unless otherwise stated, a term as used herein is given the definition as provided in the Oxford Dictionary of Biochemistry and Molecular Biology, Oxford University Press, 1997, revised 2000 and reprinted 2003, ISBN 0 19 850673 2. Several documents are cited throughout the text of this specification. The contents of all cited references (including literature references, issued patents, published patent applications as cited throughout this application and manufacturer's specifications, instructions, etc.) are hereby expressly incorporated by reference; however, there is no admission that any document cited is indeed prior art as to the present invention.

A more complete understanding can be obtained by reference to the following specific examples which are provided herein for purposes of illustration only and are not intended to limit the scope of the invention.

EXAMPLES

Example 1: Selection of Blood Donors

Clinically interesting donors were recruited, peripheral blood was drawn under appropriate informed consent and PBMCs were prepared and stored in liquid nitrogen.

The blood donors can be divided in 3 categories including healthy elderly patients with unknown HLA typing and anti-JCV titers, HLA-DRB1*04:01+ healthy donors who presented a robust JCV-specific antibody production, and patients who received monoclonal antibody therapy to treat Multiple Sclerosis and who developed symptoms of and successfully recovered from PML and PML-IRIS. Selected donors from the latter category mounted an efficient immune response with high anti-JCV antibody titers.

Human-derived antibodies targeting VP1 were identified by high-throughput analysis of complements of the human memory B-cell repertoire derived from the clinically selected donors. For VP1 antibody screening, 96-well microplates (Costar, Corning, USA) were coated overnight at 4° C. with VP1 solutions or BSA (Sigma-Aldrich, Buchs, Switzerland) diluted to a concentration of 1 µg/ml either in carbonate buffer (15 mM $Na_2CO_3$, 35 mM $NaHCO_3$, pH 9.42) or in reassociation buffer. Plates were washed in PBS-T pH 7.6 and non-specific binding sites were blocked for 1 hr at RT with PBS/0.1% Tween-20 containing 2% BSA (Sigma-Aldrich, Buchs, Switzerland). B cell conditioned medium was transferred from memory B cell culture plates to ELISA plates and incubated for one hour at RT. ELISA plates were washed in PBS-T and binding was determined using horseradish peroxidase (HRP)-conjugated anti-human immunoglobulins polyclonal antibodies (Jackson ImmunoResearch, Newmarket, UK) followed by measurement of HRP activity in a standard colorimetric assay. Only B cell cultures which have shown binding of the antibodies contained in the medium to VP1 but not to BSA were subjected to antibody cloning. High-throughput analysis was also performed to characterize the subclass of the native antibody; see Table IV. Antibody cDNAs derived from VP1-reactive memory B-cells were expressed for the determination of binding properties and VP1-reactive IgG clones were recombinantly produced in CHO for in vitro characterization. Antibodies were purified endotoxin-free by affinity chromatography, see e.g., Sheehan and O'Sullivan, Methods Mol. Biol. 244 (2004), 253-258.

VP1 antigens for recombinant full length JCV VP1 and BKV VP1 were purchased from Abcam (Cambridge, UK). Alternatively, JCV VP1 gene was fused to a 6×His tag, expressed in E. coli and purified using a nickel column. Furthermore, the antigen was incubated for 48 hours at 24° C. with shaking in reassociation buffer (1 mM $CaCl_2$ in TBS) to form the Virus-Like Particles (VLPs).

The used JCV VP1 was from the Mad-1 strain (UniProtKB/Swiss-Prot, NCBI Accession No. P03089) while the BKV VP1 was from the AS strain (UniProtKB/Swiss-Prot, NCBI Accession No. P03088).

TABLE IV

Characterization of the subclass of the antibodies of the present invention

| Antibody code | Antibody name | Antibody subclass |
| --- | --- | --- |
| A | NI-307.13G4 | IgA |
| B | NI-307.19F10 | IgG |
| C | NI-307.19F8 | IgG |
| D | NI-307.11G6 | IgG1 |
| E | NI-307.17F12 | IgG |
| F | NI-307.6A2 | IgG |
| G | NI-307.5H3 | IgA |
| H | NI-307.25G10 | IgG2 |
| I | NI-307.26E10 | IgG |
| J | NI-307.1E1 | IgG |
| K | NI-307.24C6 | IgG |

TABLE IV-continued

Characterization of the subclass of the antibodies of the present invention

| Antibody code | Antibody name | Antibody subclass |
|---|---|---|
| L | NI-307.78C3 | IgG2 |
| M | NI-307.57D5 | IgG |
| N | NI-307.43A11 | IgG |
| O | NI-307.3G4 | IgG |
| P | NI-307.61D11 | IgA |
| Q | NI-307.24F3 | IgA |
| R | NI-307.18E12 | IgG |
| S | NI-307.20F5 | IgA |
| T | NI-307.58C7 | IgG1 |
| U | NI-307.105C7 | IgG2 |
| V | NI-307.98D3 | IgG1 |
| W | NI-307.72F7 | IgG1 |
| X | NI-307.45E10 | IgG3 |
| Y | NI-307.72F10 | IgG1 |
| Z | NI-307.56A8 | IgG1 |
| A2 | NI-307.27C11 | IgG3 |
| B2 | NI-307.47B11 | IgA1 |
| C2 | NI-307.26A3 | IgG3 |
| D2 | NI-307.27C2 | IgG1 |
| E2 | NI-307.57D4 | IgA1 |
| F2 | NI-307.50H4 | IgG |
| G2 | NI-307.53B11 | IgG1 |
| H2 | NI-307.7J3 | IgA1 |
| I2 | NI-307.59A7 | IgG1 |
| J2 | NI-307.105A6 | IgG1 |
| K2 | NI-307.29B1 | IgG3 |
| L2 | NI-307.44F6B | IgA1 |
| M2 | NI-307.98H1 | IgG1 |
| N2 | NI-307.43E8 | IgG2 |
| O2 | NI-307.18F4A | IgG |

Example 2: Setup Refolding of VP1 Proteins into Virus-Like Particles

To screen and test the binding of the antibody hits to VP1 epitopes exposed on the surface of the viruses, the refolding of VP1 monomers into Virus-Like Particles (VLPs) had to be to set up. VP1 proteins (Abcam) were either diluted in carbonate ELISA coating buffer or incubated for 48 h at 24° C. in reassociation buffer (TBS containing 1 mM $CaCl_2$)). The preparations were then stained with an anti-VP1 antibody and studied by transmission electron microscopy. As shown in FIG. 1A, the VP1 proteins diluted in carbonate coating buffer do not form any structure. On the contrary, VP1 proteins incubated in reassociation buffer are reassembling into VLPs mimicking the structure of the viruses (see FIG. 1B). This procedure was further used to refold the particles to be coated on ELISA plates (referred as VP1 VLPs).

Example 3: Molecular Cloning of VP1 Antibodies

Living B cells of selected memory B cell cultures were harvested and mRNA was prepared. Immunoglobulin heavy and light chain sequences were then obtained using a nested PCR approach.

A combination of primers representing all sequence families of the human immunoglobulin germline repertoire was used for the amplifications of leader peptides, V-segments and J-segments. The first round of amplification was performed using leader peptide-specific primers in 5'-end and constant region-specific primers in 3'-end (Smith et al., Nat Protoc. 4 (2009), 372-384). For heavy chains and kappa light chains, the second round of amplification was performed using V-segment-specific primers at the 5'-end and J-segment-specific primers at the 3' end. For lambda light chains, the second round amplification was performed using V-segment-specific primers at the 5'-end and a C-region-specific primer at the 3'end (Marks et al., Mol. Biol. 222 (1991), 581-597; de Haard et al., J. Biol. Chem. 26 (1999), 18218-18230).

Identification of the antibody clone with the desired specificity was performed by re-screening on ELISA upon recombinant expression of complete antibodies. Recombinant expression of complete human IgG1 antibodies was achieved upon insertion of the variable heavy and light chain sequences "in the correct reading frame" into expression vectors that complement the variable region sequence with a sequence encoding a leader peptide at the 5'-end and at the 3'-end with a sequence encoding the appropriate constant domain(s). To that end the primers contained restriction sites designed to facilitate cloning of the variable heavy and light chain sequences into antibody expression vectors. Heavy chain immunoglobulins were expressed by inserting the immunoglobulin heavy chain RT-PCR product in frame into a heavy chain expression vector bearing a signal peptide and the constant domains of human immunoglobulin gamma 1. Kappa light chain immunoglobulins were expressed by inserting the kappa light chain RT-PCR-product in frame into a light chain expression vector providing a signal peptide and the constant domain of human kappa light chain immunoglobulin. Lambda light chain immunoglobulins were expressed by inserting the lambda light chain RT-PCR-product in frame into a lambda light chain expression vector providing a signal peptide and the constant domain of human or mouse lambda light chain immunoglobulin.

Functional recombinant monoclonal antibodies were obtained upon co-transfection into HEK 293 or CHO cells (or any other appropriate recipient cell line of human or mouse origin) of an Ig-heavy-chain expression vector and a kappa or lambda Ig-light-chain expression vector. Recombinant human monoclonal antibody was subsequently purified from the conditioned medium using a standard Protein A column purification. Recombinant human monoclonal antibody can produced in unlimited quantities using either transiently or stably transfected cells. Cell lines producing recombinant human monoclonal antibody can be established either by using the Ig-expression vectors directly or by re-cloning of Ig-variable regions into different expression vectors. Derivatives such as F(ab), $F(ab)_2$ and scFv can also be generated from these Ig-variable regions.

Antibodies used in the experiments, mouse monoclonal anti-VP1 antibody 2E4 (sc-65930, Santa Cruz Biotechnology, California, USA) and mouse monoclonal anti-VP1 antibody (ab34756, Abcam, Cambridge, UK), were used according to manufacturer's protocol. Recombinant human VP1 antibodies (A) NI-307.13G4, (B) NI-307.19F10, (C) NI-307.19F8, (D) NI-307.11G6, (E) NI-307.17F12, (F) NI-307.6A2, (G) NI-307.5H3, (H) NI-307.25G10, (I) NI-307.26E10, (J) NI-307.1E1, (K) NI-307.24C6, (L) NI-307.78C3, (M) NI-307.57D5, (N) NI-307.43A11, (O) NI-307.3G4, (P) NI-307.61D11, (Q) NI-307.24F3, (R) NI-307.18E12, (S) NI-307.20F5, (T) NI-307.58C7, (U) NI-307.105C7, (V) NI-307.98D3, (W) NI-307.72F7, (X) NI-307.45E10, (Y) NI-307.72F10, (Z) NI-307.56A8, (A2) NI-307.27C11, (B2) NI-307.47B11, (C2) NI-307.26A3, (D2) NI-307.27C2, (E2) NI-307.57D4, (F2) NI-307.50H4, (G2) NI-307.53B11, (H2) NI-307.7J3, (I2) NI-307.59A7, (J2) NI-307.105A6, (K2) NI-307.29B1, (L2) NI-307.44F6B, (M2) NI-307.98H1, (N2) NI-307.43E8 and/or (O2) NI-307.18F4A are antibodies of this invention. They were expressed in HEK 293 or CHO cells, purified from conditioned media and were directly used in subsequent applications unless otherwise stated.

Example 4: Binding Specificity of JCV VP1 Antibodies

Direct ELISA assays were performed with varying antibody concentrations to validate the binding of the antibodies to JCV VP1 and to be able to determine their half maximal effective concentration (EC50). In brief, direct ELISA was performed in 96-well microplates (Costar, Corning, USA) coated overnight at 4° C. with VP1 solutions or BSA (Sigma-Aldrich, Buchs, Switzerland) diluted to a concentration of 1 μg/ml either in carbonate ELISA coating buffer (15 mM $Na_2CO_3$, 35 mM $NaHCO_3$, pH 9.42) or in reassociation buffer. The plates coated with VP1 antigen diluted in carbonate buffer were called "VP1" while the plates coated with VP1 pre-incubated in reassociation buffer and then further diluted in reassociation buffer were called "VP1 VLP". Non-specific binding sites were blocked for 2 hr at RT with PBST containing 2% BSA (Sigma-Aldrich, Buchs, Switzerland) and 0.5% Tween20. Binding of human antibodies of the present invention was determined using a donkey anti-human IgG antibody conjugated with HRP (Jackson immunoResearch, Newmarket, UK), followed by measurement of HRP activity in a standard colorimetric assay. EC50 values were estimated by a non-linear regression using GraphPad Prism software (San Diego, USA).

For the exemplary recombinant human NI-307.13G4, NI-307.18E12, NI-307.18F4A, NI-307.19F8, NI-307.20F5 and NI-307.61D11 antibodies of the present invention and the commercial antibody Ab34756, 96-well microplates (Costar, Corning, USA) were coated with VP1 solutions or with BSA (Sigma-Aldrich, Buchs, Switzerland) diluted to a concentration of 5 μg/ml either in carbonate ELISA coating buffer (15 mM $Na_2CO_3$, 35 mM $NaHCO_3$, pH 9.4) or in reassociation buffer. The binding efficiency of the antibody was then tested. The exemplary antibodies specifically bind to VP1 from the JCV and not or weakly to VP1 from the BKV. The commercial antibody Ab34756 binds to VP1 from the JC virus and weakly to VP1 from the BKV but it was also binding to BSA and is therefore not specific as judged by ELISA. The NI-307.13G4 and NI-307.20F5 antibodies were binding much more efficiently on JCV VP1 (coating with carbonate buffer) than on JCV VP1 VLPs (coating with reassociation buffer) whereas the binding of NI-307.18E12, NI-307.19F8 and NI-307.61D11 antibodies was slightly stronger on JCV VP1 compared to JCV VP1 VLPs. Whereas, no binding was observed to BSA for the exemplary antibodies; see FIG. 2A.

The $EC_{50}$ values were estimated by a non-linear regression using GraphPad Prism (San Diego, USA) software. Recombinant human-derived antibodies NI-307.13G4, NI-307.18E12, NI-307.18F4A, NI-307.19F8, NI-307.20F5 and NI-307.61D11 bound with a high affinity to JCV VP1 with an $EC_{50}$ of 2.67 nM, 4.52 nM, 125 nM, 2.08 nM, 284 pM and 3.80 nM, respectively. Recombinant human-derived antibodies NI-307.13G4, NI-307.18E12, NI-307.19F8 and NI-307.61D11 bind with a high affinity to JCV VP1 VLP with an $EC_{50}$ of 95.4 nM, 19.9 nM, 55 nM, 6.68 nM and 17.7 nM, respectively; see FIG. 2B.

Recombinant VP1 proteins and supernatants from SVG-A cells infected or not with JCV were separated on a SDS-PAGE gel and then transferred onto nitrocellulose membranes. To prepare the viral supernatant, SVG-A (human astrocytic cell line) were grown until 60-80% confluency, washed with PBS and then infected with JCV for 1 h at 37° C. Fresh medium was added afterwards and the viral supernatant was collected after 6 to 9 days production. The supernatant was cleared of the cellular debris by spinning down at 2,500 rpm for 10 mM The viral supernatant was then stored at −80° C. If necessary, the viruses were concentrated by overlaying the supernatant on a 20% sucrose cushion and then ultra centrifuging for 2 hours at 100,000 g at 4° C.

The membranes were then probed with the exemplary antibodies.

Example 5: Binding Specificity of JCV/BKV VP1 Antibodies

Direct ELISA assays were performed with varying antibody concentrations to validate the binding of the antibodies to JCV/BKV VP1 and to be able to determine their half maximal effective concentration ($EC_{50}$). For the exemplary recombinant human NI-307.3G4, NI-307.6A2, NI-307.11G6, NI-307.19F10, NI-307.24F3, NI-307.25G10, NI-307.43A11, NI-307.44F6B, NI-307.57D5 and NI-307.78C3 antibodies, 96-well microplates (Costar, Corning, USA) were coated with VP1 solutions or with BSA (Sigma-Aldrich, Buchs, Switzerland) diluted to a concentration of 5 μg/ml either in carbonate ELISA coating buffer (15 mM $Na_2CO_3$, 35 mM $NaHCO_3$, pH 9.4) or in reassociation buffer. The binding efficiency of the antibody was then tested. The exemplary NI-307.3G4, NI-307.6A2, NI-307.11G6, NI-307.19F10, NI-307.24F3, NI-307.25G10, NI-307.43A11, NI-307.44F6B, NI-307.57D5 and NI-307.78C3 antibodies specifically bind to both VP1 from the JCV and from the BKV. The antibodies NI-307.3G4, NI-307.6A2, NI-307.11G6, NI-307.19F10, NI-307.25G10, NI-307.43A11, NI-307.44F6B, NI-307.57D5 and NI-307.78C3 are binding with the same efficiency to VP1 (coating with carbonate buffer) and VP1 VLPs (coating with reassociation buffer) independently of the virus. The antibody NI-307.24F3 is binding more strongly to the VP1 than the VP1 VLPs and better to the antigen from JCV compared to BKV. No binding is observed to BSA; see FIG. 3A.

The $EC_{50}$ values were estimated by a non-linear regression using GraphPad Prism (San Diego, USA) software. Recombinant human-derived antibodies NI-307.3G4, NI-307.6A2, NI-307.11G6, NI-307.19F10, NI-307.24F3, NI-307.25G10, NI-307.43A11, NI-307.44F6B, NI-307.57D5 and NI-307.78C3 bind with a high affinity to JCV VP1 with an $EC_{50}$ of 71.0 nM, 1.59 nM, 11.6 pM, 10.1 nM, 281 pM, 605 pM, 8.07 nM, 101 pM, 38.6 nM and 859 pM, respectively. Recombinant human-derived antibodies NI-307.3G4, NI-307.6A2, NI-307.11G6, NI-307.19F10, NI-307.24F3, NI-307.25G10, NI-307.43A11, NI-307.44F6B, NI-307.57D5 and NI-307.78C3 bind with a high affinity to JCV VP1 VLP with an EC50 of 28.2 nM, 1.39 nM, 11.8 pM, 3.41 nM, 6.95 nM, 509 pM, 6.15 nM, 83 pM, 57 nM and 932 pM, respectively. Recombinant human-derived antibodies NI-307.3G4, NI-307.6A2, NI-307.11G6, NI-307.19F10, NI-307.24F3, NI-307.25G10, NI-307.43A11, NI-307.44F6B, NI-307.57D5 and NI-307.78C3 bind with a high affinity to BKV VP1 with an $EC_{50}$ of 27.4 nM, 1.79 nM, 18.8 pM, 2.41 nM, 1.04 nM, 514 pM, 9.7 nM, 600 pM, 37.5 nM and 1.96 nM, respectively Recombinant human-derived antibodies NI-307.3G4, NI-307.6A2, NI-307.11G6, NI-307.19F10, NI-307.24F3, NI-307.25G10, NI-307.43A11, NI-307.44F6B, NI-307.57D5 and NI-307.78C3 bind with a high affinity to BKV VP1 VLP with an EC50 of 16.4 nM, 1.17 nM, 38.7 pM, 1.1 nM, 28.8 nM, 172 pM, 10 nM, 200 pM, 104 nM and 939 pM, respectively; see FIG. 3B.

Example 6: Binding Specificity of BKV VP1 Antibodies

Direct ELISA assays were performed with varying antibody concentrations to validate the binding of the exemplary antibodies of the present invention to BKV VP1 and to be able to determine their half maximal effective concentration ($EC_{50}$). For the exemplary recombinant human NI-307.1E1, NI-307.5H3, NI-307.24C6 and NI-307.26E10 antibodies, 96-well microplates (Costar, Corning, USA) were coated with VP1 solutions or with BSA (Sigma-Aldrich, Buchs, Switzerland) diluted to a concentration of 5 µg/ml either in carbonate ELISA coating buffer (15 mM $Na_2CO_3$, 35 mM $NaHCO_3$, pH 9.4) or in reassociation buffer. The binding efficiency of the antibody was then tested. The exemplary NI-307.1E1, NI-307.5H3, NI-307.24C6 and NI-307.26E10 antibodies specifically and strongly bound to VP1 from the BKV and weakly to VP1 from the JCV. The antibody NI-307.1E1 is binding more efficiently on VP1 (coating with carbonate buffer) than on VP1 VLPs (coating with reassociation buffer) while the antibodies. The antibodies NI-307.24C6 and NI-307.26E10 were bound more efficiently on VP1 VLPs than on VP1. The antibody NI-307.5H3 was bound the same way if the VP1 proteins are monomeric or reassembled into VLPs. No binding was observed to BSA; see FIG. 4A.

The $EC_{50}$ values were estimated by a non-linear regression using GraphPad Prism (San Diego, USA) software. Recombinant human-derived antibodies NI-307.1E1, NI-307.5H3, NI-307.24C6 and NI-307.26E10 bound with a high affinity to BKV VP1 with an $EC_{50}$ of 6.05 nM, 362 pM, 816 pM and 1.35 nM, respectively. Recombinant human-derived antibodies NI-307.1E1, NI-307.5H3, NI-307.24C6 and NI-307.26E10 bound with a high affinity to BKV VP1 VLP with an $EC_{50}$ of 11 nM, 288 pM, 396 pM and 740 pM, respectively. Recombinant human-derived antibodies NI-307.1E1, NI-307.5H3, NI-307.24C6 and NI-307.26E10 bound with a weaker affinity to JCV VP1 with an $EC_{50}$ of 8.04 nM, 1.54 nM, 178 nM and 22.9 nM, respectively. Recombinant human-derived antibodies NI-307.1E1, NI-307.5H3, NI-307.24C6 and NI-307.26E10 bound with a weaker affinity to JCV VP1 VLP with an $EC_{50}$ of 281 nM, 1.16 nM, 2.84 nM and 14.9 nM, respectively; see FIG. 4B.

Example 7: Assessment of the Binding Epitope of the VP1 Specific Antibodies

Figure 2:
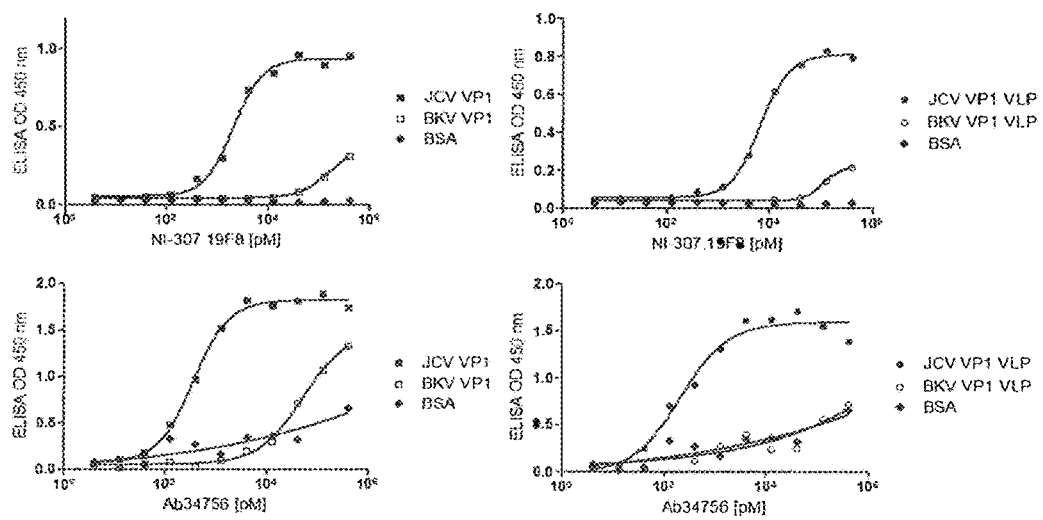
FIG. 2: Specific binding to JCV VP1 of the recombinant human-derived antibodies assessed by direct ELISA, and $EC_{50}$ determination.
- (A) Plates were incubated with the indicated concentrations of recombinant human-derived antibodies. Exemplary antibody NI-307.19F8 binds with high affinity to JCV VP1 (■, 5 μg/ml) and to JCV VP1 VLP (●, 5 μg/ml) but neither to BKV VP1 (□, 5 μg/ml) nor to BKV VP1 VLP (○, 5 μg/ml) nor to BSA (♦, 5 μg/ml). The antibody Ab34756 binds to VP1 from the JC virus (JCV) and weakly to VP1 from the BK virus (BKV) but it is also binding to BSA. The data are expressed as OD values at 450 nm.
- (B) The $EC_{50}$ values for the antibodies NI-307.13G4, NI-307.18E12, NI-307.18F4A, NI-307.19F8, NI-307.20F5, NI-307.61D11 and Ab34756 were estimated by a non-linear regression using GraphPad Prism software. N/A: not applicable
Figure 3:
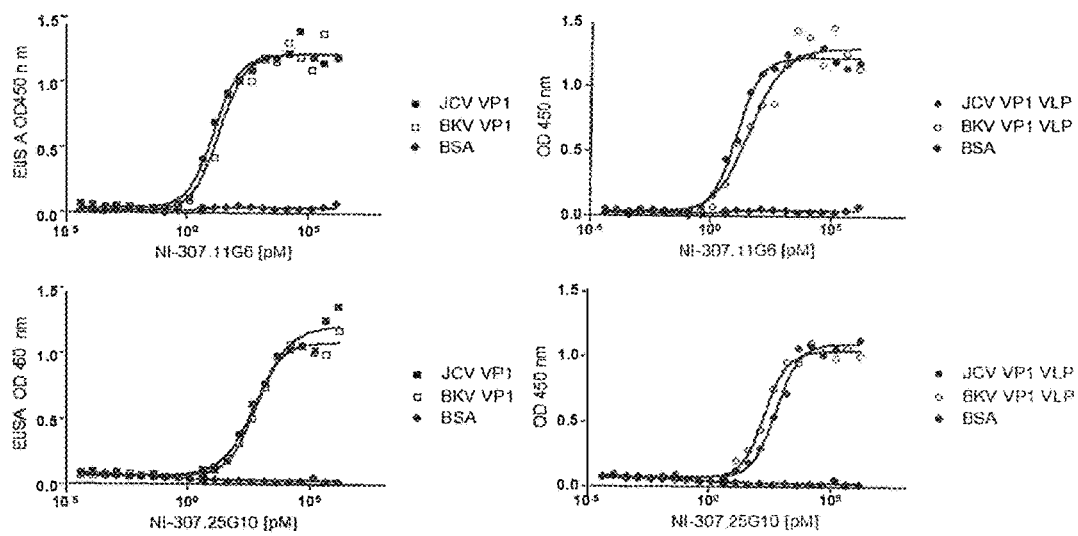
FIG. 3: Specific binding to JCV VP1 and BKV VP1 of the recombinant human-derived antibodies assessed by direct ELISA and $EC_{50}$ determination.
- (A) Plates were incubated with the indicated concentrations of recombinant human-derived antibodies. Exemplary antibodies NI-307.11G6 and NI-307.25G10 bind with high affinity to JCV VP1 (■, 5 μg/ml), JCV VP1 VLP (●, 5 μg/ml), BKV VP1 (□, 5 μg/ml) and BKV VP1 VLP (○, 5 μg/ml). The antibodies NI-307.11G6 and NI-307.25G10 do not bind to BSA (♦, 5 μg/ml). The data are expressed as OD values at 450 nm.
- (B) The $EC_{50}$ values for the antibodies NI-307.3G4, NI-307.6A2, NI-307.11G6, NI-307.19F10, NI-307.24F3, NI-307.25G10, NI-307.43A11, NI-307.44F6B, NI-307.57D5 and NI-307.78C3 were estimated by a non-linear regression using GraphPad Prism software.
Figure 4:
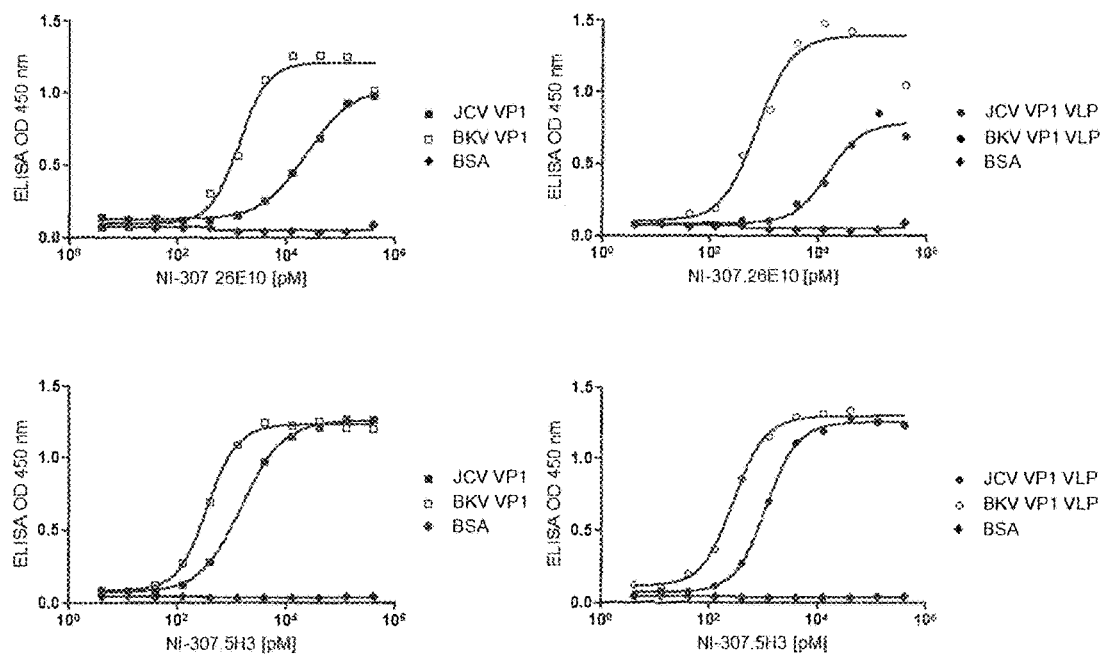
FIG. 4: Specific binding to BKV VP1 of the recombinant human-derived antibodies assessed by direct ELISA and $EC_{50}$ determination.
- (A) Plates were incubated with the indicated concentrations of recombinant human-derived antibodies. Exemplary antibodies NI-307.26E10 and NI-307.5H3 bind with high affinity to BKV VP1 (□, 5 μg/ml) and BKV VP1 VLP (○, 5 μg/ml), and weakly to JCV VP1 (■, 5 μg/ml) and JCV VP1 VLP (●, 5 μg/ml). The antibodies NI-307.26E10 and NI-307.5H3 do not bind to BSA (♦, 5 μg/ml). The data are expressed as OD values at 450 nm.
- (B) The $EC_{50}$ values for the antibodies NI-307.1E1, NI-307.5H3, NI-307.24C6 and NI-307.26E10 were estimated by a non-linear regression using GraphPad Prism software.
Figure 5:
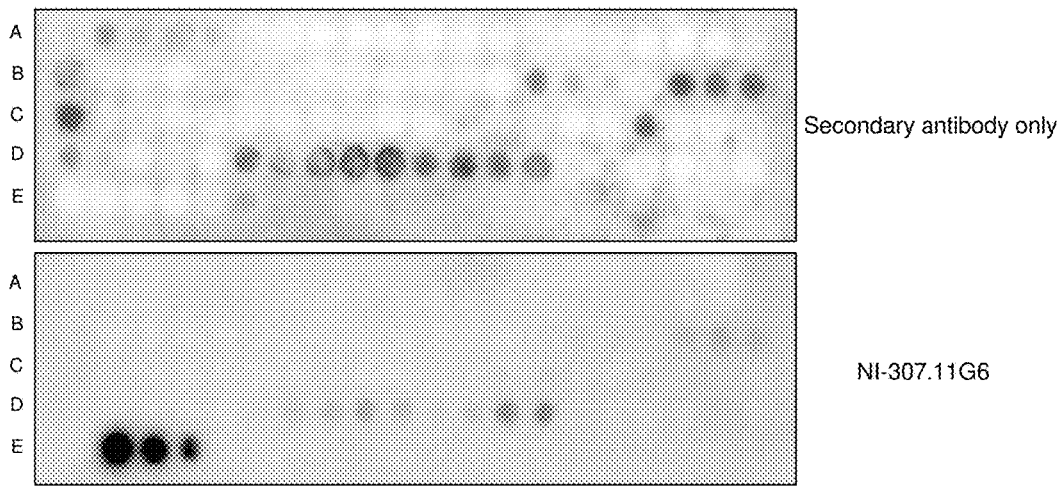
FIG. 5: VP1 binding epitopes of human-derived recombinant antibodies assessed by pepscan analysis.
- (A) Pepscan image of recombinant NI-307.11G6 human-derived antibody (1 μg/ml). NI-307.11G6 binding occurred at peptides 82, 83 and 84 (line E, 2nd, 3rd and 4th spot) covering amino acids 333-339 (peptide 82: 325-RVFEGTEELPGDPDM-339 (SEQ ID NO: 169), peptide 83: 329-GTEELPGDPDMMRYV-343 (SEQ ID NO: 170), peptide 84: 333-LPGDPDMMRYVD-KYV-343 (SEQ ID NO: 171), consensus binding sequence: LPGDPDM (SEQ ID NO: 85)). Secondary HRP-conjugated donkey anti-human IgG Fcγ only (1:20,000; secondary antibody only) was used as a control.
- (B) Identified binding epitopes of the different human-derived VP1-specific antibodies within the indicated amino acids of the VP1 protein sequence.

To determine the binding epitope of the exemplary NI-307.11G6 antibody, binding analysis was performed with overlapping peptides mapping the entire sequences of JCV VP1. Binding capacity of the antibody was tested on these peptides spotted onto a nitrocellulose membrane (JPT Peptide Technologies, Berlin, Germany) and using HRP-conjugated donkey anti-human IgG secondary antibody (Jackson immunoResearch, Newmarket, UK) followed by detection of HRP activity (FIG. 5A). In brief, epitope mapping was performed using scans of overlapping peptides. The entire sequences of JCV VP1 and BKV VP1 were synthesized as a total of respectively 86 and 88 linear 10-mer peptides with a 7 amino acid overlap between individual peptides. Those peptides were spotted onto nitrocellulose membranes (JPT Peptide Technologies, Berlin, Germany). The membrane was activated for 5 min in methanol and washed in TBS for 10 min at RT. Non-specific binding sites were blocked for 2 hours at RT with Roti®-Block (Carl Roth GmbH+Co. KG, Karlsruhe, Germany). Human antibodies (1 µg/ml) were incubated in Roti®-Block for 3 h at RT. Binding of primary antibody was determined using HRP-conjugated donkey anti-human IgG secondary antibody. Blots were developed and evaluated using ECL and ImageQuant 350 detection (GE Healthcare, Otelfingen, Switzerland).

The antibody NI-307.11G6 recognizes the spots 82, 83 and 84 (line E, 2nd, 3rd and 4th spot) which correspond to the sequence 333-LPGDPDM-339 on JCV VP1. Those amino acids are 100% conserved in the sequence of BKV VP1 what explains that this antibody is binding similarly to VP1 from JCV and BKV. The antibody NI-307.13G4 recognizes 2 regions of the JCV VP1 protein: the sequences 124-GQATHDN-130 and 340-MRYVDKYGQLQT-351. The underlined amino acids are different in the BKV VP1 protein and that would explain the fact that the antibody NI-307.13G4 binds specifically and exclusively to VP1 from the JC virus (JCV). The murine antibody Ab34756 recognizes the sequence 340-MRYVDKYGQLQT-351 (FIGS. 5A and 5B). The epitope of the other antibodies (1 and 10 µg/ml) could not be identified. This might be explained by the fact that those antibodies recognize discontinuous or conformational epitopes that cannot be identified with this method.

Example 8: Assessment of Specific Recognition of the VP1 Specific Antibodies Binding to the Virus by Electron Microscopy To determine the specific recognition of the VP1 specific antibodies to the virus, Western Blots and electron microscopy are performed. Electron microscopy is performed using VP1 preparations fixed by adding an equal volume of paraformaldehyde (4%) in PBS and incubated for 20 min at room temperature. A 7 µl droplet of the fixed sample is put on parafilm and the grid (Formvar/Carbon coated, Nickel 300 mesh) is laid on top of the droplet for 20 min. The grid is then washed 3 times for 3 min with PBS and incubated for 1 h in blocking buffer (PBS containing 10% BSA). The grid is then incubated for 30 min with the antibody Ab34756 diluted in blocking buffer. The unbound antibodies are removed by washing the grids 6 times for 3 min with PBS. The grids are then incubated for 30 min with secondary antibody (goat anti-mouse IgG, 10 nm gold). The samples are then fixed for 5 min with 1% glutaraldehyde and afterwards washed 4 times for 2 min in water. The grids are dried with filter paper and incubated for 2 min with 2% phosphotungstic acid. After final drying with a filter paper, the grids are analyzed on a Phillips EM400 at a magnification of ×25000.

Example 9: Assessment of the Neutralization Capabilities of NI-307 Antibodies Antibodies which recognize viral proteins can prevent infection e.g. by blocking the attachment of the virus to a cell, interfering with virus internalization or targeting the virus for phagocytosis or complement-mediated lysis. To test the ability of the antibodies of the present invention to block the infection by the JCV and to select antibody candidate with therapeutic potential, virus neutralization assays can be performed as outlined in the following.

In brief, antibodies which recognize viral proteins can prevent infection by neutralizing a virus in several ways, such as by blocking its attachment to a cell or interfering with uptake of the virus into a cell for uncoating and replication. To test the ability of the anti-VP1 antibodies to block the infection by the JCV, their effects on the JCV infection of some cell lines, SVG-A (human astrocytic cell line) or M03.13 (human oligodendrocytic cell line) is examined 20,000 cells are seeded on a cover slip placed in the well of a 24-well tissue culture plate. After 15-24 h of incubation at 37° C. to allow cells to adhere to the surface, the minimal concentration of the Mad-4 viral strain necessary to achieve the maximal percent infection is added to the well. The viruses are allowed to adhere to the cells for 1 h, and then the cells are cultured by standard methods in fresh media at 37° C. to allow the infection to take hold. The percent of cells infected is determined 72 h post-infection, when the cells are fixed, labeled with an antibody which recognizes viral proteins (for example Ab34756) as well as a general DNA stain, and analyzed by fluorescence microscopy to compare the total number of cells with the number of virus-containing cells. The anti-VP1 specific antibodies are added to the cells either during the viral attachment period or during post-infection incubation. The percentage of infected cells is determined in the presence and absence of anti-VP1 antibodies as described above.

In the example, the viruses were incubated for one hour at 37° C. with buffer containing either NI-307.98D3, NI-307.44F6B, NI-307.11G6, an isotype control (a human IgG1 antibody that does not bind to JCV VP1) or no antibody. The viruses were then added for one hour to SVG-A cells which were allowed to adhere on the surface of the cover slip. The cells were then washed with PBS and fresh media was added. The infection of the cells was determined 72 hours later as described above. The exemplary NI-307.98D3 and NI-307.44F6B antibodies were able to completely block the infection of the SVG-A cells by JCV while NI-307.11G6 and the isotype control antibody could not; see FIG. 10A.

The exemplary NI-307.7J3, NI-307.26A3, NI-307.27C2, NI-307.27C11, NI-307.29B1, NI-307.44F6B, NI-307.45E10, NI-307.47B11, NI-307.50H4, NI-307.53B11, NI-307.56A8, NI-307.57D4, NI-307.58C7, NI-307.59A7, NI-307.72F10, NI-307.98D3, NI-307.98H1, NI-307.105A6 and NI-307.105C7 antibodies were able to totally block the infection of the SVG-A cells by JCV in the above described conditions.

To determine the potency of the exemplary NI-307.98D3 antibody to neutralize the JCV infection, the viruses were incubated with decreasing amount of antibody before adding them to the SVG-A cells as described above. The IC50 was determined as the antibody concentration for which one the infectivity was 50% inhibited (the maximal number of infected cells was determined in the absence of antibody). The exemplary NI-307.98D3 antibody could efficiently inhibit even at low concentration the infection of the SVG-A cells with an IC50 of 0.8 ng/mL whereas the isotype control antibody did not block the infection; see FIG. 10B.

When an antibody is not effective at blocking JCV attachment to glial cells or viral replication within these cells in the assays, its ability to block the spread of the virus between cells is also tested. In this assay, the ability of an antibody to reduce the spread of the viruses from SVG-A cells to M03.13 cells is assessed. SVG-A cells are infected with Mad-4 as in the basic infection protocol, but the cells are grown post-infection with an equal number of M03.13 cells which had not been exposed to JCV. This post-infection culture includes either an antibody for a neutralization test or no antibody for a control reaction. The percentage of infected and uninfected cells is determined after one or two weeks of culture by the immunofluorescence procedure described above, with the difference that an oligodendrocyte-specific antibody (example) is added to the immunostaining in order to distinguish cells of the SVG-A astrocyte cell line from those of the M03.13 oligodendrocyte cell line. The JCV-neutralizing antibodies that are identified in the cell line assays can be further verified in primary glial cells.

To investigate complement-mediated neutralization of JCV, the infectivity rate of JCV-permissive cell lines SVG-A and M03.13 with the Mad-4 viral strain in the presence or absence of complement factors is analyzed. For these experiments free JCV virions are preincubated for 30 min with different concentrations of anti-VP1 antibodies and either heat-inactivated or untreated human sera prior to infection. The heat inactivation (56° C. for 30 min) of human sera leads to destruction of the complement factors and serves as a control. After the preincubation, the aforementioned cell lines are cultured with the pretreated viral supernatants. The infectivity rate of JCV is assayed 72 h post infection (p.i.) by staining with an anti-VP1 antibody and subsequent analysis by fluorescence microscopy, as previously explained.

Antibody-mediated phagocytosis of JCV is addressed by using the JCV Mad-4 strain preincubated with anti-VP1 antibodies and co-cultured with antigen-presenting cells. In detail, UV-inactivated (protocol) JCV supernatants are preincubated with different concentrations of anti-VP1 antibodies and co-cultured with monocyte-derived macrophages (generated by addition of M-CSF) or EBV transformed B cells from PML patients. The UV-inactivation blocks replication and spreading of the virus. Phagocytosed viruses are analyzed by treating the antigen-presenting cells with endolysosomal degradation inhibiting agents (such as Chloroquine) and subsequent staining with anti-VP1 antibody and analysis with fluorescence microscopy. As additional read-out for phagocytosis we co-cultured the antigen-presenting cells with anti-VP1-coated JCV virions and autologous JCV-specific T cells from the same PML patients as the antigen-presenting cells. These JCV-specific T cells are obtained from brain biopsies of a PML-IRIS and a JCV-Granule Cell Neuronopathy patient. As the phagocytosis of JCV virions by antigen-presenting cells lead to enhanced presentation of JCV-specific peptides on HLA molecules, these T cells are able to react due to the HLA-matching in the autologous setup. The reactivity of T cells is measured by proliferation (incorporation of CFSE) or cytokine production. To rule out, if addition of complement enhanced the antibody-mediated phagocytosis, the assays are also performed in the presence of human sera.

Antibody-mediated lysis (ADCC or CDC) of JCV-infected cells is tested by using JCV-infected cell lines incubated with different concentrations of anti-VP1 antibodies and either natural killer cells for analysis of ADCC or human sera for analysis of CDC. Lysis of JCV-infected cells is monitored by using Europium, Chromium or fluorochrome-based Cytotoxicity assays.

Example 10: Isolation of VP1 Specific Antibodies from Post-PML-IRIS Patient

To analyze whether the patients who recovered after developing PML-IRIS have mounted a protective humoral immune response against the JCV, blood samples were collected from a healthy donor and from patients that have successfully recovered from PML and PML-IRIS. While memory B cells from both groups of donors were producing similar amounts of immunoglobulins, significantly higher numbers of memory B cells producing antibodies binding strongly and specifically to VP1 were found in one donor recovered from PML and PML-IRIS while a second such donor did not show increased numbers of VP1 reactive B-cells. Interestingly, most of the VP1-specific B-cells from the high frequency donor were recognizing specifically the VP1 protein from the JC virus when properly assembled as VLP. Some antibodies were binding to the VP1 protein from JCV and BKV probably due to the high homology between the major capsid protein of those two viruses.

Those antibodies were cloned and expressed as previously described. It could be confirmed that antibodies specifically binding to the VP1 protein from JCV and not BKV could be obtained. The exemplary antibodies NI-307.58C7 and NI-307.105C7 only recognized JCV VP1 when the VLP were assembled (JCV VP1 VLP) and not when the particles were disrupted (JCV VP1); see FIG. 7A. The fact that those antibodies only recognize the VLP suggests that their binding epitope is either conformational or discontinuous. This epitope would be only presented and recognizable in correctly assembled VLPs are formed and would be a preferred epitope for a neutralizing antibody.

The exemplary antibodies obtained from the high hit frequency donor were cloned and recombinantly expressed. Direct ELISA assays were performed with varying antibody concentrations to validate the binding of the antibodies to JCV/BKV VP1 forming VLPs or not and to be able to determine their half maximal effective concentration (EC50). For the exemplary recombinant human NI-307.7J3, NI-307.26A3, NI-307.27C2, NI-307.27C11, NI-307.29B1, NI-307.43E8, NI-307.45E10, NI-307.47B11, NI-307.50H4, NI-307.53B11, NI-307.56A8, NI-307.57D4, NI-307.58C7, NI-307.59A7, NI-307.72F7, NI-307.72F10, NI-307.98D3, NI-307.98H1, NI-307.105A6 and NI-307.105C7 antibodies, 96-well microplates (Costar, Corning, USA) were coated with VP1 solutions or with BSA (Sigma-Aldrich, Buchs, Switzerland) diluted to a concentration of 5 µg/ml either in carbonate ELISA coating buffer (15 mM $Na_2CO_3$, 35 mM $NaHCO_3$, pH 9.4) or in reassociation buffer. The binding efficiency of the antibody was then tested. The exemplary NI-307.29B1, NI-307.43E8 and NI-307.72F7 antibodies specifically bind to both VP1 from the JCV and from the BKV. The antibodies NI-307.7J3, NI-307.26A3, NI-307.27C2, NI-307.27C11, NI-307.45E10, NI-307.47B11, NI-307.50H4, NI-307.53B11, NI-307.56A8, NI-307.57D4, NI-307.58C7, NI-307.59A7, NI-307.72F10, NI-307.98D3, NI-307.98H1, NI-307.105A6 and NI-307.105C7 are binding specifically and exclusively to VP1 from the JCV and not to VP1 from the BKV. The exemplary NI-307.7J3, NI-307.26A3, NI-307.27C2, NI-307.27C11, NI-307.29B1, NI-307.43E8, NI-307.47B11, NI-307.50H4, NI-307.53B11, NI-307.56A8, NI-307.57D4, NI-307.58C7, NI-307.59A7, NI-307.72F10, NI-307.98D3, NI-307.98H1, NI-307.105A6 and NI-307.105C7 antibodies are binding preferentially to the JCV VP1 when the VLPs were assembled; see FIG. 7B.

Example 11: Assessment of the Binding in Solution to VLPs and JCV

To determine the ability of the exemplary NI-307.98D3, NI-307.44F6B, and NI-307.11G6 antibodies to bind in solution to VP1 VLPs and JC virus, a flow cytometry assay was performed. In brief, latex beads were incubated with either VP1 VLPs (recombinant VP1 protein assembled into VLPs in reassociation buffer) or JCV (purified from the supernatant of infected SVG-A cells) for 30 min at room temperature to allow them to attach. The beads were then washed and incubated with the exemplary antibodies and then the secondary antibody. The binding of the exemplary antibodies to the VP1 VLPs or JCV was assessed by flow cytometry.

The exemplary NI-307.98D3, NI-307.44F6B, and NI-307.11G6 antibodies were able to bind in solution to VP1 VLPs attached to latex beads while the isotype control (human IgG1 which is not recognizing VP1) did not show any signal; see FIG. 9A.

The exemplary NI-307.98D3, NI-307.44F6B and NI-307.11G6 antibodies were also able to bind in solution to JCV attached to latex beads while the isotype control did not show any signal; see FIG. 9B.

Example 12: Binding of the Exemplary Antibodies to PML-Associated VP1 Mutants

To determine the ability of the exemplary NI-307.11G6, NI-307.98D3, NI-307.27C11, and NI-307.53B11 antibodies to neutralize the most common JCV variants, the binding of the antibodies to VP1 mutants was tested.

JC viruses isolated from the CSF of patients with PML often contain conserved mutations in the VP1 sequences. It is therefore important to study the ability of the exemplary antibodies to bind to those VP1 mutants. In brief, point mutations were introduced in the VP1 sequence with the quick change mutagenesis kit. The mutants were chosen to cover the most frequent JCV variants found in the CSF of the PML patients. The constructed VP1 mutants were VP1 L55F S269F, VP1 L55F S267F, VP1 L55F N265D, and VP1 GCN (N74S R75K T128A L158V K345R Q350 deletion T351 deletion, a mutant found in a patient with granule cell neuronopathy). 293TT were transfected with those VP1 mutants constructs, fixed and permeabilized 3-day post transfection, and stained with the exemplary NI-307.11G6, NI-307.98D3, NI-307.27C11 and NI-307.53B11 antibodies. The cells were then analyzed by flow cytometry to determine the binding of the exemplary antibodies to the VP1 mutants.

The exemplary NI-307.11G6 antibody is binding to the VP1 L55F S269F, VP1 L55F S267F, VP1 L55F N265D and VP1 GCN mutants and the WT VP1. NI-307.11G6 is known to bind to the region 333-LPGDPDM-339 on JCV VP1 which is not modified in those mutants.

The exemplary NI-307.98D3 antibody is binding to the VP1 GCN mutant and the WT VP1 but did not show binding to VP1 L55F S269F, VP1 L55F S267F and VP1 L55F N265D mutants. The binding epitope of NI-307.98D3 is not known and could be present in this region where other mutations were introduced. NI-307.98D3 was also shown to bind strongly and preferentially to the VP1 when the VLPs were properly assembled compared to the disrupted VLPs. That suggested that its binding epitope was either conformational or discontinuous and that such an epitope would be mainly presented and recognizable in correctly assembled VLPs. So the introduced mutations could destabilize or change the VLP structure and therefore block the binding of NI-307.98D3 to such mutants or hide or modify the epitope.

The exemplary NI-307.27C11 antibody is binding strongly to the VP1 GCN mutant and the WT VP1 and less strongly to VP1 L55F S269F, VP1 L55F S267F and VP1 L55F N265D mutants. The exemplary NI-307.53B11 antibody is binding strongly to the VP1 L55F S269F, VP1 GCN mutant and the WT VP1 and less strongly to VP1 L55F S267F and VP1 L55F N265D mutants. The binding epitope of the exemplary NI-307.27C11 and NI-307.53B11 antibodies is not known and could be present in this region where other mutations were introduced. NI-307.27C11 and NI-307.53B11 were also shown to bind strongly and preferentially to the VP1 when the VLPs were properly assembled compared to the disrupted VLPs. That suggested that its binding epitope was either conformational or discontinuous and that such an epitope would be mainly presented and recognizable in correctly assembled VLPs. So the introduced mutations could destabilize or change the VLP structure and therefore diminish the binding of NI-307.27C11 and NI-307.53B11 to such mutants or hide or modify the epitope; see FIG. 11.

The exemplary NI-307.72F7 and NI-307.72F10 antibodies are binding strongly to VP1 L55F S269F, VP1 GCN mutant and the WT VP1 and less strongly to VP1 L55F S267F and VP1 L55F N265D mutants. The exemplary NI-307.29B1 antibody is binding strongly to the VP1 L55F S269F mutant and the WT VP1 and less strongly to VP1 L55F S267F, VP1 L55F N265D and VP1 GCN mutants. The exemplary NI-307.56A8 and NI-307.27C2 antibodies are binding strongly to VP1 L55F S269F, VP1 GCN mutant and the WT VP1 and less strongly to VP1 L55F N265D mutant. The exemplary NI-307.44F6B antibody is binding strongly to VP1 L55F S269F, VP1 GCN mutant and the WT VP1 and less strongly to VP1 L55F S267F mutant. The exemplary NI-307.58C7 and NI-307.98H1 antibodies are binding strongly to VP1 L55F S269F, VP1 GCN mutant and the WT VP1. The exemplary NI-307.50H4 and NI-307.105A6 antibodies are binding strongly to the VP1 GCN mutant and the WT VP1 and less strongly to VP1 L55F S269F, VP1 L55F S267F and VP1 L55F N265D mutants. The exemplary NI-307.45E10, NI-307.105C7, NI-307.26A3, NI-307.7J3 and NI-307.59A7 antibodies are binding strongly to the VP1 GCN mutant and the WT VP1. The exemplary NI-307.47B11 antibody is binding strongly to the WT VP1 and less strongly to VP1 L55F S267F, VP1 L55F S269F and VP1 GCN mutants.

The invention claimed is:

1. A polynucleotide encoding at least a binding domain of a variable region of an immunoglobulin chain of a human monoclonal antibody or an antigen-binding fragment thereof capable of binding to a polyomavirus and/or antigen thereof, linked to a heterologous nucleic acid, wherein the polynucleotide is selected from the group consisting of:
  (a) a polynucleotide encoding an immunoglobulin heavy chain or a fragment thereof comprising a $V_H$ variable region comprising CDRs 1, 2, and 3 of the $V_H$ variable region amino acid sequence of
    (i) SEQ ID NO: 2, wherein the $V_H$ variable region when paired with a $V_L$ variable region comprising the amino acid sequence set forth in SEQ ID NO: 4 binds to a polyomavirus and/or an antigen thereof;
    (ii) SEQ ID NO: 6, wherein the $V_H$ variable region when paired with a $V_L$ variable region comprising the amino acid sequence set forth in SEQ ID NO: 8 binds to a polyomavirus and/or an antigen thereof;
    (iii) SEQ ID NO: 10, wherein the $V_H$ variable region when paired with a $V_L$ variable region comprising the amino acid sequence set forth in SEQ ID NO: 12 binds to a polyomavirus and/or an antigen thereof;
    (iv) SEQ ID NO: 14, wherein the $V_H$ variable region when paired with a $V_L$ variable region comprising the amino acid sequence set forth in SEQ ID NO: 16 binds to a polyomavirus and/or an antigen thereof;
    (v) SEQ ID NO: 18, wherein the $V_H$ variable region when paired with a $V_L$ variable region comprising the amino acid sequence set forth in SEQ ID NO: 20 binds to a polyomavirus and/or an antigen thereof;
    (vi) SEQ ID NO: 22, wherein the $V_H$ variable region when paired with a $V_L$ variable region comprising the amino acid sequence set forth in SEQ ID NO: 24 binds to a polyomavirus and/or an antigen thereof;
    (vii) SEQ ID NO: 26, wherein the $V_H$ variable region when paired with a $V_L$ variable region comprising the amino acid sequence set forth in SEQ ID NO: 28 binds to a polyomavirus and/or an antigen thereof;
    (viii) SEQ ID NO: 30, wherein the $V_H$ variable region when paired with a $V_L$ variable region comprising the amino acid sequence set forth in SEQ ID NO: 32 binds to a polyomavirus and/or an antigen thereof;
    (ix) SEQ ID NO: 34, wherein the $V_H$ variable region when paired with a $V_L$ variable region comprising the amino acid sequence set forth in SEQ ID NO: 36 binds to a polyomavirus and/or an antigen thereof;
    (x) SEQ ID NO: 38, wherein the $V_H$ variable region when paired with a $V_L$ variable region comprising the amino acid sequence set forth in SEQ ID NO: 40 binds to a polyomavirus and/or an antigen thereof;
(xi) SEQ ID NO: 42, wherein the $V_H$ variable region when paired with a $V_L$ variable region comprising the amino acid sequence set forth in SEQ ID NO: 44 binds to a polyomavirus and/or an antigen thereof;
(xii) SEQ ID NO: 46, wherein the $V_H$ variable region when paired with a $V_L$ variable region comprising the amino acid sequence set forth in SEQ ID NO: 48 binds to a polyomavirus and/or an antigen thereof;
(xiii) SEQ ID NO: 50, wherein the $V_H$ variable region when paired with a $V_L$ variable region comprising the amino acid sequence set forth in SEQ ID NO: 52 binds to a polyomavirus and/or an antigen thereof;
(xiv) SEQ ID NO: 54, wherein the $V_H$ variable region when paired with a $V_L$ variable region comprising the amino acid sequence set forth in SEQ ID NO: 56 binds to a polyomavirus and/or an antigen thereof;
(xv) SEQ ID NO: 58, wherein the $V_H$ variable region when paired with a $V_L$ variable region comprising the amino acid sequence set forth in SEQ ID NO: 60 binds to a polyomavirus and/or an antigen thereof;
(xvi) SEQ ID NO: 62, wherein the $V_H$ variable region when paired with a $V_L$ variable region comprising the amino acid sequence set forth in SEQ ID NO: 64 binds to a polyomavirus and/or an antigen thereof;
(xvii) SEQ ID NO: 66, wherein the $V_H$ variable region when paired with a $V_L$ variable region comprising the amino acid sequence set forth in SEQ ID NO: 68 binds to a polyomavirus and/or an antigen thereof;
(xviii) SEQ ID NO: 70, wherein the $V_H$ variable region when paired with a $V_L$ variable region comprising the amino acid sequence set forth in SEQ ID NO: 72 binds to a polyomavirus and/or an antigen thereof;
(xix) SEQ ID NO: 74, wherein the $V_H$ variable region when paired with a $V_L$ variable region comprising the amino acid sequence set forth in SEQ ID NO: 76 binds to a polyomavirus and/or an antigen thereof;
(xx) SEQ ID NO: 78, wherein the $V_H$ variable region when paired with a $V_L$ variable region comprising the amino acid sequence set forth in SEQ ID NO: 80 binds to a polyomavirus and/or an antigen thereof;
(xxi) SEQ ID NO: 82, wherein the $V_H$ variable region when paired with a $V_L$ variable region comprising the amino acid sequence set forth in SEQ ID NO: 84 binds to a polyomavirus and/or an antigen thereof;
(xxii) SEQ ID NO: 90, wherein the $V_H$ variable region when paired with a $V_L$ variable region comprising the amino acid sequence set forth in SEQ ID NO: 92 binds to a polyomavirus and/or an antigen thereof;
(xxiii) SEQ ID NO: 94, wherein the $V_H$ variable region when paired with a $V_L$ variable region comprising the amino acid sequence set forth in SEQ ID NO: 96 binds to a polyomavirus and/or an antigen thereof;
(xxiv) SEQ ID NO: 98, wherein the $V_H$ variable region when paired with a $V_L$ variable region comprising the amino acid sequence set forth in SEQ ID NO: 100 binds to a polyomavirus and/or an antigen thereof;
(xxv) SEQ ID NO: 102, wherein the $V_H$ variable region when paired with a $V_L$ variable region comprising the amino acid sequence set forth in SEQ ID NO: 104 binds to a polyomavirus and/or an antigen thereof;
(xxvi) SEQ ID NO: 106, wherein the $V_H$ variable region when paired with a $V_L$ variable region comprising the amino acid sequence set forth in SEQ ID NO: 108 binds to a polyomavirus and/or an antigen thereof;
(xxvii) SEQ ID NO: 114, wherein the $V_H$ variable region when paired with a $V_L$ variable region comprising the amino acid sequence set forth in SEQ ID NO: 116 binds to a polyomavirus and/or an antigen thereof;
(xxviii) SEQ ID NO: 118, wherein the $V_H$ variable region when paired with a $V_L$ variable region comprising the amino acid sequence set forth in SEQ ID NO: 120 binds to a polyomavirus and/or an antigen thereof;
(xxix) SEQ ID NO: 122, wherein the $V_H$ variable region when paired with a $V_L$ variable region comprising the amino acid sequence set forth in SEQ ID NO: 124 binds to a polyomavirus and/or an antigen thereof;
(xxx) SEQ ID NO: 126, wherein the $V_H$ variable region when paired with a $V_L$ variable region comprising the amino acid sequence set forth in SEQ ID NO: 128 binds to a polyomavirus and/or an antigen thereof;
(xxxi) SEQ ID NO: 130, wherein the $V_H$ variable region when paired with a $V_L$ variable region comprising the amino acid sequence set forth in SEQ ID NO: 132 binds to a polyomavirus and/or an antigen thereof;
(xxxii) SEQ ID NO: 134, wherein the $V_H$ variable region when paired with a $V_L$ variable region comprising the amino acid sequence set forth in SEQ ID NO: 136 binds to a polyomavirus and/or an antigen thereof;
(xxxiii) SEQ ID NO: 138, wherein the $V_H$ variable region when paired with a $V_L$ variable region comprising the amino acid sequence set forth in SEQ ID NO: 140 binds to a polyomavirus and/or an antigen thereof;
(xxxiv) SEQ ID NO: 142, wherein the $V_H$ variable region when paired with a $V_L$ variable region comprising the amino acid sequence set forth in SEQ ID NO: 144 binds to a polyomavirus and/or an antigen thereof;
(xxxv) SEQ ID NO: 146, wherein the $V_H$ variable region when paired with a $V_L$ variable region comprising the amino acid sequence set forth in SEQ ID NO: 148 binds to a polyomavirus and/or an antigen thereof;
(xxxvi) SEQ ID NO: 150, wherein the $V_H$ variable region when paired with a $V_L$ variable region comprising the amino acid sequence set forth in SEQ ID NO: 152 binds to a polyomavirus and/or an antigen thereof;
(xxxvii) SEQ ID NO: 154, wherein the $V_H$ variable region when paired with a $V_L$ variable region comprising the amino acid sequence set forth in SEQ ID NO: 156 binds to a polyomavirus and/or an antigen thereof;
(xxxviii) SEQ ID NO: 158, wherein the $V_H$ variable region when paired with a $V_L$ variable region comprising the amino acid sequence set forth in SEQ ID NO: 160 binds to a polyomavirus and/or an antigen thereof;
(xxxix) SEQ ID NO: 162, wherein the $V_H$ variable region when paired with a $V_L$ variable region comprising the amino acid sequence set forth in SEQ ID NO: 164 binds to a polyomavirus and/or an antigen thereof; or (xl) SEQ ID NO: 166, wherein the $V_H$ variable region when paired with a $V_L$ variable region comprising the amino acid sequence set forth in SEQ ID NO: 168 binds to a polyomavirus and/or an antigen thereof;

(b) a polynucleotide encoding an immunoglobulin light chain or a fragment thereof comprising a $V_L$ variable region comprising CDRs 1, 2, and 3 of the $V_L$ variable region amino acid sequence of (i) SEQ ID NO: 4, wherein the $V_L$ variable region when paired with a $V_H$ variable region comprising the amino acid sequence set forth in SEQ ID NO: 2 binds to a polyomavirus and/or an antigen thereof;

(ii) SEQ ED NO: 8, wherein the $V_H$ variable region when paired with a $V_L$ variable region comprising the amino acid sequence set forth in SEQ ID NO: 6 binds to a polyomavirus and/or an antigen thereof;

(iii) SEQ ID NO: 12, wherein the $V_H$ variable region when paired with a $V_L$ variable region comprising the amino acid sequence set forth in SEQ ID NO: 10 binds to a polyomavirus and/or an antigen thereof;

(iv) SEQ ID NO: 16, wherein the $V_H$ variable region when paired with a $V_L$ variable region comprising the amino acid sequence set forth in SEQ ID NO: 14 binds to a polyomavirus and/or an antigen thereof;

(v) SEQ ID NO: 20, wherein the $V_H$ variable region when paired with a $V_L$ variable region comprising the amino acid sequence set forth in SEQ ID NO: 18 binds to a polyomavirus and/or an antigen thereof;

(vi) SEQ ID NO: 24, wherein the $V_H$ variable region when paired with a $V_L$ variable region comprising the amino acid sequence set forth in SEQ ID NO: 22 binds to a polyomavirus and/or an antigen thereof;

(vii) SEQ ID NO: 28, wherein the $V_H$ variable region when paired with a $V_L$ variable region comprising the amino acid sequence set forth in SEQ ID NO: 26 binds to a polyomavirus and/or an antigen thereof;

(viii) SEQ ID NO: 32, wherein the $V_H$ variable region when paired with a $V_L$ variable region comprising the amino acid sequence set forth in SEQ ID NO: 30 binds to a polyomavirus and/or an antigen thereof;

(ix) SEQ ID NO: 36, wherein the $V_H$ variable region when paired with a $V_L$ variable region comprising the amino acid sequence set forth in SEQ ID NO: 34 binds to a polyomavirus and/or an antigen thereof;

(x) SEQ ID NO: 40, wherein the $V_H$ variable region when paired with a $V_L$ variable region comprising the amino acid sequence set forth in SEQ ID NO: 38 binds to a polyomavirus and/or an antigen thereof;

(xi) SEQ ID NO: 44, wherein the $V_H$ variable region when paired with a $V_L$ variable region comprising the amino acid sequence set forth in SEQ ID NO: 42 binds to a polyomavirus and/or an antigen thereof;

(xii) SEQ ID NO: 48, wherein the $V_H$ variable region when paired with a $V_L$ variable region comprising the amino acid sequence set forth in SEQ ID NO: 46 binds to a polyomavirus and/or an antigen thereof; #

(xiii) SEQ ID NO: 52, wherein the $V_H$ variable region when paired with a $V_L$ variable region comprising the amino acid sequence set forth in SEQ ID NO: 50 binds to a polyomavirus and/or an antigen thereof;

(xiv) SEQ ID NO: 56, wherein the $V_H$ variable region when paired with a $V_L$ variable region comprising the amino acid sequence set forth in SEQ ID NO: 54 binds to a polyomavirus and/or an antigen thereof;

(xv) SEQ ID NO: 60, wherein the $V_H$ variable region when paired with a $V_L$ variable region comprising the amino acid sequence set forth in SEQ ID NO: 58 binds to a polyomavirus and/or an antigen thereof;

(xvi) SEQ ID NO: 64, wherein the $V_H$ variable region when paired with a $V_L$ variable region comprising the amino acid sequence set forth in SEQ ID NO: 62 binds to a polyomavirus and/or an antigen thereof;

(xvii) SEQ ID NO: 68, wherein the $V_H$ variable region when paired with a $V_L$ variable region comprising the amino acid sequence set forth in SEQ ID NO: 66 binds to a polyomavirus and/or an antigen thereof;

(xviii) SEQ ID NO: 72, wherein the $V_H$ variable region when paired with a $V_L$ variable region comprising the amino acid sequence set forth in SEQ ID NO: 70 binds to a polyomavirus and/or an antigen thereof;

(xix) SEQ ID NO: 76, wherein the $V_H$ variable region when paired with a $V_L$ variable region comprising the amino acid sequence set forth in SEQ ID NO: 74 binds to a polyomavirus and/or an antigen thereof;

(xx) SEQ ID NO: 80, wherein the $V_H$ variable region when paired with a $V_L$ variable region comprising the amino acid sequence set forth in SEQ ID NO: 78 binds to a polyomavirus and/or an antigen thereof;

(xxi) SEQ ID NO: 84, wherein the $V_H$ variable region when paired with a $V_L$ variable region comprising the amino acid sequence set forth in SEQ ID NO: 82 binds to a polyomavirus and/or an antigen thereof;

(xxii) SEQ ID NO: 92, wherein the $V_H$ variable region when paired with a $V_L$ variable region comprising the amino acid sequence set forth in SEQ ID NO: 90 binds to a polyomavirus and/or an antigen thereof;

(xxiii) SEQ ID NO: 96, wherein the $V_H$ variable region when paired with a $V_L$ variable region comprising the amino acid sequence set forth in SEQ ID NO: 94 binds to a polyomavirus and/or an antigen thereof;

(xxiv) SEQ ID NO: 100, wherein the $V_H$ variable region when paired with a $V_L$ variable region comprising the amino acid sequence set forth in SEQ ID NO: 98 binds to a polyomavirus and/or an antigen thereof;

(xxv) SEQ ID NO: 104, wherein the $V_H$ variable region when paired with a $V_L$ variable region comprising the amino acid sequence set forth in SEQ ID NO: 102 binds to a polyomavirus and/or an antigen thereof;

(xxvi) SEQ ID NO: 108, wherein the $V_H$ variable region when paired with a $V_L$ variable region comprising the amino acid sequence set forth in SEQ ID NO: 106 binds to a polyomavirus and/or an antigen thereof;

(xxvii) SEQ ID NO: 116, wherein the $V_H$ variable region when paired with a $V_L$ variable region comprising the amino acid sequence set forth in SEQ ID NO: 114 binds to a polyomavirus and/or an antigen thereof;

(xxviii) SEQ ID NO: 120, wherein the $V_H$ variable region when paired with a $V_L$ variable region comprising the amino acid sequence set forth in SEQ ID NO: 118 binds to a polyomavirus and/or an antigen thereof;

(xxix) SEQ ID NO: 124, wherein the $V_H$ variable region when paired with a $V_L$ variable region comprising the amino acid sequence set forth in SEQ ID NO: 122 binds to a polyomavirus and/or an antigen thereof;
(xxx) SEQ ID NO: 128, wherein the $V_H$ variable region when paired with a $V_L$ variable region comprising the amino acid sequence set forth in SEQ ID NO: 126 binds to a polyomavirus and/or an antigen thereof;
(xxxi) SEQ ID NO: 132, wherein the $V_H$ variable region when paired with a $V_L$ variable region comprising the amino acid sequence set forth in SEQ ID NO: 130 binds to a polyomavirus and/or an antigen thereof;
(xxxii) SEQ ID NO: 136, wherein the $V_H$ variable region when paired with a $V_L$ variable region comprising the amino acid sequence set forth in SEQ ID NO: 134 binds to a polyomavirus and/or an antigen thereof;
(xxxiii) SEQ ID NO: 140, wherein the $V_H$ variable region when paired with a $V_L$ variable region comprising the amino acid sequence set forth in SEQ ID NO: 138 binds to a polyomavirus and/or an antigen thereof;
(xxxiv) SEQ ID NO: 144, wherein the $V_H$ variable region when paired with a $V_L$ variable region comprising the amino acid sequence set forth in SEQ ID NO: 142 binds to a polyomavirus and/or an antigen thereof;
(xxxv) SEQ ID NO: 148, wherein the $V_H$ variable region when paired with a $V_L$ variable region comprising the amino acid sequence set forth in SEQ ID NO: 146 binds to a polyomavirus and/or an antigen thereof;
(xxxvi) SEQ ID NO: 152, wherein the $V_H$ variable region when paired with a $V_L$ variable region comprising the amino acid sequence set forth in SEQ ID NO: 150 binds to a polyomavirus and/or an antigen thereof;
(xxxvii) SEQ ID NO: 156, wherein the $V_H$ variable region when paired with a $V_L$ variable region comprising the amino acid sequence set forth in SEQ ID NO: 154 binds to a polyomavirus and/or an antigen thereof;
(xxxviii) SEQ ID NO: 160, wherein the $V_H$ variable region when paired with a $V_L$ variable region comprising the amino acid sequence set forth in SEQ ID NO: 158 binds to a polyomavirus and/or an antigen thereof;
(xxxix) SEQ ID NO: 164, wherein the $V_H$ variable region when paired with a $V_L$ variable region comprising the amino acid sequence set forth in SEQ ID NO: 162 binds to a polyomavirus and/or an antigen thereof; or
(xl) SEQ ID NO: 168, wherein the $V_H$ variable region when paired with a $V_L$ variable region comprising the amino acid sequence set forth in SEQ ID NO: 166 binds to a polyomavirus and/or an antigen thereof;
(c) a polynucleotide encoding
an immunoglobulin heavy chain or a fragment thereof comprising a $V_H$ variable region and an immunoglobulin light chain or a fragment thereof comprising a $V_L$ variable region comprising CDRs 1, 2, and 3 of the $V_H$ and $V_L$ variable region amino acid sequences of
(i) SEQ ID NO: 2 and SEQ ID NO: 4, respectively;
(ii) SEQ ID No: 6 and SEQ NO: 8, respectively;
(iii) SEQ ID No: 10 and SEQ NO: 12, respectively;
(iv) SEQ ID No: 14 and SEQ NO: 16, respectively;
(v) SEQ ID No: 18 and SEQ NO: 20, respectively;
(vi) SEQ ID No: 22 and SEQ NO: 24, respectively;
(vii) SEQ ID No: 26 and SEQ NO: 28, respectively;
(viii) SEQ ID No: 30 and SEQ NO: 32, respectively;
(ix) SEQ ID No: 34 and SEQ NO: 36, respectively;
(x) SEQ ID No: 38 and SEQ NO: 40, respectively;
(xi) SEQ ID No: 42 and SEQ NO: 44, respectively;
(xii) SEQ ID No: 46 and SEQ NO: 48, respectively;
(xiii) SEQ ID No: 50 and SEQ NO: 52, respectively;
(xiv) SEQ ID No: 54 and SEQ NO: 56, respectively;
(xv) SEQ ID No: 58 and SEQ NO: 60, respectively;
(xvi) SEQ ID No: 62 and SEQ NO: 64, respectively;
(xvii) SEQ ID No: 66 and SEQ NO: 68, respectively;
(xviii) SEQ ID No: 70 and SEQ NO: 72, respectively;
(xix) SEQ ID No: 74 and SEQ NO: 76, respectively;
(xx) SEQ ID No: 78 and SEQ NO: 80, respectively;
(xxi) SEQ ID No: 82 and SEQ NO: 84, respectively;
(xxii) SEQ ID No: 90 and SEQ NO: 92, respectively;
(xxiii) SEQ ID No: 94 and SEQ NO: 96, respectively;
(xxiv) SEQ ID No: 98 and SEQ NO: 100, respectively;
(xxv) SEQ ID No: 102 and SEQ NO: 104, respectively;
(xxvi) SEQ ID No: 106 and SEQ NO: 108, respectively;
(xxvii) SEQ ID No: 114 and SEQ NO: 116, respectively;
(xxviii) SEQ ID No: 118 and SEQ NO: 120, respectively;
(xxix) SEQ ID No: 122 and SEQ NO: 124, respectively;
(xxx) SEQ ID No: 126 and SEQ NO: 128, respectively;
(xxxi) SEQ ID No: 130 and SEQ NO: 132, respectively;
(xxxii) SEQ ID No: 134 and SEQ NO: 136, respectively;
(xxxiii) SEQ ID No: 138 and SEQ NO: 140, respectively;
(xxxiv) SEQ ID No: 142 and SEQ NO: 144, respectively;
(xxxv) SEQ ID No: 146 and SEQ NO: 148, respectively;
(xxxvi) SEQ ID No: 150 and SEQ NO: 152, respectively;
(xxxvii) SEQ ID No: 154 and SEQ NO:156, respectively;
(xxxviii) SEQ ID No: 158 and SEQ NO: 160, respectively;
(xxxix) SEQ ID No: 162 and SEQ NO: 164, respectively; or
(xl) SEQ ID No: 166 and SEQ NO: 168, respectively;
(d) a polynucleotide encoding an immunoglobulin heavy chain or a fragment thereof comprising a $V_H$ variable region comprising the amino acid sequence set forth in
(i) SEQ ID NO: 2, wherein the $V_H$ variable region when paired with a $V_L$ variable region comprising the amino acid sequence set forth in SEQ ID NO: 4 binds to a polyomavirus and/or an antigen thereof;
(ii) SEQ ID No. 6, wherein the $V_H$ variable region when paired with a $V_L$ variable region comprising the amino acid sequence set forth in SEQ ID NO: 8 binds to a polyomavirus and/or an antigen thereof;
(iii) SEQ ID No. 10, wherein the $V_H$ variable region when paired with a $V_L$ variable region comprising the amino acid sequence set forth in SEQ ID NO: 12 binds to a polyomavirus and/or an antigen thereof;

(iv) SEQ ID No. 14, wherein the $V_H$ variable region when paired with a $V_L$ variable region comprising the amino acid sequence set forth in SEQ ID NO: 16 binds to a polyomavirus and/or an antigen thereof;

(v) SEQ ID No. 18, wherein the $V_H$ variable region when paired with a $V_L$ variable region comprising the amino acid sequence set forth in SEQ ID NO: 20 binds to a polyomavirus and/or an antigen thereof;

(vi) SEQ ID No. 22, wherein the $V_H$ variable region when paired with a $V_L$ variable region comprising the amino acid sequence set forth in SEQ ID NO: 24 binds to a polyomavirus and/or an antigen thereof;

(vii) SEQ ID No. 26, wherein the $V_H$ variable region when paired with a $V_L$ variable region comprising the amino acid sequence set forth in SEQ ID NO: 28 binds to a polyomavirus and/or an antigen thereof;

(viii) SEQ ID No. 30, wherein the $V_H$ variable region when paired with a $V_L$ variable region comprising the amino acid sequence set forth in SEQ ID NO: 32 binds to a polyomavirus and/or an antigen thereof;

(ix) SEQ ID No. 34, wherein the $V_H$ variable region when paired with a $V_L$ variable region comprising the amino acid sequence set forth in SEQ ID NO: 36 binds to a polyomavirus and/or an antigen thereof;

(x) SEQ ID No. 38, wherein the $V_H$ variable region when paired with a $V_L$ variable region comprising the amino acid sequence set forth in SEQ ID NO: 40 binds to a polyomavirus and/or an antigen thereof;

(xi) SEQ ID No. 42, wherein the $V_H$ variable region when paired with a $V_L$ variable region comprising the amino acid sequence set forth in SEQ ID NO: 44 binds to a polyomavirus and/or an antigen thereof;

(xii) SEQ ID No. 46, wherein the $V_H$ variable region when paired with a $V_L$ variable region comprising the amino acid sequence set forth in SEQ ID NO: 48 binds to a polyomavirus and/or an antigen thereof;

(xiii) SEQ ID No. 50, wherein the $V_H$ variable region when paired with a $V_L$ variable region comprising the amino acid sequence set forth in SEQ ID NO: 52 binds to a polyomavirus and/or an antigen thereof;

(xiv) SEQ ID No. 54, wherein the $V_H$ variable region when paired with a $V_L$ variable region comprising the amino acid sequence set forth in SEQ ID NO: 56 binds to a polyomavirus and/or an antigen thereof;

(xv) SEQ ID No. 58, wherein the $V_H$ variable region when paired with a $V_L$ variable region comprising the amino acid sequence set forth in SEQ ID NO: 60 binds to a polyomavirus and/or an antigen thereof;

(xvi) SEQ ID No. 62, wherein the $V_H$ variable region when paired with a $V_L$ variable region comprising the amino acid sequence set forth in SEQ ID NO: 64 binds to a polyomavirus and/or an antigen thereof;

(xvii) SEQ ID No. 66, wherein the $V_H$ variable region when paired with a $V_L$ variable region comprising the amino acid sequence set forth in SEQ ID NO: 68 binds to a polyomavirus and/or an antigen thereof;

(xviii) SEQ ID No. 70, wherein the $V_H$ variable region when paired with a $V_L$ variable region comprising the amino acid sequence set forth in SEQ ID NO: 72 binds to a polyomavirus and/or an antigen thereof;

(xix) SEQ ID No. 74, wherein the $V_H$ variable region when paired with a $V_L$ variable region comprising the amino acid sequence set forth in SEQ ID NO: 76 binds to a polyomavirus and/or an antigen thereof;

(xx) SEQ ID No. 78, wherein the $V_H$ variable region when paired with a $V_L$ variable region comprising the amino acid sequence set forth in SEQ ID NO: 80 binds to a polyomavirus and/or an antigen thereof;

(xxi) SEQ ID No. 82, wherein the $V_H$ variable region when paired with a $V_L$ variable region comprising the amino acid sequence set forth in SEQ ID NO: 84 binds to a polyomavirus and/or an antigen thereof;

(xxii) SEQ ID No. 90, wherein the $V_H$ variable region when paired with a $V_L$ variable region comprising the amino acid sequence set forth in SEQ ID NO: 92 binds to a polyomavirus and/or an antigen thereof;

(xxiii) SEQ ID No. 94, wherein the $V_H$ variable region when paired with a $V_L$ variable region comprising the amino acid sequence set forth in SEQ ID NO: 96 binds to a polyomavirus and/or an antigen thereof;

(xxiv) SEQ ID No. 98, wherein the $V_H$ variable region when paired with a $V_L$ variable region comprising the amino acid sequence set forth in SEQ ID NO: 100 binds to a polyomavirus and/or an antigen thereof;

(xxv) SEQ ID No. 102, wherein the $V_H$ variable region when paired with a $V_L$ variable region comprising the amino acid sequence set forth in SEQ ID NO: 104 binds to a polyomavirus and/or an antigen thereof;

(xxvi) SEQ ID No. 106, wherein the $V_H$ variable region when paired with a $V_L$ variable region comprising the amino acid sequence set forth in SEQ ID NO: 108 binds to a polyomavirus and/or an antigen thereof;

(xxvii) SEQ ID No. 114, wherein the $V_H$ variable region when paired with a $V_L$ variable region comprising the amino acid sequence set forth in SEQ ID NO: 116 binds to a polyomavirus and/or an antigen thereof;

(xxviii) SEQ ID No. 118, wherein the $V_H$ variable region when paired with a $V_L$ variable region comprising the amino acid sequence set forth in SEQ ID NO: 120 binds to a polyomavirus and/or an antigen thereof;

(xxix) SEQ ID No. 122, wherein the $V_H$ variable region when paired with a $V_L$ variable region comprising the amino acid sequence set forth in SEQ ID NO: 124 binds to a polyomavirus and/or an antigen thereof;

(xxx) SEQ ID No. 126, wherein the $V_H$ variable region when paired with a $V_L$ variable region comprising the amino acid sequence set forth in SEQ ID NO: 128 binds to a polyomavirus and/or an antigen thereof;

(xxxi) SEQ ID No. 130, wherein the $V_H$ variable region when paired with a $V_L$ variable region comprising the amino acid sequence set forth in SEQ ID NO: 132 binds to a polyomavirus and/or an antigen thereof;

(xxxii) SEQ ID No. 134, wherein the $V_H$ variable region when paired with a $V_L$ variable region comprising the amino acid sequence set forth in SEQ ID NO: 136 binds to a polyomavirus and/or an antigen thereof;

(xxxiii) SEQ ID No. 138, wherein the $V_H$ variable region when paired with a $V_L$ variable region comprising the amino acid sequence set forth in SEQ ID NO: 140 binds to a polyomavirus and/or an antigen thereof;

(xxxiv) SEQ ID No. 142, wherein the $V_H$ variable region when paired with a $V_L$ variable region comprising the amino acid sequence set forth in SEQ ID NO: 144 binds to a polyomavirus and/or an antigen thereof;

(xxxv) SEQ ID No. 146, wherein the $V_H$ variable region when paired with a $V_L$ variable region comprising the amino acid sequence set forth in SEQ ID NO: 148 binds to a polyomavirus and/or an antigen thereof;

(xxxvi) SEQ ID No. 150, wherein the $V_H$ variable region when paired with a $V_L$ variable region comprising the amino acid sequence set forth in SEQ ID NO: 152 binds to a polyomavirus and/or an antigen thereof;

(xxxvii) SEQ ID No. 154, wherein the $V_H$ variable region when paired with a $V_L$ variable region comprising the amino acid sequence set forth in SEQ ID NO: 156 binds to a polyomavirus and/or an antigen thereof;

(xxxviii) SEQ ID No. 158, wherein the $V_H$ variable region when paired with a $V_L$ variable region comprising the amino acid sequence set forth in SEQ ID NO: 160 binds to a polyomavirus and/or an antigen thereof;

(xxxix) SEQ ID No. 162, wherein the $V_H$ variable region when paired with a $V_L$ variable region comprising the amino acid sequence set forth in SEQ ID NO: 164 binds to a polyomavirus and/or an antigen thereof; or (xl) SEQ ID No. 166, wherein the $V_H$ variable region when paired with a $V_L$ variable region comprising the amino acid sequence set forth in SEQ ID NO: 168 binds to a polyomavirus and/or an antigen thereof;

(e) a polynucleotide encoding an immunoglobulin light chain or a fragment thereof comprising a $V_L$ variable region comprising the amino acid sequence set forth in (i) SEQ ID NO: 4, wherein the $V_L$ variable region when paired with a $V_H$ variable region comprising the amino acid sequence set forth in SEQ ID NO: 2, binds to a polyomavirus and/or an antigen thereof; and (ii) SEQ ID NO: 8, wherein the $V_L$ variable region when paired with a $V_H$ variable region comprising the amino acid sequence set forth in SEQ ID NO: 6 binds to a polyomavirus and/or an antigen thereof;

(iii) SEQ ID NO: 12, wherein the $V_L$ variable region when paired with a $V_H$ variable region comprising the amino acid sequence set forth in SEQ ID NO: 10 binds to a polyomavirus and/or an antigen thereof;

(iv) SEQ ID NO: 16, wherein the $V_L$ variable region when paired with a $V_H$ variable region comprising the amino acid sequence set forth in SEQ ID NO: 14 binds to a polyomavirus and/or an antigen thereof;

(v) SEQ ID NO: 20, wherein the $V_L$ variable region when paired with a $V_H$ variable region comprising the amino acid sequence set forth in SEQ ID NO: 18 binds to a polyomavirus and/or an antigen thereof;

(vi) SEQ ID NO: 24, wherein the $V_L$ variable region when paired with a $V_H$ variable region comprising the amino acid sequence set forth in SEQ ID NO: 22 binds to a polyomavirus and/or an antigen thereof;

(vii) SEQ ID NO: 28, wherein the $V_L$ variable region when paired with a $V_H$ variable region comprising the amino acid sequence set forth in SEQ ID NO: 26 binds to a polyomavirus and/or an antigen thereof;

(viii) SEQ ID NO: 32, wherein the $V_L$ variable region when paired with a $V_H$ variable region comprising the amino acid sequence set forth in SEQ ID NO: 30 binds to a polyomavirus and/or an antigen thereof;

(ix) SEQ ID NO: 36, wherein the $V_L$ variable region when paired with a $V_H$ variable region comprising the amino acid sequence set forth in SEQ ID NO: 34 binds to a polyomavirus and/or an antigen thereof;

(x) SEQ ID NO: 40, wherein the $V_L$ variable region when paired with a $V_H$ variable region comprising the amino acid sequence set forth in SEQ ID NO: 38 binds to a polyomavirus and/or an antigen thereof;

(xi) SEQ ID NO: 44, wherein the $V_L$ variable region when paired with a $V_H$ variable region comprising the amino acid sequence set forth in SEQ ID NO: 42 binds to a polyomavirus and/or an antigen thereof;

(xii) SEQ ID NO: 48, wherein the $V_L$ variable region when paired with a $V_H$ variable region comprising the amino acid sequence set forth in SEQ ID NO: 46 binds to a polyomavirus and/or an antigen thereof;

(xiii) SEQ ID NO: 52, wherein the $V_L$ variable region when paired with a $V_H$ variable region comprising the amino acid sequence set forth in SEQ ID NO: 50 binds to a polyomavirus and/or an antigen thereof;

(xiv) SEQ ID NO: 56, wherein the $V_L$ variable region when paired with a $V_H$ variable region comprising the amino acid sequence set forth in SEQ ID NO: 54 binds to a polyomavirus and/or an antigen thereof;

(xv) SEQ ID NO: 60, wherein the $V_L$ variable region when paired with a $V_H$ variable region comprising the amino acid sequence set forth in SEQ ID NO: 58 binds to a polyomavirus and/or an antigen thereof;

(xvi) SEQ ID NO: 64, wherein the $V_L$ variable region when paired with a $V_H$ variable region comprising the amino acid sequence set forth in SEQ ID NO: 62 binds to a polyomavirus and/or an antigen thereof;

(xvii) SEQ ID NO: 68, wherein the $V_L$ variable region when paired with a $V_H$ variable region comprising the amino acid sequence set forth in SEQ ID NO: 66 binds to a polyomavirus and/or an antigen thereof;

(xviii) SEQ ID NO: 72, wherein the $V_L$ variable region when paired with a $V_H$ variable region comprising the amino acid sequence set forth in SEQ ID NO: 70 binds to a polvomavirus and/or an antigen thereof;

(xix) SEQ ID NO: 76, wherein the $V_L$ variable region when paired with a $V_H$ variable region comprising the amino acid sequence set forth in SEQ ID NO: 74 binds to a polyomavirus and/or an antigen thereof;

(xx) SEQ ID NO: 80, wherein the $V_L$ variable region when paired with a $V_H$ variable region comprising the amino acid sequence set forth in SEQ ID NO: 78 binds to a polyomavirus and/or an antigen thereof;

(xxi) SEQ ID NO: 84, wherein the $V_L$ variable region when paired with a $V_H$ variable region comprising the amino acid sequence set forth in SEQ ID NO: 82 binds to a polyomavirus and/or an antigen thereof;

(xxii) SEQ ID NO: 92, wherein the $V_L$ variable region when paired with a $V_H$ variable region comprising the amino acid sequence set forth in SEQ ID NO: 90 binds to a polyomavirus and/or an antigen thereof;

(xxvii) SEQ ID NO: 96, wherein the $V_L$ variable region when paired with a $V_H$ variable region comprising the amino acid sequence set forth in SEQ ID NO: 94 binds to a polyomavirus and/or an antigen thereof;

(xxiv) SEQ ID NO: 100, wherein the $V_L$ variable region when paired with a $V_H$ variable region comprising the amino acid sequence set forth in SEQ ID NO: 98 binds to a polyomavirus and/or an antigen thereof;

(xxv) SEQ ID NO: 104, wherein the V$_L$ variable region when paired with a V$_H$ variable region comprising the amino acid sequence set forth in SEQ ID NO: 102 binds to a polyomavirus and/or an antigen thereof;

(xxvi) SEQ ID NO: 108, wherein the V$_L$ variable region when paired with a V$_H$ variable region comprising the amino acid sequence set forth in SEQ ID NO: 106 binds to a polyomavirus and/or an antigen thereof;

(xxvii) SEQ ID NO: 116, wherein the V$_L$ variable region when paired with a V$_H$ variable region comprising the amino acid sequence set forth in SEQ ID NO: 114 binds to a polyomavirus and/or an antigen thereof;

(xxviii) SEQ ID NO: 120, wherein the V$_L$ variable region when paired with a V$_H$ variable region comprising the amino acid sequence set forth in SEQ ID NO: 118 binds to a polyomavirus and/or an antigen thereof;

(xxix) SEQ ID NO: 124, wherein the V$_L$ variable region when paired with a V$_H$ variable region comprising the amino acid sequence set forth in SEQ ID NO: 122 binds to a polyomavirus and/or an antigen thereof;

(xxx) SEQ ID NO: 128, wherein the V$_L$ variable region when paired with a V$_H$ variable region comprising the amino acid sequence set forth in SEQ ID NO: 126 binds to a polyomavirus and/or an antigen thereof;

(xxxi) SEQ ID NO: 132, wherein the V$_L$ variable region when paired with a V$_H$ variable region comprising the amino acid sequence set forth in SEQ ID NO: 130 binds to a polyomavirus and/or an antigen thereof;

(xxxii) SEQ ID NO: 136, wherein the V$_L$ variable region when paired with a V$_H$ variable region comprising the amino acid sequence set forth in SEQ ID NO: 134 binds to a polyomavirus and/or an antigen thereof;

(xxxiii) SEQ ID NO: 140, wherein the V$_L$ variable region when paired with a V$_H$ variable region comprising the amino acid sequence set forth in SEQ ID NO: 138 binds to a polyomavirus and/or an antigen thereof;

(xxxiv) SEQ ID NO: 144, wherein the V$_L$ variable region when paired with a V$_H$ variable region comprising the amino acid sequence set forth in SEQ ID NO: 142 binds to a polyomavirus and/or an antigen thereof;

(xxxv) SEQ ID NO: 148, wherein the V$_L$ variable region when paired with a V$_H$ variable region comprising the amino acid sequence set forth in SEQ ID NO: 146 binds to a polyomavirus and/or an antigen thereof;

(xxxvi) SEQ ID NO: 152, wherein the V$_L$ variable region when paired with a V$_H$ variable region comprising the amino acid sequence set forth in SEQ ID NO: 150 binds to a polyomavirus and/or an antigen thereof;

(xxxvii) SEQ ID NO: 156, wherein the V$_L$ variable region when paired with a V$_H$ variable region comprising the amino acid sequence set forth in SEQ ID NO: 154 binds to a polyomavirus and/or an antigen thereof;

(xxxviii) SEQ ID NO: 160, wherein the V$_L$ variable region when paired with a V$_H$ variable region comprising the amino acid sequence set forth in SEQ ID NO: 158 binds to a polyomavirus and/or an antigen thereof;

(xxxix) SEQ ID NO: 164, wherein the V$_L$ variable region when paired with a V$_H$ variable region comprising the amino acid sequence set forth in SEQ ID NO: 162 binds to a polyomavirus and/or an antigen thereof; or (xl) SEQ ID NO: 168, wherein the V$_L$ variable region when paired with a V$_H$ variable region comprising the amino acid sequence set forth in SEQ ID NO: 166 binds to a polyomavirus and/or an antigen thereof;

(f) a polynucleotide encoding an immunoglobulin heavy chain or a fragment thereof comprising a V$_H$ variable region and an immunoglobulin light chain or a fragment thereof comprising a V$_L$ variable region comprising the amino acid sequences set forth in (i) SEQ ID NO: 2 and 4, respectively;
(ii) SEQ ID NO: 6 and 8, respectively;
(iii) SEQ ID NO: 10 and 12, respectively;
(iv) SEQ ID NO: 14 and 16, respectively;
(v) SEQ ID NO: 18 and 20, respectively;
(vi) SEQ ID NO: 22 and 24, respectively;
(vii) SEQ ID NO: 26 and 28, respectively;
(viii) SEQ ID NO: 30 and 32, respectively;
(ix) SEQ ID NO: 34 and 36, respectively;
(x) SEQ ID NO: 38 and 40, respectively;
(xi) SEQ ID NO: 42 and 44, respectively;
(xii) SEQ ID NO: 46 and 48, respectively;
(xiii) SEQ ID NO: 50 and 52, respectively;
(xiv) SEQ ID NO: 54 and 56, respectively;
(xv) SEQ ID NO: 58 and 60, respectively;
(xvi) SEQ ID NO: 62 and 64, respectively;
(xvii) SEQ ID NO: 66 and 68, respectively;
(xviii) SEQ ID NO: 70 and 72, respectively;
(xix) SEQ ID NO: 74 and 76, respectively;
(xx) SEQ ID NO: 78 and 80, respectively;
(xxi) SEQ ID NO: 82 and 84, respectively;
(xxii) SEQ ID NO: 90 and 92, respectively;
(xxiii) SEQ ID NO: 94 and 96, respectively;
(xxiv) SEQ ID NO: 98 and 100, respectively;
(xxv) SEQ ID NO: 102 and 104, respectively;
(xxvi) SEQ ID NO: 106 and 108, respectively;
(xxvii) SEQ ID NO: 114 and 116, respectively;
(xxviii) SEQ ID NO: 118 and 120, respectively;
(xxix) SEQ ID NO: 122 and 124, respectively;
(xxx) SEQ ID NO: 126 and 128, respectively;
(xxxi) SEQ ID NO: 130 and 132, respectively;
(xxxii) SEQ ID NO: 134 and 136, respectively;
(xxxiii) SEQ ID NO: 138 and 140, respectively;
(xxxiv) SEQ ID NO: 142 and 144, respectively;
(xxxv) SEQ ID NO: 146 and 148, respectively;
(xxxvi) SEQ ID NO: 150 and 152, respectively;
(xxxvii) SEQ ID NO: 154 and 156, respectively;
(xxxviii) SEQ ID NO: 158 and 160, respectively;
(xxxix) SEQ ID NO: 162 and 164, respectively; or
(xl) SEQ ID NO: 166 and 168, respectively.

2. One or more vector(s) comprising one or more polynucleotide(s) of claim 1.

3. The vector(s) of claim 2, further comprising a polynucleotide encoding at least a binding domain of a variable region of an immunoglobulin chain of a human monoclonal antibody or an antigen-binding fragment thereof capable of binding to a polyomavirus and/or antigen thereof, wherein the polyomavirus is JC virus (JCV) or BK virus (BKV), wherein the polynucleotide further encodes the variable region of the other immunoglobulin chain of the antibody or an antigen-binding fragment thereof.

4. An isolated host cell comprising one or more polynucleotide(s) of claim 1.

5. A composition comprising a polynucleotide of claim 1.

6. The composition of claim 5, wherein the composition:
   (a) is a pharmaceutical composition and further comprises a pharmaceutical acceptable carrier,
   or
   (b) is a diagnostic composition, and further comprises reagents conventionally used in immune- or nucleic acid based diagnostic methods.

7. The composition of claim 5, further comprising an immunomodulatory agent.

8. A kit useful in the diagnosis or monitoring of the progression of Progressive Multifocal Leukoencephalopathy (PML) and/or transplant rejection following clinical bone marrow, kidney, and other solid organs transplantations, said kit comprising the antibody or an antigen-binding fragment thereof encoded by the polynucleotide of claim 1.

9. The kit of claim 8, further comprising reagents and/or instructions for use.

10. The composition of claim 6, wherein
    the pharmaceutical composition is used for the prophylactic or therapeutic treatment of a disease, the disease is Progressive Multifocal Leukoencephalopathy (PML), infection of granule neurons, hyperchromatic nuclei, granule cell neuronopathy, cerebral autothrophy, encephalopathy, meningitis, Polyoma-induced tumors, immune reconstitution inflammatory syndrome (IRIS), hemorrhagic cystitis, pneumonia, retinitis, colitis, vasculitis, interstitial kidney disease, infections of respiratory tract, JCV nephropathy, BKV nephropathy, meningitis, Merkel cell carcinoma, trichodysplasia spinulosa, or malignant pleural mesothelioma.

11. A complementary DNA (cDNA) molecule encoding at least a binding domain of a variable region of an immunoglobulin chain of an antibody or antigen binding fragment thereof, wherein the antibody or antigen-binding fragment thereof is capable of binding to a polyomavirus or an antigen thereof, wherein the antibody or antigen-binding fragment thereof comprises in its variable region:
    (a) the complementarity determining regions (CDRs) 1, 2, and 3 of:
       (i) the $V_H$ variable region amino acid sequence of SEQ ID NO: 2 and the $V_L$ variable region amino acid sequence of SEQ ID NO: 4;
       (ii) the $V_H$ variable region amino acid sequence of SEQ ID NO: 6 and the $V_L$ variable region amino acid sequence of SEQ ID NO: 8;
       (iii) the $V_H$ variable region amino acid sequence of SEQ ID NO: 10 and the $V_L$ variable region amino acid sequence of SEQ ID NO: 12;
       (iv) the $V_H$ variable region amino acid sequence of SEQ ID NO: 14 and the $V_L$ variable region amino acid sequence of SEQ ID NO: 16;
       (v) the $V_H$ variable region amino acid sequence of SEQ ID NO: 18 and the $V_L$ variable region amino acid sequence of SEQ ID NO: 20;
       (vi) the $V_H$ variable region amino acid sequence of SEQ ID NO: 22 and the $V_L$ variable region amino acid sequence of SEQ ID NO: 24;
       (vii) the $V_H$ variable region amino acid sequence of SEQ ID NO: 26 and the $V_L$ variable region amino acid sequence of SEQ ID NO: 28;
       (viii) the $V_H$ variable region amino acid sequence of SEQ ID NO: 30 and the $V_L$ variable region amino acid sequence of SEQ ID NO: 32;
       (ix) the $V_H$ variable region amino acid sequence of SEQ ID NO: 34 and the $V_L$ variable region amino acid sequence of SEQ ID NO: 36;
       (x) the $V_H$ variable region amino acid sequence of SEQ ID NO: 38 and the $V_L$ variable region amino acid sequence of SEQ ID NO: 40;
       (xi) the $V_H$ variable region amino acid sequence of SEQ ID NO: 42 and the $V_L$ variable region amino acid sequence of SEQ ID NO: 44;
       (xii) the $V_H$ variable region amino acid sequence of SEQ ID NO: 46 and the $V_L$ variable region amino acid sequence of SEQ ID NO: 48;
       (xiii) the $V_H$ variable region amino acid sequence of SEQ ID NO: 50 and the $V_L$ variable region amino acid sequence of SEQ ID NO: 52;
       (xiv) the $V_H$ variable region amino acid sequence of SEQ ID NO: 54 and the $V_L$ variable region amino acid sequence of SEQ ID NO: 56;
       (xv) the $V_H$ variable region amino acid sequence of SEQ ID NO: 58 and the $V_L$ variable region amino acid sequence of SEQ ID NO: 60;
       (xvi) the $V_H$ variable region amino acid sequence of SEQ ID NO: 62 and the $V_L$ variable region amino acid sequence of SEQ ID NO: 64;
       (xvii) the $V_H$ variable region amino acid sequence of SEQ ID NO: 66 and the $V_L$ variable region amino acid sequence of SEQ ID NO: 68;
       (xviii) the $V_H$ variable region amino acid sequence of SEQ ID NO: 70 and the $V_L$ variable region amino acid sequence of SEQ ID NO: 72;
       (xix) the $V_H$ variable region amino acid sequence of SEQ ID NO: 74 and the $V_L$ variable region amino acid sequence of SEQ ID NO: 76;
       (xx) the $V_H$ variable region amino acid sequence of SEQ ID NO: 78 and the $V_L$ variable region amino acid sequence of SEQ ID NO: 80;
       (xxi) the $V_H$ variable region amino acid sequence of SEQ ID NO: 82 and the $V_L$ variable region amino acid sequence of SEQ ID NO: 84;
       (xxii) the $V_H$ variable region amino acid sequence of SEQ ID NO: 90 and the $V_L$ variable region amino acid sequence of SEQ ID NO: 92;
       (xxiii) the $V_H$ variable region amino acid sequence of SEQ ID NO: 94 and the $V_L$ variable region amino acid sequence of SEQ ID NO: 96;
       (xxiv) the $V_H$ variable region amino acid sequence of SEQ ID NO: 98 and the $V_L$ variable region amino acid sequence of SEQ ID NO: 100;
       (xxv) the $V_H$ variable region amino acid sequence of SEQ ID NO: 102 and the $V_L$ variable region amino acid sequence of SEQ ID NO: 104;
       (xxvi) the $V_H$ variable region amino acid sequence of SEQ ID NO: 106 and the $V_L$ variable region amino acid sequence of SEQ ID NO: 108;
       (xxvii) the $V_H$ variable region amino acid sequence of SEQ ID NO: 114 and the $V_L$ variable region amino acid sequence of SEQ ID NO: 116;
       (xxviii) the $V_H$ variable region amino acid sequence of SEQ ID NO: 118 and the $V_L$ variable region amino acid sequence of SEQ ID NO: 120;
       (xxix) the $V_H$ variable region amino acid sequence of SEQ ID NO: 122 and the $V_L$ variable region amino acid sequence of SEQ ID NO: 124;

(xxx) the V$_H$ variable region amino acid sequence of SEQ ID NO: 126 and the V$_L$ variable region amino acid sequence of SEQ ID NO: 128;
(xxxi) the V$_H$ variable region amino acid sequence of SEQ ID NO: 130 and the V$_L$ variable region amino acid sequence of SEQ ID NO: 132;
(xxxii) the V$_H$ variable region amino acid sequence of SEQ ID NO: 134 and the V$_L$ variable region amino acid sequence of SEQ ID NO: 136;
(xxxiii) the V$_H$ variable region amino acid sequence of SEQ ID NO: 138 and the V$_L$ variable region amino acid sequence of SEQ ID NO: 140;
(xxxiv) the V$_H$ variable region amino acid sequence of SEQ ID NO: 142 and the V$_L$ variable region amino acid sequence of SEQ ID NO: 144;
(xxxv) the V$_H$ variable region amino acid sequence of SEQ ID NO: 146 and the V$_L$ variable region amino acid sequence of SEQ ID NO: 148;
(xxxvi) the V$_H$ variable region amino acid sequence of SEQ ID NO: 150 and the V$_L$ variable region amino acid sequence of SEQ ID NO: 152;
(xxxvii) the V$_H$ variable region amino acid sequence of SEQ ID NO: 154 and the V$_L$ variable region amino acid sequence of SEQ ID NO: 156;
(xxxviii) the V$_H$ variable region amino acid sequence of SEQ ID NO: 158 and the V$_L$ variable region amino acid sequence of SEQ ID NO: 160;
(xxxix) the V$_H$ variable region amino acid sequence of SEQ ID NO: 162 and the V$_L$ variable region amino acid sequence of SEQ ID NO: 164; or
(xl) the V$_H$ variable region amino acid sequence of SEQ ID NO: 166 and the V$_L$ variable region amino acid sequence of SEQ ID NO: 168;
or (b) (i) an amino acid sequence of the V$_H$ variable region set forth in SEQ ID NO: 2, and the V$_L$ variable region set forth in SEQ ID NO: 4;
(ii) an amino acid sequence of the V$_H$ variable region set forth in SEQ ID NO: 6 and the V$_L$ variable region set forth in SEQ ID NO: 8;
(iii) an amino acid sequence of the V$_H$ variable region set forth in SEQ ID NO: 10 and the V$_L$ variable region set forth in SEQ ID NO: 12;
(iv) an amino acid sequence of the V$_H$ variable region set forth in SEQ ID NO: 14 and the V$_L$ variable region set forth in SEQ ID NO: 16;
(v) an amino acid sequence of the V$_H$ variable region set forth in SEQ ID NO: 18 and the V$_L$ variable region set forth in SEQ ID NO: 20;
(vi) an amino acid sequence of the V$_H$ variable region set forth in SEQ ID NO: 22 and the V$_L$ variable region set forth in SEQ ID NO: 24;
(vii) an amino acid sequence of the V$_H$ variable region set forth in SEQ ID NO: 26 and the V$_L$ variable region set forth in SEQ ID NO: 28;
(viii) an amino acid sequence of the V$_H$ variable region set forth in SEQ ID NO: 30 and the V$_L$ variable region set forth in SEQ ID NO: 32;
(ix) an amino acid sequence of the V$_H$ variable region set forth in SEQ ID NO: 34 and the V$_L$ variable region set forth in SEQ ID NO: 36;
(x) an amino acid sequence of the V$_H$ variable region set forth in SEQ ID NO: 38 and the V$_L$ variable region set forth in SEQ ID NO: 40;
(xi) an amino acid sequence of the V$_H$ variable region set forth in SEQ ID NO: 42 and the V$_L$ variable region set forth in SEQ NO: 44;

(xii) an amino acid sequence of the V$_H$ variable region set forth in SEQ ID NO: 46 and the V$_L$ variable region set forth in SEQ ID NO: 48;
(xiii) an amino acid sequence of the V$_H$ variable region set forth in SEQ ID NO: 50 and the V$_L$ variable region set forth in SEQ ID NO: 52;
(xiv) an amino acid sequence of the V$_H$ variable region set forth in SEQ ID NO: 54 and the V$_L$ variable region set forth in SEQ ID NO: 56;
(xv) an amino acid sequence of the V$_H$ variable region set forth in SEQ ID NO: 58 and the V$_L$ variable region set forth in SEQ ID NO: 60;
(xvi) an amino acid sequence of the V$_H$ variable region set forth in SEQ ID NO: 62 and the V$_L$ variable region set forth in SEQ ID NO: 64;
(xvii) an amino acid sequence of the V$_H$ variable region set forth in SEQ ID NO: 66 and the V$_L$ variable region set forth in SEQ ID NO: 68;
(xviii) an amino acid sequence of the V$_H$ variable region set forth in SEQ ID NO: 70 and the V$_L$ variable region set forth in SEQ ID NO: 72;
(xix) an amino acid sequence of the V$_H$ variable region set forth in SEQ ID NO: 74 and the V$_L$ variable region set forth in SEQ ID NO: 76;
(xx) an amino acid sequence of the V$_H$ variable region set forth in SEQ ID NO: 78 and the V$_L$ variable region set forth in SEQ ID NO: 80;
(xxi) an amino acid sequence of the V$_H$ variable region set forth in SEQ ID NO: 82 and the V$_L$ variable region set forth in SEQ ID NO: 84;
(xxii) an amino acid sequence of the V$_H$ variable region set forth in SEQ ID NO: 90 and the V$_L$ variable region set forth in SEQ ID NO: 92;
(xxiii) an amino acid sequence of the V$_H$ variable region set forth in SEQ ID NO: 94 and the V$_L$ variable region set forth in SEQ ID NO: 96;
(xxiv) an amino acid sequence of the V$_H$ variable region set forth in SEQ ID NO: 98 and the V$_L$ variable region set forth in SEQ ID NO: 100;
(xxv) an amino acid sequence of the V$_H$ variable region set forth in SEQ ID NO: 102 and the V$_L$ variable region set forth in SEQ ID NO: 104;
(xxvi) an amino acid sequence of the V$_H$ variable region set forth in SEQ ID NO: 106 and the V$_L$ variable region set forth in SEQ ID NO: 108;
(xxvii) an amino acid sequence of the V$_H$ variable region set forth in SEQ ID NO: 114 and the V$_L$ variable region set forth in SEQ ID NO: 116;
(xxviii) an amino acid sequence of the V$_H$ variable region set forth in SEQ ID NO: 118 and the V$_L$ variable region set forth in SEQ ID NO: 120;
(xxix) an amino acid sequence of the V$_H$ variable region set forth in SEQ ID NO: 122 and the V$_L$ variable region set forth in SEQ ID NO: 124;
(xxx) an amino acid sequence of the V$_H$ variable region set forth in SEQ ID NO: 126 and the V$_L$ variable region set forth in SEQ ID NO: 128;
(xxxi) an amino acid sequence of the V$_H$ variable region set forth in SEQ ID NO: 130 and the V$_L$ variable region set forth in SEQ ID NO: 132;
(xxxii) an amino acid sequence of the V$_H$ variable region set forth in SEQ ID NO: 134 and the V$_L$ variable region set forth in SEQ ID NO: 136;
(xxxiii) an amino acid sequence of the V$_H$ variable region set forth in SEQ ID NO: 138 and the V$_L$ variable region set forth in SEQ ID NO: 140;

(xxxiv) an amino acid sequence of the $V_H$ variable region set forth in SEQ ID NO: 142 and the $V_L$ variable region set forth in SEQ ID NO: 144;

(xxxv) an amino acid sequence of the $V_H$ variable region set forth in SEQ ID NO: 146 and the $V_L$ variable region set forth in SEQ ID NO: 148;

(xxxvi) an amino acid sequence of the $V_H$ variable region set forth in SEQ ID NO: 150 and the $V_L$ variable region set forth in SEQ ID NO: 152;

(xxxvii) an amino acid sequence of the $V_H$ variable region set forth in SEQ ID NO: 154 and the $V_L$ variable region set forth in SEQ ID NO: 156;

(xxxviii) an amino acid sequence of the $V_H$ variable region set forth in SEQ ID NO: 158 and the $V_L$ variable region set forth in SEQ ID NO: 160;

(xxxix) an amino acid sequence of the $V_H$ variable region set forth in SEQ ID NO: 162 and the $V_L$ variable region set forth in SEQ ID NO: 164; or (xl) an amino acid sequence of the $V_H$ variable region set forth in SEQ ID NO: 166 and the $V_L$ variable region set forth in SEQ ID NO: 168.

12. A vector comprising the cDNA of claim 11, encoding the variable region of the other immunoglobulin chain of the antibody or an antigen-binding fragment thereof.

13. The polynucleotide of claim 1, wherein the polyomavirus is JC virus (JCV) or BK virus (BKV).

14. The polynucleotide of claim 1, wherein the antibody or antigen-binding fragment thereof is capable of binding VP1 protein or a fragment thereof.

15. The polynucleotide of claim 1, wherein the antibody or antigen-binding fragment thereof is capable of recognizing an epitope exposed on the surface of the virus.

16. The polynucleotide of claim 1, wherein the antibody or antigen-binding fragment thereof does not substantially recognize serum albumin.

17. The polynucleotide of claim 16, wherein the serum albumin is bovine serum albumin (BSA).

18. The polynucleotide of claim 1, wherein the antibody or antigen-binding fragment thereof recognizes progressive multifocal leukoencephalopathy (PML)-associated VP1 mutants.

19. The vector(s) of claim 2 or 12, which is or are (an) expression vector(s).

20. An isolated host cell comprising one or more vector(s) of claim 19.

21. The composition of claim 7, wherein the agent is natalizumab, efalizumab, rituximab, infliximab, ocrelizumab, alemtuzumab, bentuximab, or vedotin.

* * * * *

SEQUENCE LISTING

```
<160> NUMBER OF SEQ ID NOS: 172

<210> SEQ ID NO 1
<211> LENGTH: 372
<212> TYPE: DNA
<213> ORGANISM: Homo sapiens
<220> FEATURE:
<221> NAME/KEY: CDS
<222> LOCATION: (1)..(372)
<223> OTHER INFORMATION: NI-307.13G4 variable heavy chain (VH) sequence
<220> FEATURE:
<221> NAME/KEY: V_region
<222> LOCATION: (76)..(105)
<223> OTHER INFORMATION: complementarity determining region (CDR) VH-
      CDR1
<220> FEATURE:
<221> NAME/KEY: V_region
<222> LOCATION: (148)..(198)
<223> OTHER INFORMATION: complementarity determining region (CDR) VH-
      CDR2
<220> FEATURE:
<221> NAME/KEY: V_region
<222> LOCATION: (295)..(339)
<223> OTHER INFORMATION: complementarity determining region (CDR) VH-
      CDR3

<400> SEQUENCE: 1 gag gtg cag ctg gtg gag tct ggg gga ggc ttg gta cag cct ggg ggg      48
Glu Val Gln Leu Val Glu Ser Gly Gly Gly Leu Val Gln Pro Gly Gly
1               5                   10                  15 tcc ctg aga ctc tcc tgt aca gcc tct gga ttc acc ttt acc tcc tat      96
Ser Leu Arg Leu Ser Cys Thr Ala Ser Gly Phe Thr Phe Thr Ser Tyr
            20                  25                  30 gcc ctg agc tgg gtc cgc cag gct cca ggg aag ggg ctg gag tgg gtc     144
Ala Leu Ser Trp Val Arg Gln Ala Pro Gly Lys Gly Leu Glu Trp Val
        35                  40                  45 tca gca att agt agt ggt cgt ggt tac aca tac tac gca gac tcc gtg     192
Ser Ala Ile Ser Ser Gly Arg Gly Tyr Thr Tyr Tyr Ala Asp Ser Val
    50                  55                  60 aag ggc cgg ttc acc atc tcc aga gac aat tcc aag aac acg ctg tat     240
Lys Gly Arg Phe Thr Ile Ser Arg Asp Asn Ser Lys Asn Thr Leu Tyr
65                  70                  75                  80 ctg caa atg aac agt ctg aga gcc gag gac acg gcc gta tat tac tgt     288
Leu Gln Met Asn Ser Leu Arg Ala Glu Asp Thr Ala Val Tyr Tyr Cys
                85                  90                  95 gcg aaa gat ggc acc cta cgt gga tac aac tat ggt tac ata gat gat     336
Ala Lys Asp Gly Thr Leu Arg Gly Tyr Asn Tyr Gly Tyr Ile Asp Asp
            100                 105                 110
```

```
atc tgg ggc caa ggc acc ctg gtc acc gtc tcc tcg                    372
Ile Trp Gly Gln Gly Thr Leu Val Thr Val Ser Ser
            115                 120

<210> SEQ ID NO 2
<211> LENGTH: 124
<212> TYPE: PRT
<213> ORGANISM: Homo sapiens

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Thr Ser Tyr
            20                  25                  30

Ala Leu Ser Trp Val Arg Gln Ala Pro Gly Lys Gly Leu Glu Trp Val
        35                  40                  45

Ser Ala Ile Ser Ser Gly Arg Gly Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Thr Leu Arg Gly Tyr Asn Tyr Gly Tyr Ile Asp Asp
            100                 105                 110

Ile Trp Gly Gln Gly Thr Leu Val Thr Val Ser Ser
            115                 120

<210> SEQ ID NO 3
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-307.13G4 variable K-light chain (VK)
      sequence
<220> FEATURE:
<221> NAME/KEY: V_region
<222> LOCATION: (70)..(102)
<223> OTHER INFORMATION: complementarity determining region (CDR) VK-
      CDR1
<220> FEATURE:
<221> NAME/KEY: V_region
<222> LOCATION: (148)..(171)
<223> OTHER INFORMATION: complementarity determining region (CDR) VK-
      CDR2
<220> FEATURE:
<221> NAME/KEY: V_region
<222> LOCATION: (265)..(291)
<223> OTHER INFORMATION: complementarity determining region (CDR) VK-
      CDR3

<400> SEQUENCE: 3 gac atc cag atg acc cag tct cca tcg tca ctg tct gca tct gta gga    48
Asp Ile Gln Met Thr Gln Ser Pro Ser Ser Leu Ser Ala Ser Val Gly
1               5                   10                  15 gac aga gtc acc atc act tgt cgg gcg agt cag ggc atc agc aat tat    96
Asp Arg Val Thr Ile Thr Cys Arg Ala Ser Gln Gly Ile Ser Asn Tyr
            20                  25                  30 tta gcc tgg ctt cag cag aaa cca ggg aaa gcc cct aag ccc ctg atc    144
Leu Ala Trp Leu Gln Gln Lys Pro Gly Lys Ala Pro Lys Pro Leu Ile
        35                  40                  45 tat gcc gta tcc att ttg caa agt ggg gtc cca tca aag ttc agc ggc    192
Tyr Ala Val Ser Ile Leu Gln Ser Gly Val Pro Ser Lys Phe Ser Gly
    50                  55                  60
```

-continued

```
agt gga tct ggg aca gat ttc act ctc acc atc agc agc ctg cag cct      240
Ser Gly Ser Gly Thr Asp Phe Thr Leu Thr Ile Ser Ser Leu Gln Pro
 65                  70                  75                  80 gag gat ttt gca act tat tac tgc caa cag tat aag agt tac cct tac      288
Glu Asp Phe Ala Thr Tyr Tyr Cys Gln Gln Tyr Lys Ser Tyr Pro Tyr
                 85                  90                  95 acc ttt ggc cag ggg acc aag ctg gag atc aaa                          321
Thr Phe Gly Gln Gly Thr Lys Leu Glu Ile Lys
            100                 105

<210> SEQ ID NO 4
<211> LENGTH: 107
<212> TYPE: PRT
<213> ORGANISM: Homo sapiens

<400> SEQUENCE: 4

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Tyr
             20                  25                  30

Leu Ala Trp Leu Gln Gln Lys Pro Gly Lys Ala Pro Lys Pro Leu Ile
         35                  40                  45

Tyr Ala Val Ser Ile Leu Gln Ser Gly Val Pro Ser Lys Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Lys Ser Tyr Pro Tyr
                 85                  90                  95

Thr Phe Gly Gln Gly Thr Lys Leu Glu Ile Lys
            100                 105

<210> SEQ ID NO 5
<211> LENGTH: 351
<212> TYPE: DNA
<213> ORGANISM: Homo sapiens
<220> FEATURE:
<221> NAME/KEY: CDS
<222> LOCATION: (1)..(351)
<223> OTHER INFORMATION: NI-307.19F10 VH  variable heavy chain (VH)
      sequence
<220> FEATURE:
<221> NAME/KEY: V_region
<222> LOCATION: (76)..(105)
<223> OTHER INFORMATION: complementarity determining region (CDR) VH-
      CDR1
<220> FEATURE:
<221> NAME/KEY: V_region
<222> LOCATION: (148)..(198)
<223> OTHER INFORMATION: complementarity determining region (CDR) VH-
      CDR2
<220> FEATURE:
<221> NAME/KEY: V_region
<222> LOCATION: (295)..(318)
<223> OTHER INFORMATION: complementarity determining region (CDR) VH-
      CDR3

<400> SEQUENCE: 5 gag gtg cag ctg gtg gag tct ggg gga ggc tta gtt cag ccg ggg ggg      48
Glu Val Gln Leu Val Glu Ser Gly Gly Gly Leu Val Gln Pro Gly Gly
 1               5                  10                  15 tcc gtg agc ctc tcc tgt gca gcc tct gga ttc acc ttc cct gtc tac      96
Ser Val Ser Leu Ser Cys Ala Ala Ser Gly Phe Thr Phe Pro Val Tyr
             20                  25                  30 tgg atg cac tgg gtc cgc caa gct cca gag aag ggc ctg atg tgg gtc     144
```

```
Trp Met His Trp Val Arg Gln Ala Pro Glu Lys Gly Leu Met Trp Val
        35                  40                  45 tca cgg att agt cct gat ggg acc ata gta gac tac gcg ggc tcc gtg       192
Ser Arg Ile Ser Pro Asp Gly Thr Ile Val Asp Tyr Ala Gly Ser Val
    50                  55                  60 aag ggc cga ttc acc gtc tcc aga gac aac gcc aag aac att ctt tat       240
Lys Gly Arg Phe Thr Val Ser Arg Asp Asn Ala Lys Asn Ile Leu Tyr
65                  70                  75                  80 ctg caa att caa cgt ctg act gcc gag gac acg gct gtg tat ttc tgt       288
Leu Gln Ile Gln Arg Leu Thr Ala Glu Asp Thr Ala Val Tyr Phe Cys
                85                  90                  95 aca aag gac ttc gat gtt gcg agt gga ttc tgg ggc cag gga acc ctg       336
Thr Lys Asp Phe Asp Val Ala Ser Gly Phe Trp Gly Gln Gly Thr Leu
                100                 105                 110 gtc acc gtc tcc tcg                                                   351
Val Thr Val Ser Ser
        115

<210> SEQ ID NO 6
<211> LENGTH: 117
<212> TYPE: PRT
<213> ORGANISM: Homo sapiens

<400> SEQUENCE: 6

Glu Val Gln Leu Val Glu Ser Gly Gly Gly Leu Val Gln Pro Gly Gly
1               5                   10                  15

Ser Val Ser Leu Ser Cys Ala Ala Ser Gly Phe Thr Phe Pro Val Tyr
            20                  25                  30

Trp Met His Trp Val Arg Gln Ala Pro Glu Lys Gly Leu Met Trp Val
        35                  40                  45

Ser Arg Ile Ser Pro Asp Gly Thr Ile Val Asp Tyr Ala Gly Ser Val
    50                  55                  60

Lys Gly Arg Phe Thr Val Ser Arg Asp Asn Ala Lys Asn Ile Leu Tyr
65                  70                  75                  80

Leu Gln Ile Gln Arg Leu Thr Ala Glu Asp Thr Ala Val Tyr Phe Cys
                85                  90                  95

Thr Lys Asp Phe Asp Val Ala Ser Gly Phe Trp Gly Gln Gly Thr Leu
                100                 105                 110

Val Thr Val Ser Ser
        115

<210> SEQ ID NO 7
<211> LENGTH: 330
<212> TYPE: DNA
<213> ORGANISM: Homo sapiens
<220> FEATURE:
<221> NAME/KEY: CDS
<222> LOCATION: (1)..(330)
<223> OTHER INFORMATION: NI-307.19F10 VL  variable light chain (VL)
      sequence
<220> FEATURE:
<221> NAME/KEY: V_region
<222> LOCATION: (68)..(108)
<223> OTHER INFORMATION: complementarity determining region (CDR) VL-
      CDR1
<220> FEATURE:
<221> NAME/KEY: V_region
<222> LOCATION: (154)..(174)
<223> OTHER INFORMATION: complementarity determining region (CDR) VL-
      CDR2
<220> FEATURE:
<221> NAME/KEY: V_region
<222> LOCATION: (271)..(300)
<223> OTHER INFORMATION: complementarity determining region (CDR) VL-
```

CDR3

<400> SEQUENCE: 7

| | | | | | | | | | | | | | | | |
|---|---|---|---|---|---|---|---|---|---|---|---|---|---|---|---|
| cag | tct | gcc | ctg | act | cag | cct | ccc | tcc | gcg | tcc | ggg | tct | cct | gga | cag | 48 |
| Gln | Ser | Ala | Leu | Thr | Gln | Pro | Pro | Ser | Ala | Ser | Gly | Ser | Pro | Gly | Gln |
| 1 | | | | 5 | | | | | 10 | | | | | 15 | |

| tca | gtc | acc | atc | tcc | tgc | act | gga | tcc | aaa | agt | gac | gtt | ggt | act | tgt | 96 |
| Ser | Val | Thr | Ile | Ser | Cys | Thr | Gly | Ser | Lys | Ser | Asp | Val | Gly | Thr | Cys |
| | | | 20 | | | | | 25 | | | | | 30 | | |

| cac | ttt | gtc | tcc | tgg | tac | cag | cag | cac | cca | ggc | aaa | gtc | ccc | aaa | ctc | 144 |
| His | Phe | Val | Ser | Trp | Tyr | Gln | Gln | His | Pro | Gly | Lys | Val | Pro | Lys | Leu |
| | | | 35 | | | | | 40 | | | | | 45 | | |

| gtc | att | tat | gag | ggc | aat | aag | cgg | ccc | tca | ggg | gtc | cct | gat | cgc | ttc | 192 |
| Val | Ile | Tyr | Glu | Gly | Asn | Lys | Arg | Pro | Ser | Gly | Val | Pro | Asp | Arg | Phe |
| 50 | | | | | 55 | | | | | 60 | | | | | |

| tct | gcc | tcc | aag | tct | ggc | aac | acg | gcc | tcc | ctc | acc | atc | tct | ggg | ctg | 240 |
| Ser | Ala | Ser | Lys | Ser | Gly | Asn | Thr | Ala | Ser | Leu | Thr | Ile | Ser | Gly | Leu |
| 65 | | | | | 70 | | | | | 75 | | | | | 80 |

| cag | cct | ggc | gac | gag | gcg | gac | tat | tat | tgc | agc | aca | tgt | gca | ggc | ccc | 288 |
| Gln | Pro | Gly | Asp | Glu | Ala | Asp | Tyr | Tyr | Cys | Ser | Thr | Cys | Ala | Gly | Pro |
| | | | | 85 | | | | | 90 | | | | | 95 | |

| aac | aac | tat | gtc | ttc | gga | act | ggg | acc | aag | gtc | acc | gtc | ctt | | | 330 |
| Asn | Asn | Tyr | Val | Phe | Gly | Thr | Gly | Thr | Lys | Val | Thr | Val | Leu |
| | | | 100 | | | | | 105 | | | | | 110 |

<210> SEQ ID NO 8
<211> LENGTH: 110
<212> TYPE: PRT
<213> ORGANISM: Homo sapiens

<400> SEQUENCE: 8

Gln Ser Ala Leu Thr Gln Pro Pro Ser Ala Ser Gly Ser Pro Gly Gln
1               5                   10                  15

Ser Val Thr Ile Ser Cys Thr Gly Ser Lys Ser Asp Val Gly Thr Cys
            20                  25                  30

His Phe Val Ser Trp Tyr Gln Gln His Pro Gly Lys Val Pro Lys Leu
        35                  40                  45

Val Ile Tyr Glu Gly Asn Lys Arg Pro Ser Gly Val Pro Asp Arg Phe
    50                  55                  60

Ser Ala Ser Lys Ser Gly Asn Thr Ala Ser Leu Thr Ile Ser Gly Leu
65                  70                  75                  80

Gln Pro Gly Asp Glu Ala Asp Tyr Tyr Cys Ser Thr Cys Ala Gly Pro
                85                  90                  95

Asn Asn Tyr Val Phe Gly Thr Gly Thr Lys Val Thr Val Leu
            100                 105                 110

<210> SEQ ID NO 9
<211> LENGTH: 363
<212> TYPE: DNA
<213> ORGANISM: Homo sapiens
<220> FEATURE:
<221> NAME/KEY: CDS
<222> LOCATION: (1)..(363)
<223> OTHER INFORMATION: NI-307.19F8 variable heavy chain (VH) sequence
<220> FEATURE:
<221> NAME/KEY: V_region
<222> LOCATION: (76)..(105)
<223> OTHER INFORMATION: complementarity determining region (CDR) VH-
      CDR1
<220> FEATURE:
<221> NAME/KEY: V_region
<222> LOCATION: (148)..(198)
<223> OTHER INFORMATION: complementarity determining region (CDR) VH-

```
        CDR2
<220> FEATURE:
<221> NAME/KEY: V_region
<222> LOCATION: (295)..(330)
<223> OTHER INFORMATION: complementarity determining region (CDR) VH-
      CDR3

<400> SEQUENCE: 9 gag gtg cag ctg gtg gag tct ggg gga ggc ctg gtc aag cct ggg ggg        48
Glu Val Gln Leu Val Glu Ser Gly Gly Gly Leu Val Lys Pro Gly Gly
1               5                   10                  15 tcc ctg aga ctc tcc tgt gca gcc tct gga ttc acc ttc agt agc tat        96
Ser Leu Arg Leu Ser Cys Ala Ala Ser Gly Phe Thr Phe Ser Ser Tyr
            20                  25                  30 tac atg aac tgg gtc cgc cag gct cca ggg aag ggg ctg gag tgg gtc       144
Tyr Met Asn Trp Val Arg Gln Ala Pro Gly Lys Gly Leu Glu Trp Val
        35                  40                  45 tca tcc att agt agt agt agt agt tac ata tac tac gca gac tca gtg       192
Ser Ser Ile Ser Ser Ser Ser Ser Tyr Ile Tyr Tyr Ala Asp Ser Val
    50                  55                  60 aag ggc cga ttc acc atc tcc aga gac aac gcc aag aac tca ctg tat       240
Lys Gly Arg Phe Thr Ile Ser Arg Asp Asn Ala Lys Asn Ser Leu Tyr
65                  70                  75                  80 ctg caa atg aac agc ctg aca gcc gag gac acg gct gtg tat tac tgt       288
Leu Gln Met Asn Ser Leu Thr Ala Glu Asp Thr Ala Val Tyr Tyr Cys
                85                  90                  95 gcg aga gat ccc cgc cta caa cta tgg ttc atg ttt gac tac tgg ggc       336
Ala Arg Asp Pro Arg Leu Gln Leu Trp Phe Met Phe Asp Tyr Trp Gly
            100                 105                 110 cag gga acc ctg gtc acc gtc tcc tcg                                   363
Gln Gly Thr Leu Val Thr Val Ser Ser
        115                 120

<210> SEQ ID NO 10
<211> LENGTH: 121
<212> TYPE: PRT
<213> ORGANISM: Homo sapiens

<400> SEQUENCE: 10

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Tyr Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Thr Ala Glu Asp Thr Ala Val Tyr Tyr Cys
                85                  90                  95

Ala Arg Asp Pro Arg Leu Gln Leu Trp Phe Met Phe Asp Tyr Trp Gly
            100                 105                 110

Gln Gly Thr Leu Val Thr Val Ser Ser
        115                 120

<210> SEQ ID NO 11
<211> LENGTH: 348
<212> TYPE: DNA
<213> ORGANISM: Homo sapiens
<220> FEATURE:
```

```
<221> NAME/KEY: CDS
<222> LOCATION: (1)..(348)
<223> OTHER INFORMATION: NI-307.19F8 VL variable light chain (VL)
      sequence
<220> FEATURE:
<221> NAME/KEY: V_region
<222> LOCATION: (67)..(102)
<223> OTHER INFORMATION: complementarity determining region (CDR) VL-
      CDR1
<220> FEATURE:
<221> NAME/KEY: V_region
<222> LOCATION: (148)..(168)
<223> OTHER INFORMATION: complementarity determining region (CDR) VL-
      CDR2
<220> FEATURE:
<221> NAME/KEY: V_region
<222> LOCATION: (280)..(318)
<223> OTHER INFORMATION: complementarity determining region (CDR) VL-
      CDR3

<400> SEQUENCE: 11 cag cct gtg ctg act cag cca cct tct gca tca gcc tcc ctg gga gcc        48
Gln Pro Val Leu Thr Gln Pro Pro Ser Ala Ser Ala Ser Leu Gly Ala
1               5                   10                  15 tcg gtc aca ctc acc tgc acc ctg agc agc ggc tac agt aat tat aaa        96
Ser Val Thr Leu Thr Cys Thr Leu Ser Ser Gly Tyr Ser Asn Tyr Lys
            20                  25                  30 gtg gac tgg tac cag cag aga cca ggg gag ggc ccc cgc ttt gtg atg       144
Val Asp Trp Tyr Gln Gln Arg Pro Gly Glu Gly Pro Arg Phe Val Met
        35                  40                  45 cga gtg ggc act ggt ggg att gtg gga tcc aag ggg gat ggc atc cct       192
Arg Val Gly Thr Gly Gly Ile Val Gly Ser Lys Gly Asp Gly Ile Pro
    50                  55                  60 gat cgc ttc tca gtc ttg ggc tca ggc ctg aat cgg tac ctg acc atc       240
Asp Arg Phe Ser Val Leu Gly Ser Gly Leu Asn Arg Tyr Leu Thr Ile
65                  70                  75                  80 aag gac atc cag gaa gag gat gag agt gac tac cac tgt ggg gca gac       288
Lys Asp Ile Gln Glu Glu Asp Glu Ser Asp Tyr His Cys Gly Ala Asp
                85                  90                  95 cat ggc agt ggg agc aac ttc gtg tat gtc ttc gga act ggg acc aag       336
His Gly Ser Gly Ser Asn Phe Val Tyr Val Phe Gly Thr Gly Thr Lys
                100                 105                 110 gtc acc gtc cta                                                       348
Val Thr Val Leu
            115

<210> SEQ ID NO 12
<211> LENGTH: 116
<212> TYPE: PRT
<213> ORGANISM: Homo sapiens

<400> SEQUENCE: 12

Gln Pro Val Leu Thr Gln Pro Pro Ser Ala Ser Ala Ser Leu Gly Ala
1               5                   10                  15

Ser Val Thr Leu Thr Cys Thr Leu Ser Ser Gly Tyr Ser Asn Tyr Lys
            20                  25                  30

Val Asp Trp Tyr Gln Gln Arg Pro Gly Glu Gly Pro Arg Phe Val Met
        35                  40                  45

Arg Val Gly Thr Gly Gly Ile Val Gly Ser Lys Gly Asp Gly Ile Pro
    50                  55                  60

Asp Arg Phe Ser Val Leu Gly Ser Gly Leu Asn Arg Tyr Leu Thr Ile
65                  70                  75                  80

Lys Asp Ile Gln Glu Glu Asp Glu Ser Asp Tyr His Cys Gly Ala Asp
                85                  90                  95
```

```
His Gly Ser Gly Ser Asn Phe Val Tyr Val Phe Gly Thr Gly Thr Lys
            100                 105                 110

Val Thr Val Leu
        115

<210> SEQ ID NO 13
<211> LENGTH: 360
<212> TYPE: DNA
<213> ORGANISM: Homo sapiens
<220> FEATURE:
<221> NAME/KEY: CDS
<222> LOCATION: (1)..(360)
<223> OTHER INFORMATION: NI-307.11G6 variable heavy chain (VH) sequence
<220> FEATURE:
<221> NAME/KEY: V_region
<222> LOCATION: (76)..(105)
<223> OTHER INFORMATION: complementarity determining region (CDR) VH-
      CDR1
<220> FEATURE:
<221> NAME/KEY: V_region
<222> LOCATION: (148)..(198)
<223> OTHER INFORMATION: complementarity determining region (CDR) VH-
      CDR2
<220> FEATURE:
<221> NAME/KEY: V_region
<222> LOCATION: (295)..(327)
<223> OTHER INFORMATION: complementarity determining region (CDR) VH-
      CDR3

<400> SEQUENCE: 13 cag gtg cag ctg gtg gag tct ggg gga gac ttg gtc aag cct gga ggg      48
Gln Val Gln Leu Val Glu Ser Gly Gly Asp Leu Val Lys Pro Gly Gly
1               5                   10                  15 tcc ctg aga ctc tcc tgt gca gcc tct gga ttc acc ttc agt gac cac      96
Ser Leu Arg Leu Ser Cys Ala Ala Ser Gly Phe Thr Phe Ser Asp His
            20                  25                  30 tac atg agc tgg atc cgc cag gct cca ggg aag ggg ctg gaa tgg gtt     144
Tyr Met Ser Trp Ile Arg Gln Ala Pro Gly Lys Gly Leu Glu Trp Val
        35                  40                  45 tca tac att agt act aga agt act tac aca aac tac gca gac tct gtg     192
Ser Tyr Ile Ser Thr Arg Ser Thr Tyr Thr Asn Tyr Ala Asp Ser Val
    50                  55                  60 aag ggc cga ttc acc atc tcc aga gac aac gcc aag aac tca cta tat     240
Lys Gly Arg Phe Thr Ile Ser Arg Asp Asn Ala Lys Asn Ser Leu Tyr
65                  70                  75                  80 ctg cac atg aac agc ctg aga acc gag gac acg gct gtt tat tac tgt     288
Leu His Met Asn Ser Leu Arg Thr Glu Asp Thr Ala Val Tyr Tyr Cys
                85                  90                  95 gcg aga gat tac tct gat act agt gga ccc cct gac tac tgg ggc cag     336
Ala Arg Asp Tyr Ser Asp Thr Ser Gly Pro Pro Asp Tyr Trp Gly Gln
            100                 105                 110 ggc acc ctg gtc acc gtc tcc tcg                                     360
Gly Thr Leu Val Thr Val Ser Ser
        115                 120

<210> SEQ ID NO 14
<211> LENGTH: 120
<212> TYPE: PRT
<213> ORGANISM: Homo sapiens

<400> SEQUENCE: 14

Gln Val Gln Leu Val Glu Ser Gly Gly Asp Leu Val Lys Pro Gly Gly
1               5                   10                  15

Ser Leu Arg Leu Ser Cys Ala Ala Ser Gly Phe Thr Phe Ser Asp His
            20                  25                  30
```

```
Tyr Met Ser Trp Ile Arg Gln Ala Pro Gly Lys Gly Leu Glu Trp Val
         35                  40                  45

Ser Tyr Ile Ser Thr Arg Ser Thr Tyr Thr Asn Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu His Met Asn Ser Leu Arg Thr Glu Asp Thr Ala Val Tyr Tyr Cys
                 85                  90                  95

Ala Arg Asp Tyr Ser Asp Thr Ser Gly Pro Pro Asp Tyr Trp Gly Gln
                100                 105                 110

Gly Thr Leu Val Thr Val Ser Ser
            115                 120

<210> SEQ ID NO 15
<211> LENGTH: 330
<212> TYPE: DNA
<213> ORGANISM: Homo sapiens
<220> FEATURE:
<221> NAME/KEY: CDS
<222> LOCATION: (1)..(330)
<223> OTHER INFORMATION: NI-307.11G6 variable light chain (VL) sequence
<220> FEATURE:
<221> NAME/KEY: V_region
<222> LOCATION: (67)..(105)
<223> OTHER INFORMATION: complementarity determining region (CDR) VL-
      CDR1
<220> FEATURE:
<221> NAME/KEY: V_region
<222> LOCATION: (151)..(171)
<223> OTHER INFORMATION: complementarity determining region (CDR) VL-
      CDR2
<220> FEATURE:
<221> NAME/KEY: V_region
<222> LOCATION: (268)..(300)
<223> OTHER INFORMATION: complementarity determining region (CDR) VL-
      CDR3

<400> SEQUENCE: 15 cag tct gtg ctg act cag cca ccc tca gcg tct ggg acc ccc ggg cag        48
Gln Ser Val Leu Thr Gln Pro Pro Ser Ala Ser Gly Thr Pro Gly Gln
 1               5                  10                  15 agg gtc acc atc tct tgt tct ggg agc aac tcc aac atc gga agt aat        96
Arg Val Thr Ile Ser Cys Ser Gly Ser Asn Ser Asn Ile Gly Ser Asn
             20                  25                  30 tat gta tac tgg tac cag cag ctc cca gga acg gcc ccc aaa ctc gtc       144
Tyr Val Tyr Trp Tyr Gln Gln Leu Pro Gly Thr Ala Pro Lys Leu Val
         35                  40                  45 atc tat agg aat act cag cgg ccc tca ggg gtc cct gac cga ttc tct       192
Ile Tyr Arg Asn Thr Gln Arg Pro Ser Gly Val Pro Asp Arg Phe Ser
 50                  55                  60 ggc tcc aag tct ggc acc tca gcc tcc ctg gcc atc agt ggg ctc cgg       240
Gly Ser Lys Ser Gly Thr Ser Ala Ser Leu Ala Ile Ser Gly Leu Arg
 65                  70                  75                  80 tcc gaa gat gag gct gat tat tac tgt gca gca tgg gat gac agc ctg       288
Ser Glu Asp Glu Ala Asp Tyr Tyr Cys Ala Ala Trp Asp Asp Ser Leu
                 85                  90                  95 agt ggt ctg gtg ttc ggc gga ggg acc aag ctg acc gtc ctg               330
Ser Gly Leu Val Phe Gly Gly Gly Thr Lys Leu Thr Val Leu
                100                 105                 110

<210> SEQ ID NO 16
<211> LENGTH: 110
<212> TYPE: PRT
<213> ORGANISM: Homo sapiens
```

<400> SEQUENCE: 16

Gln Ser Val Leu Thr Gln Pro Pro Ser Ala Ser Gly Thr Pro Gly Gln
1               5                   10                  15

Arg Val Thr Ile Ser Cys Ser Gly Ser Asn Ser Asn Ile Gly Ser Asn
            20                  25                  30

Tyr Val Tyr Trp Tyr Gln Gln Leu Pro Gly Thr Ala Pro Lys Leu Val
        35                  40                  45

Ile Tyr Arg Asn Thr Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Leu Val Phe Gly Gly Gly Thr Lys Leu Thr Val Leu
            100                 105                 110

<210> SEQ ID NO 17
<211> LENGTH: 357
<212> TYPE: DNA
<213> ORGANISM: Homo sapiens
<220> FEATURE:
<221> NAME/KEY: CDS
<222> LOCATION: (1)..(357)
<223> OTHER INFORMATION: NI-307.17F12 variable heavy chain (VH) sequence
<220> FEATURE:
<221> NAME/KEY: V_region
<222> LOCATION: (76)..(108)
<223> OTHER INFORMATION: complementarity determining region (CDR) VH-
      CDR1
<220> FEATURE:
<221> NAME/KEY: V_region
<222> LOCATION: (151)..(198)
<223> OTHER INFORMATION: complementarity determining region (CDR) VH-
      CDR2
<220> FEATURE:
<221> NAME/KEY: V_region
<222> LOCATION: (295)..(324)
<223> OTHER INFORMATION: complementarity determining region (CDR) VH-
      CDR3

<400> SEQUENCE: 17 cag ctg cag ctg cag gag tcg ggc cca gga ctg gtg aag cct tcg ggg      48
Gln Leu Gln Leu Gln Glu Ser Gly Pro Gly Leu Val Lys Pro Ser Gly
1               5                   10                  15 acc ctg tcc ctc acc tgc gct gtc tct ggt gac tcc atc acc aat act      96
Thr Leu Ser Leu Thr Cys Ala Val Ser Gly Asp Ser Ile Thr Asn Thr
            20                  25                  30 aac tgg tgg tgt tgg gtc cgc cag ccc cca ggg aag ggg ctg gag tgg     144
Asn Trp Trp Cys Trp Val Arg Gln Pro Pro Gly Lys Gly Leu Glu Trp
        35                  40                  45 att ggg gaa atc ttt cat agt ggg ggc acc aac tac aac ccg tcc ctc     192
Ile Gly Glu Ile Phe His Ser Gly Gly Thr Asn Tyr Asn Pro Ser Leu
    50                  55                  60 aag agt cga gtc acc atg tca gta gac aag gcc aag aac cag ttc tcc     240
Lys Ser Arg Val Thr Met Ser Val Asp Lys Ala Lys Asn Gln Phe Ser
65                  70                  75                  80 ctg aag gtg aac tct gtg acc gcc gcg gac acg gcc gtg tac ttc tgt     288
Leu Lys Val Asn Ser Val Thr Ala Ala Asp Thr Ala Val Tyr Phe Cys
                85                  90                  95 acg acc aac ccc ggg ggg gga gat ggc tac agt tac tgg ggc cag ggc     336
Thr Thr Asn Pro Gly Gly Gly Asp Gly Tyr Ser Tyr Trp Gly Gln Gly
            100                 105                 110

```
acc ctg gtc acc gtc tcc tcg                                    357
Thr Leu Val Thr Val Ser Ser
        115
```

<210> SEQ ID NO 18
<211> LENGTH: 119
<212> TYPE: PRT
<213> ORGANISM: Homo sapiens

<400> SEQUENCE: 18

```
Gln Leu Gln Leu Gln Glu Ser Gly Pro Gly Leu Val Lys Pro Ser Gly
1               5                   10                  15

Thr Leu Ser Leu Thr Cys Ala Val Ser Gly Asp Ser Ile Thr Asn Thr
            20                  25                  30

Asn Trp Trp Cys Trp Val Arg Gln Pro Pro Gly Lys Gly Leu Glu Trp
        35                  40                  45

Ile Gly Glu Ile Phe His Ser Gly Gly Thr Asn Tyr Asn Pro Ser Leu
    50                  55                  60

Lys Ser Arg Val Thr Met Ser Val Asp Lys Ala Lys Asn Gln Phe Ser
65                  70                  75                  80

Leu Lys Val Asn Ser Val Thr Ala Ala Asp Thr Ala Val Tyr Phe Cys
                85                  90                  95

Thr Thr Asn Pro Gly Gly Gly Asp Gly Tyr Ser Tyr Trp Gly Gln Gly
            100                 105                 110

Thr Leu Val Thr Val Ser Ser
        115
```

<210> SEQ ID NO 19
<211> LENGTH: 327
<212> TYPE: DNA
<213> ORGANISM: Homo sapiens
<220> FEATURE:
<221> NAME/KEY: CDS
<222> LOCATION: (1)..(327)
<223> OTHER INFORMATION: NI-307.17F12 variable light chain (VL) sequence
<220> FEATURE:
<221> NAME/KEY: V_region
<222> LOCATION: (67)..(108)
<223> OTHER INFORMATION: complementarity determining region (CDR) VL-
      CDR1
<220> FEATURE:
<221> NAME/KEY: V_region
<222> LOCATION: (154)..(174)
<223> OTHER INFORMATION: complementarity determining region (CDR) VL-
      CDR2
<220> FEATURE:
<221> NAME/KEY: V_region
<222> LOCATION: (271)..(300)
<223> OTHER INFORMATION: complementarity determining region (CDR) VL-
      CDR3

<400> SEQUENCE: 19

```
cag tct gcc ctg act cag cct cgc tca gtg tcc ggg tct cct gga cag    48
Gln Ser Ala Leu Thr Gln Pro Arg Ser Val Ser Gly Ser Pro Gly Gln
1               5                   10                  15 tca gtc acc atc tcc tgc act gga acc agc agt gat gtt ggt ggt tat    96
Ser Val Thr Ile Ser Cys Thr Gly Thr Ser Ser Asp Val Gly Gly Tyr
            20                  25                  30 aac tat gtc tcc tgg tac caa caa cac cca ggc aaa gcc ccc aat ctc   144
Asn Tyr Val Ser Trp Tyr Gln Gln His Pro Gly Lys Ala Pro Asn Leu
        35                  40                  45 atg att tct gag gtc agt aag cgg ccc tca ggg gtc cct gat cgc ttc   192
Met Ile Ser Glu Val Ser Lys Arg Pro Ser Gly Val Pro Asp Arg Phe
    50                  55                  60
```

```
tct ggc tcc aag tct ggc aac acg gcc tcc ctg acc atc tct ggg ctc      240
Ser Gly Ser Lys Ser Gly Asn Thr Ala Ser Leu Thr Ile Ser Gly Leu
 65                  70                  75                  80 cag gct gag gat gag gct gat tat ttc tgc tgc tca tat gca ggc agt      288
Gln Ala Glu Asp Glu Ala Asp Tyr Phe Cys Cys Ser Tyr Ala Gly Ser
                 85                  90                  95 tac agg gtc ttc gga act ggg acc aag gtc acc gtc cta                  327
Tyr Arg Val Phe Gly Thr Gly Thr Lys Val Thr Val Leu
            100                 105
```

<210> SEQ ID NO 20
<211> LENGTH: 109
<212> TYPE: PRT
<213> ORGANISM: Homo sapiens

<400> SEQUENCE: 20

```
Gln Ser Ala Leu Thr Gln Pro Arg Ser Val Ser Gly Ser Pro Gly Gln
 1               5                  10                  15

Ser Val Thr Ile Ser Cys Thr Gly Thr Ser Ser Asp Val Gly Gly Tyr
             20                  25                  30

Asn Tyr Val Ser Trp Tyr Gln Gln His Pro Gly Lys Ala Pro Asn Leu
         35                  40                  45

Met Ile Ser Glu Val Ser Lys Arg Pro Ser Gly Val Pro Asp Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Phe Cys Cys Ser Tyr Ala Gly Ser
                 85                  90                  95

Tyr Arg Val Phe Gly Thr Gly Thr Lys Val Thr Val Leu
            100                 105
```

<210> SEQ ID NO 21
<211> LENGTH: 372
<212> TYPE: DNA
<213> ORGANISM: Homo sapiens
<220> FEATURE:
<221> NAME/KEY: CDS
<222> LOCATION: (1)..(372)
<223> OTHER INFORMATION: NI-307.6A2 variable heavy chain (VH) sequence
<220> FEATURE:
<221> NAME/KEY: V_region
<222> LOCATION: (76)..(108)
<223> OTHER INFORMATION: complementarity determining region (CDR) VH-CDR1
<220> FEATURE:
<221> NAME/KEY: V_region
<222> LOCATION: (151)..(198)
<223> OTHER INFORMATION: complementarity determining region (CDR) VH-CDR2
<220> FEATURE:
<221> NAME/KEY: V_region
<222> LOCATION: (295)..(339)
<223> OTHER INFORMATION: complementarity determining region (CDR) VH-CDR3

<400> SEQUENCE: 21

```
cag gtg cag ctg cag gag tcg ggc cca gga ctg gtg aag cct tcg gag       48
Gln Val Gln Leu Gln Glu Ser Gly Pro Gly Leu Val Lys Pro Ser Glu
 1               5                  10                  15 acc ctg tcc ctc acc tgc gct gtc tct gga ggc tcc gtc agc agt agt       96
Thr Leu Ser Leu Thr Cys Ala Val Ser Gly Gly Ser Val Ser Ser Ser
             20                  25                  30 tac tgg tac agt tgg gtc cgc cag ctc cca gga agg ggg ctg gaa tgg      144
Tyr Trp Tyr Ser Trp Val Arg Gln Leu Pro Gly Lys Gly Leu Glu Trp
         35                  40                  45
```

```
atc gga gaa atc ttt cat act ggg gac acc aac tac aac ccg tcc ctc      192
Ile Gly Glu Ile Phe His Thr Gly Asp Thr Asn Tyr Asn Pro Ser Leu
        50                  55                  60 gag agt cga gtc acc att tca ata gac acg tcc aag aac cag ttg tcc      240
Glu Ser Arg Val Thr Ile Ser Ile Asp Thr Ser Lys Asn Gln Leu Ser
65                  70                  75                  80 ctg gat gtg acc tct gcg acc gcc gcg gac acg gcc gta tac tac tgc      288
Leu Asp Val Thr Ser Ala Thr Ala Ala Asp Thr Ala Val Tyr Tyr Cys
                85                  90                  95 gcg aga gat tat tgt act gat agc ggt tgc gac tct gat gct ctt gat      336
Ala Arg Asp Tyr Cys Thr Asp Ser Gly Cys Asp Ser Asp Ala Leu Asp
            100                 105                 110 gtc tgg ggc cac ggg aca atg gtc acc gtc tct tcg                      372
Val Trp Gly His Gly Thr Met Val Thr Val Ser Ser
        115                 120
```

<210> SEQ ID NO 22
<211> LENGTH: 124
<212> TYPE: PRT
<213> ORGANISM: Homo sapiens

<400> SEQUENCE: 22

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Gly Ser Val Ser Ser Ser
            20                  25                  30

Tyr Trp Tyr Ser Trp Val Arg Gln Leu Pro Gly Lys Gly Leu Glu Trp
        35                  40                  45

Ile Gly Glu Ile Phe His Thr Gly Asp Thr Asn Tyr Asn Pro Ser Leu
    50                  55                  60

Glu Ser Arg Val Thr Ile Ser Ile Asp Thr Ser Lys Asn Gln Leu Ser
65                  70                  75                  80

Leu Asp Val Thr Ser Ala Thr Ala Ala Asp Thr Ala Val Tyr Tyr Cys
                85                  90                  95

Ala Arg Asp Tyr Cys Thr Asp Ser Gly Cys Asp Ser Asp Ala Leu Asp
            100                 105                 110

Val Trp Gly His Gly Thr Met Val Thr Val Ser Ser
        115                 120
```

<210> SEQ ID NO 23
<211> LENGTH: 330
<212> TYPE: DNA
<213> ORGANISM: Homo sapiens
<220> FEATURE:
<221> NAME/KEY: CDS
<222> LOCATION: (1)..(330)
<223> OTHER INFORMATION: NI-307.6A2 variable light chain (VL) sequence
<220> FEATURE:
<221> NAME/KEY: V_region
<222> LOCATION: (67)..(108)
<223> OTHER INFORMATION: complementarity determining region (CDR) VL-
      CDR1
<220> FEATURE:
<221> NAME/KEY: V_region
<222> LOCATION: (154)..(174)
<223> OTHER INFORMATION: complementarity determining region (CDR) VL-
      CDR2
<220> FEATURE:
<221> NAME/KEY: V_region
<222> LOCATION: (271)..(300)
<223> OTHER INFORMATION: complementarity determining region (CDR) VL-
      CDR3

<400> SEQUENCE: 23

```
cag tct gcc ctg act cag cct gcc tcc gtg tct ggg tct cct gga cag    48
Gln Ser Ala Leu Thr Gln Pro Ala Ser Val Ser Gly Ser Pro Gly Gln
1               5                   10                  15 tcg atc acc atc tcc tgc act gga acc acc aaa gat gtt gga aat tat    96
Ser Ile Thr Ile Ser Cys Thr Gly Thr Thr Lys Asp Val Gly Asn Tyr
            20                  25                  30 aac ctt gtc tcc tgg tac caa cag cac ccg ggc aaa gcc ccc aga ctc   144
Asn Leu Val Ser Trp Tyr Gln Gln His Pro Gly Lys Ala Pro Arg Leu
        35                  40                  45 gtg att tat gag gtc agt gag cgg ccc tca ggg gtt tct aat cgc ttc   192
Val Ile Tyr Glu Val Ser Glu Arg Pro Ser Gly Val Ser Asn Arg Phe
50                  55                  60 tct ggc tcc aag tct ggc aac acg gcc tcc ctg aca atc tct ggg ctc   240
Ser Gly Ser Lys Ser Gly Asn Thr Ala Ser Leu Thr Ile Ser Gly Leu
65                  70                  75                  80 cag gct gag gac gag gct gat tat cac tgc tgc tca tat gca ggt agt   288
Gln Ala Glu Asp Glu Ala Asp Tyr His Cys Cys Ser Tyr Ala Gly Ser
                85                  90                  95 ggc aca tcg gta ttc ggc gga ggg acc aag gtg acc gtc cta           330
Gly Thr Ser Val Phe Gly Gly Gly Thr Lys Val Thr Val Leu
                100                 105                 110

<210> SEQ ID NO 24
<211> LENGTH: 110
<212> TYPE: PRT
<213> ORGANISM: Homo sapiens

<400> SEQUENCE: 24

Gln Ser Ala Leu Thr Gln Pro Ala Ser Val Ser Gly Ser Pro Gly Gln
1               5                   10                  15

Ser Ile Thr Ile Ser Cys Thr Gly Thr Thr Lys Asp Val Gly Asn Tyr
            20                  25                  30

Asn Leu Val Ser Trp Tyr Gln Gln His Pro Gly Lys Ala Pro Arg Leu
        35                  40                  45

Val Ile Tyr Glu Val Ser Glu Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr His Cys Cys Ser Tyr Ala Gly Ser
                85                  90                  95

Gly Thr Ser Val Phe Gly Gly Gly Thr Lys Val Thr Val Leu
                100                 105                 110

<210> SEQ ID NO 25
<211> LENGTH: 375
<212> TYPE: DNA
<213> ORGANISM: Homo sapiens
<220> FEATURE:
<221> NAME/KEY: CDS
<222> LOCATION: (1)..(375)
<223> OTHER INFORMATION: NI-307.5H3 variable heavy chain (VH) sequence
<220> FEATURE:
<221> NAME/KEY: V_region
<222> LOCATION: (76)..(108)
<223> OTHER INFORMATION: complementarity determining region (CDR) VH-
      CDR1
<220> FEATURE:
<221> NAME/KEY: V_region
<222> LOCATION: (151)..(198)
<223> OTHER INFORMATION: complementarity determining region (CDR) VH-
      CDR2
<220> FEATURE:
<221> NAME/KEY: V_region
```

```
<222> LOCATION: (295)..(342)
<223> OTHER INFORMATION: complementarity determining region (CDR) VH-
      CDR3

<400> SEQUENCE: 25 cag gtg cag ctg cag gag tcc ggc cca gga ctg ctg aag cct ttg gga       48
Gln Val Gln Leu Gln Glu Ser Gly Pro Gly Leu Leu Lys Pro Leu Gly
1               5                   10                  15 acc ctg tcc ctc atc tgc gat gtc tct ggt gac tcc atc agt agt agt       96
Thr Leu Ser Leu Ile Cys Asp Val Ser Gly Asp Ser Ile Ser Ser Ser
            20                  25                  30 aac tgg tgg agt tgg gtc cgc cag tcc ccc cgg aag ggg ctg gag tgg      144
Asn Trp Trp Ser Trp Val Arg Gln Ser Pro Arg Lys Gly Leu Glu Trp
        35                  40                  45 att ggc gaa atc tat cat agt ggg agg acc aac tac aat ccg tca ctc      192
Ile Gly Glu Ile Tyr His Ser Gly Arg Thr Asn Tyr Asn Pro Ser Leu
    50                  55                  60 acg aat cga gtt acc att tca gtg gac aag tcc aag aac cag ttc tcc      240
Thr Asn Arg Val Thr Ile Ser Val Asp Lys Ser Lys Asn Gln Phe Ser
65                  70                  75                  80 ctg aat ctg aac tct gtg acc gcc gcg gac acg ggt gta tat tat tgt      288
Leu Asn Leu Asn Ser Val Thr Ala Ala Asp Thr Gly Val Tyr Tyr Cys
                85                  90                  95 gcg aga tgg gat tat tat tat aat aat gat tat tat atc cgc ggt ttt      336
Ala Arg Trp Asp Tyr Tyr Tyr Asn Asn Asp Tyr Tyr Ile Arg Gly Phe
            100                 105                 110 gat ata tgg ggc caa ggg aca atg gtc acc gtc tct tcg                  375
Asp Ile Trp Gly Gln Gly Thr Met Val Thr Val Ser Ser
        115                 120                 125

<210> SEQ ID NO 26
<211> LENGTH: 125
<212> TYPE: PRT
<213> ORGANISM: Homo sapiens

<400> SEQUENCE: 26

Gln Val Gln Leu Gln Glu Ser Gly Pro Gly Leu Leu Lys Pro Leu Gly
1               5                   10                  15

Thr Leu Ser Leu Ile Cys Asp Val Ser Gly Asp Ser Ile Ser Ser Ser
            20                  25                  30

Asn Trp Trp Ser Trp Val Arg Gln Ser Pro Arg Lys Gly Leu Glu Trp
        35                  40                  45

Ile Gly Glu Ile Tyr His Ser Gly Arg Thr Asn Tyr Asn Pro Ser Leu
    50                  55                  60

Thr Asn Arg Val Thr Ile Ser Val Asp Lys Ser Lys Asn Gln Phe Ser
65                  70                  75                  80

Leu Asn Leu Asn Ser Val Thr Ala Ala Asp Thr Gly Val Tyr Tyr Cys
                85                  90                  95

Ala Arg Trp Asp Tyr Tyr Tyr Asn Asn Asp Tyr Tyr Ile Arg Gly Phe
            100                 105                 110

Asp Ile Trp Gly Gln Gly Thr Met Val Thr Val Ser Ser
        115                 120                 125

<210> SEQ ID NO 27
<211> LENGTH: 327
<212> TYPE: DNA
<213> ORGANISM: Homo sapiens
<220> FEATURE:
<221> NAME/KEY: CDS
<222> LOCATION: (1)..(327)
<223> OTHER INFORMATION: NI-307.5H3 variable K-light chain (VK) sequence
```

```
<220> FEATURE:
<221> NAME/KEY: V_region
<222> LOCATION: (70)..(105)
<223> OTHER INFORMATION: complementarity determining region (CDR) VK-
      CDR1
<220> FEATURE:
<221> NAME/KEY: V_region
<222> LOCATION: (151)..(171)
<223> OTHER INFORMATION: complementarity determining region (CDR) VK-
      CDR2
<220> FEATURE:
<221> NAME/KEY: V_region
<222> LOCATION: (268)..(297)
<223> OTHER INFORMATION: complementarity determining region (CDR) VK-
      CDR3

<400> SEQUENCE: 27 gaa att gtg ttg acg cag tct cca ggc atc ctg tct ttg tct cca ggg     48
Glu Ile Val Leu Thr Gln Ser Pro Gly Ile Leu Ser Leu Ser Pro Gly
1               5                   10                  15 gaa aga gcc acc ctc tcc tgc agg gcc agt cag agt gtt gac agc aac     96
Glu Arg Ala Thr Leu Ser Cys Arg Ala Ser Gln Ser Val Asp Ser Asn
            20                  25                  30 tac cta gcc tgg tac cag cag aaa cct ggc cag gct ccc agg ctc ctc    144
Tyr Leu Ala Trp Tyr Gln Gln Lys Pro Gly Gln Ala Pro Arg Leu Leu
        35                  40                  45 atc tat agt aca tcc acc agg gcc gct ggc gtc cca gac agg ttc agt    192
Ile Tyr Ser Thr Ser Thr Arg Ala Ala Gly Val Pro Asp Arg Phe Ser
    50                  55                  60 ggc agt ggg tct ggg aca gac ttc gct ctc acc atc agc gga ctg gag    240
Gly Ser Gly Ser Gly Thr Asp Phe Ala Leu Thr Ile Ser Gly Leu Glu
65                  70                  75                  80 cct gaa gat ttt gca gtg tat tac tgt cag cag tgg ggt ggc tca cct    288
Pro Glu Asp Phe Ala Val Tyr Tyr Cys Gln Gln Trp Gly Gly Ser Pro
                85                  90                  95 ccg atc acc ttc ggc caa ggg aca cga ctg gag att aaa                327
Pro Ile Thr Phe Gly Gln Gly Thr Arg Leu Glu Ile Lys
            100                 105

<210> SEQ ID NO 28
<211> LENGTH: 109
<212> TYPE: PRT
<213> ORGANISM: Homo sapiens

<400> SEQUENCE: 28

Glu Ile Val Leu Thr Gln Ser Pro Gly Ile Leu Ser Leu Ser Pro Gly
1               5                   10                  15

Glu Arg Ala Thr Leu Ser Cys Arg Ala Ser Gln Ser Val Asp Ser Asn
            20                  25                  30

Tyr Leu Ala Trp Tyr Gln Gln Lys Pro Gly Gln Ala Pro Arg Leu Leu
        35                  40                  45

Ile Tyr Ser Thr Ser Thr Arg Ala Ala Gly Val Pro Asp Arg Phe Ser
    50                  55                  60

Gly Ser Gly Ser Gly Thr Asp Phe Ala Leu Thr Ile Ser Gly Leu Glu
65                  70                  75                  80

Pro Glu Asp Phe Ala Val Tyr Tyr Cys Gln Gln Trp Gly Gly Ser Pro
                85                  90                  95

Pro Ile Thr Phe Gly Gln Gly Thr Arg Leu Glu Ile Lys
            100                 105

<210> SEQ ID NO 29
<211> LENGTH: 372
<212> TYPE: DNA
```

```
<213> ORGANISM: Homo sapiens
<220> FEATURE:
<221> NAME/KEY: CDS
<222> LOCATION: (1)..(372)
<223> OTHER INFORMATION: NI-307.25G10 variable heavy chain (VH) sequence
<220> FEATURE:
<221> NAME/KEY: V_region
<222> LOCATION: (76)..(105)
<223> OTHER INFORMATION: complementarity determining region (CDR) VH-
      CDR1
<220> FEATURE:
<221> NAME/KEY: V_region
<222> LOCATION: (148)..(195)
<223> OTHER INFORMATION: complementarity determining region (CDR) VH-
      CDR2
<220> FEATURE:
<221> NAME/KEY: V_region
<222> LOCATION: (292)..(339)
<223> OTHER INFORMATION: complementarity determining region (CDR) VH-
      CDR3

<400> SEQUENCE: 29 gag gtg cag ctg gtg gag tct ggg gga ggc tta gta cag ccg ggg ggg       48
Glu Val Gln Leu Val Glu Ser Gly Gly Gly Leu Val Gln Pro Gly Gly
1               5                   10                  15 tcc ctg aga ctc tcc tgt gtg gcc tct gga atc atc ttc aaa gac tac       96
Ser Leu Arg Leu Ser Cys Val Ala Ser Gly Ile Ile Phe Lys Asp Tyr
            20                  25                  30 gac ttc cac tgg gtc cga caa gtt aaa gaa aaa ggt ctg gag tgg gtc      144
Asp Phe His Trp Val Arg Gln Val Lys Glu Lys Gly Leu Glu Trp Val
        35                  40                  45 tca gct att ggt act gct ggt gac cca tat tat gca gct tcc gtg aag      192
Ser Ala Ile Gly Thr Ala Gly Asp Pro Tyr Tyr Ala Ala Ser Val Lys
    50                  55                  60 ggc cgc ttc acc gtc tcc agg gaa aat ggc aag aac tcc gtg tat ctt      240
Gly Arg Phe Thr Val Ser Arg Glu Asn Gly Lys Asn Ser Val Tyr Leu
65                  70                  75                  80 cga atg aac aac gtg gga gcc ggt gac acg gct ctg tat tat tgt acg      288
Arg Met Asn Asn Val Gly Ala Gly Asp Thr Ala Leu Tyr Tyr Cys Thr
                85                  90                  95 agc ggc aat tac ttc gat aga ggt tct ttc agg ccg agt gct ttt gat      336
Ser Gly Asn Tyr Phe Asp Arg Gly Ser Phe Arg Pro Ser Ala Phe Asp
            100                 105                 110 atg tgg ggc caa ggg aca atg gtc acc gtc tct tcg                      372
Met Trp Gly Gln Gly Thr Met Val Thr Val Ser Ser
        115                 120

<210> SEQ ID NO 30
<211> LENGTH: 124
<212> TYPE: PRT
<213> ORGANISM: Homo sapiens

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Val Ala Ser Gly Ile Ile Phe Lys Asp Tyr
            20                  25                  30

Asp Phe His Trp Val Arg Gln Val Lys Glu Lys Gly Leu Glu Trp Val
        35                  40                  45

Ser Ala Ile Gly Thr Ala Gly Asp Pro Tyr Tyr Ala Ala Ser Val Lys
    50                  55                  60

Gly Arg Phe Thr Val Ser Arg Glu Asn Gly Lys Asn Ser Val Tyr Leu
65                  70                  75                  80

Arg Met Asn Asn Val Gly Ala Gly Asp Thr Ala Leu Tyr Tyr Cys Thr
```

```
                    85                  90                  95
Ser Gly Asn Tyr Phe Asp Arg Gly Ser Phe Arg Pro Ser Ala Phe Asp
                100                 105                 110
Met Trp Gly Gln Gly Thr Met Val Thr Val Ser Ser
                115                 120
```

<210> SEQ ID NO 31
<211> LENGTH: 333
<212> TYPE: DNA
<213> ORGANISM: Homo sapiens
<220> FEATURE:
<221> NAME/KEY: CDS
<222> LOCATION: (1)..(333)
<223> OTHER INFORMATION: NI-307.25G10 variable K-light chain (VK)
      sequence
<220> FEATURE:
<221> NAME/KEY: V_region
<222> LOCATION: (70)..(105)
<223> OTHER INFORMATION: complementarity determining region (CDR) VK-
      CDR1
<220> FEATURE:
<221> NAME/KEY: V_region
<222> LOCATION: (151)..(171)
<223> OTHER INFORMATION: complementarity determining region (CDR) VK-
      CDR2
<220> FEATURE:
<221> NAME/KEY: V_region
<222> LOCATION: (268)..(303)
<223> OTHER INFORMATION: complementarity determining region (CDR) VK-
      CDR3

<400> SEQUENCE: 31

```
gaa att gtg ctg act cag tct cca ggc acc ctg tct ttg tct cca ggg         48
Glu Ile Val Leu Thr Gln Ser Pro Gly Thr Leu Ser Leu Ser Pro Gly
1               5                   10                  15 gaa aga gcc acc ctc tcc tgc tgg gcc agt cag agt gtt tct agc aac         96
Glu Arg Ala Thr Leu Ser Cys Trp Ala Ser Gln Ser Val Ser Ser Asn
            20                  25                  30 tac tta gcc tgg tat cag cac aaa cct ggc cag gct ccc aga ctc ctc        144
Tyr Leu Ala Trp Tyr Gln His Lys Pro Gly Gln Ala Pro Arg Leu Leu
        35                  40                  45 atc ttt cgc gca tct cgt agg gcc act gac atc cca gag agg ttc agt        192
Ile Phe Arg Ala Ser Arg Arg Ala Thr Asp Ile Pro Glu Arg Phe Ser
    50                  55                  60 gcc gga ggg tct ggg aca gac ttc act ctc acc atc agc aga ctg gaa        240
Ala Gly Gly Ser Gly Thr Asp Phe Thr Leu Thr Ile Ser Arg Leu Glu
65                  70                  75                  80 gct gaa gac tct gca gtc tat tac tgt cag gag tat ggt agt gca cct        288
Ala Glu Asp Ser Ala Val Tyr Tyr Cys Gln Glu Tyr Gly Ser Ala Pro
                85                  90                  95 ccg gcg tcg atc acg ttc ggc caa ggg aca cga ctg gag att aaa            333
Pro Ala Ser Ile Thr Phe Gly Gln Gly Thr Arg Leu Glu Ile Lys
                100                 105                 110
```

<210> SEQ ID NO 32
<211> LENGTH: 111
<212> TYPE: PRT
<213> ORGANISM: Homo sapiens

<400> SEQUENCE: 32

```
Glu Ile Val Leu Thr Gln Ser Pro Gly Thr Leu Ser Leu Ser Pro Gly
1               5                   10                  15

Glu Arg Ala Thr Leu Ser Cys Trp Ala Ser Gln Ser Val Ser Ser Asn
            20                  25                  30

Tyr Leu Ala Trp Tyr Gln His Lys Pro Gly Gln Ala Pro Arg Leu Leu
```

```
                35                  40                  45
Ile Phe Arg Ala Ser Arg Arg Ala Thr Asp Ile Pro Glu Arg Phe Ser
    50                  55                  60

Ala Gly Gly Ser Gly Thr Asp Phe Thr Leu Thr Ile Ser Arg Leu Glu
65                  70                  75                  80

Ala Glu Asp Ser Ala Val Tyr Tyr Cys Gln Glu Tyr Gly Ser Ala Pro
                85                  90                  95

Pro Ala Ser Ile Thr Phe Gly Gln Gly Thr Arg Leu Glu Ile Lys
                100                 105                 110

<210> SEQ ID NO 33
<211> LENGTH: 339
<212> TYPE: DNA
<213> ORGANISM: Homo sapiens
<220> FEATURE:
<221> NAME/KEY: CDS
<222> LOCATION: (1)..(339)
<223> OTHER INFORMATION: NI-307.26E10 variable heavy chain (VH) sequence
<220> FEATURE:
<221> NAME/KEY: V_region
<222> LOCATION: (76)..(105)
<223> OTHER INFORMATION: complementarity determining region (CDR) VH-
      CDR1
<220> FEATURE:
<221> NAME/KEY: V_region
<222> LOCATION: (148)..(195)
<223> OTHER INFORMATION: complementarity determining region (CDR) VH-
      CDR2
<220> FEATURE:
<221> NAME/KEY: V_region
<222> LOCATION: (292)..(306)
<223> OTHER INFORMATION: complementarity determining region (CDR) VH-
      CDR3

<400> SEQUENCE: 33 gag gtg cag ctg gtg gag tct ggg gga ggc ctg gtc ctg ccg ggg ggg        48
Glu Val Gln Leu Val Glu Ser Gly Gly Gly Leu Val Leu Pro Gly Gly
1               5                   10                  15 tcc ctg aga ctc tcc tgt gca gtc tct gga ttc act gtc aga aat gag       96
Ser Leu Arg Leu Ser Cys Ala Val Ser Gly Phe Thr Val Arg Asn Glu
            20                  25                  30 tac atg agg tgg gcc cgc cag gct cca ggg agg ggg ctg gag tgg gtc      144
Tyr Met Arg Trp Ala Arg Gln Ala Pro Gly Arg Gly Leu Glu Trp Val
        35                  40                  45 tca gtg att tac aga gat ggc cag aca cac cac gca gac acc gtg aag      192
Ser Val Ile Tyr Arg Asp Gly Gln Thr His His Ala Asp Thr Val Lys
    50                  55                  60 ggc aga ttc gac gtc tcc aaa gac act tcc aag aac acg atg tac ctt      240
Gly Arg Phe Asp Val Ser Lys Asp Thr Ser Lys Asn Thr Met Tyr Leu
65                  70                  75                  80 cag atg cac aat ctg aga gtc gac gac acg gcc atc tat tac tgt gcg      288
Gln Met His Asn Leu Arg Val Asp Asp Thr Ala Ile Tyr Tyr Cys Ala
                85                  90                  95 agg ggg cat tac ggt cct tgg ggc cag ggc acc ctg gtc acc gtc tcc      336
Arg Gly His Tyr Gly Pro Trp Gly Gln Gly Thr Leu Val Thr Val Ser
                100                 105                 110 tcg                                                                   339
Ser

<210> SEQ ID NO 34
<211> LENGTH: 113
<212> TYPE: PRT
<213> ORGANISM: Homo sapiens

<400> SEQUENCE: 34
```

```
Glu Val Gln Leu Val Glu Ser Gly Gly Gly Leu Val Leu Pro Gly Gly
1               5                   10                  15

Ser Leu Arg Leu Ser Cys Ala Val Ser Gly Phe Thr Val Arg Asn Glu
            20                  25                  30

Tyr Met Arg Trp Ala Arg Gln Ala Pro Gly Arg Gly Leu Glu Trp Val
        35                  40                  45

Ser Val Ile Tyr Arg Asp Gly Gln Thr His His Ala Asp Thr Val Lys
50                  55                  60

Gly Arg Phe Asp Val Ser Lys Asp Thr Ser Lys Asn Thr Met Tyr Leu
65                  70                  75                  80

Gln Met His Asn Leu Arg Val Asp Asp Thr Ala Ile Tyr Tyr Cys Ala
                85                  90                  95

Arg Gly His Tyr Gly Pro Trp Gly Gln Gly Thr Leu Val Thr Val Ser
            100                 105                 110

Ser

<210> SEQ ID NO 35
<211> LENGTH: 327
<212> TYPE: DNA
<213> ORGANISM: Homo sapiens
<220> FEATURE:
<221> NAME/KEY: CDS
<222> LOCATION: (1)..(327)
<223> OTHER INFORMATION: NI-307.26E10 variable K-light chain (VK)
      sequence
<220> FEATURE:
<221> NAME/KEY: V_region
<222> LOCATION: (70)..(102)
<223> OTHER INFORMATION: complementarity determining region (CDR) VK-
      CDR1
<220> FEATURE:
<221> NAME/KEY: V_region
<222> LOCATION: (148)..(168)
<223> OTHER INFORMATION: complementarity determining region (CDR) VK-
      CDR2
<220> FEATURE:
<221> NAME/KEY: V_region
<222> LOCATION: (265)..(297)
<223> OTHER INFORMATION: complementarity determining region (CDR) VK-
      CDR3

<400> SEQUENCE: 35 gac atc cag atg acc cag tct cct tcc acc ctg cct gca tct gta gga      48
Asp Ile Gln Met Thr Gln Ser Pro Ser Thr Leu Pro Ala Ser Val Gly
1               5                   10                  15 gac aga gtc acc atc act tgc cgg gcc agt cag agt att aat aat tgg      96
Asp Arg Val Thr Ile Thr Cys Arg Ala Ser Gln Ser Ile Asn Asn Trp
            20                  25                  30 ttg gcc tgg tat cag cag aag cca ggg aaa gcc cct aac ctc ctg att     144
Leu Ala Trp Tyr Gln Gln Lys Pro Gly Lys Ala Pro Asn Leu Leu Ile
        35                  40                  45 tat gat gcc tcc aat ttg gaa act ggg gtc cca tca agg ttc agc ggc     192
Tyr Asp Ala Ser Asn Leu Glu Thr Gly Val Pro Ser Arg Phe Ser Gly
50                  55                  60 agt gga tct ggg aca gaa ttc act ctc acc atc agc agc ctg cag cct     240
Ser Gly Ser Gly Thr Glu Phe Thr Leu Thr Ile Ser Ser Leu Gln Pro
65                  70                  75                  80 gat gat ttt gca act tat tac tgt cag cag tat aat agt cat tct cac     288
Asp Asp Phe Ala Thr Tyr Tyr Cys Gln Gln Tyr Asn Ser His Ser His
                85                  90                  95 acg tgg acg ttc ggc caa ggg acc aag gtg gaa atc aaa                 327
Thr Trp Thr Phe Gly Gln Gly Thr Lys Val Glu Ile Lys
            100                 105
```

<210> SEQ ID NO 36
<211> LENGTH: 109
<212> TYPE: PRT
<213> ORGANISM: Homo sapiens

<400> SEQUENCE: 36

Asp Ile Gln Met Thr Gln Ser Pro Ser Thr Leu Pro Ala Ser Val Gly
1               5                   10                  15

Asp Arg Val Thr Ile Thr Cys Arg Ala Ser Gln Ser Ile Asn Asn Trp
            20                  25                  30

Leu Ala Trp Tyr Gln Gln Lys Pro Gly Lys Ala Pro Asn Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser His Ser His
                85                  90                  95

Thr Trp Thr Phe Gly Gln Gly Thr Lys Val Glu Ile Lys
            100                 105

<210> SEQ ID NO 37
<211> LENGTH: 348
<212> TYPE: DNA
<213> ORGANISM: Homo sapiens
<220> FEATURE:
<221> NAME/KEY: CDS
<222> LOCATION: (1)..(348)
<223> OTHER INFORMATION: NI-307.1E1 variable heavy chain (VH) sequence
<220> FEATURE:
<221> NAME/KEY: V_region
<222> LOCATION: (76)..(105)
<223> OTHER INFORMATION: complementarity determining region (CDR) VH-
      CDR1
<220> FEATURE:
<221> NAME/KEY: V_region
<222> LOCATION: (148)..(204)
<223> OTHER INFORMATION: complementarity determining region (CDR) VH-
      CDR2
<220> FEATURE:
<221> NAME/KEY: V_region
<222> LOCATION: (301)..(315)
<223> OTHER INFORMATION: complementarity determining region (CDR) VH-
      CDR3

<400> SEQUENCE: 37 gag gtg cag ctg gtg gag tct ggg gga ggc ttg gta aag ccg ggg ggg      48
Glu Val Gln Leu Val Glu Ser Gly Gly Gly Leu Val Lys Pro Gly Gly
1               5                   10                  15 tcc ctt aga ctc tcc tgt gca gcc tct gga ttc ata ttt agt gac gcc      96
Ser Leu Arg Leu Ser Cys Ala Ala Ser Gly Phe Ile Phe Ser Asp Ala
            20                  25                  30 tgg atg aac tgg gtc cgc cag gct cca ggg aag gga ctg gag tgg gtt     144
Trp Met Asn Trp Val Arg Gln Ala Pro Gly Lys Gly Leu Glu Trp Val
        35                  40                  45 ggc cat att aaa agc aga cct gct ggt ggg aca act gag tac gct gca     192
Gly His Ile Lys Ser Arg Pro Ala Gly Gly Thr Thr Glu Tyr Ala Ala
    50                  55                  60 ccc gtg aaa ggc aga ttc acc atc tca aga gat gat tct aca gac aca     240
Pro Val Lys Gly Arg Phe Thr Ile Ser Arg Asp Asp Ser Thr Asp Thr
65                  70                  75                  80 cta tat ctc caa atg aac aac ctg aaa gcc gag gac aca gcc gtc tat     288
Leu Tyr Leu Gln Met Asn Asn Leu Lys Ala Glu Asp Thr Ala Val Tyr

```
                          85                  90                  95
tac tgt tcc aca ggg cac tat ggt gtc tat ggg ctg gga acc ctg gtc      336
Tyr Cys Ser Thr Gly His Tyr Gly Val Tyr Gly Leu Gly Thr Leu Val
            100                 105                 110 acc gtc tcc tcg                                                      348
Thr Val Ser Ser
        115

<210> SEQ ID NO 38
<211> LENGTH: 116
<212> TYPE: PRT
<213> ORGANISM: Homo sapiens

<400> SEQUENCE: 38

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Ser Asp Ala
            20                  25                  30

Trp Met Asn Trp Val Arg Gln Ala Pro Gly Lys Gly Leu Glu Trp Val
        35                  40                  45

Gly His Ile Lys Ser Arg Pro Ala Gly Gly Thr Thr Glu Tyr Ala Ala
    50                  55                  60

Pro Val Lys Gly Arg Phe Thr Ile Ser Arg Asp Asp Ser Thr Asp Thr
65                  70                  75                  80

Leu Tyr Leu Gln Met Asn Asn Leu Lys Ala Glu Asp Thr Ala Val Tyr
                85                  90                  95

Tyr Cys Ser Thr Gly His Tyr Gly Val Tyr Gly Leu Gly Thr Leu Val
            100                 105                 110

Thr Val Ser Ser
        115

<210> SEQ ID NO 39
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: NI-307.1E1 variable K-light chain (VK) sequence
<220> FEATURE:
<221> NAME/KEY: V_region
<222> LOCATION: (70)..(102)
<223> OTHER INFORMATION: complementarity determining region (CDR) VK-
      CDR1
<220> FEATURE:
<221> NAME/KEY: V_region
<222> LOCATION: (148)..(168)
<223> OTHER INFORMATION: complementarity determining region (CDR) VK-
      CDR2
<220> FEATURE:
<221> NAME/KEY: V_region
<222> LOCATION: (265)..(294)
<223> OTHER INFORMATION: complementarity determining region (CDR) VK-
      CDR3

<400> SEQUENCE: 39 gac atc cag atg acc cag tct cct tcc acc ctg tct gca tct gta gga       48
Asp Ile Gln Met Thr Gln Ser Pro Ser Thr Leu Ser Ala Ser Val Gly
1               5                   10                  15 gac aga gtc acc atc act tgc cgg gcc agt cag agt att aga gac tac       96
Asp Arg Val Thr Ile Thr Cys Arg Ala Ser Gln Ser Ile Arg Asp Tyr
            20                  25                  30 ttg gcc tgg tat cag cag aaa cca ggg aaa gcc cct aaa ctt cta atc      144
Leu Ala Trp Tyr Gln Gln Lys Pro Gly Lys Ala Pro Lys Leu Leu Ile
```

```
                35                  40                  45
tat gat ggc tcc att ttg gaa ggt ggg gtc cca tca agg ttc agc ggc      192
Tyr Asp Gly Ser Ile Leu Glu Gly Gly Val Pro Ser Arg Phe Ser Gly
     50                  55                  60 agt gta tct ggg aca gat ttc act ctc acc atc agc agt ctg cag tct      240
Ser Val Ser Gly Thr Asp Phe Thr Leu Thr Ile Ser Ser Leu Gln Ser
 65                  70                  75                  80 gat gat ttt gca act tat tac tgc caa cag tat act agt tat tct tcg      288
Asp Asp Phe Ala Thr Tyr Tyr Cys Gln Gln Tyr Thr Ser Tyr Ser Ser
                 85                  90                  95 tgg acg ttc ggc caa ggg acc aag gtg gaa atc aaa                      324
Trp Thr Phe Gly Gln Gly Thr Lys Val Glu Ile Lys
             100                 105

<210> SEQ ID NO 40
<211> LENGTH: 108
<212> TYPE: PRT
<213> ORGANISM: Homo sapiens

<400> SEQUENCE: 40

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Arg Asp Tyr
             20                  25                  30

Leu Ala Trp Tyr Gln Gln Lys Pro Gly Lys Ala Pro Lys Leu Leu Ile
         35                  40                  45

Tyr Asp Gly Ser Ile Leu Glu Gly Gly Val Pro Ser Arg Phe Ser Gly
     50                  55                  60

Ser Val Ser Gly Thr Asp Phe Thr Leu Thr Ile Ser Ser Leu Gln Ser
 65                  70                  75                  80

Asp Asp Phe Ala Thr Tyr Tyr Cys Gln Gln Tyr Thr Ser Tyr Ser Ser
                 85                  90                  95

Trp Thr Phe Gly Gln Gly Thr Lys Val Glu Ile Lys
             100                 105

<210> SEQ ID NO 41
<211> LENGTH: 378
<212> TYPE: DNA
<213> ORGANISM: Homo sapiens
<220> FEATURE:
<221> NAME/KEY: CDS
<222> LOCATION: (1)..(378)
<223> OTHER INFORMATION: NI-307.24C6 variable heavy chain (VH) sequence
<220> FEATURE:
<221> NAME/KEY: V_region
<222> LOCATION: (76)..(111)
<223> OTHER INFORMATION: complementarity determining region (CDR) VH-
      CDR1
<220> FEATURE:
<221> NAME/KEY: V_region
<222> LOCATION: (154)..(201)
<223> OTHER INFORMATION: complementarity determining region (CDR) VH-
      CDR2
<220> FEATURE:
<221> NAME/KEY: V_region
<222> LOCATION: (298)..(345)
<223> OTHER INFORMATION: complementarity determining region (CDR) VH-
      CDR3

<400> SEQUENCE: 41 cag ctg cag ctg cag gag tcg ggc cca gga ctg gtg aag ccc tcg ggg       48
Gln Leu Gln Leu Gln Glu Ser Gly Pro Gly Leu Val Lys Pro Ser Gly
 1               5                  10                  15 acc ctg tcc ctc att tgt gtt gtc tct ggt tcc tcc atc aga agt aat       96
```

```
               Thr Leu Ser Leu Ile Cys Val Val Ser Gly Ser Ser Ile Arg Ser Asn
                            20                  25                  30 att tgg tgg tgg aat tgg gtc cgc cag tcc cca ggg aag ggg ctt gag        144
Ile Trp Trp Trp Asn Trp Val Arg Gln Ser Pro Gly Lys Gly Leu Glu
                35                  40                  45 tgg att ggg gaa atc tat cat agt ggg agt acc aat tac agc ccg tcc        192
Trp Ile Gly Glu Ile Tyr His Ser Gly Ser Thr Asn Tyr Ser Pro Ser
 50                  55                  60 ctc aag agt cga gtc acc atg tca gta gac aac tcc aag aac cag ttc        240
Leu Lys Ser Arg Val Thr Met Ser Val Asp Asn Ser Lys Asn Gln Phe
 65                  70                  75                  80 tcc ctg aaa atg agc tct gtg acc gcc gcg gac acg gcc gta tat ttc        288
Ser Leu Lys Met Ser Ser Val Thr Ala Ala Asp Thr Ala Val Tyr Phe
                85                  90                  95 tgt gcg ata aac acc agg act tcg atc tct gga gtg ctc tat gat act        336
Cys Ala Ile Asn Thr Arg Thr Ser Ile Ser Gly Val Leu Tyr Asp Thr
                100                 105                 110 ttt gat gtc tgg ggc caa ggg aca atg gtc acc gtc tct tcg                378
Phe Asp Val Trp Gly Gln Gly Thr Met Val Thr Val Ser Ser
                115                 120                 125
```

<210> SEQ ID NO 42
<211> LENGTH: 126
<212> TYPE: PRT
<213> ORGANISM: Homo sapiens

<400> SEQUENCE: 42

```
Gln Leu Gln Leu Gln Glu Ser Gly Pro Gly Leu Val Lys Pro Ser Gly
 1               5                  10                  15

Thr Leu Ser Leu Ile Cys Val Val Ser Gly Ser Ser Ile Arg Ser Asn
                20                  25                  30

Ile Trp Trp Trp Asn Trp Val Arg Gln Ser Pro Gly Lys Gly Leu Glu
                35                  40                  45

Trp Ile Gly Glu Ile Tyr His Ser Gly Ser Thr Asn Tyr Ser Pro Ser
 50                  55                  60

Leu Lys Ser Arg Val Thr Met Ser Val Asp Asn Ser Lys Asn Gln Phe
 65                  70                  75                  80

Ser Leu Lys Met Ser Ser Val Thr Ala Ala Asp Thr Ala Val Tyr Phe
                85                  90                  95

Cys Ala Ile Asn Thr Arg Thr Ser Ile Ser Gly Val Leu Tyr Asp Thr
                100                 105                 110

Phe Asp Val Trp Gly Gln Gly Thr Met Val Thr Val Ser Ser
                115                 120                 125
```

<210> SEQ ID NO 43
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: NI-307.24C6 variable K-light chain (VK)
      sequence
<220> FEATURE:
<221> NAME/KEY: V_region
<222> LOCATION: (70)..(102)
<223> OTHER INFORMATION: complementarity determining region (CDR) VK-
      CDR1
<220> FEATURE:
<221> NAME/KEY: V_region
<222> LOCATION: (148)..(168)
<223> OTHER INFORMATION: complementarity determining region (CDR) VK-
      CDR2

```
<220> FEATURE:
<221> NAME/KEY: V_region
<222> LOCATION: (265)..(294)
<223> OTHER INFORMATION: complementarity determining region (CDR) VK-
      CDR3

<400> SEQUENCE: 43 gaa att gtg ctg act cag tct cca gcc acc ctg tct ttg tct tca ggg      48
Glu Ile Val Leu Thr Gln Ser Pro Ala Thr Leu Ser Leu Ser Ser Gly
1               5                   10                  15 gaa aga gcc acc ctc tcc tgc agg gcc agt cag agt gtt agc ggc tac      96
Glu Arg Ala Thr Leu Ser Cys Arg Ala Ser Gln Ser Val Ser Gly Tyr
            20                  25                  30 tta gcc tgg tac caa cag aaa cct ggc cag gct ccc agg ctc ctc atc     144
Leu Ala Trp Tyr Gln Gln Lys Pro Gly Gln Ala Pro Arg Leu Leu Ile
        35                  40                  45 tat gat ggg tcc aac agg gcc act ggc atc cca gcc agg ttt agt ggc     192
Tyr Asp Gly Ser Asn Arg Ala Thr Gly Ile Pro Ala Arg Phe Ser Gly
    50                  55                  60 agt ggg tct ggg aca gac ttc act ctc acc atc agc agc ctg gaa cct     240
Ser Gly Ser Gly Thr Asp Phe Thr Leu Thr Ile Ser Ser Leu Glu Pro
65                  70                  75                  80 gaa gat ttt gca gtt tat tac tgt cag cat cgt agc aac tgg ccc atg     288
Glu Asp Phe Ala Val Tyr Tyr Cys Gln His Arg Ser Asn Trp Pro Met
                85                  90                  95 tac act ttt ggc cag ggg acc aag ctg gag atc aaa                     324
Tyr Thr Phe Gly Gln Gly Thr Lys Leu Glu Ile Lys
            100                 105

<210> SEQ ID NO 44
<211> LENGTH: 108
<212> TYPE: PRT
<213> ORGANISM: Homo sapiens

<400> SEQUENCE: 44

Glu Ile Val Leu Thr Gln Ser Pro Ala Thr Leu Ser Leu Ser Ser Gly
1               5                   10                  15

Glu Arg Ala Thr Leu Ser Cys Arg Ala Ser Gln Ser Val Ser Gly Tyr
            20                  25                  30

Leu Ala Trp Tyr Gln Gln Lys Pro Gly Gln Ala Pro Arg Leu Leu Ile
        35                  40                  45

Tyr Asp Gly Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln His Arg Ser Asn Trp Pro Met
                85                  90                  95

Tyr Thr Phe Gly Gln Gly Thr Lys Leu Glu Ile Lys
            100                 105

<210> SEQ ID NO 45
<211> LENGTH: 354
<212> TYPE: DNA
<213> ORGANISM: Homo sapiens
<220> FEATURE:
<221> NAME/KEY: CDS
<222> LOCATION: (1)..(354)
<223> OTHER INFORMATION: NI-307.78C3 variable heavy chain (VH) sequence
<220> FEATURE:
<221> NAME/KEY: V_region
<222> LOCATION: (76)..(108)
<223> OTHER INFORMATION: complementarity determining region (CDR) VH-
      CDR1
```

```
<220> FEATURE:
<221> NAME/KEY: V_region
<222> LOCATION: (151)..(198)
<223> OTHER INFORMATION: complementarity determining region (CDR) VH-
      CDR2
<220> FEATURE:
<221> NAME/KEY: V_region
<222> LOCATION: (295)..(321)
<223> OTHER INFORMATION: complementarity determining region (CDR) VH-
      CDR3

<400> SEQUENCE: 45 cag gtg cag ctg cag gag tcg ggc cca gga ctg gtg aag cct tcg ggg       48
Gln Val Gln Leu Gln Glu Ser Gly Pro Gly Leu Val Lys Pro Ser Gly
1               5                   10                  15 acc ctg tcc ctc acc tgc act gtc tct ggt ggc tcc atc agc ggt cgt       96
Thr Leu Ser Leu Thr Cys Thr Val Ser Gly Gly Ser Ile Ser Gly Arg
                20                  25                  30 atc tgg tgg agc tgg gtc cgc cag ccc cca ggg aag ggg ctg gag tgg      144
Ile Trp Trp Ser Trp Val Arg Gln Pro Pro Gly Lys Gly Leu Glu Trp
            35                  40                  45 att ggg gaa atc tat cat agt ggg agc acc aac tac agc ccg tcc ctc      192
Ile Gly Glu Ile Tyr His Ser Gly Ser Thr Asn Tyr Ser Pro Ser Leu
        50                  55                  60 agg ggt cga gtc acc ata tca gtg gac acg tcc aag cag cac ttc tcc      240
Arg Gly Arg Val Thr Ile Ser Val Asp Thr Ser Lys Gln His Phe Ser
65                  70                  75                  80 ctg aag atg acc tct gtg acc gcc gcg gac acg gcc atg tat tac tgt      288
Leu Lys Met Thr Ser Val Thr Ala Ala Asp Thr Ala Met Tyr Tyr Cys
                85                  90                  95 gtg aga ggc gaa cta gca ctc ggc ttc gac tcc tgg ggc cag gga acc      336
Val Arg Gly Glu Leu Ala Leu Gly Phe Asp Ser Trp Gly Gln Gly Thr
                100                 105                 110 ctg gtc acc gtc tcc tcg                                              354
Leu Val Thr Val Ser Ser
        115

<210> SEQ ID NO 46
<211> LENGTH: 118
<212> TYPE: PRT
<213> ORGANISM: Homo sapiens

<400> SEQUENCE: 46

Gln Val Gln Leu Gln Glu Ser Gly Pro Gly Leu Val Lys Pro Ser Gly
1               5                   10                  15

Thr Leu Ser Leu Thr Cys Thr Val Ser Gly Gly Ser Ile Ser Gly Arg
                20                  25                  30

Ile Trp Trp Ser Trp Val Arg Gln Pro Pro Gly Lys Gly Leu Glu Trp
            35                  40                  45

Ile Gly Glu Ile Tyr His Ser Gly Ser Thr Asn Tyr Ser Pro Ser Leu
        50                  55                  60

Arg Gly Arg Val Thr Ile Ser Val Asp Thr Ser Lys Gln His Phe Ser
65                  70                  75                  80

Leu Lys Met Thr Ser Val Thr Ala Ala Asp Thr Ala Met Tyr Tyr Cys
                85                  90                  95

Val Arg Gly Glu Leu Ala Leu Gly Phe Asp Ser Trp Gly Gln Gly Thr
                100                 105                 110

Leu Val Thr Val Ser Ser
        115

<210> SEQ ID NO 47
```

```
<211> LENGTH: 330
<212> TYPE: DNA
<213> ORGANISM: Homo sapiens
<220> FEATURE:
<221> NAME/KEY: CDS
<222> LOCATION: (1)..(330)
<223> OTHER INFORMATION: NI-307.78C3 variable light chain (VL) sequence
<220> FEATURE:
<221> NAME/KEY: V_region
<222> LOCATION: (67)..(108)
<223> OTHER INFORMATION: complementarity determining region (CDR) VL-
      CDR1
<220> FEATURE:
<221> NAME/KEY: V_region
<222> LOCATION: (154)..(174)
<223> OTHER INFORMATION: complementarity determining region (CDR) VL-
      CDR2
<220> FEATURE:
<221> NAME/KEY: V_region
<222> LOCATION: (271)..(300)
<223> OTHER INFORMATION: complementarity determining region (CDR) VL-
      CDR3

<400> SEQUENCE: 47 cag tct gcc ctg act cag cct ccc tcc gcg tcc ggg tct cct gga cag         48
Gln Ser Ala Leu Thr Gln Pro Pro Ser Ala Ser Gly Ser Pro Gly Gln
1               5                   10                  15 tca gtc acc atc tcc tgc act gga acc agc agt gac gtt ggt ggt tat         96
Ser Val Thr Ile Ser Cys Thr Gly Thr Ser Ser Asp Val Gly Gly Tyr
                20                  25                  30 aac tct gtc tcc tgg tac caa cag cac cca cgc aga gcc ccc aaa ctc        144
Asn Ser Val Ser Trp Tyr Gln Gln His Pro Arg Arg Ala Pro Lys Leu
            35                  40                  45 atg att tat gag gtc agt aag cgg ccc tca ggg gtc cct gat cgc ttc        192
Met Ile Tyr Glu Val Ser Lys Arg Pro Ser Gly Val Pro Asp Arg Phe
        50                  55                  60 tct ggc tcc aag tct ggc aac acg gcc tcc ctg acc gtc tct ggc ctc        240
Ser Gly Ser Lys Ser Gly Asn Thr Ala Ser Leu Thr Val Ser Gly Leu
65                  70                  75                  80 cag gct gac gat gag gct cat tat tac tgc agc tca tat gca ggc agc        288
Gln Ala Asp Asp Glu Ala His Tyr Tyr Cys Ser Ser Tyr Ala Gly Ser
                85                  90                  95 aac aat ttg gtg ttc ggc gga ggg acc atg ctg acc gtc cta                330
Asn Asn Leu Val Phe Gly Gly Gly Thr Met Leu Thr Val Leu
                100                 105                 110

<210> SEQ ID NO 48
<211> LENGTH: 110
<212> TYPE: PRT
<213> ORGANISM: Homo sapiens

<400> SEQUENCE: 48

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Ser Val Ser Trp Tyr Gln Gln His Pro Arg Arg Ala Pro Lys Leu
            35                  40                  45

Met Ile Tyr Glu Val Ser Lys Arg Pro Ser Gly Val Pro Asp Arg Phe
        50                  55                  60

Ser Gly Ser Lys Ser Gly Asn Thr Ala Ser Leu Thr Val Ser Gly Leu
65                  70                  75                  80

Gln Ala Asp Asp Glu Ala His Tyr Tyr Cys Ser Ser Tyr Ala Gly Ser
                85                  90                  95
```

```
Asn Asn Leu Val Phe Gly Gly Gly Thr Met Leu Thr Val Leu
        100             105             110
```

<210> SEQ ID NO 49
<211> LENGTH: 387
<212> TYPE: DNA
<213> ORGANISM: Homo sapiens
<220> FEATURE:
<221> NAME/KEY: CDS
<222> LOCATION: (1)..(387)
<223> OTHER INFORMATION: NI-307.57D5 variable heavy chain (VH) sequence
<220> FEATURE:
<221> NAME/KEY: V_region
<222> LOCATION: (76)..(105)
<223> OTHER INFORMATION: complementarity determining region (CDR) VH-CDR1
<220> FEATURE:
<221> NAME/KEY: V_region
<222> LOCATION: (148)..(198)
<223> OTHER INFORMATION: complementarity determining region (CDR) VH-CDR2
<220> FEATURE:
<221> NAME/KEY: V_region
<222> LOCATION: (295)..(354)
<223> OTHER INFORMATION: complementarity determining region (CDR) VH-CDR3

<400> SEQUENCE: 49

```
gag gtg cag ctg gtg gag tct ggg gga ggc ttg gca cag ccg ggg ggg      48
Glu Val Gln Leu Val Glu Ser Gly Gly Gly Leu Ala Gln Pro Gly Gly
1               5                   10                  15 tcc ctg aga ctc tcc tgt gca ggc tct gga ttc aca ctc agt gat ttt      96
Ser Leu Arg Leu Ser Cys Ala Gly Ser Gly Phe Thr Leu Ser Asp Phe
            20                  25                  30 gcc atg agt tgg gtc cgc cgg gct cca ggg aag ggg ctg gaa tgg gtc     144
Ala Met Ser Trp Val Arg Arg Ala Pro Gly Lys Gly Leu Glu Trp Val
        35                  40                  45 tcg tcg ctt act cct tcc ggt cga aat tca ttt tat tca gac tcc gtg     192
Ser Ser Leu Thr Pro Ser Gly Arg Asn Ser Phe Tyr Ser Asp Ser Val
    50                  55                  60 aag ggc cgg ttc acc atc tcc aga gac aat tgg aag aac aca ctg tat     240
Lys Gly Arg Phe Thr Ile Ser Arg Asp Asn Trp Lys Asn Thr Leu Tyr
65                  70                  75                  80 tta gaa atg aat ctc ctg aga ccc gag gac acg gcc gtc tat tac tgt     288
Leu Glu Met Asn Leu Leu Arg Pro Glu Asp Thr Ala Val Tyr Tyr Cys
                85                  90                  95 gcg aga ccc ggc gcc cct aag aat tct gac agt aaa tat tcc tat gtg     336
Ala Arg Pro Gly Ala Pro Lys Asn Ser Asp Ser Lys Tyr Ser Tyr Val
            100                 105                 110 aga gtg gac ttc cag cac tgg ggc cag ggc acc ctg gtc acc gtc tcc     384
Arg Val Asp Phe Gln His Trp Gly Gln Gly Thr Leu Val Thr Val Ser
        115                 120                 125 tcg                                                                  387
Ser
```

<210> SEQ ID NO 50
<211> LENGTH: 129
<212> TYPE: PRT
<213> ORGANISM: Homo sapiens

<400> SEQUENCE: 50

```
Glu Val Gln Leu Val Glu Ser Gly Gly Gly Leu Ala Gln Pro Gly Gly
1               5                   10                  15

Ser Leu Arg Leu Ser Cys Ala Gly Ser Gly Phe Thr Leu Ser Asp Phe
            20                  25                  30
```

```
Ala Met Ser Trp Val Arg Arg Ala Pro Gly Lys Gly Leu Glu Trp Val
         35                  40                  45

Ser Ser Leu Thr Pro Ser Gly Arg Asn Ser Phe Tyr Ser Asp Ser Val
 50                  55                  60

Lys Gly Arg Phe Thr Ile Ser Arg Asp Asn Trp Lys Asn Thr Leu Tyr
 65                  70                  75                  80

Leu Glu Met Asn Leu Leu Arg Pro Glu Asp Thr Ala Val Tyr Tyr Cys
                 85                  90                  95

Ala Arg Pro Gly Ala Pro Lys Asn Ser Asp Ser Lys Tyr Ser Tyr Val
             100                 105                 110

Arg Val Asp Phe Gln His Trp Gly Gln Gly Thr Leu Val Thr Val Ser
             115                 120                 125

Ser
```

```
<210> SEQ ID NO 51
<211> LENGTH: 330
<212> TYPE: DNA
<213> ORGANISM: Homo sapiens
<220> FEATURE:
<221> NAME/KEY: CDS
<222> LOCATION: (1)..(330)
<223> OTHER INFORMATION: NI-307.57D5 variable light chain (VL) sequence
<220> FEATURE:
<221> NAME/KEY: V_region
<222> LOCATION: (67)..(105)
<223> OTHER INFORMATION: complementarity determining region (CDR) VL-
      CDR1
<220> FEATURE:
<221> NAME/KEY: V_region
<222> LOCATION: (151)..(171)
<223> OTHER INFORMATION: complementarity determining region (CDR) VL-
      CDR2
<220> FEATURE:
<221> NAME/KEY: V_region
<222> LOCATION: (274)..(300)
<223> OTHER INFORMATION: complementarity determining region (CDR) VL-
      CDR3

<400> SEQUENCE: 51 aat ttt atg ctg act cag ccc cac tct gtg tcg gag tct ccg ggg agg      48
Asn Phe Met Leu Thr Gln Pro His Ser Val Ser Glu Ser Pro Gly Arg
 1               5                  10                  15 acg gtt acc att tcg tgc acc cgc agc agc ggc agc att gcc aac aac      96
Thr Val Thr Ile Ser Cys Thr Arg Ser Ser Gly Ser Ile Ala Asn Asn
             20                  25                  30 ttt gtg cag tgg tac cag cac cgc ccg ggc agt gcc ccc acc act ttg     144
Phe Val Gln Trp Tyr Gln His Arg Pro Gly Ser Ala Pro Thr Thr Leu
         35                  40                  45 atc tat gag gat gat cag aga ccc tct ggg gtc cct gat cga ttc tct     192
Ile Tyr Glu Asp Asp Gln Arg Pro Ser Gly Val Pro Asp Arg Phe Ser
 50                  55                  60 ggc tcc gtc gac agt ttt tcc aac tct gcc tcc ctc acc atc tct ggg     240
Gly Ser Val Asp Ser Phe Ser Asn Ser Ala Ser Leu Thr Ile Ser Gly
 65                  70                  75                  80 ctg aag act gag gac gag gct gac tac ttc tgt cag tct tat gat aac     288
Leu Lys Thr Glu Asp Glu Ala Asp Tyr Phe Cys Gln Ser Tyr Asp Asn
                 85                  90                  95 cac aat tgg gtt ttc ggc ggt ggg acc acg ctg acc gtc cta             330
His Asn Trp Val Phe Gly Gly Gly Thr Thr Leu Thr Val Leu
            100                 105                 110

<210> SEQ ID NO 52
<211> LENGTH: 110
<212> TYPE: PRT
```

<213> ORGANISM: Homo sapiens

<400> SEQUENCE: 52

```
Asn Phe Met Leu Thr Gln Pro His Ser Val Ser Glu Ser Pro Gly Arg
1               5                   10                  15

Thr Val Thr Ile Ser Cys Thr Arg Ser Ser Gly Ser Ile Ala Asn Asn
            20                  25                  30

Phe Val Gln Trp Tyr Gln His Arg Pro Gly Ser Ala Pro Thr Thr Leu
        35                  40                  45

Ile Tyr Glu Asp Asp Gln Arg Pro Ser Gly Val Pro Asp Arg Phe Ser
    50                  55                  60

Gly Ser Val Asp Ser Phe Ser Asn Ser Ala Ser Leu Thr Ile Ser Gly
65                  70                  75                  80

Leu Lys Thr Glu Asp Glu Ala Asp Tyr Phe Cys Gln Ser Tyr Asp Asn
                85                  90                  95

His Asn Trp Val Phe Gly Gly Gly Thr Thr Leu Thr Val Leu
            100                 105                 110
```

<210> SEQ ID NO 53
<211> LENGTH: 375
<212> TYPE: DNA
<213> ORGANISM: Homo sapiens
<220> FEATURE:
<221> NAME/KEY: CDS
<222> LOCATION: (1)..(375)
<223> OTHER INFORMATION: NI-307.43A11 variable heavy chain (VH) sequence
<220> FEATURE:
<221> NAME/KEY: V_region
<222> LOCATION: (76)..(108)
<223> OTHER INFORMATION: complementarity determining region (CDR) VH-CDR1
<220> FEATURE:
<221> NAME/KEY: V_region
<222> LOCATION: (151)..(198)
<223> OTHER INFORMATION: complementarity determining region (CDR) VH-CDR2
<220> FEATURE:
<221> NAME/KEY: V_region
<222> LOCATION: (295)..(342)
<223> OTHER INFORMATION: complementarity determining region (CDR) VH-CDR3

<400> SEQUENCE: 53

```
cag gtg cag ctg cag gag tcg ggc cca gga ctg gtg aag cct tcg ggg        48
Gln Val Gln Leu Gln Glu Ser Gly Pro Gly Leu Val Lys Pro Ser Gly
1               5                   10                  15 acc ctg tcc ctc acc tgc gct gtt act ggt ggc tcc atc agt agt agt        96
Thr Leu Ser Leu Thr Cys Ala Val Thr Gly Gly Ser Ile Ser Ser Ser
            20                  25                  30 aat tgg tgg agt tgg gtc cgc cag tcc cca gga aag ggg ctg gag tgg       144
Asn Trp Trp Ser Trp Val Arg Gln Ser Pro Gly Lys Gly Leu Glu Trp
        35                  40                  45 att gga gaa att cat cat gat gga aat ctc aac tac aat cca ctc ctc       192
Ile Gly Glu Ile His His Asp Gly Asn Leu Asn Tyr Asn Pro Leu Leu
    50                  55                  60 aag agt cga gtc agc atg tca cta gac aga tcc aag aac caa ttt tct       240
Lys Ser Arg Val Ser Met Ser Leu Asp Arg Ser Lys Asn Gln Phe Ser
65                  70                  75                  80 ctg aag ctg acc tct gtg aca gcc gcg gac acg gcc gta tat tat tgt       288
Leu Lys Leu Thr Ser Val Thr Ala Ala Asp Thr Ala Val Tyr Tyr Cys
                85                  90                  95 gcg aga tgg gat ttc ttt ttt gat agt tct tat tat att cgt ggt ttt       336
Ala Arg Trp Asp Phe Phe Phe Asp Ser Ser Tyr Tyr Ile Arg Gly Phe
            100                 105                 110
```

```
gat ctc tgg ggc cag ggg aca atg gtc acc gtc tct tcg        375
Asp Leu Trp Gly Gln Gly Thr Met Val Thr Val Ser Ser
        115                 120                 125

<210> SEQ ID NO 54
<211> LENGTH: 125
<212> TYPE: PRT
<213> ORGANISM: Homo sapiens

<400> SEQUENCE: 54

Gln Val Gln Leu Gln Glu Ser Gly Pro Gly Leu Val Lys Pro Ser Gly
1               5                   10                  15

Thr Leu Ser Leu Thr Cys Ala Val Thr Gly Gly Ser Ile Ser Ser Ser
            20                  25                  30

Asn Trp Trp Ser Trp Val Arg Gln Ser Pro Gly Lys Gly Leu Glu Trp
        35                  40                  45

Ile Gly Glu Ile His His Asp Gly Asn Leu Asn Tyr Asn Pro Leu Leu
    50                  55                  60

Lys Ser Arg Val Ser Met Ser Leu Asp Arg Ser Lys Asn Gln Phe Ser
65                  70                  75                  80

Leu Lys Leu Thr Ser Val Thr Ala Ala Asp Thr Ala Val Tyr Tyr Cys
                85                  90                  95

Ala Arg Trp Asp Phe Phe Phe Asp Ser Ser Tyr Tyr Ile Arg Gly Phe
            100                 105                 110

Asp Leu Trp Gly Gln Gly Thr Met Val Thr Val Ser Ser
        115                 120                 125

<210> SEQ ID NO 55
<211> LENGTH: 327
<212> TYPE: DNA
<213> ORGANISM: Homo sapiens
<220> FEATURE:
<221> NAME/KEY: CDS
<222> LOCATION: (1)..(327)
<223> OTHER INFORMATION: NI-307.43A11 variable K-light chain (VK)
      sequence
<220> FEATURE:
<221> NAME/KEY: V_region
<222> LOCATION: (70)..(105)
<223> OTHER INFORMATION: complementarity determining region (CDR) VK-
      CDR1
<220> FEATURE:
<221> NAME/KEY: V_region
<222> LOCATION: (151)..(171)
<223> OTHER INFORMATION: complementarity determining region (CDR) VK-
      CDR2
<220> FEATURE:
<221> NAME/KEY: V_region
<222> LOCATION: (268)..(297)
<223> OTHER INFORMATION: complementarity determining region (CDR) VK-
      CDR3

<400> SEQUENCE: 55 gaa acg aca ctc acg cag tct cca ggc acc ctg tct ttg tct cca ggg   48
Glu Thr Thr Leu Thr Gln Ser Pro Gly Thr Leu Ser Leu Ser Pro Gly
1               5                   10                  15 gaa aga gtc acc ctc tct tgc agg gcc agt cag agt gtt gac agg aac   96
Glu Arg Val Thr Leu Ser Cys Arg Ala Ser Gln Ser Val Asp Arg Asn
            20                  25                  30 tat tta gcc tgg tac cag cag aaa cct ggc cag tct ccc agg ctc ctc   144
Tyr Leu Ala Trp Tyr Gln Gln Lys Pro Gly Gln Ser Pro Arg Leu Leu
        35                  40                  45 atc tat agt gca tcc aga agg gcc act ggc atc cca gac agg ttc agt   192
Ile Tyr Ser Ala Ser Arg Arg Ala Thr Gly Ile Pro Asp Arg Phe Ser
```

```
                   50                   55                  60
ggc agt ggg tct ggg aca gac ttc act ctc acc atc agc aga ctg gag        240
Gly Ser Gly Ser Gly Thr Asp Phe Thr Leu Thr Ile Ser Arg Leu Glu
 65                  70                  75                  80 cct gaa gat ttt gta gtg tat tat tgt cag cag tat ggt ggc tca ccg        288
Pro Glu Asp Phe Val Val Tyr Tyr Cys Gln Gln Tyr Gly Gly Ser Pro
                     85                  90                  95 ccg atc acc ttc ggc cag ggg aca cga ctg gag att aaa                    327
Pro Ile Thr Phe Gly Gln Gly Thr Arg Leu Glu Ile Lys
                100                 105

<210> SEQ ID NO 56
<211> LENGTH: 109
<212> TYPE: PRT
<213> ORGANISM: Homo sapiens

<400> SEQUENCE: 56

Glu Thr Thr Leu Thr Gln Ser Pro Gly Thr Leu Ser Leu Ser Pro Gly
 1               5                  10                  15

Glu Arg Val Thr Leu Ser Cys Arg Ala Ser Gln Ser Val Asp Arg Asn
                20                  25                  30

Tyr Leu Ala Trp Tyr Gln Gln Lys Pro Gly Ser Pro Arg Leu Leu
            35                  40                  45

Ile Tyr Ser Ala Ser Arg Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Val Val Tyr Tyr Cys Gln Gln Tyr Gly Gly Ser Pro
                     85                  90                  95

Pro Ile Thr Phe Gly Gln Gly Thr Arg Leu Glu Ile Lys
                100                 105

<210> SEQ ID NO 57
<211> LENGTH: 369
<212> TYPE: DNA
<213> ORGANISM: Homo sapiens
<220> FEATURE:
<221> NAME/KEY: CDS
<222> LOCATION: (1)..(369)
<223> OTHER INFORMATION: NI-307.3G4 variable heavy chain (VH) sequence
<220> FEATURE:
<221> NAME/KEY: V_region
<222> LOCATION: (76)..(105)
<223> OTHER INFORMATION: complementarity determining region (CDR) VH-
      CDR1
<220> FEATURE:
<221> NAME/KEY: V_region
<222> LOCATION: (148)..(198)
<223> OTHER INFORMATION: complementarity determining region (CDR) VH-
      CDR2
<220> FEATURE:
<221> NAME/KEY: V_region
<222> LOCATION: (295)..(336)
<223> OTHER INFORMATION: complementarity determining region (CDR) VH-
      CDR3

<400> SEQUENCE: 57 cag gtg cag ctg gtg cag tct gga gct gaa ttg aag aag cct ggg gcc        48
Gln Val Gln Leu Val Gln Ser Gly Ala Glu Leu Lys Lys Pro Gly Ala
 1               5                  10                  15 gca gtg aag gtc tcc tgc cag gct tct ggg tac aac ttc ctt agt tat        96
Ala Val Lys Val Ser Cys Gln Ala Ser Gly Tyr Asn Phe Leu Ser Tyr
                20                  25                  30 ggt att aat tgg gtg cga cag atc cct gga caa ggg ctt cag tgg ttg        144
```

```
                Gly Ile Asn Trp Val Arg Gln Ile Pro Gly Gln Gly Leu Gln Trp Leu
                             35                  40                  45 gga tgg atc agc act tat gat ggg acc atg aac tat gac cag aag ccc         192
Gly Trp Ile Ser Thr Tyr Asp Gly Thr Met Asn Tyr Asp Gln Lys Pro
         50                  55                  60 gac aac aga gtc acc gtg acc aca gac aca tcc tcg agt aca gtc tat         240
Asp Asn Arg Val Thr Val Thr Thr Asp Thr Ser Ser Ser Thr Val Tyr
 65                  70                  75                  80 ttg gaa ctg agg ggc ctg aga tct gac gac acg ggc gtt tat tac tgt         288
Leu Glu Leu Arg Gly Leu Arg Ser Asp Asp Thr Gly Val Tyr Tyr Cys
                     85                  90                  95 gtg agg gat cgt tgt gct ggt gct ggc tgc tcc cac tcc ctc ggc tat         336
Val Arg Asp Arg Cys Ala Gly Ala Gly Cys Ser His Ser Leu Gly Tyr
                100                 105                 110 tgg ggc cag gga acc ctg gtc acc gtc tcc tcg                             369
Trp Gly Gln Gly Thr Leu Val Thr Val Ser Ser
            115                 120
```

<210> SEQ ID NO 58
<211> LENGTH: 123
<212> TYPE: PRT
<213> ORGANISM: Homo sapiens

<400> SEQUENCE: 58

```
Gln Val Gln Leu Val Gln Ser Gly Ala Glu Leu Lys Lys Pro Gly Ala
 1               5                  10                  15

Ala Val Lys Val Ser Cys Gln Ala Ser Gly Tyr Asn Phe Leu Ser Tyr
             20                  25                  30

Gly Ile Asn Trp Val Arg Gln Ile Pro Gly Gln Gly Leu Gln Trp Leu
             35                  40                  45

Gly Trp Ile Ser Thr Tyr Asp Gly Thr Met Asn Tyr Asp Gln Lys Pro
     50                  55                  60

Asp Asn Arg Val Thr Val Thr Thr Asp Thr Ser Ser Ser Thr Val Tyr
 65                  70                  75                  80

Leu Glu Leu Arg Gly Leu Arg Ser Asp Asp Thr Gly Val Tyr Tyr Cys
                 85                  90                  95

Val Arg Asp Arg Cys Ala Gly Ala Gly Cys Ser His Ser Leu Gly Tyr
                100                 105                 110

Trp Gly Gln Gly Thr Leu Val Thr Val Ser Ser
            115                 120
```

<210> SEQ ID NO 59
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-307.3G4 variable K-light chain (VK) sequence
<220> FEATURE:
<221> NAME/KEY: V_region
<222> LOCATION: (70)..(102)
<223> OTHER INFORMATION: complementarity determining region (CDR) VK-
      CDR1
<220> FEATURE:
<221> NAME/KEY: V_region
<222> LOCATION: (148)..(168)
<223> OTHER INFORMATION: complementarity determining region (CDR) VK-
      CDR2
<220> FEATURE:
<221> NAME/KEY: V_region
<222> LOCATION: (265)..(291)
<223> OTHER INFORMATION: complementarity determining region (CDR) VK-
      CDR3

<400> SEQUENCE: 59

```
gac atc cag atg acc cag tct cca tcc gcc ctg tct gca tct gta gga        48
Asp Ile Gln Met Thr Gln Ser Pro Ser Ala Leu Ser Ala Ser Val Gly
1               5                   10                  15 gac aga gtc acc atc tct tgc cgg gca agt cag aac att aat acc cag        96
Asp Arg Val Thr Ile Ser Cys Arg Ala Ser Gln Asn Ile Asn Thr Gln
            20                  25                  30 tta aat tgg tat cag gag aaa cca ggg aaa gcc cca gag tta ttg atc       144
Leu Asn Trp Tyr Gln Glu Lys Pro Gly Lys Ala Pro Glu Leu Leu Ile
         35                 40                  45 tat ggt gca ttc aat ttg caa agt ggg gcc cca tca acg ttc agt ggc       192
Tyr Gly Ala Phe Asn Leu Gln Ser Gly Ala Pro Ser Thr Phe Ser Gly
    50                  55                  60 agt ggt tct ggg aca gat ttc act ctc acc atc acc agt ctg caa cct       240
Ser Gly Ser Gly Thr Asp Phe Thr Leu Thr Ile Thr Ser Leu Gln Pro
65                  70                  75                  80 gaa gat ttt gca agt tac tac tgt caa cag ggt ttc cat gcc ccg tac       288
Glu Asp Phe Ala Ser Tyr Tyr Cys Gln Gln Gly Phe His Ala Pro Tyr
                85                  90                  95 act ttt ggc cgg ggg acc aaa gtg gat atc aaa                           321
Thr Phe Gly Arg Gly Thr Lys Val Asp Ile Lys
            100                 105
```

<210> SEQ ID NO 60
<211> LENGTH: 107
<212> TYPE: PRT
<213> ORGANISM: Homo sapiens

<400> SEQUENCE: 60

```
Asp Ile Gln Met Thr Gln Ser Pro Ser Ala Leu Ser Ala Ser Val Gly
1               5                   10                  15

Asp Arg Val Thr Ile Ser Cys Arg Ala Ser Gln Asn Ile Asn Thr Gln
            20                  25                  30

Leu Asn Trp Tyr Gln Glu Lys Pro Gly Lys Ala Pro Glu Leu Leu Ile
         35                 40                  45

Tyr Gly Ala Phe Asn Leu Gln Ser Gly Ala Pro Ser Thr Phe Ser Gly
    50                  55                  60

Ser Gly Ser Gly Thr Asp Phe Thr Leu Thr Ile Thr Ser Leu Gln Pro
65                  70                  75                  80

Glu Asp Phe Ala Ser Tyr Tyr Cys Gln Gln Gly Phe His Ala Pro Tyr
                85                  90                  95

Thr Phe Gly Arg Gly Thr Lys Val Asp Ile Lys
            100                 105
```

<210> SEQ ID NO 61
<211> LENGTH: 360
<212> TYPE: DNA
<213> ORGANISM: Homo sapiens
<220> FEATURE:
<221> NAME/KEY: CDS
<222> LOCATION: (1)..(360)
<223> OTHER INFORMATION: NI-307.61D11 variable heavy chain (VH) sequence
<220> FEATURE:
<221> NAME/KEY: V_region
<222> LOCATION: (76)..(105)
<223> OTHER INFORMATION: complementarity determining region (CDR) VH-CDR1
<220> FEATURE:
<221> NAME/KEY: V_region
<222> LOCATION: (148)..(198)
<223> OTHER INFORMATION: complementarity determining region (CDR) VH-CDR2

```
<220> FEATURE:
<221> NAME/KEY: V_region
<222> LOCATION: (295)..(327)
<223> OTHER INFORMATION: complementarity determining region (CDR) VH-
      CDR3

<400> SEQUENCE: 61 gag gtg cag ctg gtg cag tct ggg gct gag gtg aag aaa cct ggg gcc        48
Glu Val Gln Leu Val Gln Ser Gly Ala Glu Val Lys Lys Pro Gly Ala
1               5                   10                  15 tca gtg aag gtc tcc tgc aag act tct gga tac acc ttc atc ggc cac        96
Ser Val Lys Val Ser Cys Lys Thr Ser Gly Tyr Thr Phe Ile Gly His
            20                  25                  30 tac atg cag tgg gtg cga cag gtc cct gga caa ggg ttt gag tgg atg       144
Tyr Met Gln Trp Val Arg Gln Val Pro Gly Gln Gly Phe Glu Trp Met
        35                  40                  45 gga tgg atc aac cct aac acc ggt act aca aag tat gca ctg aag ttt       192
Gly Trp Ile Asn Pro Asn Thr Gly Thr Thr Lys Tyr Ala Leu Lys Phe
    50                  55                  60 aag gac cgg gtc acc gtg acc agg gac acg tcc aca gca aca gtg tac       240
Lys Asp Arg Val Thr Val Thr Arg Asp Thr Ser Thr Ala Thr Val Tyr
65                  70                  75                  80 atg gag ttt cat gga ctg aca tct gac gac acg gcc gtg tat tac tgc       288
Met Glu Phe His Gly Leu Thr Ser Asp Asp Thr Ala Val Tyr Tyr Cys
                85                  90                  95 gcg aga gcc agt gcc tat caa ctg gca aac tat gac tac tgg ggc cag       336
Ala Arg Ala Ser Ala Tyr Gln Leu Ala Asn Tyr Asp Tyr Trp Gly Gln
            100                 105                 110 gga acc ctg gtc acc gtc tcc tcg                                        360
Gly Thr Leu Val Thr Val Ser Ser
        115                 120

<210> SEQ ID NO 62
<211> LENGTH: 120
<212> TYPE: PRT
<213> ORGANISM: Homo sapiens

<400> SEQUENCE: 62

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Ile Gly His
            20                  25                  30

Tyr Met Gln Trp Val Arg Gln Val Pro Gly Gln Gly Phe Glu Trp Met
        35                  40                  45

Gly Trp Ile Asn Pro Asn Thr Gly Thr Thr Lys Tyr Ala Leu Lys Phe
    50                  55                  60

Lys Asp Arg Val Thr Val Thr Arg Asp Thr Ser Thr Ala Thr Val Tyr
65                  70                  75                  80

Met Glu Phe His Gly Leu Thr Ser Asp Asp Thr Ala Val Tyr Tyr Cys
                85                  90                  95

Ala Arg Ala Ser Ala Tyr Gln Leu Ala Asn Tyr Asp Tyr Trp Gly Gln
            100                 105                 110

Gly Thr Leu Val Thr Val Ser Ser
        115                 120

<210> SEQ ID NO 63
<211> LENGTH: 336
<212> TYPE: DNA
<213> ORGANISM: Homo sapiens
<220> FEATURE:
<221> NAME/KEY: CDS
```

<222> LOCATION: (1)..(336)
<223> OTHER INFORMATION: NI-307.61D11 variable light chain (VL) sequence
<220> FEATURE:
<221> NAME/KEY: V_region
<222> LOCATION: (67)..(108)
<223> OTHER INFORMATION: complementarity determining region (CDR) VL-
      CDR1
<220> FEATURE:
<221> NAME/KEY: V_region
<222> LOCATION: (154)..(174)
<223> OTHER INFORMATION: complementarity determining region (CDR) VL-
      CDR2
<220> FEATURE:
<221> NAME/KEY: V_region
<222> LOCATION: (271)..(306)
<223> OTHER INFORMATION: complementarity determining region (CDR) VL-
      CDR3

<400> SEQUENCE: 63

```
cag tct gcc ctg act cag cct gcc tcc gtg tct ggg tct cct gga cag      48
Gln Ser Ala Leu Thr Gln Pro Ala Ser Val Ser Gly Ser Pro Gly Gln
1               5                   10                  15 tcg atc acc atc tcc tgc gct gga acc agc aat gac gtt ggt gat gat      96
Ser Ile Thr Ile Ser Cys Ala Gly Thr Ser Asn Asp Val Gly Asp Asp
                20                  25                  30 gac ttt gtc tcc tgg tac caa cac caa cca ggg aaa gcc ccc aga ctc     144
Asp Phe Val Ser Trp Tyr Gln His Gln Pro Gly Lys Ala Pro Arg Leu
            35                  40                  45 atg att tat gag gtc act aat cgg ccc tca ggg gtt tct act cgc ttc     192
Met Ile Tyr Glu Val Thr Asn Arg Pro Ser Gly Val Ser Thr Arg Phe
        50                  55                  60 tct ggc tcc aag tct ggc aac acg gcc tcc ctg acc atc tct gga ctc     240
Ser Gly Ser Lys Ser Gly Asn Thr Ala Ser Leu Thr Ile Ser Gly Leu
65                  70                  75                  80 cag gct gaa gac gag ggt gat tat tac tgt atg tca tat aca aag aac     288
Gln Ala Glu Asp Glu Gly Asp Tyr Tyr Cys Met Ser Tyr Thr Lys Asn
                85                  90                  95 agc gct ctc ggt tat gtc ttc gga ggt ggg acc aag gtc acc gtc cta     336
Ser Ala Leu Gly Tyr Val Phe Gly Gly Gly Thr Lys Val Thr Val Leu
            100                 105                 110
```

<210> SEQ ID NO 64
<211> LENGTH: 112
<212> TYPE: PRT
<213> ORGANISM: Homo sapiens

<400> SEQUENCE: 64

```
Gln Ser Ala Leu Thr Gln Pro Ala Ser Val Ser Gly Ser Pro Gly Gln
1               5                   10                  15

Ser Ile Thr Ile Ser Cys Ala Gly Thr Ser Asn Asp Val Gly Asp Asp
                20                  25                  30

Asp Phe Val Ser Trp Tyr Gln His Gln Pro Gly Lys Ala Pro Arg Leu
            35                  40                  45

Met Ile Tyr Glu Val Thr Asn Arg Pro Ser Gly Val Ser Thr Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Gly Asp Tyr Tyr Cys Met Ser Tyr Thr Lys Asn
                85                  90                  95

Ser Ala Leu Gly Tyr Val Phe Gly Gly Gly Thr Lys Val Thr Val Leu
            100                 105                 110
```

<210> SEQ ID NO 65

-continued

```
<211> LENGTH: 363
<212> TYPE: DNA
<213> ORGANISM: Homo sapiens
<220> FEATURE:
<221> NAME/KEY: CDS
<222> LOCATION: (1)..(363)
<223> OTHER INFORMATION: NI-307.24F3 variable heavy chain (VH) sequence
<220> FEATURE:
<221> NAME/KEY: V_region
<222> LOCATION: (76)..(105)
<223> OTHER INFORMATION: complementarity determining region (CDR) VH-
      CDR1
<220> FEATURE:
<221> NAME/KEY: V_region
<222> LOCATION: (148)..(198)
<223> OTHER INFORMATION: complementarity determining region (CDR) VH-
      CDR2
<220> FEATURE:
<221> NAME/KEY: V_region
<222> LOCATION: (295)..(330)
<223> OTHER INFORMATION: complementarity determining region (CDR) VH-
      CDR3

<400> SEQUENCE: 65 cag gtg cag ctg cag gag tcg ggg gga ggc gtg gtc cag cct ggg agg      48
Gln Val Gln Leu Gln Glu Ser Gly Gly Gly Val Val Gln Pro Gly Arg
1               5                   10                  15 tcc cta aga ctc tcc tgt gca gcg tca gga ttc agc ttc aat agg tat      96
Ser Leu Arg Leu Ser Cys Ala Ala Ser Gly Phe Ser Phe Asn Arg Tyr
            20                  25                  30 ggc atg cac tgg gtc cgc cag gct cca ggc aag ggg ctg gag tgg ttg     144
Gly Met His Trp Val Arg Gln Ala Pro Gly Lys Gly Leu Glu Trp Leu
        35                  40                  45 gca gtc atc tca aat gat gga gtc aat aca cac tac gca gac tcc gtg     192
Ala Val Ile Ser Asn Asp Gly Val Asn Thr His Tyr Ala Asp Ser Val
    50                  55                  60 aag ggc cga ttc acc atc tcc aga gac aat tcc aag agc acg ctg tat     240
Lys Gly Arg Phe Thr Ile Ser Arg Asp Asn Ser Lys Ser Thr Leu Tyr
65                  70                  75                  80 ttg caa gcg agc agc ctg aga gtt gag gac acg gct gtg tat tac tgt     288
Leu Gln Ala Ser Ser Leu Arg Val Glu Asp Thr Ala Val Tyr Tyr Cys
                85                  90                  95 gcg ggg tat tac tat ggt tcg ggg act tca ctt ttc ttc tac tgg ggc     336
Ala Gly Tyr Tyr Tyr Gly Ser Gly Thr Ser Leu Phe Phe Tyr Trp Gly
            100                 105                 110 cag gga acc ctg gtc acc gtc tcc tcg                                 363
Gln Gly Thr Leu Val Thr Val Ser Ser
        115                 120

<210> SEQ ID NO 66
<211> LENGTH: 121
<212> TYPE: PRT
<213> ORGANISM: Homo sapiens

<400> SEQUENCE: 66

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Ser Phe Asn Arg Tyr
            20                  25                  30

Gly Met His Trp Val Arg Gln Ala Pro Gly Lys Gly Leu Glu Trp Leu
        35                  40                  45

Ala Val Ile Ser Asn Asp Gly Val Asn Thr His Tyr Ala Asp Ser Val
    50                  55                  60

Lys Gly Arg Phe Thr Ile Ser Arg Asp Asn Ser Lys Ser Thr Leu Tyr
65                  70                  75                  80
```

```
Leu Gln Ala Ser Ser Leu Arg Val Glu Asp Thr Ala Val Tyr Tyr Cys
                85                  90                  95

Ala Gly Tyr Tyr Tyr Gly Ser Gly Thr Ser Leu Phe Phe Tyr Trp Gly
            100                 105                 110

Gln Gly Thr Leu Val Thr Val Ser Ser
        115                 120

<210> SEQ ID NO 67
<211> LENGTH: 339
<212> TYPE: DNA
<213> ORGANISM: Homo sapiens
<220> FEATURE:
<221> NAME/KEY: CDS
<222> LOCATION: (1)..(339)
<223> OTHER INFORMATION: NI-307.24F3 variable K-light chain (VK)
      sequence
<220> FEATURE:
<221> NAME/KEY: V_region
<222> LOCATION: (70)..(120)
<223> OTHER INFORMATION: complementarity determining region (CDR) VK-
      CDR1
<220> FEATURE:
<221> NAME/KEY: V_region
<222> LOCATION: (166)..(186)
<223> OTHER INFORMATION: complementarity determining region (CDR) VK-
      CDR2
<220> FEATURE:
<221> NAME/KEY: V_region
<222> LOCATION: (283)..(309)
<223> OTHER INFORMATION: complementarity determining region (CDR) VK-
      CDR3

<400> SEQUENCE: 67 gaa att gtg ctg act cag tct cca gac tcc ctg gct gtg tct ctg ggc      48
Glu Ile Val Leu Thr Gln Ser Pro Asp Ser Leu Ala Val Ser Leu Gly
1               5                   10                  15 gag agg gcc acc atc aac tgc aag tcc agc cag act gtt tta tac agc     96
Glu Arg Ala Thr Ile Asn Cys Lys Ser Ser Gln Thr Val Leu Tyr Ser
                20                  25                  30 tcc aac aat cag aac tac tta gct tgg tac cag cag aaa cca gga cag    144
Ser Asn Asn Gln Asn Tyr Leu Ala Trp Tyr Gln Gln Lys Pro Gly Gln
            35                  40                  45 cct cct aag ctg ctc ctt tac tgg gca tct acc cgg gaa tcc ggg gtc    192
Pro Pro Lys Leu Leu Leu Tyr Trp Ala Ser Thr Arg Glu Ser Gly Val
        50                  55                  60 cct gac cgg ttc agt ggc agc ggg tct ggg aca gat ttc act ctc acc    240
Pro Asp Arg Phe Ser Gly Ser Gly Ser Gly Thr Asp Phe Thr Leu Thr
65                  70                  75                  80 atc agc agc ctg cag cct gaa gat gtg gca gtt tat tac tgt cag caa    288
Ile Ser Ser Leu Gln Pro Glu Asp Val Ala Val Tyr Tyr Cys Gln Gln
                85                  90                  95 tat tat act gct ccg tac act ttt ggc cag ggg acc aag gtg gag atc    336
Tyr Tyr Thr Ala Pro Tyr Thr Phe Gly Gln Gly Thr Lys Val Glu Ile
            100                 105                 110 aaa                                                                 339
Lys

<210> SEQ ID NO 68
<211> LENGTH: 113
<212> TYPE: PRT
<213> ORGANISM: Homo sapiens

<400> SEQUENCE: 68

Glu Ile Val Leu Thr Gln Ser Pro Asp Ser Leu Ala Val Ser Leu Gly
1               5                   10                  15
```

-continued

```
Glu Arg Ala Thr Ile Asn Cys Lys Ser Ser Gln Thr Val Leu Tyr Ser
            20                  25                  30

Ser Asn Asn Gln Asn Tyr Leu Ala Trp Tyr Gln Gln Lys Pro Gly Gln
        35                  40                  45

Pro Pro Lys Leu Leu Leu Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Pro Glu Asp Val Ala Val Tyr Tyr Cys Gln Gln
                85                  90                  95

Tyr Tyr Thr Ala Pro Tyr Thr Phe Gly Gln Gly Thr Lys Val Glu Ile
            100                 105                 110

Lys

<210> SEQ ID NO 69
<211> LENGTH: 363
<212> TYPE: DNA
<213> ORGANISM: Homo sapiens
<220> FEATURE:
<221> NAME/KEY: CDS
<222> LOCATION: (1)..(363)
<223> OTHER INFORMATION: NI-307.18E12 variable heavy chain (VH) sequence
<220> FEATURE:
<221> NAME/KEY: V_region
<222> LOCATION: (76)..(99)
<223> OTHER INFORMATION: complementarity determining region (CDR) VH-
    CDR1
<220> FEATURE:
<221> NAME/KEY: V_region
<222> LOCATION: (148)..(195)
<223> OTHER INFORMATION: complementarity determining region (CDR) VH-
    CDR2
<220> FEATURE:
<221> NAME/KEY: V_region
<222> LOCATION: (292)..(330)
<223> OTHER INFORMATION: complementarity determining region (CDR) VH-
    CDR3

<400> SEQUENCE: 69 cag gtg cag cta cag cag tgg ggc gca ggg ctg ttg aag cct tcg gag      48
Gln Val Gln Leu Gln Gln Trp Gly Ala Gly Leu Leu Lys Pro Ser Glu
1               5                   10                  15 acc ctg tcc ctc acg tgc gct gta tat ggt gac tcc ttc agt ggt ttc      96
Thr Leu Ser Leu Thr Cys Ala Val Tyr Gly Asp Ser Phe Ser Gly Phe
            20                  25                  30 ttc tgg gcc tgg atc cgc cag act cca ggg acg ggg ctg gag tgg att     144
Phe Trp Ala Trp Ile Arg Gln Thr Pro Gly Thr Gly Leu Glu Trp Ile
        35                  40                  45 ggg gaa atc caa cat ggt gga agc ccc acg tac aat ccg tcg ttc gag     192
Gly Glu Ile Gln His Gly Gly Ser Pro Thr Tyr Asn Pro Ser Phe Glu
50                  55                  60 agt cga ctc acc ata tcg act gac gcg tct aag agt caa gtc tct ctt     240
Ser Arg Leu Thr Ile Ser Thr Asp Ala Ser Lys Ser Gln Val Ser Leu
65                  70                  75                  80 aaa atg aca tct gtg acc gtc acg gac acg gct ata tat tgt gcg         288
Lys Met Thr Ser Val Thr Val Thr Asp Thr Ala Ile Tyr Tyr Cys Ala
                85                  90                  95 agg tgt atc cgg ggt aaa tat ggt tcg ggc agt ttg cag ttg tgg agt     336
Arg Cys Ile Arg Gly Lys Tyr Gly Ser Gly Ser Leu Gln Leu Trp Ser
            100                 105                 110 cag ggc acc ctg gtc acc gtc tcc tcg                                 363
Gln Gly Thr Leu Val Thr Val Ser Ser
        115                 120
```

<210> SEQ ID NO 70
<211> LENGTH: 121
<212> TYPE: PRT
<213> ORGANISM: Homo sapiens

<400> SEQUENCE: 70

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Asp Ser Phe Ser Gly Phe
            20                  25                  30

Phe Trp Ala Trp Ile Arg Gln Thr Pro Gly Thr Gly Leu Glu Trp Ile
        35                  40                  45

Gly Glu Ile Gln His Gly Gly Ser Pro Thr Tyr Asn Pro Ser Phe Glu
    50                  55                  60

Ser Arg Leu Thr Ile Ser Thr Asp Ala Ser Lys Ser Gln Val Ser Leu
65                  70                  75                  80

Lys Met Thr Ser Val Thr Val Asp Thr Ala Ile Tyr Tyr Cys Ala
                85                  90                  95

Arg Cys Ile Arg Gly Lys Tyr Gly Ser Gly Ser Leu Gln Leu Trp Ser
            100                 105                 110

Gln Gly Thr Leu Val Thr Val Ser Ser
            115                 120

<210> SEQ ID NO 71
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-307.18E12 variable K-light chain (VK)
      sequence
<220> FEATURE:
<221> NAME/KEY: V_region
<222> LOCATION: (70)..(102)
<223> OTHER INFORMATION: complementarity determining region (CDR) VK-
      CDR1
<220> FEATURE:
<221> NAME/KEY: V_region
<222> LOCATION: (148)..(168)
<223> OTHER INFORMATION: complementarity determining region (CDR) VK-
      CDR2
<220> FEATURE:
<221> NAME/KEY: V_region
<222> LOCATION: (265)..(291)
<223> OTHER INFORMATION: complementarity determining region (CDR) VK-
      CDR3

<400> SEQUENCE: 71 gac atc cag ttg acc cag tct cca tcc ttc ctg tct gca tct gtg gga      48
Asp Ile Gln Leu Thr Gln Ser Pro Ser Phe Leu Ser Ala Ser Val Gly
1               5                   10                  15 gac aga gtc acc atc act tgc cgg gcc agt cag gac att aat tat cat      96
Asp Arg Val Thr Ile Thr Cys Arg Ala Ser Gln Asp Ile Asn Tyr His
            20                  25                  30 tta gcc tgg tat cgg cag aag cca gga aaa gcc cct gac ctc ctg atc     144
Leu Ala Trp Tyr Arg Gln Lys Pro Gly Lys Ala Pro Asp Leu Leu Ile
        35                  40                  45 cat agt gcg cac act ttg cac att ggg gtc tca tcg agg ttc agc ggc     192
His Ser Ala His Thr Leu His Ile Gly Val Ser Ser Arg Phe Ser Gly
    50                  55                  60 agt gga tct ggg aca gaa ttc act ctc aca atc cac acc ttg cag cct     240
Ser Gly Ser Gly Thr Glu Phe Thr Leu Thr Ile His Thr Leu Gln Pro

```
                    65                  70                  75                  80
gaa gat ttt gca acc tat tat tgt cac cag cct aaa act ttt cct ccc        288
Glu Asp Phe Ala Thr Tyr Tyr Cys His Gln Pro Lys Thr Phe Pro Pro
                    85                  90                  95 act ttc ggc ggc ggg acc aaa gtg gat atc aaa                            321
Thr Phe Gly Gly Gly Thr Lys Val Asp Ile Lys
                100                 105

<210> SEQ ID NO 72
<211> LENGTH: 107
<212> TYPE: PRT
<213> ORGANISM: Homo sapiens

<400> SEQUENCE: 72

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Asp Ile Asn Tyr His
                20                  25                  30

Leu Ala Trp Tyr Arg Gln Lys Pro Gly Lys Ala Pro Asp Leu Leu Ile
            35                  40                  45

His Ser Ala His Thr Leu His Ile Gly Val Ser Ser Arg Phe Ser Gly
        50                  55                  60

Ser Gly Ser Gly Thr Glu Phe Thr Leu Thr Ile His Thr Leu Gln Pro
65                  70                  75                  80

Glu Asp Phe Ala Thr Tyr Tyr Cys His Gln Pro Lys Thr Phe Pro Pro
                85                  90                  95

Thr Phe Gly Gly Gly Thr Lys Val Asp Ile Lys
            100                 105

<210> SEQ ID NO 73
<211> LENGTH: 381
<212> TYPE: DNA
<213> ORGANISM: Homo sapiens
<220> FEATURE:
<221> NAME/KEY: CDS
<222> LOCATION: (1)..(381)
<223> OTHER INFORMATION: NI-307.20F5 variable heavy chain (VH) sequence
<220> FEATURE:
<221> NAME/KEY: V_region
<222> LOCATION: (76)..(105)
<223> OTHER INFORMATION: complementarity determining region (CDR) VH-
      CDR1
<220> FEATURE:
<221> NAME/KEY: V_region
<222> LOCATION: (148)..(198)
<223> OTHER INFORMATION: complementarity determining region (CDR) VH-
      CDR2
<220> FEATURE:
<221> NAME/KEY: V_region
<222> LOCATION: (295)..(348)
<223> OTHER INFORMATION: complementarity determining region (CDR) VH-
      CDR3

<400> SEQUENCE: 73 gag gtg cag ctg gtg gag tct ggg gga ggc gtg gtc cag cct ggg acg        48
Glu Val Gln Leu Val Glu Ser Gly Gly Gly Val Val Gln Pro Gly Thr
1               5                   10                  15 tcc ctg aga ctc tcc tgt gca gcg tct ggg ttt agt ttc aat aaa tat        96
Ser Leu Arg Leu Ser Cys Ala Ala Ser Gly Phe Ser Phe Asn Lys Tyr
                20                  25                  30 ggc gta cac tgg gtc cgc cag gct cct ggc aag ggg ctg gag tgg gtg       144
Gly Val His Trp Val Arg Gln Ala Pro Gly Lys Gly Leu Glu Trp Val
            35                  40                  45 gcg aat att tgg tat gat gga act aat cct ttt tat gca gac ttc gtg       192
```

```
                Ala Asn Ile Trp Tyr Asp Gly Thr Asn Pro Phe Tyr Ala Asp Phe Val
                    50                  55                  60 aag ggc cgg ttc gtc atc tcc aga gac act tcc aag aac acg att tat       240
Lys Gly Arg Phe Val Ile Ser Arg Asp Thr Ser Lys Asn Thr Ile Tyr
 65                  70                  75                  80 ctg caa atg aac aga ctg agg gcc gag gac acg gct gtg tat tat tgt       288
Leu Gln Met Asn Arg Leu Arg Ala Glu Asp Thr Ala Val Tyr Tyr Cys
                    85                  90                  95 gcg aga gat gca ttt tgt ggt gga gac tgt tat ggt ggc cta tta cac       336
Ala Arg Asp Ala Phe Cys Gly Gly Asp Cys Tyr Gly Gly Leu Leu His
                    100                 105                 110 ggt ttg gac gtc tgg ggc caa ggg acc acg gtc acc gtc tcc tcg           381
Gly Leu Asp Val Trp Gly Gln Gly Thr Thr Val Thr Val Ser Ser
                    115                 120                 125

<210> SEQ ID NO 74
<211> LENGTH: 127
<212> TYPE: PRT
<213> ORGANISM: Homo sapiens

<400> SEQUENCE: 74

Glu Val Gln Leu Val Glu Ser Gly Gly Gly Val Val Gln Pro Gly Thr
 1               5                   10                  15

Ser Leu Arg Leu Ser Cys Ala Ala Ser Gly Phe Ser Phe Asn Lys Tyr
                20                  25                  30

Gly Val His Trp Val Arg Gln Ala Pro Gly Lys Gly Leu Glu Trp Val
            35                  40                  45

Ala Asn Ile Trp Tyr Asp Gly Thr Asn Pro Phe Tyr Ala Asp Phe Val
    50                  55                  60

Lys Gly Arg Phe Val Ile Ser Arg Asp Thr Ser Lys Asn Thr Ile Tyr
 65                  70                  75                  80

Leu Gln Met Asn Arg Leu Arg Ala Glu Asp Thr Ala Val Tyr Tyr Cys
                85                  90                  95

Ala Arg Asp Ala Phe Cys Gly Gly Asp Cys Tyr Gly Gly Leu Leu His
                100                 105                 110

Gly Leu Asp Val Trp Gly Gln Gly Thr Thr Val Thr Val Ser Ser
            115                 120                 125

<210> SEQ ID NO 75
<211> LENGTH: 333
<212> TYPE: DNA
<213> ORGANISM: Homo sapiens
<220> FEATURE:
<221> NAME/KEY: CDS
<222> LOCATION: (1)..(333)
<223> OTHER INFORMATION: NI-307.20F5 variable K-light chain (VK)
      sequence
<220> FEATURE:
<221> NAME/KEY: V_region
<222> LOCATION: (70)..(117)
<223> OTHER INFORMATION: complementarity determining region (CDR) VK-
      CDR1
<220> FEATURE:
<221> NAME/KEY: V_region
<222> LOCATION: (163)..(183)
<223> OTHER INFORMATION: complementarity determining region (CDR) VK-
      CDR2
<220> FEATURE:
<221> NAME/KEY: V_region
<222> LOCATION: (280)..(303)
<223> OTHER INFORMATION: complementarity determining region (CDR) VK-
      CDR3

<400> SEQUENCE: 75
```

```
gat gtt gtg atg act cag tct cca ctc tcc ctg ccc gtc act cct gga     48
Asp Val Val Met Thr Gln Ser Pro Leu Ser Leu Pro Val Thr Pro Gly
 1               5                  10                  15 gag ccg gcc tcc atc tcc tgc agg tct agt cag agc ctc ctg cat agt     96
Glu Pro Ala Ser Ile Ser Cys Arg Ser Ser Gln Ser Leu Leu His Ser
             20                  25                  30 aat ggg ctc aat tat tta gat tgg tac ctg cag aag cca gga cag tct    144
Asn Gly Leu Asn Tyr Leu Asp Trp Tyr Leu Gln Lys Pro Gly Gln Ser
         35                  40                  45 cca cag ctc ctg atc tat ttg ggt tct aat cgg gcc ccc ggg gtc cct    192
Pro Gln Leu Leu Ile Tyr Leu Gly Ser Asn Arg Ala Pro Gly Val Pro
     50                  55                  60 gac agg ttc agt ggc agt gga tca ggc aca gat ttt aca ctg aaa atc    240
Asp Arg Phe Ser Gly Ser Gly Ser Gly Thr Asp Phe Thr Leu Lys Ile
 65                  70                  75                  80 agc aga gtg gag gct gag gat gtt ggg gtt tat tac tgc ttg caa gct    288
Ser Arg Val Glu Ala Glu Asp Val Gly Val Tyr Tyr Cys Leu Gln Ala
                 85                  90                  95 cta caa act ccg gcg ttc ggc cag ggg acc aag gtg gaa atc aaa        333
Leu Gln Thr Pro Ala Phe Gly Gln Gly Thr Lys Val Glu Ile Lys
             100                 105                 110

<210> SEQ ID NO 76
<211> LENGTH: 111
<212> TYPE: PRT
<213> ORGANISM: Homo sapiens

<400> SEQUENCE: 76

Asp Val Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
             20                  25                  30

Asn Gly Leu Asn Tyr Leu Asp Trp Tyr Leu Gln Lys Pro Gly Gln Ser
         35                  40                  45

Pro Gln Leu Leu Ile Tyr Leu Gly Ser Asn Arg Ala Pro Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Leu Gln Ala
                 85                  90                  95

Leu Gln Thr Pro Ala Phe Gly Gln Gly Thr Lys Val Glu Ile Lys
             100                 105                 110

<210> SEQ ID NO 77
<211> LENGTH: 369
<212> TYPE: DNA
<213> ORGANISM: Homo sapiens
<220> FEATURE:
<221> NAME/KEY: CDS
<222> LOCATION: (1)..(369)
<223> OTHER INFORMATION: NI-307.58C7 variable heavy chain (VH) sequence
<220> FEATURE:
<221> NAME/KEY: V_region
<222> LOCATION: (76)..(105)
<223> OTHER INFORMATION: complementarity determining region (CDR) VH-
      CDR1
<220> FEATURE:
<221> NAME/KEY: V_region
<222> LOCATION: (148)..(198)
<223> OTHER INFORMATION: complementarity determining region (CDR) VH-
      CDR2
<220> FEATURE:
<221> NAME/KEY: V_region
<222> LOCATION: (295)..(336)
```

<223> OTHER INFORMATION: complementarity determining region (CDR) VH-CDR3

<400> SEQUENCE: 77

```
gag gtg cag ctg gtg gag tcc ggg gga ggc ttg gtc aag cct gga ggg      48
Glu Val Gln Leu Val Glu Ser Gly Gly Gly Leu Val Lys Pro Gly Gly
 1               5                  10                  15 tcc ctg aga ctc tcc tgt gca gcc tct gga ttc acc ttc agt gac tac      96
Ser Leu Arg Leu Ser Cys Ala Ala Ser Gly Phe Thr Phe Ser Asp Tyr
                20                  25                  30 tac gtc aac tgg atc cgc cag gct cca ggg aag ggg ctg gag tgg gtt     144
Tyr Val Asn Trp Ile Arg Gln Ala Pro Gly Lys Gly Leu Glu Trp Val
            35                  40                  45 gca tgc att agt agt agt ggt cgt acc ata cac tac gca gac tcc gtg     192
Ala Cys Ile Ser Ser Ser Gly Arg Thr Ile His Tyr Ala Asp Ser Val
50                  55                  60 aag ggc cga ttc acc atc tcc agg gac aac gcc aag aac tca ctg tat     240
Lys Gly Arg Phe Thr Ile Ser Arg Asp Asn Ala Lys Asn Ser Leu Tyr
65                  70                  75                  80 ctg caa atg aac agc ctg aga gcc gag gac acg gcc ttt tat tac tgt     288
Leu Gln Met Asn Ser Leu Arg Ala Glu Asp Thr Ala Phe Tyr Tyr Cys
                85                  90                  95 gcg aga gac ctg gac aaa gca gca act ggc aga ccc tac ttt gac tac     336
Ala Arg Asp Leu Asp Lys Ala Ala Thr Gly Arg Pro Tyr Phe Asp Tyr
                100                 105                 110 tgg ggc cag gga acc ctg gtc acc gtc tcc tcg                          369
Trp Gly Gln Gly Thr Leu Val Thr Val Ser Ser
            115                 120
```

<210> SEQ ID NO 78
<211> LENGTH: 123
<212> TYPE: PRT
<213> ORGANISM: Homo sapiens

<400> SEQUENCE: 78

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
                20                  25                  30

Tyr Val Asn Trp Ile Arg Gln Ala Pro Gly Lys Gly Leu Glu Trp Val
            35                  40                  45

Ala Cys Ile Ser Ser Ser Gly Arg Thr Ile His Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Phe Tyr Tyr Cys
                85                  90                  95

Ala Arg Asp Leu Asp Lys Ala Ala Thr Gly Arg Pro Tyr Phe Asp Tyr
                100                 105                 110

Trp Gly Gln Gly Thr Leu Val Thr Val Ser Ser
            115                 120
```

<210> SEQ ID NO 79
<211> LENGTH: 330
<212> TYPE: DNA
<213> ORGANISM: Homo sapiens
<220> FEATURE:
<221> NAME/KEY: CDS
<222> LOCATION: (1)..(330)
<223> OTHER INFORMATION: NI-307.58C7 variable light chain (VL) sequence
<220> FEATURE:

```
<221> NAME/KEY: V_region
<222> LOCATION: (67)..(105)
<223> OTHER INFORMATION: complementarity determining region (CDR) VL-
      CDR1
<220> FEATURE:
<221> NAME/KEY: V_region
<222> LOCATION: (151)..(171)
<223> OTHER INFORMATION: complementarity determining region (CDR) VL-
      CDR2
<220> FEATURE:
<221> NAME/KEY: V_region
<222> LOCATION: (268)..(300)
<223> OTHER INFORMATION: complementarity determining region (CDR) VL-
      CDR3

<400> SEQUENCE: 79 cag tct gtg ctg act cag cca ccc tca gcg tct ggg acc ccc ggg cag      48
Gln Ser Val Leu Thr Gln Pro Pro Ser Ala Ser Gly Thr Pro Gly Gln
1               5                   10                  15 agg gtc acc atc tct tgt tct gga agc agc tcc aac atc gga ggt aat      96
Arg Val Thr Ile Ser Cys Ser Gly Ser Ser Ser Asn Ile Gly Gly Asn
            20                  25                  30 gct gtg aac tgg ttc caa cag ctc cca gga acg gcc ccc aaa ctc ctc     144
Ala Val Asn Trp Phe Gln Gln Leu Pro Gly Thr Ala Pro Lys Leu Leu
        35                  40                  45 atc tat ggt aat act cag cgg ccc tca ggg gtc cct gac cga ttc tct     192
Ile Tyr Gly Asn Thr Gln Arg Pro Ser Gly Val Pro Asp Arg Phe Ser
    50                  55                  60 ggc tcc aag tct ggc acc tca gcc tcc ctg gcc atc agt ggg ctc cag     240
Gly Ser Lys Ser Gly Thr Ser Ala Ser Leu Ala Ile Ser Gly Leu Gln
65                  70                  75                  80 tct gaa gat gag act aat tat tac tgt gca gca tgg gat gac agc ctg     288
Ser Glu Asp Glu Thr Asn Tyr Tyr Cys Ala Ala Trp Asp Asp Ser Leu
                85                  90                  95 aat ggt gtg gta ttc ggc gga ggg acc aag ctg acc gtc cta             330
Asn Gly Val Val Phe Gly Gly Gly Thr Lys Leu Thr Val Leu
                100                 105                 110

<210> SEQ ID NO 80
<211> LENGTH: 110
<212> TYPE: PRT
<213> ORGANISM: Homo sapiens

<400> SEQUENCE: 80

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Gly Asn
            20                  25                  30

Ala Val Asn Trp Phe Gln Gln Leu Pro Gly Thr Ala Pro Lys Leu Leu
        35                  40                  45

Ile Tyr Gly Asn Thr Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Thr Asn Tyr Tyr Cys Ala Ala Trp Asp Asp Ser Leu
                85                  90                  95

Asn Gly Val Val Phe Gly Gly Gly Thr Lys Leu Thr Val Leu
                100                 105                 110

<210> SEQ ID NO 81
<211> LENGTH: 378
<212> TYPE: DNA
<213> ORGANISM: Homo sapiens
```

```
<220> FEATURE:
<221> NAME/KEY: CDS
<222> LOCATION: (1)..(378)
<223> OTHER INFORMATION: NI-307.105C7 variable heavy chain (VH) sequence
<220> FEATURE:
<221> NAME/KEY: V_region
<222> LOCATION: (76)..(105)
<223> OTHER INFORMATION: complementarity determining region (CDR) VH-
      CDR1
<220> FEATURE:
<221> NAME/KEY: V_region
<222> LOCATION: (148)..(198)
<223> OTHER INFORMATION: complementarity determining region (CDR) VH-
      CDR2
<220> FEATURE:
<221> NAME/KEY: V_region
<222> LOCATION: (295)..(345)
<223> OTHER INFORMATION: complementarity determining region (CDR) VH-
      CDR3

<400> SEQUENCE: 81 gag gtg cag ctg gtg gag tct ggg gga ggc ttg gta cag cct ggg ggg      48
Glu Val Gln Leu Val Glu Ser Gly Gly Gly Leu Val Gln Pro Gly Gly
1               5                   10                  15 tcc ctg aga ctc tcc tgt gca gcc tct gga ttc tcc ttt gga ttc tat      96
Ser Leu Arg Leu Ser Cys Ala Ala Ser Gly Phe Ser Phe Gly Phe Tyr
            20                  25                  30 gcc atg aac tgg gtc cgc cag gct cca ggg aag ggg ctg gag tac gtc     144
Ala Met Asn Trp Val Arg Gln Ala Pro Gly Lys Gly Leu Glu Tyr Val
        35                  40                  45 tca ggt gtc agt ggt ggt ggt ggt agc aca tac tac gca gac tcc gtg     192
Ser Gly Val Ser Gly Gly Gly Gly Ser Thr Tyr Tyr Ala Asp Ser Val
    50                  55                  60 aag ggc cgg ttc acc atc tcc aga gac aat tcc aag aac acg ctg tat     240
Lys Gly Arg Phe Thr Ile Ser Arg Asp Asn Ser Lys Asn Thr Leu Tyr
65                  70                  75                  80 ctg caa atg aag agc ctg aga gcc gag gac acg gcc ata tat tac tgt     288
Leu Gln Met Lys Ser Leu Arg Ala Glu Asp Thr Ala Ile Tyr Tyr Cys
                85                  90                  95 gcg aaa gat cag tct tac tgt agt ggt ggt agc tgc cac ccc tac tac     336
Ala Lys Asp Gln Ser Tyr Cys Ser Gly Gly Ser Cys His Pro Tyr Tyr
            100                 105                 110 tta gac tac tgg ggc cag gga acc ctg gtc acc gtc tcc tcg             378
Leu Asp Tyr Trp Gly Gln Gly Thr Leu Val Thr Val Ser Ser
        115                 120                 125

<210> SEQ ID NO 82
<211> LENGTH: 126
<212> TYPE: PRT
<213> ORGANISM: Homo sapiens

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Gly Phe Tyr
            20                  25                  30

Ala Met Asn Trp Val Arg Gln Ala Pro Gly Lys Gly Leu Glu Tyr Val
        35                  40                  45

Ser Gly Val Ser Gly Gly Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Lys Ser Leu Arg Ala Glu Asp Thr Ala Ile Tyr Tyr Cys
                85                  90                  95
```

```
Ala Lys Asp Gln Ser Tyr Cys Ser Gly Gly Ser Cys His Pro Tyr Tyr
            100                 105                 110

Leu Asp Tyr Trp Gly Gln Gly Thr Leu Val Thr Val Ser Ser
            115                 120                 125

<210> SEQ ID NO 83
<211> LENGTH: 327
<212> TYPE: DNA
<213> ORGANISM: Homo sapiens
<220> FEATURE:
<221> NAME/KEY: CDS
<222> LOCATION: (1)..(327)
<223> OTHER INFORMATION: NI-307.105C7 variable light chain (VL) sequence
<220> FEATURE:
<221> NAME/KEY: V_region
<222> LOCATION: (67)..(99)
<223> OTHER INFORMATION: complementarity determining region (CDR) VL-
      CDR1
<220> FEATURE:
<221> NAME/KEY: V_region
<222> LOCATION: (145)..(165)
<223> OTHER INFORMATION: complementarity determining region (CDR) VL-
      CDR2
<220> FEATURE:
<221> NAME/KEY: V_region
<222> LOCATION: (262)..(297)
<223> OTHER INFORMATION: complementarity determining region (CDR) VL-
      CDR3

<400> SEQUENCE: 83 tcc tat gtg ctg act cag cca ccc tcg gtg tcc gtg gcc cca gga cag       48
Ser Tyr Val Leu Thr Gln Pro Pro Ser Val Ser Val Ala Pro Gly Gln
1               5                   10                  15 acg gcc agg att acc tgt ggg gga aat aac att gga agt aaa agt gtg       96
Thr Ala Arg Ile Thr Cys Gly Gly Asn Asn Ile Gly Ser Lys Ser Val
            20                  25                  30 cac tgg tac cag cag aag cca ggc cag gcc cct gtg gtg gtc gtc tat      144
His Trp Tyr Gln Gln Lys Pro Gly Gln Ala Pro Val Val Val Val Tyr
        35                  40                  45 gat gat agc ggc cgg ccc tca ggt atc cct gag cga ttc tct ggc tcc      192
Asp Asp Ser Gly Arg Pro Ser Gly Ile Pro Glu Arg Phe Ser Gly Ser
50                  55                  60 aat tct ggg aac acg gcc acc ctg acc atc agc agg gtc gaa gcc ggg      240
Asn Ser Gly Asn Thr Ala Thr Leu Thr Ile Ser Arg Val Glu Ala Gly
65                  70                  75                  80 gat gag gcc gac tat tac tgt cag gtg tgg gat agt agt agt gat cat      288
Asp Glu Ala Asp Tyr Tyr Cys Gln Val Trp Asp Ser Ser Ser Asp His
                85                  90                  95 cct tat gtc ttc gga act ggg acc aag gtc acc gtc cta                  327
Pro Tyr Val Phe Gly Thr Gly Thr Lys Val Thr Val Leu
            100                 105

<210> SEQ ID NO 84
<211> LENGTH: 109
<212> TYPE: PRT
<213> ORGANISM: Homo sapiens

<400> SEQUENCE: 84

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Val Val Val Tyr
        35                  40                  45
```

```
Asp Asp Ser Gly Arg Pro Ser Gly Ile Pro Glu Arg Phe Ser Gly Ser
            50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                85                  90                  95

Pro Tyr Val Phe Gly Thr Gly Thr Lys Val Thr Val Leu
            100                 105
```

<210> SEQ ID NO 85
<211> LENGTH: 7
<212> TYPE: PRT
<213> ORGANISM: Artificial Sequence
<220> FEATURE:
<223> OTHER INFORMATION: Epitope recognized by NI-307.11G6 antibody
<220> FEATURE:
<221> NAME/KEY: PEPTIDE
<222> LOCATION: (1)..(7)
<223> OTHER INFORMATION: Epitope of NI-307.11G6 antibody, aa 333 to aa 339

<400> SEQUENCE: 85

```
Leu Pro Gly Asp Pro Asp Met
1               5
```

<210> SEQ ID NO 86
<211> LENGTH: 7
<212> TYPE: PRT
<213> ORGANISM: Artificial Sequence
<220> FEATURE:
<223> OTHER INFORMATION: Epitope recognized by NI-307.13G4 antibody
<220> FEATURE:
<221> NAME/KEY: PEPTIDE
<222> LOCATION: (1)..(7)
<223> OTHER INFORMATION: Epitope of NI-307.13G4 antibody, aa124 to aa130
<220> FEATURE:
<221> NAME/KEY: PEPTIDE
<222> LOCATION: (1)..(7)
<223> OTHER INFORMATION: Epitope of NI-307.13G4 antibody, aa 124 to aa 130

<400> SEQUENCE: 86

```
Gly Gln Ala Thr His Asp Asn
1               5
```

<210> SEQ ID NO 87
<211> LENGTH: 12
<212> TYPE: PRT
<213> ORGANISM: Artificial Sequence
<220> FEATURE:
<223> OTHER INFORMATION: Epitope recognized by NI-307.13G4 antibody
<220> FEATURE:
<221> NAME/KEY: PEPTIDE
<222> LOCATION: (1)..(12)
<223> OTHER INFORMATION: Epitope of NI-307.13G4 antibody, aa 340 to aa 351

<400> SEQUENCE: 87

```
Met Arg Tyr Val Asp Lys Tyr Gly Gln Leu Gln Thr
1               5                   10
```

<210> SEQ ID NO 88
<211> LENGTH: 11
<212> TYPE: PRT
<213> ORGANISM: Artificial Sequence
<220> FEATURE:
<223> OTHER INFORMATION: Epitope recognized by NI-307.61D11 antibody
<220> FEATURE:
<221> NAME/KEY: PEPTIDE

```
<222> LOCATION: (1)..(11)
<223> OTHER INFORMATION: Epitope of NI-307.61D11 antibody, aa 325 to aa
      335

<400> SEQUENCE: 88

Arg Val Phe Glu Gly Thr Glu Glu Leu Pro Gly
1               5                   10

<210> SEQ ID NO 89
<211> LENGTH: 369
<212> TYPE: DNA
<213> ORGANISM: Homo sapiens
<220> FEATURE:
<221> NAME/KEY: CDS
<222> LOCATION: (1)..(369)
<223> OTHER INFORMATION: NI-307.98D3 variable heavy chain (VH) sequence
<220> FEATURE:
<221> NAME/KEY: V_region
<222> LOCATION: (76)..(105)
<223> OTHER INFORMATION: Complementarity determining region (CDR) VH-
      CDR1
<220> FEATURE:
<221> NAME/KEY: V_region
<222> LOCATION: (148)..(195)
<223> OTHER INFORMATION: Complementarity determining region (CDR) VH-
      CDR2
<220> FEATURE:
<221> NAME/KEY: V_region
<222> LOCATION: (295)..(336)
<223> OTHER INFORMATION: Complementarity determining region (CDR) VH-
      CDR3

<400> SEQUENCE: 89 gag gtg cag ctg gtg gag tct ggg gga ggc gtg gtc cag cct ggg agg       48
Glu Val Gln Leu Val Glu Ser Gly Gly Gly Val Val Gln Pro Gly Arg
1               5                   10                  15 tcc ctg aga ctc tcc tgt gca gcc tct gga ttc acc ttc agc agc tcc       96
Ser Leu Arg Leu Ser Cys Ala Ala Ser Gly Phe Thr Phe Ser Ser Ser
            20                  25                  30 gct atg cac tgg gtc cgc cag gct cca ggc aag ggg ctg gag tgg gtg      144
Ala Met His Trp Val Arg Gln Ala Pro Gly Lys Gly Leu Glu Trp Val
        35                  40                  45 gca gtt ata tca tat gat ggg aat aat caa tta tac gca gac tcc gtg      192
Ala Val Ile Ser Tyr Asp Gly Asn Asn Gln Leu Tyr Ala Asp Ser Val
    50                  55                  60 aag ggc cga tta acc atc tcc aga gac aat tcc aag aat gca ctg tat      240
Lys Gly Arg Leu Thr Ile Ser Arg Asp Asn Ser Lys Asn Ala Leu Tyr
65                  70                  75                  80 ctt caa ctg aac agc ctg aga act gag gac acg gct gtt tat ttc tgt      288
Leu Gln Leu Asn Ser Leu Arg Thr Glu Asp Thr Ala Val Tyr Phe Cys
                85                  90                  95 gcg aga gat ggg ggt gga tac agc ttt ggc act tac ttc ttt gac ttc      336
Ala Arg Asp Gly Gly Gly Tyr Ser Phe Gly Thr Tyr Phe Phe Asp Phe
            100                 105                 110 tgg ggc cag gga acc ctg gtc acc gtc tcc tcg                          369
Trp Gly Gln Gly Thr Leu Val Thr Val Ser Ser
        115                 120

<210> SEQ ID NO 90
<211> LENGTH: 123
<212> TYPE: PRT
<213> ORGANISM: Homo sapiens

<400> SEQUENCE: 90

Glu Val Gln Leu Val Glu Ser Gly Gly Gly Val Val Gln Pro Gly Arg
1               5                   10                  15
```

```
Ser Leu Arg Leu Ser Cys Ala Ala Ser Gly Phe Thr Phe Ser Ser
        20                  25                  30

Ala Met His Trp Val Arg Gln Ala Pro Gly Lys Gly Leu Glu Trp Val
            35                  40                  45

Ala Val Ile Ser Tyr Asp Gly Asn Asn Gln Leu Tyr Ala Asp Ser Val
50                  55                  60

Lys Gly Arg Leu Thr Ile Ser Arg Asp Asn Ser Lys Asn Ala Leu Tyr
65                  70                  75                  80

Leu Gln Leu Asn Ser Leu Arg Thr Glu Asp Thr Ala Val Tyr Phe Cys
                85                  90                  95

Ala Arg Asp Gly Gly Gly Tyr Ser Phe Gly Thr Tyr Phe Phe Asp Phe
            100                 105                 110

Trp Gly Gln Gly Thr Leu Val Thr Val Ser Ser
            115                 120

<210> SEQ ID NO 91
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-307.98D3 variable kappa-light chain (VK)
      sequence
<220> FEATURE:
<221> NAME/KEY: V_region
<222> LOCATION: (70)..(102)
<223> OTHER INFORMATION: Complementarity determining region (CDR) VK-
      CDR1
<220> FEATURE:
<221> NAME/KEY: V_region
<222> LOCATION: (148)..(168)
<223> OTHER INFORMATION: Complementarity determining region (CDR) VK-
      CDR2
<220> FEATURE:
<221> NAME/KEY: V_region
<222> LOCATION: (265)..(291)
<223> OTHER INFORMATION: Complementarity determining region (CDR) VK-
      CDR3

<400> SEQUENCE: 91 gac atc cag atg acc cag tct cca tcc tcc ctg tct gca tct gta gga    48
Asp Ile Gln Met Thr Gln Ser Pro Ser Ser Leu Ser Ala Ser Val Gly
1               5                   10                  15 gag aga gtc acc atc act tgt cgg gca agt cag agg att agc aac tat    96
Glu Arg Val Thr Ile Thr Cys Arg Ala Ser Gln Arg Ile Ser Asn Tyr
            20                  25                  30 tta aat tgg tat cag cag aaa cca ggg aaa gcc cct aag ctc ctg atc   144
Leu Asn Trp Tyr Gln Gln Lys Pro Gly Lys Ala Pro Lys Leu Leu Ile
        35                  40                  45 tat gct gca tcc act ttg caa agt ggg gtc cca tca agg ttc agt ggc   192
Tyr Ala Ala Ser Thr Leu Gln Ser Gly Val Pro Ser Arg Phe Ser Gly
50                  55                  60 agt gga tct ggg aca gat ttc act ctc acc atc agc agt ctg caa cct   240
Ser Gly Ser Gly Thr Asp Phe Thr Leu Thr Ile Ser Ser Leu Gln Pro
65                  70                  75                  80 gaa gat ttt gca act tac tac tgt caa cag agt tac agt agt ccc ccc   288
Glu Asp Phe Ala Thr Tyr Tyr Cys Gln Gln Ser Tyr Ser Ser Pro Pro
                85                  90                  95 act ttc ggc cct ggg acc aaa gtg gat atc aaa                       321
Thr Phe Gly Pro Gly Thr Lys Val Asp Ile Lys
            100                 105

<210> SEQ ID NO 92
```

<211> LENGTH: 107
<212> TYPE: PRT
<213> ORGANISM: Homo sapiens

<400> SEQUENCE: 92

Asp Ile Gln Met Thr Gln Ser Pro Ser Ser Leu Ser Ala Ser Val Gly
1               5                   10                  15

Glu Arg Val Thr Ile Thr Cys Arg Ala Ser Gln Arg Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Pro Pro
                85                  90                  95

Thr Phe Gly Pro Gly Thr Lys Val Asp Ile Lys
            100                 105

<210> SEQ ID NO 93
<211> LENGTH: 384
<212> TYPE: DNA
<213> ORGANISM: Homo sapiens
<220> FEATURE:
<221> NAME/KEY: CDS
<222> LOCATION: (1)..(384)
<223> OTHER INFORMATION: NI-307.72F7 variable heavy chain (VH) sequence
<220> FEATURE:
<221> NAME/KEY: V_region
<222> LOCATION: (76)..(105)
<223> OTHER INFORMATION: Complementarity determining region (CDR) VH-
      CDR1
<220> FEATURE:
<221> NAME/KEY: V_region
<222> LOCATION: (148)..(198)
<223> OTHER INFORMATION: Complementarity determining region (CDR) VH-
      CDR2
<220> FEATURE:
<221> NAME/KEY: V_region
<222> LOCATION: (295)..(351)
<223> OTHER INFORMATION: Complementarity determining region (CDR) VH-
      CDR2

<400> SEQUENCE: 93 gag gtg cag ctg gtg gag tct ggg gga ggc ttg gta cag cct gga ggg         48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttc agt agt tat         96
Ser Leu Arg Leu Ser Cys Ala Ala Ser Gly Phe Thr Phe Ser Ser Tyr
            20                  25                  30 gaa atg aac tgg gtc cgc cag gct cca ggg aag ggg ctg gag tgg att        144
Glu Met Asn Trp Val Arg Gln Ala Pro Gly Lys Gly Leu Glu Trp Ile
        35                  40                  45 tca tac att agt agt cgt ggg agt acc ata cac tac gca gac tct gtg        192
Ser Tyr Ile Ser Ser Arg Gly Ser Thr Ile His Tyr Ala Asp Ser Val
    50                  55                  60 aag ggc cga ttc acc atc tcc aga gac gac gcc aag aac tca ctg tat        240
Lys Gly Arg Phe Thr Ile Ser Arg Asp Asp Ala Lys Asn Ser Leu Tyr
65                  70                  75                  80 ctg caa atg aac agc ctg aga gcc gag gac acg gct att tat tac tgt        288
Leu Gln Met Asn Ser Leu Arg Ala Glu Asp Thr Ala Ile Tyr Tyr Cys
                85                  90                  95 gcg aga gat cgg tac gat ttc tgg agt ggt tgc atc aag ggg tgc tac        336

```
Ala Arg Asp Arg Tyr Asp Phe Trp Ser Gly Cys Ile Lys Gly Cys Tyr
            100                 105                 110 tac ggc atg gac gtc tgg ggc caa ggg tcc acg gtc acc gtc tcc tcg    384
Tyr Gly Met Asp Val Trp Gly Gln Gly Ser Thr Val Thr Val Ser Ser
        115                 120                 125

<210> SEQ ID NO 94
<211> LENGTH: 128
<212> TYPE: PRT
<213> ORGANISM: Homo sapiens

<400> SEQUENCE: 94

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Ile
        35                  40                  45

Ser Tyr Ile Ser Ser Arg Gly Ser Thr Ile His Tyr Ala Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Ile Tyr Tyr Cys
                85                  90                  95

Ala Arg Asp Arg Tyr Asp Phe Trp Ser Gly Cys Ile Lys Gly Cys Tyr
            100                 105                 110

Tyr Gly Met Asp Val Trp Gly Gln Gly Ser Thr Val Thr Val Ser Ser
        115                 120                 125

<210> SEQ ID NO 95
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-307.72F7 variable kappa-light chain (VK)
      sequence
<220> FEATURE:
<221> NAME/KEY: V_region
<222> LOCATION: (70)..(105)
<223> OTHER INFORMATION: Complementarity determining region (CDR) VK-
      CDR1
<220> FEATURE:
<221> NAME/KEY: V_region
<222> LOCATION: (151)..(171)
<223> OTHER INFORMATION: Complementarity determining region (CDR) VK-
      CDR2
<220> FEATURE:
<221> NAME/KEY: V_region
<222> LOCATION: (268)..(291)
<223> OTHER INFORMATION: Complementarity determining region (CDR) VK-
      CDR3

<400> SEQUENCE: 95 gaa att gtg ttg acg cag tct cca ggc acc ctg tct ttg tct cca ggg     48
Glu Ile Val Leu Thr Gln Ser Pro Gly Thr Leu Ser Leu Ser Pro Gly
1               5                   10                  15 caa aga gcc acc ctc tcc tgc agg gcc agt cag agc att agc agc agc    96
Gln Arg Ala Thr Leu Ser Cys Arg Ala Ser Gln Ser Ile Ser Ser Ser
            20                  25                  30 tac ttg gcc tgg tac cag cag aga cgt ggc cag gct ccc agg ctc ctc    144
Tyr Leu Ala Trp Tyr Gln Gln Arg Arg Gly Gln Ala Pro Arg Leu Leu
        35                  40                  45
```

-continued

| | | |
|---|---|---|
| atc tat ggt gca tcc agc agg gcc act ggc atc cca gac agg ttc agt<br>Ile Tyr Gly Ala Ser Ser Arg Ala Thr Gly Ile Pro Asp Arg Phe Ser<br>50                             55                             60 | 192 | |
| ggc agt ggg tct ggg aca gac ttc act ctc acc atc agc aga ctg gag<br>Gly Ser Gly Ser Gly Thr Asp Phe Thr Leu Thr Ile Ser Arg Leu Glu<br>65                           70                           75                        80 | 240 | |
| cct gaa gat ttt gca gtg tat tac tgt cag cac tat ggt acc aca ctg<br>Pro Glu Asp Phe Ala Val Tyr Tyr Cys Gln His Tyr Gly Thr Thr Leu<br>85                           90                           95 | 288 | |
| acg ttc ggc caa ggg acc aaa gtg gat atc aaa<br>Thr Phe Gly Gln Gly Thr Lys Val Asp Ile Lys<br>100                         105 | 321 | |

<210> SEQ ID NO 96
<211> LENGTH: 107
<212> TYPE: PRT
<213> ORGANISM: Homo sapiens

<400> SEQUENCE: 96

Glu Ile Val Leu Thr Gln Ser Pro Gly Thr Leu Ser Leu Ser Pro Gly
1               5                   10                  15

Gln Arg Ala Thr Leu Ser Cys Arg Ala Ser Gln Ser Ile Ser Ser Ser
            20                  25                  30

Tyr Leu Ala Trp Tyr Gln Gln Arg Arg Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Thr Thr Leu
                85                  90                  95

Thr Phe Gly Gln Gly Thr Lys Val Asp Ile Lys
            100                 105

<210> SEQ ID NO 97
<211> LENGTH: 378
<212> TYPE: DNA
<213> ORGANISM: Homo sapiens
<220> FEATURE:
<221> NAME/KEY: CDS
<222> LOCATION: (1)..(378)
<223> OTHER INFORMATION: NI-307.45E10 variable heavy chain (VH) sequence
<220> FEATURE:
<221> NAME/KEY: V_region
<222> LOCATION: (76)..(105)
<223> OTHER INFORMATION: Complementarity determining region (CDR) VH-
      CDR1
<220> FEATURE:
<221> NAME/KEY: V_region
<222> LOCATION: (148)..(198)
<223> OTHER INFORMATION: Complementarity determining region (CDR) VH-
      CDR2
<220> FEATURE:
<221> NAME/KEY: V_region
<222> LOCATION: (295)..(345)
<223> OTHER INFORMATION: Complementarity determining region (CDR) VH-
      CDR3

<400> SEQUENCE: 97

| | | |
|---|---|---|
| gag gtg cag ctg gtg gag tct ggg gga ggc ttg gtg cag cct ggg ggg<br>Glu Val Gln Leu Val Glu Ser Gly Gly Gly Leu Val Gln Pro Gly Gly<br>1                   5                       10                     15 | 48 | |
| tcc ctg aga ctc tcc tgt gca gcc tct gga ttc tcc ttt aga ttc tat<br>Ser Leu Arg Leu Ser Cys Ala Ala Ser Gly Phe Ser Phe Arg Phe Tyr<br>          20                       25                       30 | 96 | |

```
gcc atg aac tgg gtc cgc cag gct cca ggg aag ggg ctg gag tac gtc      144
Ala Met Asn Trp Val Arg Gln Ala Pro Gly Lys Gly Leu Glu Tyr Val
         35                  40                  45 tca ggt atc agt ggt ggt ggt act aca tac tac gca gac tcc gtg           192
Ser Gly Ile Ser Gly Gly Gly Thr Thr Tyr Tyr Ala Asp Ser Val
 50                  55                  60 aag ggc cgg ttc acc atc tcc aga gac aat tcc aag aac acc ctg tat      240
Lys Gly Arg Phe Thr Ile Ser Arg Asp Asn Ser Lys Asn Thr Leu Tyr
 65                  70                  75                  80 ctg caa atg aag agc ctg aga gcc gag gac acg gcc ata tat tac tgt      288
Leu Gln Met Lys Ser Leu Arg Ala Glu Asp Thr Ala Ile Tyr Tyr Cys
                 85                  90                  95 gcg aaa gat cag tct tac tgt agt ggt gct ggc tgc cac ccc tac tac      336
Ala Lys Asp Gln Ser Tyr Cys Ser Gly Ala Gly Cys His Pro Tyr Tyr
             100                 105                 110 tta gac tac tgg ggc cag gga acc ctg gtc acc gtc tcc tcg              378
Leu Asp Tyr Trp Gly Gln Gly Thr Leu Val Thr Val Ser Ser
         115                 120                 125

<210> SEQ ID NO 98
<211> LENGTH: 126
<212> TYPE: PRT
<213> ORGANISM: Homo sapiens

<400> SEQUENCE: 98

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Phe Arg Phe Tyr
             20                  25                  30

Ala Met Asn Trp Val Arg Gln Ala Pro Gly Lys Gly Leu Glu Tyr Val
         35                  40                  45

Ser Gly Ile Ser Gly Gly Gly Thr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Lys Ser Leu Arg Ala Glu Asp Thr Ala Ile Tyr Tyr Cys
                 85                  90                  95

Ala Lys Asp Gln Ser Tyr Cys Ser Gly Ala Gly Cys His Pro Tyr Tyr
             100                 105                 110

Leu Asp Tyr Trp Gly Gln Gly Thr Leu Val Thr Val Ser Ser
         115                 120                 125

<210> SEQ ID NO 99
<211> LENGTH: 327
<212> TYPE: DNA
<213> ORGANISM: Homo sapiens
<220> FEATURE:
<221> NAME/KEY: CDS
<222> LOCATION: (1)..(327)
<223> OTHER INFORMATION: NI-307.45E10 variable light chain (VL) sequence
<220> FEATURE:
<221> NAME/KEY: V_region
<222> LOCATION: (67)..(99)
<223> OTHER INFORMATION: Complementarity determining region (CDR) VL-
      CDR1
<220> FEATURE:
<221> NAME/KEY: V_region
<222> LOCATION: (145)..(165)
<223> OTHER INFORMATION: Complementarity determining region (CDR) VL-
      CDR2
<220> FEATURE:
<221> NAME/KEY: V_region
<222> LOCATION: (262)..(297)
```

<223> OTHER INFORMATION: Complementarity determining region (CDR) VL-CDR3

<400> SEQUENCE: 99

| | | | | | | | | | | | | | | | | |
|---|---|---|---|---|---|---|---|---|---|---|---|---|---|---|---|---|
| tcc | tat | gtg | ctg | act | cag | cca | ccc | tcg | gtg | tcc | gtg | gcc | cca | gga | cag | 48 |
| Ser | Tyr | Val | Leu | Thr | Gln | Pro | Pro | Ser | Val | Ser | Val | Ala | Pro | Gly | Gln | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| acg | gcc | agg | att | acc | tgt | ggg | gga | aat | aac | att | gga | agt | aaa | agt | gtg | 96 |
| Thr | Ala | Arg | Ile | Thr | Cys | Gly | Gly | Asn | Asn | Ile | Gly | Ser | Lys | Ser | Val | |
| | | | 20 | | | | | 25 | | | | | 30 | | | |

| | | | | | | | | | | | | | | | | |
|---|---|---|---|---|---|---|---|---|---|---|---|---|---|---|---|---|
| cac | tgg | tac | cag | cag | aag | cca | ggc | cag | gcc | cct | gtg | gtg | gtc | gtc | tat | 144 |
| His | Trp | Tyr | Gln | Gln | Lys | Pro | Gly | Gln | Ala | Pro | Val | Val | Val | Val | Tyr | |
| | | | 35 | | | | | 40 | | | | | 45 | | | |

| | | | | | | | | | | | | | | | | |
|---|---|---|---|---|---|---|---|---|---|---|---|---|---|---|---|---|
| gat | agt | ggc | cgg | ccc | tca | ggg | atg | cct | gag | cga | ttc | tct | ggc | tcc | | 192 |
| Asp | Asp | Ser | Gly | Arg | Pro | Ser | Gly | Met | Pro | Glu | Arg | Phe | Ser | Gly | Ser | |
| 50 | | | | | 55 | | | | | 60 | | | | | | |

| | | | | | | | | | | | | | | | | |
|---|---|---|---|---|---|---|---|---|---|---|---|---|---|---|---|---|
| aac | tct | ggg | aac | acg | gcc | acc | ctg | acc | atc | agc | agg | gtc | gaa | gcc | ggg | 240 |
| Asn | Ser | Gly | Asn | Thr | Ala | Thr | Leu | Thr | Ile | Ser | Arg | Val | Glu | Ala | Gly | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| gat | gag | gcc | gac | tat | tac | tgt | cag | gtg | tgg | gat | agt | agt | agt | gat | cat | 288 |
| Asp | Glu | Ala | Asp | Tyr | Tyr | Cys | Gln | Val | Trp | Asp | Ser | Ser | Ser | Asp | His | |
| | | | | 85 | | | | | 90 | | | | | 95 | | |

| | | | | | | | | | | | | | |
|---|---|---|---|---|---|---|---|---|---|---|---|---|---|
| ctt | tat | gtc | ttc | gga | act | ggg | acc | aag | gtc | acc | gtc | cta | 327 |
| Leu | Tyr | Val | Phe | Gly | Thr | Gly | Thr | Lys | Val | Thr | Val | Leu | |
| | | | 100 | | | | | 105 | | | | | |

<210> SEQ ID NO 100
<211> LENGTH: 109
<212> TYPE: PRT
<213> ORGANISM: Homo sapiens

<400> SEQUENCE: 100

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Val Val Val Tyr
        35                  40                  45

Asp Asp Ser Gly Arg Pro Ser Gly Met Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Leu Tyr Val Phe Gly Thr Gly Thr Lys Val Thr Val Leu
            100                 105

<210> SEQ ID NO 101
<211> LENGTH: 363
<212> TYPE: DNA
<213> ORGANISM: Homo sapiens
<220> FEATURE:
<221> NAME/KEY: CDS
<222> LOCATION: (1)..(363)
<223> OTHER INFORMATION: NI-307.72F10 variable heavy chain (VH) sequence
<220> FEATURE:
<221> NAME/KEY: V_region
<222> LOCATION: (76)..(105)
<223> OTHER INFORMATION: Complementarity determining region (CDR) VH-CDR1
<220> FEATURE:
<221> NAME/KEY: V_region
<222> LOCATION: (148)..(192)

```
<223> OTHER INFORMATION: Complementarity determining region (CDR) VH-
      CDR2
<220> FEATURE:
<221> NAME/KEY: V_region
<222> LOCATION: (295)..(330)
<223> OTHER INFORMATION: Complementarity determining region (CDR) VH-
      CDR3

<400> SEQUENCE: 101 gag gtg cag ctg gtg gag tct ggg gga ggc gtg gta cag cct ggc agg      48
Glu Val Gln Leu Val Glu Ser Gly Gly Gly Val Val Gln Pro Gly Arg
1               5                   10                  15 tcc ctg aga ctc tcc tgt gca acc tct gga ttc acc ttt gat gat tat      96
Ser Leu Arg Leu Ser Cys Ala Thr Ser Gly Phe Thr Phe Asp Asp Tyr
            20                  25                  30 gcc atg cac tgg gtc cgg caa gct cca ggg aag ggc ctg gag tgg gtc     144
Ala Met His Trp Val Arg Gln Ala Pro Gly Lys Gly Leu Glu Trp Val
        35                  40                  45 tca ggt ctg act tgg agt agt agt ggc gtt ggc tat gcc gac tct gtg     192
Ser Gly Leu Thr Trp Ser Ser Ser Gly Val Gly Tyr Ala Asp Ser Val
    50                  55                  60 aag ggc cga ttc acc atc tcc aga gac aac gcc aag aac tcc ctg tat     240
Lys Gly Arg Phe Thr Ile Ser Arg Asp Asn Ala Lys Asn Ser Leu Tyr
65                  70                  75                  80 ctg caa atg aac agt ctg aga gct gag gac acg gcc ttg tat tac tgt     288
Leu Gln Met Asn Ser Leu Arg Ala Glu Asp Thr Ala Leu Tyr Tyr Cys
                85                  90                  95 gca aaa ggt tcc ggg gag tgg cta cga tta gga caa gac tac tgg ggc     336
Ala Lys Gly Ser Gly Glu Trp Leu Arg Leu Gly Gln Asp Tyr Trp Gly
            100                 105                 110 cag gga acc ctg gtc acc gtc tcc tcg                                  363
Gln Gly Thr Leu Val Thr Val Ser Ser
        115                 120

<210> SEQ ID NO 102
<211> LENGTH: 121
<212> TYPE: PRT
<213> ORGANISM: Homo sapiens

<400> SEQUENCE: 102

Glu Val Gln Leu Val Glu Ser Gly Gly Gly Val Val Gln Pro Gly Arg
1               5                   10                  15

Ser Leu Arg Leu Ser Cys Ala Thr Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Leu Thr Trp Ser Ser Ser Gly Val Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly Ser Gly Glu Trp Leu Arg Leu Gly Gln Asp Tyr Trp Gly
            100                 105                 110

Gln Gly Thr Leu Val Thr Val Ser Ser
        115                 120

<210> SEQ ID NO 103
<211> LENGTH: 333
<212> TYPE: DNA
<213> ORGANISM: Homo sapiens
```

```
<220> FEATURE:
<221> NAME/KEY: CDS
<222> LOCATION: (1)..(333)
<223> OTHER INFORMATION: NI-307.72F10 variable light chain (VL)
      sequence
<220> FEATURE:
<221> NAME/KEY: V_region
<222> LOCATION: (67)..(108)
<223> OTHER INFORMATION: Complementarity determining region (CDR) VL-
      CDR1
<220> FEATURE:
<221> NAME/KEY: V_region
<222> LOCATION: (154)..(174)
<223> OTHER INFORMATION: Complementarity determining region (CDR) VL-
      CDR2
<220> FEATURE:
<221> NAME/KEY: V_region
<222> LOCATION: (271)..(303)
<223> OTHER INFORMATION: Complementarity determining region (CDR) VL-
      CDR3

<400> SEQUENCE: 103 cag tct gtg ctg act cag cca ccc tca gtc tct ggg acc cca ggg cag      48
Gln Ser Val Leu Thr Gln Pro Pro Ser Val Ser Gly Thr Pro Gly Gln
1               5                   10                  15 agg gtc acc atc tcc tgc act ggg agc agc tcc aac atc ggg gca ggt      96
Arg Val Thr Ile Ser Cys Thr Gly Ser Ser Ser Asn Ile Gly Ala Gly
            20                  25                  30 tat gat gta cac tgg tac cag cag ctt cca gga aca gcc ccc aaa ctc     144
Tyr Asp Val His Trp Tyr Gln Gln Leu Pro Gly Thr Ala Pro Lys Leu
        35                  40                  45 ctc atc tat gat aac agt aat cgg ccc tca ggg gtc cct gac cga ttc     192
Leu Ile Tyr Asp Asn Ser Asn Arg Pro Ser Gly Val Pro Asp Arg Phe
    50                  55                  60 tct ggc tcc aag tct ggc acc tca gcc tcc ctg gcc atc act ggg ctc     240
Ser Gly Ser Lys Ser Gly Thr Ser Ala Ser Leu Ala Ile Thr Gly Leu
65                  70                  75                  80 cag gct gag gat gag gct cat tat tac tgc cag tcc ttt gac agc agc     288
Gln Ala Glu Asp Glu Ala His Tyr Tyr Cys Gln Ser Phe Asp Ser Ser
                85                  90                  95 ctg agt ggt tcg gtt ttc ggc gga ggg acc aag ctg gcc gtc cta         333
Leu Ser Gly Ser Val Phe Gly Gly Gly Thr Lys Leu Ala Val Leu
            100                 105                 110

<210> SEQ ID NO 104
<211> LENGTH: 111
<212> TYPE: PRT
<213> ORGANISM: Homo sapiens

<400> SEQUENCE: 104

Gln Ser Val Leu Thr Gln Pro Pro Ser Val Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala His Tyr Tyr Cys Gln Ser Phe Asp Ser Ser
                85                  90                  95

Leu Ser Gly Ser Val Phe Gly Gly Gly Thr Lys Leu Ala Val Leu
            100                 105                 110
```

```
<210> SEQ ID NO 105
<211> LENGTH: 354
<212> TYPE: DNA
<213> ORGANISM: Homo sapiens
<220> FEATURE:
<221> NAME/KEY: CDS
<222> LOCATION: (1)..(354)
<223> OTHER INFORMATION: NI-307.56A8 variable heavy chain (VH) sequence
<220> FEATURE:
<221> NAME/KEY: V_region
<222> LOCATION: (76)..(105)
<223> OTHER INFORMATION: Complementarity determining region (CDR) VH-
      CDR1
<220> FEATURE:
<221> NAME/KEY: V_region
<222> LOCATION: (148)..(198)
<223> OTHER INFORMATION: Complementarity determining region (CDR) VH-
      CDR2
<220> FEATURE:
<221> NAME/KEY: V_region
<222> LOCATION: (295)..(321)
<223> OTHER INFORMATION: Complementarity determining region (CDR) VH-
      CDR3

<400> SEQUENCE: 105 gag gtg cag ctg gtg gag tct ggg gga ggc ctg gtc aag cct ggg ggg      48
Glu Val Gln Leu Val Glu Ser Gly Gly Gly Leu Val Lys Pro Gly Gly
1               5                   10                  15 tcc ctg aga ctc tcc tgt gca gcc tct gga ttc acc ttc agt agc tat      96
Ser Leu Arg Leu Ser Cys Ala Ala Ser Gly Phe Thr Phe Ser Ser Tyr
            20                  25                  30 aga atg aac tgg gtc cgc cag gct cca ggg aag ggg ctg gag tgg gtc     144
Arg Met Asn Trp Val Arg Gln Ala Pro Gly Lys Gly Leu Glu Trp Val
        35                  40                  45 tca tcc att agt agt agc agt agt tac ata tac tat gga gac tca gtg     192
Ser Ser Ile Ser Ser Ser Ser Ser Tyr Ile Tyr Tyr Gly Asp Ser Val
    50                  55                  60 aag ggc cga ttc acc atc tcc aga gac aac gcc aag aac tca ctg tat     240
Lys Gly Arg Phe Thr Ile Ser Arg Asp Asn Ala Lys Asn Ser Leu Tyr
65                  70                  75                  80 ctg caa atg agc agc ctg aga gcc gag gac acg gct gtg tat tac tgt     288
Leu Gln Met Ser Ser Leu Arg Ala Glu Asp Thr Ala Val Tyr Tyr Cys
                85                  90                  95 gcg aga tac gcg cac gac tgg aac att gac tac tgg ggc cag gga acc     336
Ala Arg Tyr Ala His Asp Trp Asn Ile Asp Tyr Trp Gly Gln Gly Thr
            100                 105                 110 ctg gtc acc gtc tcc tcg                                             354
Leu Val Thr Val Ser Ser
        115

<210> SEQ ID NO 106
<211> LENGTH: 118
<212> TYPE: PRT
<213> ORGANISM: Homo sapiens

<400> SEQUENCE: 106

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Arg Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Gly Asp Ser Val
    50                  55                  60
```

```
Lys Gly Arg Phe Thr Ile Ser Arg Asp Asn Ala Lys Asn Ser Leu Tyr
 65                  70                  75                  80

Leu Gln Met Ser Ser Leu Arg Ala Glu Asp Thr Ala Val Tyr Tyr Cys
                 85                  90                  95

Ala Arg Tyr Ala His Asp Trp Asn Ile Asp Tyr Trp Gly Gln Gly Thr
            100                 105                 110

Leu Val Thr Val Ser Ser
            115

<210> SEQ ID NO 107
<211> LENGTH: 330
<212> TYPE: DNA
<213> ORGANISM: Homo sapiens
<220> FEATURE:
<221> NAME/KEY: CDS
<222> LOCATION: (1)..(330)
<223> OTHER INFORMATION: NI-307.56A8 variable light chain (VL) sequence
<220> FEATURE:
<221> NAME/KEY: V_region
<222> LOCATION: (67)..(105)
<223> OTHER INFORMATION: Complementarity determining region (CDR) VL-
      CDR1
<220> FEATURE:
<221> NAME/KEY: V_region
<222> LOCATION: (151)..(171)
<223> OTHER INFORMATION: Complementarity determining region (CDR) VL-
      CDR2
<220> FEATURE:
<221> NAME/KEY: V_region
<222> LOCATION: (268)..(300)
<223> OTHER INFORMATION: Complementarity determining region (CDR) VL-
      CDR3

<400> SEQUENCE: 107 cag tct gtg ctg act cag cca ccc tca gcg tct ggg acc ccc ggg cag      48
Gln Ser Val Leu Thr Gln Pro Pro Ser Ala Ser Gly Thr Pro Gly Gln
1               5                  10                  15 agg gtc acc atc tct tgt tct gga agc agc tcc aac atc gga agt aat      96
Arg Val Thr Ile Ser Cys Ser Gly Ser Ser Ser Asn Ile Gly Ser Asn
            20                  25                  30 act gta aac tgg tac cag cag ctc cca gga acg gcc ccc aaa ctc ctc     144
Thr Val Asn Trp Tyr Gln Gln Leu Pro Gly Thr Ala Pro Lys Leu Leu
        35                  40                  45 atc tat agt aat agt cag cgg ccc tca ggg gtc cct gac cga ttc tct     192
Ile Tyr Ser Asn Ser Gln Arg Pro Ser Gly Val Pro Asp Arg Phe Ser
    50                  55                  60 ggc tcc aag tct ggc acc tca gcc tcc ctg gcc atc agt ggg ctc cag     240
Gly Ser Lys Ser Gly Thr Ser Ala Ser Leu Ala Ile Ser Gly Leu Gln
65                  70                  75                  80 tct gag gat gag gct gat tat tac tgt gca gca tgg gat gac agc ctg     288
Ser Glu Asp Glu Ala Asp Tyr Tyr Cys Ala Ala Trp Asp Asp Ser Leu
                85                  90                  95 aat ggt tgg gtg ttc ggc gga ggg acc aag ctg acc gtc cta             330
Asn Gly Trp Val Phe Gly Gly Gly Thr Lys Leu Thr Val Leu
            100                 105                 110

<210> SEQ ID NO 108
<211> LENGTH: 110
<212> TYPE: PRT
<213> ORGANISM: Homo sapiens

<400> SEQUENCE: 108

Gln Ser Val Leu Thr Gln Pro Pro Ser Ala Ser Gly Thr Pro Gly Gln
1               5                  10                  15
```

```
Arg Val Thr Ile Ser Cys Ser Gly Ser Ser Asn Ile Gly Ser Asn
             20                  25                  30

Thr Val Asn Trp Tyr Gln Gln Leu Pro Gly Thr Ala Pro Lys Leu Leu
         35                  40                  45

Ile Tyr Ser Asn Ser Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Ser Leu
             85                  90                  95

Asn Gly Trp Val Phe Gly Gly Gly Thr Lys Leu Thr Val Leu
            100                 105                 110

<210> SEQ ID NO 109
<211> LENGTH: 381
<212> TYPE: DNA
<213> ORGANISM: Homo sapiens
<220> FEATURE:
<221> NAME/KEY: CDS
<222> LOCATION: (1)..(381)
<223> OTHER INFORMATION: NI-307.27C11 variable heavy chain (VH) sequence
<220> FEATURE:
<221> NAME/KEY: V_region
<222> LOCATION: (76)..(108)
<223> OTHER INFORMATION: complementarity determining region (CDR) VH-
      CDR1
<220> FEATURE:
<221> NAME/KEY: V_region
<222> LOCATION: (151)..(198)
<223> OTHER INFORMATION: complementarity determining region (CDR) VH-
      CDR2
<220> FEATURE:
<221> NAME/KEY: V_region
<222> LOCATION: (295)..(348)
<223> OTHER INFORMATION: complementarity determining region (CDR) VH-
      CDR3

<400> SEQUENCE: 109 cag gtg cag ctg cag gag tcg ggc cca gga ctg gtg aag cct tcg ggg      48
Gln Val Gln Leu Gln Glu Ser Gly Pro Gly Leu Val Lys Pro Ser Gly
 1               5                  10                  15 acc ctg tcc ctc acc tgc gct gtc tct ggt gac tct atc agc agt agt      96
Thr Leu Ser Leu Thr Cys Ala Val Ser Gly Asp Ser Ile Ser Ser Ser
             20                  25                  30 aac tgg tgg agt tgg gtc cgc cag ccc cca ggg aag ggg ctg gag tgg     144
Asn Trp Trp Ser Trp Val Arg Gln Pro Pro Gly Lys Gly Leu Glu Trp
         35                  40                  45 att ggg gag atc tat cat agt ggg ggc acc aag tac aac ccg tcc ctc     192
Ile Gly Glu Ile Tyr His Ser Gly Gly Thr Lys Tyr Asn Pro Ser Leu
 50                  55                  60 aag agt cga gtc acc att tca gta gac aag tcc aag aat cac ttc tcc     240
Lys Ser Arg Val Thr Ile Ser Val Asp Lys Ser Lys Asn His Phe Ser
 65                  70                  75                  80 ctg aag ctg agg tct gtg acc gcc gcg acg gcc gtg tat tat tgt         288
Leu Lys Leu Arg Ser Val Thr Ala Ala Asp Thr Ala Val Tyr Tyr Cys
             85                  90                  95 gcg aga aat agg tgg ttc gac aat aac cgg ggg tac tac tac tac         336
Ala Arg Asn Arg Trp Phe Asp Asn Asn Arg Gly Tyr Tyr Tyr Tyr
            100                 105                 110 ggc atg gac gtc tgg ggc caa ggg acc acg gtc acc gtc tcc tcg         381
Gly Met Asp Val Trp Gly Gln Gly Thr Thr Val Thr Val Ser Ser
            115                 120                 125

<210> SEQ ID NO 110
```

```
<211> LENGTH: 127
<212> TYPE: PRT
<213> ORGANISM: Homo sapiens

<400> SEQUENCE: 110

Gln Val Gln Leu Gln Glu Ser Gly Pro Gly Leu Val Lys Pro Ser Gly
1               5                   10                  15

Thr Leu Ser Leu Thr Cys Ala Val Ser Gly Asp Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Gly Thr Lys Tyr Asn Pro Ser Leu
50                  55                  60

Lys Ser Arg Val Thr Ile Ser Val Asp Lys Ser Lys Asn His Phe Ser
65                  70                  75                  80

Leu Lys Leu Arg Ser Val Thr Ala Ala Asp Thr Ala Val Tyr Tyr Cys
                85                  90                  95

Ala Arg Asn Arg Trp Phe Asp Asn Asn Arg Gly Gly Tyr Tyr Tyr Tyr
            100                 105                 110

Gly Met Asp Val Trp Gly Gln Gly Thr Thr Val Thr Val Ser Ser
        115                 120                 125

<210> SEQ ID NO 111
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-307.27C11 variable K-light chain (VK)
      sequence
<220> FEATURE:
<221> NAME/KEY: V_region
<222> LOCATION: (70)..(102)
<223> OTHER INFORMATION: complementarity determining region (CDR) VK-
      CDR1
<220> FEATURE:
<221> NAME/KEY: V_region
<222> LOCATION: (148)..(168)
<223> OTHER INFORMATION: complementarity determining region (CDR) VK-
      CDR2
<220> FEATURE:
<221> NAME/KEY: V_region
<222> LOCATION: (265)..(291)
<223> OTHER INFORMATION: complementarity determining region (CDR) VK-
      CDR3

<400> SEQUENCE: 111 gac atc cag atg acc cag tct cca tcc tcc ctg tct gca tct gtg gga      48
Asp Ile Gln Met Thr Gln Ser Pro Ser Ser Leu Ser Ala Ser Val Gly
1               5                   10                  15 gac aga gtc acc atc act tgc cgg gca agt cag ggc atc agt agt tat      96
Asp Arg Val Thr Ile Thr Cys Arg Ala Ser Gln Gly Ile Ser Ser Tyr
            20                  25                  30 tta aat tgg tat cag cag aaa cca ggg aaa gcc cct aaa ctc ctg atc     144
Leu Asn Trp Tyr Gln Gln Lys Pro Gly Lys Ala Pro Lys Leu Leu Ile
        35                  40                  45 tct gct aca tcc gat ttg caa agt ggg gtc cca tca agg ttc agt ggc     192
Ser Ala Thr Ser Asp Leu Gln Ser Gly Val Pro Ser Arg Phe Ser Gly
50                  55                  60 agt gga tct ggg aca gat ttc act ctc acc atc agc agt ctg caa cct     240
Ser Gly Ser Gly Thr Asp Phe Thr Leu Thr Ile Ser Ser Leu Gln Pro
65                  70                  75                  80 gaa gat ttt gct act tac tac tgt caa cag agt tac agt acc ccg tac     288
Glu Asp Phe Ala Thr Tyr Tyr Cys Gln Gln Ser Tyr Ser Thr Pro Tyr
```

```
                Glu Asp Phe Ala Thr Tyr Tyr Cys Gln Gln Ser Tyr Ser Thr Pro Tyr
                                85                  90                  95 act ttt ggc cag ggg acc aag ctg gag atc aaa                              321
Thr Phe Gly Gln Gly Thr Lys Leu Glu Ile Lys
            100                 105

<210> SEQ ID NO 112
<211> LENGTH: 107
<212> TYPE: PRT
<213> ORGANISM: Homo sapiens

<400> SEQUENCE: 112

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Ser Ala Thr Ser Asp Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105

<210> SEQ ID NO 113
<211> LENGTH: 369
<212> TYPE: DNA
<213> ORGANISM: Homo sapiens
<220> FEATURE:
<221> NAME/KEY: CDS
<222> LOCATION: (1)..(369)
<223> OTHER INFORMATION: NI-307.47B11  variable heavy chain (VH)
      sequence
<220> FEATURE:
<221> NAME/KEY: V_region
<222> LOCATION: (76)..(105)
<223> OTHER INFORMATION: complementarity determining region (CDR) VH-
      CDR1
<220> FEATURE:
<221> NAME/KEY: V_region
<222> LOCATION: (148)..(198)
<223> OTHER INFORMATION: complementarity determining region (CDR) VH-
      CDR2
<220> FEATURE:
<221> NAME/KEY: V_region
<222> LOCATION: (295)..(336)
<223> OTHER INFORMATION: complementarity determining region (CDR) VH-
      CDR3

<400> SEQUENCE: 113 gag gtg cag ctg gtg gag tct ggg gga ggc ttg gtc aag cct gga ggg    48
Glu Val Gln Leu Val Glu Ser Gly Gly Gly Leu Val Lys Pro Gly Gly
1               5                   10                  15 tcc ctg aga ctc tcc tgt gca gcc tct gga ttc acc ttc agt gac tac    96
Ser Leu Arg Leu Ser Cys Ala Ala Ser Gly Phe Thr Phe Ser Asp Tyr
            20                  25                  30 tac atg aac tgg atc cgc cag gct cca ggg aag ggg ctg gag tgg ctt   144
Tyr Met Asn Trp Ile Arg Gln Ala Pro Gly Lys Gly Leu Glu Trp Leu
        35                  40                  45 tca tgc att agt agt agt ggt aat acc att tac tac gca gac tct gtg   192
Ser Cys Ile Ser Ser Ser Gly Asn Thr Ile Tyr Tyr Ala Asp Ser Val
    50                  55                  60
```

```
aag ggc cga ttc acc atc tcc agg gac aac gcc aag aac tca ctg tat      240
Lys Gly Arg Phe Thr Ile Ser Arg Asp Asn Ala Lys Asn Ser Leu Tyr
 65                  70                  75                  80 ctg caa atg aac agc ctg aga gcc gag gac acg gcc gta tat tac tgt      288
Leu Gln Met Asn Ser Leu Arg Ala Glu Asp Thr Ala Val Tyr Tyr Cys
                 85                  90                  95 gcg aga gat ttg gac aaa gca gca act ggc aga ccc tac ttt gac tac      336
Ala Arg Asp Leu Asp Lys Ala Ala Thr Gly Arg Pro Tyr Phe Asp Tyr
            100                 105                 110 tgg ggc cag gga acc ctg gtc acc gtc tcc tcg                          369
Trp Gly Gln Gly Thr Leu Val Thr Val Ser Ser
        115                 120
```

<210> SEQ ID NO 114
<211> LENGTH: 123
<212> TYPE: PRT
<213> ORGANISM: Homo sapiens

<400> SEQUENCE: 114

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
            20                  25                  30

Tyr Met Asn Trp Ile Arg Gln Ala Pro Gly Lys Gly Leu Glu Trp Leu
         35                  40                  45

Ser Cys Ile Ser Ser Ser Gly Asn Thr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Asp Lys Ala Ala Thr Gly Arg Pro Tyr Phe Asp Tyr
            100                 105                 110

Trp Gly Gln Gly Thr Leu Val Thr Val Ser Ser
        115                 120
```

<210> SEQ ID NO 115
<211> LENGTH: 330
<212> TYPE: DNA
<213> ORGANISM: Homo sapiens
<220> FEATURE:
<221> NAME/KEY: CDS
<222> LOCATION: (1)..(330)
<223> OTHER INFORMATION: NI-307.47B11 variable L-light chain (VL)
      sequence
<220> FEATURE:
<221> NAME/KEY: V_region
<222> LOCATION: (67)..(105)
<223> OTHER INFORMATION: complementarity determining region (CDR) VL-
      CDR1
<220> FEATURE:
<221> NAME/KEY: V_region
<222> LOCATION: (151)..(171)
<223> OTHER INFORMATION: complementarity determining region (CDR) VL-
      CDR2
<220> FEATURE:
<221> NAME/KEY: V_region
<222> LOCATION: (268)..(300)
<223> OTHER INFORMATION: complementarity determining region (CDR) VL-
      CDR3

<400> SEQUENCE: 115

```
cag tct gtg ctg act cag cca ccc tca gcg tct ggg acc ccc ggg cag       48
Gln Ser Val Leu Thr Gln Pro Pro Ser Ala Ser Gly Thr Pro Gly Gln
```

```
              1               5              10              15
agg gtc acc atc tct tgt tct gga agc agc tcc aac atc gga agt aat         96
Arg Val Thr Ile Ser Cys Ser Gly Ser Ser Ser Asn Ile Gly Ser Asn
              20                      25                      30 act gta aac tgg tac cag cag ctc cca gga acg gcc ccc aaa ctc ctc        144
Thr Val Asn Trp Tyr Gln Gln Leu Pro Gly Thr Ala Pro Lys Leu Leu
              35                      40                      45 atc tat agt aat aat cag cgg ccc tca ggg gtc cct gac cga ttc tct        192
Ile Tyr Ser Asn Asn Gln Arg Pro Ser Gly Val Pro Asp Arg Phe Ser
        50                      55                      60 ggc tcc agg tct ggc acc tca gcc tcc ctg gcc atc agt gga ctc cag        240
Gly Ser Arg Ser Gly Thr Ser Ala Ser Leu Ala Ile Ser Gly Leu Gln
65                      70                      75                      80 tct gag gat gag gct gat tat tac tgt gca gca tgg gat gac agc ctg        288
Ser Glu Asp Glu Ala Asp Tyr Tyr Cys Ala Ala Trp Asp Asp Ser Leu
                    85                      90                      95 aat ggt gtg gta ttc ggc gga ggg acc aag ctg acc gtc cta                330
Asn Gly Val Val Phe Gly Gly Gly Thr Lys Leu Thr Val Leu
                100                     105                     110

<210> SEQ ID NO 116
<211> LENGTH: 110
<212> TYPE: PRT
<213> ORGANISM: Homo sapiens

<400> SEQUENCE: 116

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Arg Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu
            100                 105                 110

<210> SEQ ID NO 117
<211> LENGTH: 372
<212> TYPE: DNA
<213> ORGANISM: Homo sapiens
<220> FEATURE:
<221> NAME/KEY: CDS
<222> LOCATION: (1)..(372)
<223> OTHER INFORMATION: NI-307.26A3 variable heavy chain (VH) sequence
<220> FEATURE:
<221> NAME/KEY: V_region
<222> LOCATION: (76)..(105)
<223> OTHER INFORMATION: complementarity determining region (CDR) VH-
      CDR1
<220> FEATURE:
<221> NAME/KEY: V_region
<222> LOCATION: (148)..(198)
<223> OTHER INFORMATION: complementarity determining region (CDR) VH-
      CDR2
<220> FEATURE:
<221> NAME/KEY: V_region
<222> LOCATION: (295)..(339)
<223> OTHER INFORMATION: complementarity determining region (CDR) VH-
      CDR3
```

<400> SEQUENCE: 117

| | | | | | | | | | | | | | | | | |
|---|---|---|---|---|---|---|---|---|---|---|---|---|---|---|---|---|
| gag | gtg | cag | ctg | gtg | gag | tct | ggg | gga | gtc | ttg | gta | cag | cct | ggg | ggg | 48 |
| Glu | Val | Gln | Leu | Val | Glu | Ser | Gly | Gly | Val | Leu | Val | Gln | Pro | Gly | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tcc | ctg | aga | ctc | tcc | tgt | gca | gcc | tct | gga | ttc | acc | ttt | agc | agc | tat | 96 |
| Ser | Leu | Arg | Leu | Ser | Cys | Ala | Ala | Ser | Gly | Phe | Thr | Phe | Ser | Ser | Tyr | |
| | | | 20 | | | | | 25 | | | | | 30 | | | |

| | | | | | | | | | | | | | | | | |
|---|---|---|---|---|---|---|---|---|---|---|---|---|---|---|---|---|
| gcc | atg | acc | tgg | gtc | cgc | cag | gct | cca | gag | aag | ggg | ctg | gag | tgg | gtc | 144 |
| Ala | Met | Thr | Trp | Val | Arg | Gln | Ala | Pro | Glu | Lys | Gly | Leu | Glu | Trp | Val | |
| | | 35 | | | | | 40 | | | | | 45 | | | | |

| | | | | | | | | | | | | | | | | |
|---|---|---|---|---|---|---|---|---|---|---|---|---|---|---|---|---|
| tca | act | att | att | ggt | aat | ggt | gct | tac | aca | tac | tac | gca | gac | tcc | gtg | 192 |
| Ser | Thr | Ile | Ile | Gly | Asn | Gly | Ala | Tyr | Thr | Tyr | Tyr | Ala | Asp | Ser | Val | |
| | 50 | | | | | 55 | | | | | 60 | | | | | |

| | | | | | | | | | | | | | | | | |
|---|---|---|---|---|---|---|---|---|---|---|---|---|---|---|---|---|
| aag | ggc | cgg | ttc | acc | atc | tcc | aga | gac | aat | tcc | aag | aac | acg | ctg | att | 240 |
| Lys | Gly | Arg | Phe | Thr | Ile | Ser | Arg | Asp | Asn | Ser | Lys | Asn | Thr | Leu | Ile | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ctg | caa | atg | aac | agc | ctg | aga | gcc | gac | gac | gcg | gcc | gta | tat | tac | tgt | 288 |
| Leu | Gln | Met | Asn | Ser | Leu | Arg | Ala | Asp | Asp | Ala | Ala | Val | Tyr | Tyr | Cys | |
| | | | | 85 | | | | | 90 | | | | | 95 | | |

| | | | | | | | | | | | | | | | | |
|---|---|---|---|---|---|---|---|---|---|---|---|---|---|---|---|---|
| gcg | aaa | ggc | aca | gaa | tta | gcc | ccc | tac | tac | tac | tac | ttc | gct | ttg | gac | 336 |
| Ala | Lys | Gly | Thr | Glu | Leu | Ala | Pro | Tyr | Tyr | Tyr | Tyr | Phe | Ala | Leu | Asp | |
| | | | 100 | | | | | 105 | | | | | 110 | | | |

| | | | | | | | | | | |
|---|---|---|---|---|---|---|---|---|---|---|
| gtc | tgg | ggc | caa | ggg | acc | acg | gtc | acc | gtc | tcc | tcg | 372 |
| Val | Trp | Gly | Gln | Gly | Thr | Thr | Val | Thr | Val | Ser | Ser | |
| | | 115 | | | | | 120 | | | | | |

<210> SEQ ID NO 118
<211> LENGTH: 124
<212> TYPE: PRT
<213> ORGANISM: Homo sapiens

<400> SEQUENCE: 118

Glu Val Gln Leu Val Glu Ser Gly Gly Val Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Glu Lys Gly Leu Glu Trp Val
        35                  40                  45

Ser Thr Ile Ile Gly Asn Gly Ala Tyr Thr Tyr Tyr Ala Asp Ser Val
    50                  55                  60

Lys Gly Arg Phe Thr Ile Ser Arg Asp Asn Ser Lys Asn Thr Leu Ile
65                  70                  75                  80

Leu Gln Met Asn Ser Leu Arg Ala Asp Asp Ala Ala Val Tyr Tyr Cys
                85                  90                  95

Ala Lys Gly Thr Glu Leu Ala Pro Tyr Tyr Tyr Tyr Phe Ala Leu Asp
            100                 105                 110

Val Trp Gly Gln Gly Thr Thr Val Thr Val Ser Ser
        115                 120

<210> SEQ ID NO 119
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: NI-307.26A3 variable K-light chain (VK)
      sequence
<220> FEATURE:
<221> NAME/KEY: V_region

```
<222> LOCATION: (70)..(105)
<223> OTHER INFORMATION: complementarity determining region (CDR) VK-
      CDR1
<220> FEATURE:
<221> NAME/KEY: V_region
<222> LOCATION: (151)..(171)
<223> OTHER INFORMATION: complementarity determining region (CDR) VK-
      CDR2
<220> FEATURE:
<221> NAME/KEY: V_region
<222> LOCATION: (268)..(294)
<223> OTHER INFORMATION: complementarity determining region (CDR) VK-
      CDR3

<400> SEQUENCE: 119 gaa att gtg ttg acg cag tct cca ggc acc ctg tct ttg tct cca ggg      48
Glu Ile Val Leu Thr Gln Ser Pro Gly Thr Leu Ser Leu Ser Pro Gly
1               5                   10                  15 gaa aga gcc acc ctc tcc tgc agg gcc agt cag agt att agc agc agc      96
Glu Arg Ala Thr Leu Ser Cys Arg Ala Ser Gln Ser Ile Ser Ser Ser
            20                  25                  30 cac tta gcc tgg tac cag cag aaa cct ggc cag gct ccc agg ctc ctc      144
His Leu Ala Trp Tyr Gln Gln Lys Pro Gly Gln Ala Pro Arg Leu Leu
        35                  40                  45 atc tat ggt gca tcc agc agg gcc act ggc atc cca gac agg ttc agt      192
Ile Tyr Gly Ala Ser Ser Arg Ala Thr Gly Ile Pro Asp Arg Phe Ser
50                  55                  60 ggc ggt ggg tct ggg aca gac ttc act ctc acc atc acc aga ctg gag      240
Gly Gly Gly Ser Gly Thr Asp Phe Thr Leu Thr Ile Thr Arg Leu Glu
65                  70                  75                  80 cct gaa gat ttt gca gtg tat tac tgt cag cag tat ggt agc tct ccg      288
Pro Glu Asp Phe Ala Val Tyr Tyr Cys Gln Gln Tyr Gly Ser Ser Pro
                85                  90                  95 tac act ttt ggc cag ggg acc aag ctg gag atc aaa                      324
Tyr Thr Phe Gly Gln Gly Thr Lys Leu Glu Ile Lys
            100                 105

<210> SEQ ID NO 120
<211> LENGTH: 108
<212> TYPE: PRT
<213> ORGANISM: Homo sapiens

<400> SEQUENCE: 120

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Ser
            20                  25                  30

His Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Gly Gly Ser Gly Thr Asp Phe Thr Leu Thr Ile Thr Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys
            100                 105

<210> SEQ ID NO 121
<211> LENGTH: 354
<212> TYPE: DNA
<213> ORGANISM: Homo sapiens
<220> FEATURE:
```

```
<221> NAME/KEY: CDS
<222> LOCATION: (1)..(354)
<223> OTHER INFORMATION: NI-307.27C2 variable heavy chain (VH) sequence
<220> FEATURE:
<221> NAME/KEY: V_region
<222> LOCATION: (76)..(105)
<223> OTHER INFORMATION: complementarity determining region (CDR) VH-
      CDR1
<220> FEATURE:
<221> NAME/KEY: V_region
<222> LOCATION: (148)..(198)
<223> OTHER INFORMATION: complementarity determining region (CDR) VH-
      CDR2
<220> FEATURE:
<221> NAME/KEY: V_region
<222> LOCATION: (244)..(252)
<223> OTHER INFORMATION: complementarity determining region (CDR) VH-
      CDR3

<400> SEQUENCE: 121 gag gtg cag ctg gtg gag tct ggg gga ggc ctg gtc aag cct ggg ggg       48
Glu Val Gln Leu Val Glu Ser Gly Gly Gly Leu Val Lys Pro Gly Gly
1               5                   10                  15 tcc ctg aga ctc tcc tgt gca gcc tct gga ttc acc ttc agt agc tat       96
Ser Leu Arg Leu Ser Cys Ala Ala Ser Gly Phe Thr Phe Ser Ser Tyr
            20                  25                  30 acc atg aac tgg gtc cgc cag gct cca ggg aag ggg ctg cag tgg gtc      144
Thr Met Asn Trp Val Arg Gln Ala Pro Gly Lys Gly Leu Gln Trp Val
        35                  40                  45 tca tcc atc agt agt agt agt acc tac atg tac tac gga gac tca gtg      192
Ser Ser Ile Ser Ser Ser Ser Thr Tyr Met Tyr Tyr Gly Asp Ser Val
50                  55                  60 aag ggc cga ttc acc atc tcc aga gac aac gcc agg aac tca ctc tat      240
Lys Gly Arg Phe Thr Ile Ser Arg Asp Asn Ala Arg Asn Ser Leu Tyr
65                  70                  75                  80 ctg caa atg aac agc ctg aga gtc gag gac acg gct gta tat tac tgt      288
Leu Gln Met Asn Ser Leu Arg Val Glu Asp Thr Ala Val Tyr Tyr Cys
                85                  90                  95 gcg aga tac gcg cac gac tgg aac gtt gac tac tgg ggc cag gga acc      336
Ala Arg Tyr Ala His Asp Trp Asn Val Asp Tyr Trp Gly Gln Gly Thr
            100                 105                 110 ctg gtc acc gtc tcc tcg                                              354
Leu Val Thr Val Ser Ser
        115

<210> SEQ ID NO 122
<211> LENGTH: 118
<212> TYPE: PRT
<213> ORGANISM: Homo sapiens

<400> SEQUENCE: 122

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Thr Met Asn Trp Val Arg Gln Ala Pro Gly Lys Gly Leu Gln Trp Val
        35                  40                  45

Ser Ser Ile Ser Ser Ser Ser Thr Tyr Met Tyr Tyr Gly Asp Ser Val
50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Val Glu Asp Thr Ala Val Tyr Tyr Cys
                85                  90                  95
```

```
Ala Arg Tyr Ala His Asp Trp Asn Val Asp Tyr Trp Gly Gln Gly Thr
            100                 105                 110

Leu Val Thr Val Ser Ser
        115

<210> SEQ ID NO 123
<211> LENGTH: 330
<212> TYPE: DNA
<213> ORGANISM: Homo sapiens
<220> FEATURE:
<221> NAME/KEY: CDS
<222> LOCATION: (1)..(330)
<223> OTHER INFORMATION: NI-307.27C2 variable L-light chain (VL)
      sequence
<220> FEATURE:
<221> NAME/KEY: V_region
<222> LOCATION: (67)..(105)
<223> OTHER INFORMATION: complementarity determining region (CDR) VL-
      CDR1
<220> FEATURE:
<221> NAME/KEY: V_region
<222> LOCATION: (151)..(171)
<223> OTHER INFORMATION: complementarity determining region (CDR) VL-
      CDR2
<220> FEATURE:
<221> NAME/KEY: V_region
<222> LOCATION: (268)..(300)
<223> OTHER INFORMATION: complementarity determining region (CDR) VL-
      CDR3

<400> SEQUENCE: 123 cag tct gtg ctg act cag cca ccc tca gcg tct ggg acc ccc ggg cag    48
Gln Ser Val Leu Thr Gln Pro Pro Ser Ala Ser Gly Thr Pro Gly Gln
1               5                   10                  15 agg gtc acc atc tct tgt tct gga ggc agc tcc aac atc gga agt aat    96
Arg Val Thr Ile Ser Cys Ser Gly Gly Ser Ser Asn Ile Gly Ser Asn
            20                  25                  30 cct gtg aac tgg ttc caa caa ttc cca gga acg gcc ccc aaa ctc ctc   144
Pro Val Asn Trp Phe Gln Gln Phe Pro Gly Thr Ala Pro Lys Leu Leu
        35                  40                  45 atc tat gct aat act cag cgg ccc tca ggg gtc cct gac cga ttc tct   192
Ile Tyr Ala Asn Thr Gln Arg Pro Ser Gly Val Pro Asp Arg Phe Ser
    50                  55                  60 ggc tcc aag tct ggc acc tca gtt tcc ctg gcc atc agt ggg ctc cag   240
Gly Ser Lys Ser Gly Thr Ser Val Ser Leu Ala Ile Ser Gly Leu Gln
65                  70                  75                  80 tct gag gat gag ggt gat tat cac tgt gca gca tgg gat gac agc ctg   288
Ser Glu Asp Glu Gly Asp Tyr His Cys Ala Ala Trp Asp Asp Ser Leu
                85                  90                  95 aag ggt tgg gtg ttc ggc gga ggg acc aag ctg acc gtc cta            330
Lys Gly Trp Val Phe Gly Gly Gly Thr Lys Leu Thr Val Leu
            100                 105                 110

<210> SEQ ID NO 124
<211> LENGTH: 110
<212> TYPE: PRT
<213> ORGANISM: Homo sapiens

<400> SEQUENCE: 124

Gln Ser Val Leu Thr Gln Pro Pro Ser Ala Ser Gly Thr Pro Gly Gln
1               5                   10                  15

Arg Val Thr Ile Ser Cys Ser Gly Gly Ser Ser Asn Ile Gly Ser Asn
            20                  25                  30

Pro Val Asn Trp Phe Gln Gln Phe Pro Gly Thr Ala Pro Lys Leu Leu
        35                  40                  45
```

```
Ile Tyr Ala Asn Thr Gln Arg Pro Ser Gly Val Pro Asp Arg Phe Ser
    50                  55                  60

Gly Ser Lys Ser Gly Thr Ser Val Ser Leu Ala Ile Ser Gly Leu Gln
 65                  70                  75                  80

Ser Glu Asp Glu Gly Asp Tyr His Cys Ala Ala Trp Asp Asp Ser Leu
                 85                  90                  95

Lys Gly Trp Val Phe Gly Gly Gly Thr Lys Leu Thr Val Leu
            100                 105                 110
```

<210> SEQ ID NO 125
<211> LENGTH: 363
<212> TYPE: DNA
<213> ORGANISM: Homo sapiens
<220> FEATURE:
<221> NAME/KEY: CDS
<222> LOCATION: (1)..(363)
<223> OTHER INFORMATION: NI-307.57D4 variable heavy chain (VH) sequence
<220> FEATURE:
<221> NAME/KEY: V_region
<222> LOCATION: (76)..(105)
<223> OTHER INFORMATION: complementarity determining region (CDR) VH-CDR1
<220> FEATURE:
<221> NAME/KEY: V_region
<222> LOCATION: (148)..(198)
<223> OTHER INFORMATION: complementarity determining region (CDR) VH-CDR2
<220> FEATURE:
<221> NAME/KEY: V_region
<222> LOCATION: (295)..(330)
<223> OTHER INFORMATION: complementarity determining region (CDR) VH-CDR3

<400> SEQUENCE: 125

```
gag gtg cag ctg gtg gag tct ggg gga ggc ctg gta cag cct ggc agg      48
Glu Val Gln Leu Val Glu Ser Gly Gly Gly Leu Val Gln Pro Gly Arg
 1               5                  10                  15 tcc ctg aga ctc tcc tgt gca gcc tct gga ttc acc ttt gat cat tat      96
Ser Leu Arg Leu Ser Cys Ala Ala Ser Gly Phe Thr Phe Asp His Tyr
             20                  25                  30 gcc atg cac tgg gtc cgg caa gtt cca ggg agg ggc ctg gag tgg gtc     144
Ala Met His Trp Val Arg Gln Val Pro Gly Arg Gly Leu Glu Trp Val
         35                  40                  45 tca ggt gtt act tgg aat agt ggt atc ata ggc tat gcg gac tct gtg     192
Ser Gly Val Thr Trp Asn Ser Gly Ile Ile Gly Tyr Ala Asp Ser Val
 50                  55                  60 aag ggc cga ttc acc atc tcc aga gac aat gcc aag aat tcc ctc tat     240
Lys Gly Arg Phe Thr Ile Ser Arg Asp Asn Ala Lys Asn Ser Leu Tyr
 65                  70                  75                  80 ctg caa atg acc agt ctg aga gct gag gac acg gcc ttg tat tac tgt     288
Leu Gln Met Thr Ser Leu Arg Ala Glu Asp Thr Ala Leu Tyr Tyr Cys
                 85                  90                  95 gca aaa ggg aca aat gac ttc gta agc tac ggt ttg gac gtc tgg ggc     336
Ala Lys Gly Thr Asn Asp Phe Val Ser Tyr Gly Leu Asp Val Trp Gly
            100                 105                 110 caa ggg acc acg gtc acc gtc tcc tcg                                  363
Gln Gly Thr Thr Val Thr Val Ser Ser
            115                 120
```

<210> SEQ ID NO 126
<211> LENGTH: 121
<212> TYPE: PRT
<213> ORGANISM: Homo sapiens

<400> SEQUENCE: 126

-continued

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp His Tyr
            20                  25                  30

Ala Met His Trp Val Arg Gln Val Pro Gly Arg Gly Leu Glu Trp Val
            35                  40                  45

Ser Gly Val Thr Trp Asn Ser Gly Ile Ile Gly Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Thr Ser Leu Arg Ala Glu Asp Thr Ala Leu Tyr Tyr Cys
            85                  90                  95

Ala Lys Gly Thr Asn Asp Phe Val Ser Tyr Gly Leu Asp Val Trp Gly
            100                 105                 110

Gln Gly Thr Thr Val Thr Val Ser Ser
            115                 120

<210> SEQ ID NO 127
<211> LENGTH: 333
<212> TYPE: DNA
<213> ORGANISM: Homo sapiens
<220> FEATURE:
<221> NAME/KEY: CDS
<222> LOCATION: (1)..(333)
<223> OTHER INFORMATION: NI-307.57D4 variable L-light chain (VL)
      sequence
<220> FEATURE:
<221> NAME/KEY: V_region
<222> LOCATION: (67)..(108)
<223> OTHER INFORMATION: complementarity determining region (CDR) VL-
      CDR1
<220> FEATURE:
<221> NAME/KEY: V_region
<222> LOCATION: (154)..(174)
<223> OTHER INFORMATION: complementarity determining region (CDR) VL-
      CDR2
<220> FEATURE:
<221> NAME/KEY: V_region
<222> LOCATION: (271)..(303)
<223> OTHER INFORMATION: complementarity determining region (CDR) VL-
      CDR3

<400> SEQUENCE: 127 cag tct gtg ttg acg cag ccg ccc tca gtg tct ggg gcc cca ggg cag     48
Gln Ser Val Leu Thr Gln Pro Pro Ser Val Ser Gly Ala Pro Gly Gln
1               5                   10                  15 agg gtc tcc atc tcc tgc act ggg acc agc tcc aac ctc ggg gca ggt     96
Arg Val Ser Ile Ser Cys Thr Gly Thr Ser Ser Asn Leu Gly Ala Gly
            20                  25                  30 ttt gat gta cac tgg tac cag cag att cca aga aaa gcc ccc gaa ctc    144
Phe Asp Val His Trp Tyr Gln Gln Ile Pro Arg Lys Ala Pro Glu Leu
            35                  40                  45 ctc atc tat ggt aac agc att cgg ccc tca ggg gtc cct gac cga ttc    192
Leu Ile Tyr Gly Asn Ser Ile Arg Pro Ser Gly Val Pro Asp Arg Phe
50                  55                  60 tct ggc tcc aag tct ggc acc tca gcc tcc ctg gcc atc act ggg ctc    240
Ser Gly Ser Lys Ser Gly Thr Ser Ala Ser Leu Ala Ile Thr Gly Leu
65                  70                  75                  80 cag gct gag gat gag gct gat tat tac tgc cag tcc tat gac agc agg    288
Gln Ala Glu Asp Glu Ala Asp Tyr Tyr Cys Gln Ser Tyr Asp Ser Arg
            85                  90                  95 ttg agt ggc tcg gtg ttc ggc ggg ggg acc aag ctg acc gtc cta        333
Leu Ser Gly Ser Val Phe Gly Gly Gly Thr Lys Leu Thr Val Leu
            100                 105                 110
```

<210> SEQ ID NO 128
<211> LENGTH: 111
<212> TYPE: PRT
<213> ORGANISM: Homo sapiens

<400> SEQUENCE: 128

Gln Ser Val Leu Thr Gln Pro Pro Ser Val Ser Gly Ala Pro Gly Gln
1               5                   10                  15

Arg Val Ser Ile Ser Cys Thr Gly Thr Ser Ser Asn Leu Gly Ala Gly
            20                  25                  30

Phe Asp Val His Trp Tyr Gln Gln Ile Pro Arg Lys Ala Pro Glu Leu
        35                  40                  45

Leu Ile Tyr Gly Asn Ser Ile Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Arg
                85                  90                  95

Leu Ser Gly Ser Val Phe Gly Gly Gly Thr Lys Leu Thr Val Leu
            100                 105                 110

<210> SEQ ID NO 129
<211> LENGTH: 381
<212> TYPE: DNA
<213> ORGANISM: Homo sapiens
<220> FEATURE:
<221> NAME/KEY: CDS
<222> LOCATION: (1)..(381)
<223> OTHER INFORMATION: NI-307.50H4 variable heavy chain (VH) sequence
<220> FEATURE:
<221> NAME/KEY: V_region
<222> LOCATION: (76)..(108)
<223> OTHER INFORMATION: complementarity determining region (CDR) VH-
      CDR1
<220> FEATURE:
<221> NAME/KEY: V_region
<222> LOCATION: (151)..(198)
<223> OTHER INFORMATION: complementarity determining region (CDR) VH-
      CDR2
<220> FEATURE:
<221> NAME/KEY: V_region
<222> LOCATION: (295)..(348)
<223> OTHER INFORMATION: complementarity determining region (CDR) VH-
      CDR3

<400> SEQUENCE: 129 cag gtg cag ctg cag gag tcg ggc cca gga ctg gtg aag cct tcg ggg        48
Gln Val Gln Leu Gln Glu Ser Gly Pro Gly Leu Val Lys Pro Ser Gly
1               5                   10                  15 acc ctg tcc ctc acc tgc gct gtc tct ggt gac tcc atc agc agt agt        96
Thr Leu Ser Leu Thr Cys Ala Val Ser Gly Asp Ser Ile Ser Ser Ser
            20                  25                  30 aac tgg tgg agt tgg gtc cgc cag ccc cca ggg aag agg ctg gag tgg       144
Asn Trp Trp Ser Trp Val Arg Gln Pro Pro Gly Lys Arg Leu Glu Trp
        35                  40                  45 att ggg gag atc tat cat agt ggg ggc acc aag tac aac ccg tcc ctc       192
Ile Gly Glu Ile Tyr His Ser Gly Gly Thr Lys Tyr Asn Pro Ser Leu
    50                  55                  60 aag agt cga gtc acc att tca gtg gac aag tcc aag aac cac ttc tcc       240
Lys Ser Arg Val Thr Ile Ser Val Asp Lys Ser Lys Asn His Phe Ser
65                  70                  75                  80 ctg aag ctg agg tct gtg acc gcc gcg gac acg gcc gtg tat tat tgt       288
Leu Lys Leu Arg Ser Val Thr Ala Ala Asp Thr Ala Val Tyr Tyr Cys

```
                 85                  90                  95
gcg aga aat agg tgg ttc gac aat aac cgg ggg ggc tac tac tat tac       336
Ala Arg Asn Arg Trp Phe Asp Asn Asn Arg Gly Gly Tyr Tyr Tyr Tyr
            100                 105                 110 ggc atg gac gtc tgg ggc caa ggg aca atg gtc acc gtc tct tcg           381
Gly Met Asp Val Trp Gly Gln Gly Thr Met Val Thr Val Ser Ser
        115                 120                 125
```

<210> SEQ ID NO 130
<211> LENGTH: 127
<212> TYPE: PRT
<213> ORGANISM: Homo sapiens

<400> SEQUENCE: 130

```
Gln Val Gln Leu Gln Glu Ser Gly Pro Gly Leu Val Lys Pro Ser Gly
1               5                   10                  15

Thr Leu Ser Leu Thr Cys Ala Val Ser Gly Asp Ser Ile Ser Ser Ser
            20                  25                  30

Asn Trp Trp Ser Trp Val Arg Gln Pro Pro Gly Lys Arg Leu Glu Trp
        35                  40                  45

Ile Gly Glu Ile Tyr His Ser Gly Gly Thr Lys Tyr Asn Pro Ser Leu
    50                  55                  60

Lys Ser Arg Val Thr Ile Ser Val Asp Lys Ser Lys Asn His Phe Ser
65                  70                  75                  80

Leu Lys Leu Arg Ser Val Thr Ala Ala Asp Thr Ala Val Tyr Tyr Cys
                85                  90                  95

Ala Arg Asn Arg Trp Phe Asp Asn Asn Arg Gly Gly Tyr Tyr Tyr Tyr
            100                 105                 110

Gly Met Asp Val Trp Gly Gln Gly Thr Met Val Thr Val Ser Ser
        115                 120                 125
```

<210> SEQ ID NO 131
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-307.50H4 variable K-light chain (VK)
      sequence
<220> FEATURE:
<221> NAME/KEY: V_region
<222> LOCATION: (70)..(102)
<223> OTHER INFORMATION: complementarity determining region (CDR) VK-
      CDR1
<220> FEATURE:
<221> NAME/KEY: V_region
<222> LOCATION: (148)..(168)
<223> OTHER INFORMATION: complementarity determining region (CDR) VK-
      CDR2
<220> FEATURE:
<221> NAME/KEY: V_region
<222> LOCATION: (265)..(291)
<223> OTHER INFORMATION: complementarity determining region (CDR) VK-
      CDR3

<400> SEQUENCE: 131

```
gac atc cag atg acc cag tct cca tcc tcc ctg tct gca tct gtg gga       48
Asp Ile Gln Met Thr Gln Ser Pro Ser Ser Leu Ser Ala Ser Val Gly
1               5                   10                  15 gac aga gtc acc atc act tgc cgg gca ggt cag ggc att agc acc tat       96
Asp Arg Val Thr Ile Thr Cys Arg Ala Gly Gln Gly Ile Ser Thr Tyr
            20                  25                  30 tta aat tgg tat cag cag aaa cca ggg aaa gcc cct aac ctc ctg atc      144
```

```
Leu Asn Trp Tyr Gln Gln Lys Pro Gly Lys Ala Pro Asn Leu Leu Ile
         35                  40                  45 tat gct aca tcc gat ttg caa agt ggg gtc cca tca agg ttc agt ggc       192
Tyr Ala Thr Ser Asp Leu Gln Ser Gly Val Pro Ser Arg Phe Ser Gly
     50                  55                  60 agt gga tct ggg aca gat ttc act ctc acc atc agc agt ctg caa cct       240
Ser Gly Ser Gly Thr Asp Phe Thr Leu Thr Ile Ser Ser Leu Gln Pro
 65                  70                  75                  80 gaa gat ttt gct act tac tac tgt caa cag agt tac aat aac ccg tac       288
Glu Asp Phe Ala Thr Tyr Tyr Cys Gln Gln Ser Tyr Asn Asn Pro Tyr
                 85                  90                  95 act ttt ggc cag ggg acc aag gtg gag atc aaa                           321
Thr Phe Gly Gln Gly Thr Lys Val Glu Ile Lys
             100                 105

<210> SEQ ID NO 132
<211> LENGTH: 107
<212> TYPE: PRT
<213> ORGANISM: Homo sapiens

<400> SEQUENCE: 132

Asp Ile Gln Met Thr Gln Ser Pro Ser Ser Leu Ser Ala Ser Val Gly
 1               5                  10                  15

Asp Arg Val Thr Ile Thr Cys Arg Ala Gly Gln Gly Ile Ser Thr Tyr
             20                  25                  30

Leu Asn Trp Tyr Gln Gln Lys Pro Gly Lys Ala Pro Asn Leu Leu Ile
         35                  40                  45

Tyr Ala Thr Ser Asp Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Asn Asn Pro Tyr
                 85                  90                  95

Thr Phe Gly Gln Gly Thr Lys Val Glu Ile Lys
             100                 105

<210> SEQ ID NO 133
<211> LENGTH: 360
<212> TYPE: DNA
<213> ORGANISM: Homo sapiens
<220> FEATURE:
<221> NAME/KEY: CDS
<222> LOCATION: (1)..(360)
<223> OTHER INFORMATION: NI-307.53B11 variable heavy chain (VH) sequence
<220> FEATURE:
<221> NAME/KEY: V_region
<222> LOCATION: (76)..(105)
<223> OTHER INFORMATION: complementarity determining region (CDR) VH-
      CDR1
<220> FEATURE:
<221> NAME/KEY: V_region
<222> LOCATION: (148)..(198)
<223> OTHER INFORMATION: complementarity determining region (CDR) VH-
      CDR2
<220> FEATURE:
<221> NAME/KEY: V_region
<222> LOCATION: (295)..(327)
<223> OTHER INFORMATION: complementarity determining region (CDR) VH-
      CDR3

<400> SEQUENCE: 133 gag gtg cag ctg gtg cag tct gga gca gag gtg aaa aag ccc ggg gaa        48
Glu Val Gln Leu Val Gln Ser Gly Ala Glu Val Lys Lys Pro Gly Glu
 1               5                  10                  15
```

```
tct ctg aag atc tcc tgt aag ggt tct gga tac agc ttt acc agc tac        96
Ser Leu Lys Ile Ser Cys Lys Gly Ser Gly Tyr Ser Phe Thr Ser Tyr
         20                  25                  30 tgg atc ggc tgg gtg cgc cag atg ccc ggg aaa ggc ctg gag tgg atg       144
Trp Ile Gly Trp Val Arg Gln Met Pro Gly Lys Gly Leu Glu Trp Met
         35                  40                  45 ggg atc atc tat cct ggt gac tct gat acc aga tac agc ccg tcc ttc       192
Gly Ile Ile Tyr Pro Gly Asp Ser Asp Thr Arg Tyr Ser Pro Ser Phe
 50                  55                  60 caa ggc cag gtc acc atc tca gcc gac aag tcc atc acc acc gcc tac       240
Gln Gly Gln Val Thr Ile Ser Ala Asp Lys Ser Ile Thr Thr Ala Tyr
 65                  70                  75                  80 ctg cag tgg agc agc ctg aag gcc tcg gac acc gcc tta tat tac tgt       288
Leu Gln Trp Ser Ser Leu Lys Ala Ser Asp Thr Ala Leu Tyr Tyr Cys
             85                  90                  95 gcg aga cgg ggt agt ggg agc ttc tcc aac tat gac ttc tgg ggc cag       336
Ala Arg Arg Gly Ser Gly Ser Phe Ser Asn Tyr Asp Phe Trp Gly Gln
                100                 105                 110 ggc acc ctg gtc acc gtc tcc tcg                                       360
Gly Thr Leu Val Thr Val Ser Ser
        115                 120
```

<210> SEQ ID NO 134
<211> LENGTH: 120
<212> TYPE: PRT
<213> ORGANISM: Homo sapiens

<400> SEQUENCE: 134

```
Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
         20                  25                  30

Trp Ile Gly Trp Val Arg Gln Met Pro Gly Lys Gly Leu Glu Trp Met
         35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Ile Thr Thr Ala Tyr
 65                  70                  75                  80

Leu Gln Trp Ser Ser Leu Lys Ala Ser Asp Thr Ala Leu Tyr Tyr Cys
             85                  90                  95

Ala Arg Arg Gly Ser Gly Ser Phe Ser Asn Tyr Asp Phe Trp Gly Gln
                100                 105                 110

Gly Thr Leu Val Thr Val Ser Ser
        115                 120
```

<210> SEQ ID NO 135
<211> LENGTH: 330
<212> TYPE: DNA
<213> ORGANISM: Homo sapiens
<220> FEATURE:
<221> NAME/KEY: CDS
<222> LOCATION: (1)..(330)
<223> OTHER INFORMATION: NI-307.53B11 variable K-light chain (VK)
      sequence
<220> FEATURE:
<221> NAME/KEY: V_region
<222> LOCATION: (67)..(108)
<223> OTHER INFORMATION: complementarity determining region (CDR) VK-
      CDR1
<220> FEATURE:
<221> NAME/KEY: V_region
<222> LOCATION: (154)..(174)
<223> OTHER INFORMATION: complementarity determining region (CDR) VK- CDR2
<220> FEATURE:
<221> NAME/KEY: V_region
<222> LOCATION: (271)..(300)
<223> OTHER INFORMATION: complementarity determining region (CDR) VK-
      CDR3

<400> SEQUENCE: 135

```
cag tct gcc ctg act cag cct cgc tca gtg tcc ggg tct cct ggg cag        48
Gln Ser Ala Leu Thr Gln Pro Arg Ser Val Ser Gly Ser Pro Gly Gln
1               5                   10                  15 tca gtc acc atc tcc tgc act gga acc agc agt gat gtt ggt gct tat        96
Ser Val Thr Ile Ser Cys Thr Gly Thr Ser Ser Asp Val Gly Ala Tyr
            20                  25                  30 aac tat gtc tcc tgg tac caa cag cac cca gtc aaa gcc ccc aaa ctc       144
Asn Tyr Val Ser Trp Tyr Gln Gln His Pro Val Lys Ala Pro Lys Leu
        35                  40                  45 atg att tat gat gtc agt aag cgg ccc tca ggg gtc cct gat cgc ttc       192
Met Ile Tyr Asp Val Ser Lys Arg Pro Ser Gly Val Pro Asp Arg Phe
    50                  55                  60 tct ggc tcc agg tct ggc aac acg gcc tcc ctg acc atc tct ggg ctc       240
Ser Gly Ser Arg Ser Gly Asn Thr Ala Ser Leu Thr Ile Ser Gly Leu
65                  70                  75                  80 cag gct gac gat gag gct gat tat tac tgc tgc tca tat gca ggc acc       288
Gln Ala Asp Asp Glu Ala Asp Tyr Tyr Cys Cys Ser Tyr Ala Gly Thr
                85                  90                  95 tac act gtg ctt ttc ggc gga ggg acc aag ctg acc gtc cta               330
Tyr Thr Val Leu Phe Gly Gly Gly Thr Lys Leu Thr Val Leu
                100                 105                 110
```

<210> SEQ ID NO 136
<211> LENGTH: 110
<212> TYPE: PRT
<213> ORGANISM: Homo sapiens

<400> SEQUENCE: 136

```
Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Ala Tyr
            20                  25                  30

Asn Tyr Val Ser Trp Tyr Gln Gln His Pro Val Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Arg Ser Gly Asn Thr Ala Ser Leu Thr Ile Ser Gly Leu
65                  70                  75                  80

Gln Ala Asp Asp Glu Ala Asp Tyr Tyr Cys Cys Ser Tyr Ala Gly Thr
                85                  90                  95

Tyr Thr Val Leu Phe Gly Gly Gly Thr Lys Leu Thr Val Leu
                100                 105                 110
```

<210> SEQ ID NO 137
<211> LENGTH: 384
<212> TYPE: DNA
<213> ORGANISM: Homo sapiens
<220> FEATURE:
<221> NAME/KEY: CDS
<222> LOCATION: (1)..(384)
<223> OTHER INFORMATION: NI-307.7J3 variable heavy chain (VH) sequence
<220> FEATURE:
<221> NAME/KEY: V_region
<222> LOCATION: (76)..(111)
<223> OTHER INFORMATION: complementarity determining region (CDR) VH-

```
        CDR1
<220> FEATURE:
<221> NAME/KEY: V_region
<222> LOCATION: (154)..(201)
<223> OTHER INFORMATION: complementarity determining region (CDR) VH-
      CDR2
<220> FEATURE:
<221> NAME/KEY: V_region
<222> LOCATION: (298)..(351)
<223> OTHER INFORMATION: complementarity determining region (CDR) VH-
      CDR3

<400> SEQUENCE: 137 cag gtg cag ctg cag gag tcg ggc cca gga ctg gtg aag cct tca cag       48
Gln Val Gln Leu Gln Glu Ser Gly Pro Gly Leu Val Lys Pro Ser Gln
1               5                   10                  15 acc ctg tcc ctc acc tgc act gtc tct ggt ggc tcc atc agc agt ggt       96
Thr Leu Ser Leu Thr Cys Thr Val Ser Gly Gly Ser Ile Ser Ser Gly
            20                  25                  30 gat tac tac tgg agt tgg atc cgc cag ccc cca ggg aag ggc ctg gag      144
Asp Tyr Tyr Trp Ser Trp Ile Arg Gln Pro Pro Gly Lys Gly Leu Glu
        35                  40                  45 tgg att ggg tac atc tat tac agt ggg acc acc tac tac aac ccg tcc      192
Trp Ile Gly Tyr Ile Tyr Tyr Ser Gly Thr Thr Tyr Tyr Asn Pro Ser
50                  55                  60 ctc aag agt cga gtt acc ata tca gta gac acg tcc aag aac cag ttc      240
Leu Lys Ser Arg Val Thr Ile Ser Val Asp Thr Ser Lys Asn Gln Phe
65                  70                  75                  80 tcc ctg aag ctg agt ttt gtg act gtc gca gac acg gcc gtg tat tac      288
Ser Leu Lys Leu Ser Phe Val Thr Val Ala Asp Thr Ala Val Tyr Tyr
                85                  90                  95 tgt gcc aga gat ggc cgt ttt act atg gtt cgg gga ggc tac tac tac      336
Cys Ala Arg Asp Gly Arg Phe Thr Met Val Arg Gly Gly Tyr Tyr Tyr
            100                 105                 110 tac ggt atg gac gtc tgg ggc caa ggg acc acg gtc acc gtc tcc tcg      384
Tyr Gly Met Asp Val Trp Gly Gln Gly Thr Thr Val Thr Val Ser Ser
        115                 120                 125

<210> SEQ ID NO 138
<211> LENGTH: 128
<212> TYPE: PRT
<213> ORGANISM: Homo sapiens

<400> SEQUENCE: 138

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Pro Pro Gly Lys Gly Leu Glu
        35                  40                  45

Trp Ile Gly Tyr Ile Tyr Tyr Ser Gly Thr Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Phe Val Thr Val Ala Asp Thr Ala Val Tyr Tyr
                85                  90                  95

Cys Ala Arg Asp Gly Arg Phe Thr Met Val Arg Gly Gly Tyr Tyr Tyr
            100                 105                 110

Tyr Gly Met Asp Val Trp Gly Gln Gly Thr Thr Val Thr Val Ser Ser
        115                 120                 125
```

```
<210> SEQ ID NO 139
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-307.7J3 variable K-light chain (VK) sequence
<220> FEATURE:
<221> NAME/KEY: V_region
<222> LOCATION: (70)..(102)
<223> OTHER INFORMATION: complementarity determining region (CDR) VK-
      CDR1
<220> FEATURE:
<221> NAME/KEY: V_region
<222> LOCATION: (148)..(168)
<223> OTHER INFORMATION: complementarity determining region (CDR) VK-
      CDR2
<220> FEATURE:
<221> NAME/KEY: V_region
<222> LOCATION: (265)..(291)
<223> OTHER INFORMATION: complementarity determining region (CDR) VK-
      CDR3

<400> SEQUENCE: 139 gac atc cag atg acc cag tct cca tcc tcc ctg tct gta tct gta gga      48
Asp Ile Gln Met Thr Gln Ser Pro Ser Ser Leu Ser Val Ser Val Gly
1               5                   10                  15 gac aga gtc acc atc act tgc cgg gca agt cag agc att agc agc tat      96
Asp Arg Val Thr Ile Thr Cys Arg Ala Ser Gln Ser Ile Ser Ser Tyr
            20                  25                  30 tta aat tgg tat cag cag aaa tta ggg aaa gcc cct aag ctc ctg att     144
Leu Asn Trp Tyr Gln Gln Lys Leu Gly Lys Ala Pro Lys Leu Leu Ile
        35                  40                  45 tat gat gca tcc agt ttg caa agt ggg gtc cca tca agg ttc agt ggc     192
Tyr Asp Ala Ser Ser Leu Gln Ser Gly Val Pro Ser Arg Phe Ser Gly
    50                  55                  60 agt gga tct ggg aca gat ttc act ctc acc atc agc agt ctg caa cct     240
Ser Gly Ser Gly Thr Asp Phe Thr Leu Thr Ile Ser Ser Leu Gln Pro
65                  70                  75                  80 gaa gat ttt gca act tac tac tgt caa cag agt tac act acc cct cga     288
Glu Asp Phe Ala Thr Tyr Tyr Cys Gln Gln Ser Tyr Thr Thr Pro Arg
                85                  90                  95 acg ttc ggc caa ggg acc aag gtg gag atc aaa                         321
Thr Phe Gly Gln Gly Thr Lys Val Glu Ile Lys
                100                 105

<210> SEQ ID NO 140
<211> LENGTH: 107
<212> TYPE: PRT
<213> ORGANISM: Homo sapiens

<400> SEQUENCE: 140

Asp Ile Gln Met Thr Gln Ser Pro Ser Ser Leu Ser Val Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Leu Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Arg
                85                  90                  95
```

-continued

```
Thr Phe Gly Gln Gly Thr Lys Val Glu Ile Lys
            100                 105

<210> SEQ ID NO 141
<211> LENGTH: 369
<212> TYPE: DNA
<213> ORGANISM: Homo sapiens
<220> FEATURE:
<221> NAME/KEY: CDS
<222> LOCATION: (1)..(369)
<223> OTHER INFORMATION: NI-307.59A7 variable heavy chain (VH) sequence
<220> FEATURE:
<221> NAME/KEY: V_region
<222> LOCATION: (76)..(105)
<223> OTHER INFORMATION: complementarity determining region (CDR) VH-
      CDR1
<220> FEATURE:
<221> NAME/KEY: V_region
<222> LOCATION: (148)..(198)
<223> OTHER INFORMATION: complementarity determining region (CDR) VH-
      CDR2
<220> FEATURE:
<221> NAME/KEY: V_region
<222> LOCATION: (295)..(336)
<223> OTHER INFORMATION: complementarity determining region (CDR) VH-
      CDR3

<400> SEQUENCE: 141 gag gtg cag ctg gtg gag tct ggg gga ggc ttg gta cag cct gga ggg         48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttc agt agt tat         96
Ser Leu Arg Leu Ser Cys Ala Ala Ser Gly Phe Thr Phe Ser Ser Tyr
                20                  25                  30 gaa atg aac tgg gtc cgc cag gct cca ggg aag ggg ctg gag tgg gtt        144
Glu Met Asn Trp Val Arg Gln Ala Pro Gly Lys Gly Leu Glu Trp Val
            35                  40                  45 tca tac att agt agt agt ggt acc aac ata tac cac gca gac tct gtg        192
Ser Tyr Ile Ser Ser Ser Gly Thr Asn Ile Tyr His Ala Asp Ser Val
    50                  55                  60 aag ggc cga ttc acc atc tcc aga gac aac gcc aag aac tca ctg tat        240
Lys Gly Arg Phe Thr Ile Ser Arg Asp Asn Ala Lys Asn Ser Leu Tyr
65                  70                  75                  80 ctg caa atg aac agc ctg aga gcc gag gac acg gct gtt tat tac tgt        288
Leu Gln Met Asn Ser Leu Arg Ala Glu Asp Thr Ala Val Tyr Tyr Cys
                85                  90                  95 gcg aga gat ggt cct tca cca cgc gga cac aac tat ggt cat gac tac        336
Ala Arg Asp Gly Pro Ser Pro Arg Gly His Asn Tyr Gly His Asp Tyr
            100                 105                 110 tgg ggc caa ggc acc ctg gtc acc gtc tcc tcg                            369
Trp Gly Gln Gly Thr Leu Val Thr Val Ser Ser
    115                 120

<210> SEQ ID NO 142
<211> LENGTH: 123
<212> TYPE: PRT
<213> ORGANISM: Homo sapiens

<400> SEQUENCE: 142

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Glu Met Asn Trp Val Arg Gln Ala Pro Gly Lys Gly Leu Glu Trp Val
            35                  40                  45
```

```
Ser Tyr Ile Ser Ser Gly Thr Asn Ile Tyr His Ala Asp Ser Val
    50              55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Pro Ser Pro Arg Gly His Asn Tyr Gly His Asp Tyr
            100                 105                 110

Trp Gly Gln Gly Thr Leu Val Thr Val Ser Ser
            115                 120
```

<210> SEQ ID NO 143
<211> LENGTH: 330
<212> TYPE: DNA
<213> ORGANISM: Homo sapiens
<220> FEATURE:
<221> NAME/KEY: CDS
<222> LOCATION: (1)..(330)
<223> OTHER INFORMATION: NI-307.59A7 variable L-light chain (VL)
      sequence
<220> FEATURE:
<221> NAME/KEY: V_region
<222> LOCATION: (67)..(105)
<223> OTHER INFORMATION: complementarity determining region (CDR) VL-
      CDR1
<220> FEATURE:
<221> NAME/KEY: V_region
<222> LOCATION: (151)..(171)
<223> OTHER INFORMATION: complementarity determining region (CDR) VL-
      CDR2
<220> FEATURE:
<221> NAME/KEY: V_region
<222> LOCATION: (268)..(300)
<223> OTHER INFORMATION: complementarity determining region (CDR) VL-
      CDR3

<400> SEQUENCE: 143

```
cag tct gtg ctg act cag cca ccc tca gcg tct ggg acc ccc ggg cag      48
Gln Ser Val Leu Thr Gln Pro Pro Ser Ala Ser Gly Thr Pro Gly Gln
1               5                   10                  15 agg gtc acc atc tct tgt tct gga agc agc tcc aac atc gga agt aat      96
Arg Val Thr Ile Ser Cys Ser Gly Ser Ser Ser Asn Ile Gly Ser Asn
                20                  25                  30 gct gta aac tgg tac cag cag gtc cca gga acg gcc ccc aaa ctc ctc     144
Ala Val Asn Trp Tyr Gln Gln Val Pro Gly Thr Ala Pro Lys Leu Leu
            35                  40                  45 atc tat act aat aat cag cgg ccc tca ggg gtc cct gac cga ttc tct     192
Ile Tyr Thr Asn Asn Gln Arg Pro Ser Gly Val Pro Asp Arg Phe Ser
    50                  55                  60 ggc tcc aag tct ggc acc tca gcc tcc ctg gcc atc agt ggg ctc cag     240
Gly Ser Lys Ser Gly Thr Ser Ala Ser Leu Ala Ile Ser Gly Leu Gln
65                  70                  75                  80 tct gag gat gag act gat tat tac tgt gca gca tgg gat gac agc ctg     288
Ser Glu Asp Glu Thr Asp Tyr Tyr Cys Ala Ala Trp Asp Asp Ser Leu
                85                  90                  95 ggt ggt ccg gtt ttc ggc gga ggg acc aag ctg acc gtc cta             330
Gly Gly Pro Val Phe Gly Gly Gly Thr Lys Leu Thr Val Leu
            100                 105                 110
```

<210> SEQ ID NO 144
<211> LENGTH: 110
<212> TYPE: PRT
<213> ORGANISM: Homo sapiens

<400> SEQUENCE: 144

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Ala Val Asn Trp Tyr Gln Gln Val Pro Gly Thr Ala Pro Lys Leu Leu
        35                  40                  45

Ile Tyr Thr Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Thr Asp Tyr Tyr Cys Ala Ala Trp Asp Asp Ser Leu
                85                  90                  95

Gly Gly Pro Val Phe Gly Gly Gly Thr Lys Leu Thr Val Leu
            100                 105                 110

<210> SEQ ID NO 145
<211> LENGTH: 363
<212> TYPE: DNA
<213> ORGANISM: Homo sapiens
<220> FEATURE:
<221> NAME/KEY: CDS
<222> LOCATION: (1)..(363)
<223> OTHER INFORMATION: NI-307.105A6 variable heavy chain (VH) sequence
<220> FEATURE:
<221> NAME/KEY: V_region
<222> LOCATION: (76)..(105)
<223> OTHER INFORMATION: complementarity determining region (CDR) VH-
      CDR1
<220> FEATURE:
<221> NAME/KEY: V_region
<222> LOCATION: (148)..(198)
<223> OTHER INFORMATION: complementarity determining region (CDR) VH-
      CDR2
<220> FEATURE:
<221> NAME/KEY: V_region
<222> LOCATION: (295)..(330)
<223> OTHER INFORMATION: complementarity determining region (CDR) VH-
      CDR3

<400> SEQUENCE: 145 gaa gtg cag ctg gtg gag tct ggg gga ggc ttg gta cag cct ggc agg      48
Glu Val Gln Leu Val Glu Ser Gly Gly Gly Leu Val Gln Pro Gly Arg
1               5                   10                  15 tcc ctg aga ctc tcc tgt gca gcc tct gga ttc acc ttt gat gat tat      96
Ser Leu Arg Leu Ser Cys Ala Ala Ser Gly Phe Thr Phe Asp Asp Tyr
            20                  25                  30 gcc atg cac tgg gtc cgg caa gct cca ggg aag ggc ttg gag tgg gtc     144
Ala Met His Trp Val Arg Gln Ala Pro Gly Lys Gly Leu Glu Trp Val
        35                  40                  45 tca ggt att act tgg aat agt ggt agt ata ggc tat gcg gac tct gtg     192
Ser Gly Ile Thr Trp Asn Ser Gly Ser Ile Gly Tyr Ala Asp Ser Val
50                  55                  60 aag ggc cga ttc acc atc tcc aga gac aac gcc aag aac tcc cta tat     240
Lys Gly Arg Phe Thr Ile Ser Arg Asp Asn Ala Lys Asn Ser Leu Tyr
65                  70                  75                  80 ctg caa atg aac agt ctg agc gct gag gac acg gcc ttg tat tac tgt     288
Leu Gln Met Asn Ser Leu Ser Ala Glu Asp Thr Ala Leu Tyr Tyr Cys
                85                  90                  95 gca aaa ggg gcg cgt gac tac tta agc tat ggt atg gac gtc tgg ggc     336
Ala Lys Gly Ala Arg Asp Tyr Leu Ser Tyr Gly Met Asp Val Trp Gly
            100                 105                 110 caa ggg acc acg gtc acc gtc tcc tcg                                  363
Gln Gly Thr Thr Val Thr Val Ser Ser
```

<210> SEQ ID NO 146
<211> LENGTH: 121
<212> TYPE: PRT
<213> ORGANISM: Homo sapiens

<400> SEQUENCE: 146

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Thr Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Ser Ala Glu Asp Thr Ala Leu Tyr Tyr Cys
                85                  90                  95

Ala Lys Gly Ala Arg Asp Tyr Leu Ser Tyr Gly Met Asp Val Trp Gly
            100                 105                 110

Gln Gly Thr Thr Val Thr Val Ser Ser
        115                 120

<210> SEQ ID NO 147
<211> LENGTH: 333
<212> TYPE: DNA
<213> ORGANISM: Homo sapiens
<220> FEATURE:
<221> NAME/KEY: CDS
<222> LOCATION: (1)..(333)
<223> OTHER INFORMATION: NI-307.105A6 variable L-light chain (VL)
      sequence
<220> FEATURE:
<221> NAME/KEY: V_region
<222> LOCATION: (67)..(108)
<223> OTHER INFORMATION: complementarity determining region (CDR) VL-
      CDR1
<220> FEATURE:
<221> NAME/KEY: V_region
<222> LOCATION: (154)..(174)
<223> OTHER INFORMATION: complementarity determining region (CDR) VL-
      CDR2
<220> FEATURE:
<221> NAME/KEY: V_region
<222> LOCATION: (271)..(303)
<223> OTHER INFORMATION: complementarity determining region (CDR) VL-
      CDR3

<400> SEQUENCE: 147 cag tct gtc gtg acg cag ccg ccc tca gtg tct ggg gcc cca ggg cag    48
Gln Ser Val Val Thr Gln Pro Pro Ser Val Ser Gly Ala Pro Gly Gln
1               5                   10                  15 agg gtc acc atc tcc tgc act ggg agc agt tcc aac atc ggg gca ggt    96
Arg Val Thr Ile Ser Cys Thr Gly Ser Ser Ser Asn Ile Gly Ala Gly
            20                  25                  30 tat gat gta cac tgg tac cag cag ctt cca gga aca gcc ccc aaa ctc    144
Tyr Asp Val His Trp Tyr Gln Gln Leu Pro Gly Thr Ala Pro Lys Leu
        35                  40                  45 ctc atc ttt agt aac acc att cgg ccc tca ggg gtc cct gac cga ttc    192
Leu Ile Phe Ser Asn Thr Ile Arg Pro Ser Gly Val Pro Asp Arg Phe
    50                  55                  60 tct ggc tcc aag tct ggc acc tca gcc tcc ctg gcc atc act ggg ctc    240

```
Ser Gly Ser Lys Ser Gly Thr Ser Ala Ser Leu Ala Ile Thr Gly Leu
 65                  70                  75                  80 cag gct gag gat gag gct aat tat tac tgc cag tct tat gac agc agc      288
Gln Ala Glu Asp Glu Ala Asn Tyr Tyr Cys Gln Ser Tyr Asp Ser Ser
                 85                  90                  95 ctg agt ggt tcg gtg ttc ggc gga ggg acc aag ctg acc gtc cta          333
Leu Ser Gly Ser Val Phe Gly Gly Gly Thr Lys Leu Thr Val Leu
            100                 105                 110
```

<210> SEQ ID NO 148
<211> LENGTH: 111
<212> TYPE: PRT
<213> ORGANISM: Homo sapiens

<400> SEQUENCE: 148

```
Gln Ser Val Val Thr Gln Pro Pro Ser Val Ser Gly Ala Pro Gly Gln
  1               5                  10                  15

Arg Val Thr Ile Ser Cys Thr Gly Ser Ser Asn Ile Gly Ala Gly
             20                  25                  30

Tyr Asp Val His Trp Tyr Gln Gln Leu Pro Gly Thr Ala Pro Lys Leu
             35                  40                  45

Leu Ile Phe Ser Asn Thr Ile Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asn Tyr Tyr Cys Gln Ser Tyr Asp Ser Ser
                 85                  90                  95

Leu Ser Gly Ser Val Phe Gly Gly Gly Thr Lys Leu Thr Val Leu
            100                 105                 110
```

<210> SEQ ID NO 149
<211> LENGTH: 372
<212> TYPE: DNA
<213> ORGANISM: Homo sapiens
<220> FEATURE:
<221> NAME/KEY: CDS
<222> LOCATION: (1)..(372)
<223> OTHER INFORMATION: NI-307.29B1 variable heavy chain (VH) sequence
<220> FEATURE:
<221> NAME/KEY: V_region
<222> LOCATION: (76)..(105)
<223> OTHER INFORMATION: complementarity determining region (CDR) VH-
      CDR1
<220> FEATURE:
<221> NAME/KEY: V_region
<222> LOCATION: (148)..(198)
<223> OTHER INFORMATION: complementarity determining region (CDR) VH-
      CDR2
<220> FEATURE:
<221> NAME/KEY: V_region
<222> LOCATION: (295)..(339)
<223> OTHER INFORMATION: complementarity determining region (CDR) VH-
      CDR3

<400> SEQUENCE: 149

```
gag gtg cag ctg gtg gag tct ggg gga ggc ttg gta aag cct ggg ggg       48
Glu Val Gln Leu Val Glu Ser Gly Gly Gly Leu Val Lys Pro Gly Gly
  1               5                  10                  15 tcc ctg aga ctc tcc tgt gca gcc tct gga atc acc ttt caa tac tat       96
Ser Leu Arg Leu Ser Cys Ala Ala Ser Gly Ile Thr Phe Gln Tyr Tyr
             20                  25                  30 gcc atg aat tgg gtc cgc cag gct cca ggg aag ggg ctg gag tgg gtc      144
Ala Met Asn Trp Val Arg Gln Ala Pro Gly Lys Gly Leu Glu Trp Val
             35                  40                  45
```

```
tct tct att ggc ggt cgt ggt gat acc aca tac tac aca gac tcc gtg      192
Ser Ser Ile Gly Gly Arg Gly Asp Thr Thr Tyr Tyr Thr Asp Ser Val
50                  55                  60 aag ggc cgc ttc acc atc tcc aga gac aat tcc aag agc aca cta tat      240
Lys Gly Arg Phe Thr Ile Ser Arg Asp Asn Ser Lys Ser Thr Leu Tyr
65                  70                  75                  80 ctg caa atg aac agc ctg aga gcc gag gac acg gcc gtc tat tac tgt      288
Leu Gln Met Asn Ser Leu Arg Ala Glu Asp Thr Ala Val Tyr Tyr Cys
                85                  90                  95 gcg aaa gag cca ttt gac agt agt ggt gat cac cga ggc gtc ttt gac      336
Ala Lys Glu Pro Phe Asp Ser Ser Gly Asp His Arg Gly Val Phe Asp
            100                 105                 110 tac tgg ggc cag gga acc ctg gtc acc gtc tcc tcg                      372
Tyr Trp Gly Gln Gly Thr Leu Val Thr Val Ser Ser
        115                 120
```

<210> SEQ ID NO 150
<211> LENGTH: 124
<212> TYPE: PRT
<213> ORGANISM: Homo sapiens

<400> SEQUENCE: 150

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Ile Thr Phe Gln Tyr Tyr
            20                  25                  30

Ala Met Asn Trp Val Arg Gln Ala Pro Gly Lys Gly Leu Glu Trp Val
        35                  40                  45

Ser Ser Ile Gly Gly Arg Gly Asp Thr Thr Tyr Tyr Thr Asp Ser Val
    50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Pro Phe Asp Ser Ser Gly Asp His Arg Gly Val Phe Asp
            100                 105                 110

Tyr Trp Gly Gln Gly Thr Leu Val Thr Val Ser Ser
        115                 120
```

<210> SEQ ID NO 151
<211> LENGTH: 330
<212> TYPE: DNA
<213> ORGANISM: Homo sapiens
<220> FEATURE:
<221> NAME/KEY: CDS
<222> LOCATION: (1)..(330)
<223> OTHER INFORMATION: NI-307.29B1 variable L-light chain (VL) sequence
<220> FEATURE:
<221> NAME/KEY: V_region
<222> LOCATION: (67)..(108)
<223> OTHER INFORMATION: complementarity determining region (CDR) VL-CDR1
<220> FEATURE:
<221> NAME/KEY: V_region
<222> LOCATION: (154)..(174)
<223> OTHER INFORMATION: complementarity determining region (CDR) VL-CDR2
<220> FEATURE:
<221> NAME/KEY: V_region
<222> LOCATION: (271)..(300)
<223> OTHER INFORMATION: complementarity determining region (CDR) VL-CDR3

<400> SEQUENCE: 151

```
cag tct gtc gtg acg cag ccg ccc tca gtg tct ggg gcc cca ggg cag      48
Gln Ser Val Val Thr Gln Pro Pro Ser Val Ser Gly Ala Pro Gly Gln
1               5                   10                  15 agg gtc acc atc tcc tgc gct ggg agc agg tcc aac atc ggg gca ggt      96
Arg Val Thr Ile Ser Cys Ala Gly Ser Arg Ser Asn Ile Gly Ala Gly
                20                  25                  30 tat gat gta aat tgg tac cag caa ctt cca aga act gcc ccc aaa ctg     144
Tyr Asp Val Asn Trp Tyr Gln Gln Leu Pro Arg Thr Ala Pro Lys Leu
            35                  40                  45 ctc atc tat gat aac acc agg cgg ccg tca ggt gtc cct gcc cga ttc     192
Leu Ile Tyr Asp Asn Thr Arg Arg Pro Ser Gly Val Pro Ala Arg Phe
        50                  55                  60 tct ggt tcc aag tct ggc tcc tca gcc tcc ctg acc atc act ggg ctc     240
Ser Gly Ser Lys Ser Gly Ser Ser Ala Ser Leu Thr Ile Thr Gly Leu
65                  70                  75                  80 cag gct gaa gat gag gct gat tat tac tgc cag tcc tat gac agc aaa     288
Gln Ala Glu Asp Glu Ala Asp Tyr Tyr Cys Gln Ser Tyr Asp Ser Lys
                85                  90                  95 ctg aat aaa gtg ttc ggc gga ggg acc aag ttg acc gtc cta             330
Leu Asn Lys Val Phe Gly Gly Gly Thr Lys Leu Thr Val Leu
            100                 105                 110
```

<210> SEQ ID NO 152
<211> LENGTH: 110
<212> TYPE: PRT
<213> ORGANISM: Homo sapiens

<400> SEQUENCE: 152

```
Gln Ser Val Val Thr Gln Pro Pro Ser Val Ser Gly Ala Pro Gly Gln
1               5                   10                  15

Arg Val Thr Ile Ser Cys Ala Gly Ser Arg Ser Asn Ile Gly Ala Gly
                20                  25                  30

Tyr Asp Val Asn Trp Tyr Gln Gln Leu Pro Arg Thr Ala Pro Lys Leu
            35                  40                  45

Leu Ile Tyr Asp Asn Thr Arg Arg Pro Ser Gly Val Pro Ala Arg Phe
        50                  55                  60

Ser Gly Ser Lys Ser Gly Ser Ser Ala Ser Leu Thr Ile Thr Gly Leu
65                  70                  75                  80

Gln Ala Glu Asp Glu Ala Asp Tyr Tyr Cys Gln Ser Tyr Asp Ser Lys
                85                  90                  95

Leu Asn Lys Val Phe Gly Gly Gly Thr Lys Leu Thr Val Leu
            100                 105                 110
```

<210> SEQ ID NO 153
<211> LENGTH: 363
<212> TYPE: DNA
<213> ORGANISM: Homo sapiens
<220> FEATURE:
<221> NAME/KEY: CDS
<222> LOCATION: (1)..(363)
<223> OTHER INFORMATION: NI-307.44F6B variable heavy chain (VH) sequence
<220> FEATURE:
<221> NAME/KEY: V_region
<222> LOCATION: (76)..(105)
<223> OTHER INFORMATION: complementarity determining region (CDR) VH-
      CDR1
<220> FEATURE:
<221> NAME/KEY: V_region
<222> LOCATION: (148)..(198)
<223> OTHER INFORMATION: complementarity determining region (CDR) VH-
      CDR2
<220> FEATURE:
<221> NAME/KEY: V_region
<222> LOCATION: (295)..(330)
<223> OTHER INFORMATION: complementarity determining region (CDR) VH-CDR3

<400> SEQUENCE: 153

```
gag gtg cag ctg gtg gag tct ggg gga agt gtg gtt cgg cct ggg ggg      48
Glu Val Gln Leu Val Glu Ser Gly Gly Ser Val Val Arg Pro Gly Gly
1               5                   10                  15 tcc ctg aga ctt gcc tgt gaa gtg tct gga ctc agg ttt gat gat ttc      96
Ser Leu Arg Leu Ala Cys Glu Val Ser Gly Leu Arg Phe Asp Asp Phe
            20                  25                  30 gcc atg agt tgg gtc cgc caa gtt cca ggg aag ggg ctg gag tgg atc     144
Ala Met Ser Trp Val Arg Gln Val Pro Gly Lys Gly Leu Glu Trp Ile
        35                  40                  45 gct ggc att ttt tgg aac agt ggt ggc aca ctt tat gcg gat tct gtg     192
Ala Gly Ile Phe Trp Asn Ser Gly Gly Thr Leu Tyr Ala Asp Ser Val
    50                  55                  60 aag ggc cga ttc acc atc tcc aga gac aac gcc gaa aat tcc ctg tat     240
Lys Gly Arg Phe Thr Ile Ser Arg Asp Asn Ala Glu Asn Ser Leu Tyr
65                  70                  75                  80 ttg caa atg aac agt ctg aga gcc gag gac acg gcc tta tat cga tgt     288
Leu Gln Met Asn Ser Leu Arg Ala Glu Asp Thr Ala Leu Tyr Arg Cys
                85                  90                  95 gtg aga gga agg tca cac gcc gcc tac tac ggc atg gac gtc tgg ggc     336
Val Arg Gly Arg Ser His Ala Ala Tyr Tyr Gly Met Asp Val Trp Gly
            100                 105                 110 aaa ggg acc acg gtc acc gtc tcc tcg                                 363
Lys Gly Thr Thr Val Thr Val Ser Ser
        115                 120
```

<210> SEQ ID NO 154
<211> LENGTH: 121
<212> TYPE: PRT
<213> ORGANISM: Homo sapiens

<400> SEQUENCE: 154

```
Glu Val Gln Leu Val Glu Ser Gly Gly Ser Val Val Arg Pro Gly Gly
1               5                   10                  15

Ser Leu Arg Leu Ala Cys Glu Val Ser Gly Leu Arg Phe Asp Asp Phe
            20                  25                  30

Ala Met Ser Trp Val Arg Gln Val Pro Gly Lys Gly Leu Glu Trp Ile
        35                  40                  45

Ala Gly Ile Phe Trp Asn Ser Gly Gly Thr Leu Tyr Ala Asp Ser Val
    50                  55                  60

Lys Gly Arg Phe Thr Ile Ser Arg Asp Asn Ala Glu Asn Ser Leu Tyr
65                  70                  75                  80

Leu Gln Met Asn Ser Leu Arg Ala Glu Asp Thr Ala Leu Tyr Arg Cys
                85                  90                  95

Val Arg Gly Arg Ser His Ala Ala Tyr Tyr Gly Met Asp Val Trp Gly
            100                 105                 110

Lys Gly Thr Thr Val Thr Val Ser Ser
        115                 120
```

<210> SEQ ID NO 155
<211> LENGTH: 336
<212> TYPE: DNA
<213> ORGANISM: Homo sapiens
<220> FEATURE:
<221> NAME/KEY: CDS
<222> LOCATION: (1)..(336)
<223> OTHER INFORMATION: NI-307.44F6B variable K-light chain (VK)

```
                    sequence
<220> FEATURE:
<221> NAME/KEY: V_region
<222> LOCATION: (70)..(117)
<223> OTHER INFORMATION: complementarity determining region (CDR) VK-
      CDR1
<220> FEATURE:
<221> NAME/KEY: V_region
<222> LOCATION: (163)..(183)
<223> OTHER INFORMATION: complementarity determining region (CDR) VK-
      CDR2
<220> FEATURE:
<221> NAME/KEY: V_region
<222> LOCATION: (280)..(306)
<223> OTHER INFORMATION: complementarity determining region (CDR) VK-
      CDR3

<400> SEQUENCE: 155 gaa att gtg ctg act cag tct cca ctc tcc ctg ccc gtc acc cct gga      48
Glu Ile Val Leu Thr Gln Ser Pro Leu Ser Leu Pro Val Thr Pro Gly
1               5                   10                  15 gag ccg gcc tcc atc tcc tgc agg tct agt cag agc ctc ctc cac agt      96
Glu Pro Ala Ser Ile Ser Cys Arg Ser Ser Gln Ser Leu Leu His Ser
            20                  25                  30 aat gga tac aac tat ttg gac tgg tac ctg cag aag cca ggg cag tct     144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct     192
Pro Gln Leu Leu Ile Tyr Leu Gly Ser Asn Arg Ala Ser Gly Val Pro
50                  55                  60 gac agg ttc agt ggc agt gga tca ggc aca gat ttc aca ctg aca atc     240
Asp Arg Phe Ser Gly Ser Gly Ser Gly Thr Asp Phe Thr Leu Thr Ile
65                  70                  75                  80 agc aga gtg gag gct gag gat gtt ggg att tat tac tgc atg caa gca     288
Ser Arg Val Glu Ala Glu Asp Val Gly Ile Tyr Tyr Cys Met Gln Ala
                85                  90                  95 cta cag aac gcg ctc gct ttc ggc gga ggg acc aag ctg gag atc aaa     336
Leu Gln Asn Ala Leu Ala Phe Gly Gly Gly Thr Lys Leu Glu Ile Lys
            100                 105                 110

<210> SEQ ID NO 156
<211> LENGTH: 112
<212> TYPE: PRT
<213> ORGANISM: Homo sapiens

<400> SEQUENCE: 156

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
50                  55                  60

Asp Arg Phe Ser Gly Ser Gly Ser Gly Thr Asp Phe Thr Leu Thr Ile
65                  70                  75                  80

Ser Arg Val Glu Ala Glu Asp Val Gly Ile Tyr Tyr Cys Met Gln Ala
                85                  90                  95

Leu Gln Asn Ala Leu Ala Phe Gly Gly Gly Thr Lys Leu Glu Ile Lys
            100                 105                 110

<210> SEQ ID NO 157
<211> LENGTH: 387
```

```
<212> TYPE: DNA
<213> ORGANISM: Homo sapiens
<220> FEATURE:
<221> NAME/KEY: CDS
<222> LOCATION: (1)..(387)
<223> OTHER INFORMATION: NI-307.98H1 variable heavy chain (VH) sequence
<220> FEATURE:
<221> NAME/KEY: V_region
<222> LOCATION: (76)..(111)
<223> OTHER INFORMATION: complementarity determining region (CDR) VH-
      CDR1
<220> FEATURE:
<221> NAME/KEY: V_region
<222> LOCATION: (154)..(201)
<223> OTHER INFORMATION: complementarity determining region (CDR) VH-
      CDR2
<220> FEATURE:
<221> NAME/KEY: V_region
<222> LOCATION: (298)..(354)
<223> OTHER INFORMATION: complementarity determining region (CDR) VH-
      CDR3

<400> SEQUENCE: 157 cag ctg cag ctg cag gag tcg ggc cca gga ctg gtg aag cct tca cag         48
Gln Leu Gln Leu Gln Glu Ser Gly Pro Gly Leu Val Lys Pro Ser Gln
1               5                   10                  15 acc ctg tcc ctc acc tgc gct gtc tct ggt gcc tcc atc agc agt ggt         96
Thr Leu Ser Leu Thr Cys Ala Val Ser Gly Ala Ser Ile Ser Ser Gly
            20                  25                  30 act tac tac tgg ggc tgg atc cga cag cac cca ggg aag ggc ctg gag        144
Thr Tyr Tyr Trp Gly Trp Ile Arg Gln His Pro Gly Lys Gly Leu Glu
        35                  40                  45 tgg att ggg tac atc tat ccc agt ggg agc acc tac tac aac ccg tcc        192
Trp Ile Gly Tyr Ile Tyr Pro Ser Gly Ser Thr Tyr Tyr Asn Pro Ser
    50                  55                  60 ctc aag agt cga gtt atc ata tca tta gac acg tct aag agc cag ttc        240
Leu Lys Ser Arg Val Ile Ile Ser Leu Asp Thr Ser Lys Ser Gln Phe
65                  70                  75                  80 tcc ctg aac ctg agc tct gtg act gcc gcg gac acg gcc gtg tat tac        288
Ser Leu Asn Leu Ser Ser Val Thr Ala Ala Asp Thr Ala Val Tyr Tyr
                85                  90                  95 tgt gcg aga gat tac tac gat agt agt ggc cat atg ggg ggc tac tac        336
Cys Ala Arg Asp Tyr Tyr Asp Ser Ser Gly His Met Gly Gly Tyr Tyr
            100                 105                 110 cac tac gct atg gac gtc tgg ggc caa ggg acc acg gtc acc gtc tcc        384
His Tyr Ala Met Asp Val Trp Gly Gln Gly Thr Thr Val Thr Val Ser
        115                 120                 125 tcg                                                                    387
Ser

<210> SEQ ID NO 158
<211> LENGTH: 129
<212> TYPE: PRT
<213> ORGANISM: Homo sapiens

<400> SEQUENCE: 158

Gln Leu Gln Leu Gln Glu Ser Gly Pro Gly Leu Val Lys Pro Ser Gln
1               5                   10                  15

Thr Leu Ser Leu Thr Cys Ala Val Ser Gly Ala Ser Ile Ser Ser Gly
            20                  25                  30

Thr Tyr Tyr Trp Gly Trp Ile Arg Gln His Pro Gly Lys Gly Leu Glu
        35                  40                  45

Trp Ile Gly Tyr Ile Tyr Pro Ser Gly Ser Thr Tyr Tyr Asn Pro Ser
    50                  55                  60
```

```
Leu Lys Ser Arg Val Ile Ile Ser Leu Asp Thr Ser Lys Ser Gln Phe
 65                  70                  75                  80

Ser Leu Asn Leu Ser Ser Val Thr Ala Ala Asp Thr Ala Val Tyr Tyr
                 85                  90                  95

Cys Ala Arg Asp Tyr Tyr Asp Ser Ser Gly His Met Gly Gly Tyr Tyr
            100                 105                 110

His Tyr Ala Met Asp Val Trp Gly Gln Gly Thr Thr Val Thr Val Ser
        115                 120                 125

Ser

<210> SEQ ID NO 159
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-307.98H1 variable K-light chain (VK)
      sequence
<220> FEATURE:
<221> NAME/KEY: V_region
<222> LOCATION: (70)..(102)
<223> OTHER INFORMATION: complementarity determining region (CDR) VK-
      CDR1
<220> FEATURE:
<221> NAME/KEY: V_region
<222> LOCATION: (148)..(168)
<223> OTHER INFORMATION: complementarity determining region (CDR) VK-
      CDR2
<220> FEATURE:
<221> NAME/KEY: V_region
<222> LOCATION: (265)..(291)
<223> OTHER INFORMATION: complementarity determining region (CDR) VK-
      CDR3

<400> SEQUENCE: 159 gac atc cag ttg acc cag tct cca tcc tcc ctg tct gca tct gta gga      48
Asp Ile Gln Leu Thr Gln Ser Pro Ser Ser Leu Ser Ala Ser Val Gly
  1               5                  10                  15 gac aga gtc acc atc act tgc cgg gca agt cag agc att agt agc cat      96
Asp Arg Val Thr Ile Thr Cys Arg Ala Ser Gln Ser Ile Ser Ser His
             20                  25                  30 tta aat tgg tat cag cag aaa cca ggg aaa gtc cct aag ctc ctg atc     144
Leu Asn Trp Tyr Gln Gln Lys Pro Gly Lys Val Pro Lys Leu Leu Ile
         35                  40                  45 tat gct gca tcc acc ttg caa agt ggg gtc cca tca agg ttc agt ggc     192
Tyr Ala Ala Ser Thr Leu Gln Ser Gly Val Pro Ser Arg Phe Ser Gly
     50                  55                  60 agt gga tct ggg aca gat ttc act ctc gcc atc agc agt ctg caa cct     240
Ser Gly Ser Gly Thr Asp Phe Thr Leu Ala Ile Ser Ser Leu Gln Pro
 65                  70                  75                  80 gca gat ttt gca act tat tac tgt caa cag agt tac agt acc cct cgg     288
Ala Asp Phe Ala Thr Tyr Tyr Cys Gln Gln Ser Tyr Ser Thr Pro Arg
                 85                  90                  95 acg ttc ggc caa ggg acc aaa gtg gat atc aaa                         321
Thr Phe Gly Gln Gly Thr Lys Val Asp Ile Lys
            100                 105

<210> SEQ ID NO 160
<211> LENGTH: 107
<212> TYPE: PRT
<213> ORGANISM: Homo sapiens

<400> SEQUENCE: 160

Asp Ile Gln Leu Thr Gln Ser Pro Ser Ser Leu Ser Ala Ser Val Gly
```

```
                1               5                   10                  15
            Asp Arg Val Thr Ile Thr Cys Arg Ala Ser Gln Ser Ile Ser Ser His
                                20                  25                  30

Leu Asn Trp Tyr Gln Gln Lys Pro Gly Lys Val Pro Lys Leu Leu Ile
                        35                  40                  45

Tyr Ala Ala Ser Thr Leu Gln Ser Gly Val Pro Ser Arg Phe Ser Gly
                    50                  55                  60

Ser Gly Ser Gly Thr Asp Phe Thr Leu Ala Ile Ser Ser Leu Gln Pro
            65                  70                  75                  80

Ala Asp Phe Ala Thr Tyr Tyr Cys Gln Gln Ser Tyr Ser Thr Pro Arg
                            85                  90                  95

Thr Phe Gly Gln Gly Thr Lys Val Asp Ile Lys
                            100                 105

<210> SEQ ID NO 161
<211> LENGTH: 360
<212> TYPE: DNA
<213> ORGANISM: Homo sapiens
<220> FEATURE:
<221> NAME/KEY: CDS
<222> LOCATION: (1)..(360)
<223> OTHER INFORMATION: NI-307.43E8 variable heavy chain (VH) sequence
<220> FEATURE:
<221> NAME/KEY: V_region
<222> LOCATION: (76)..(105)
<223> OTHER INFORMATION: complementarity determining region (CDR) VH-
      CDR1
<220> FEATURE:
<221> NAME/KEY: V_region
<222> LOCATION: (148)..(195)
<223> OTHER INFORMATION: complementarity determining region (CDR) VH-
      CDR2
<220> FEATURE:
<221> NAME/KEY: V_region
<222> LOCATION: (292)..(327)
<223> OTHER INFORMATION: complementarity determining region (CDR) VH-
      CDR3

<400> SEQUENCE: 161 gag gtg cag ctg gtg gag tct ggg gga gac gtg gtc cag cct ggg agg       48
Glu Val Gln Leu Val Glu Ser Gly Gly Asp Val Val Gln Pro Gly Arg
1               5                   10                  15 tcc ctg aga ctc tcc tgt gca gcc tct gga ttc gcc ttc agt att tat       96
Ser Leu Arg Leu Ser Cys Ala Ala Ser Gly Phe Ala Phe Ser Ile Tyr
            20                  25                  30 gct atg aac tgg gtc cgc cag gct cca ggc aag ggg ctg gag tgg gtg      144
Ala Met Asn Trp Val Arg Gln Ala Pro Gly Lys Gly Leu Glu Trp Val
        35                  40                  45 gca ctt ata tca act tct gga act gaa cac tac gca gac tcc gtg aag      192
Ala Leu Ile Ser Thr Ser Gly Thr Glu His Tyr Ala Asp Ser Val Lys
    50                  55                  60 ggc cga ttc acc atc tcc aga gac aat tcc aag aac acg ttg ttt ctg      240
Gly Arg Phe Thr Ile Ser Arg Asp Asn Ser Lys Asn Thr Leu Phe Leu
65                  70                  75                  80 caa att aat agt ctg aga gtt gag gac acg gct gtg tat tac tgt gcg      288
Gln Ile Asn Ser Leu Arg Val Glu Asp Thr Ala Val Tyr Tyr Cys Ala
                85                  90                  95 aga gat ctt gac agt act ggt tat tac gag aat aac tac tgg ggc cag      336
Arg Asp Leu Asp Ser Thr Gly Tyr Tyr Glu Asn Asn Tyr Trp Gly Gln
            100                 105                 110 ggc acc ctg gtc acc gtc tcc tcg                                      360
Gly Thr Leu Val Thr Val Ser Ser
            115                 120
```

<210> SEQ ID NO 162
<211> LENGTH: 120
<212> TYPE: PRT
<213> ORGANISM: Homo sapiens

<400> SEQUENCE: 162

Glu Val Gln Leu Val Glu Ser Gly Gly Asp Val Val Gln Pro Gly Arg
1               5                   10                  15

Ser Leu Arg Leu Ser Cys Ala Ala Ser Gly Phe Ala Phe Ser Ile Tyr
            20                  25                  30

Ala Met Asn Trp Val Arg Gln Ala Pro Gly Lys Gly Leu Glu Trp Val
        35                  40                  45

Ala Leu Ile Ser Thr Ser Gly Thr Glu His Tyr Ala Asp Ser Val Lys
    50                  55                  60

Gly Arg Phe Thr Ile Ser Arg Asp Asn Ser Lys Asn Thr Leu Phe Leu
65                  70                  75                  80

Gln Ile Asn Ser Leu Arg Val Glu Asp Thr Ala Val Tyr Tyr Cys Ala
                85                  90                  95

Arg Asp Leu Asp Ser Thr Gly Tyr Tyr Glu Asn Asn Tyr Trp Gly Gln
            100                 105                 110

Gly Thr Leu Val Thr Val Ser Ser
        115                 120

<210> SEQ ID NO 163
<211> LENGTH: 336
<212> TYPE: DNA
<213> ORGANISM: Homo sapiens
<220> FEATURE:
<221> NAME/KEY: CDS
<222> LOCATION: (1)..(336)
<223> OTHER INFORMATION: NI-307.43E8 complementarity determining region
      (CDR) VK-CDR1
<220> FEATURE:
<221> NAME/KEY: V_region
<222> LOCATION: (70)..(117)
<223> OTHER INFORMATION: complementarity determining region (CDR) VK-
      CDR1
<220> FEATURE:
<221> NAME/KEY: V_region
<222> LOCATION: (163)..(183)
<223> OTHER INFORMATION: complementarity determining region (CDR) VK-
      CDR2
<220> FEATURE:
<221> NAME/KEY: V_region
<222> LOCATION: (280)..(306)
<223> OTHER INFORMATION: complementarity determining region (CDR) VK-
      CDR3

<400> SEQUENCE: 163 gat gtt gtg atg act cag tct cca ctc tcc tca cct gtc agt ctt gga       48
Asp Val Val Met Thr Gln Ser Pro Leu Ser Ser Pro Val Ser Leu Gly
1               5                   10                  15 cag ccg gcc tcc atc tcc tgc agg tct agt cac agc ctc gta cac agt       96
Gln Pro Ala Ser Ile Ser Cys Arg Ser Ser His Ser Leu Val His Ser
            20                  25                  30 aat gga gat acc tac ttg agt tgg ctt cag cag agg cca ggc cag cct      144
Asn Gly Asp Thr Tyr Leu Ser Trp Leu Gln Gln Arg Pro Gly Gln Pro
        35                  40                  45 cca aga ctg cta atc tat aag att tct aac cga ttc tct ggg gtc cca      192
Pro Arg Leu Leu Ile Tyr Lys Ile Ser Asn Arg Phe Ser Gly Val Pro
    50                  55                  60 gac aga ttc agt ggc agt ggg gca ggg aca gat ttc aca ctg aaa atc      240
Asp Arg Phe Ser Gly Ser Gly Ala Gly Thr Asp Phe Thr Leu Lys Ile
65                  70                  75                  80

```
agc agg gtg gaa gct gag gat gtc ggg gtc tat ttc tgc atg caa gct    288
Ser Arg Val Glu Ala Glu Asp Val Gly Val Tyr Phe Cys Met Gln Ala
                85                  90                  95 acg tct ttt cct cga aca ttc ggc caa ggg acc aag gtg gaa atc aaa    336
Thr Ser Phe Pro Arg Thr Phe Gly Gln Gly Thr Lys Val Glu Ile Lys
            100                 105                 110

<210> SEQ ID NO 164
<211> LENGTH: 112
<212> TYPE: PRT
<213> ORGANISM: Homo sapiens

<400> SEQUENCE: 164

Asp Val Val Met Thr Gln Ser Pro Leu Ser Ser Pro Val Ser Leu Gly
1               5                   10                  15

Gln Pro Ala Ser Ile Ser Cys Arg Ser Ser His Ser Leu Val His Ser
            20                  25                  30

Asn Gly Asp Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Phe Cys Met Gln Ala
                85                  90                  95

Thr Ser Phe Pro Arg Thr Phe Gly Gln Gly Thr Lys Val Glu Ile Lys
            100                 105                 110

<210> SEQ ID NO 165
<211> LENGTH: 360
<212> TYPE: DNA
<213> ORGANISM: Homo sapiens
<220> FEATURE:
<221> NAME/KEY: CDS
<222> LOCATION: (1)..(360)
<223> OTHER INFORMATION: NI-307.18F4A variable heavy chain (VH) sequence
<220> FEATURE:
<221> NAME/KEY: V_region
<222> LOCATION: (76)..(105)
<223> OTHER INFORMATION: complementarity determining region (CDR) VH-
      CDR1
<220> FEATURE:
<221> NAME/KEY: V_region
<222> LOCATION: (148)..(198)
<223> OTHER INFORMATION: complementarity determining region (CDR) VH-
      CDR2
<220> FEATURE:
<221> NAME/KEY: V_region
<222> LOCATION: (295)..(327)
<223> OTHER INFORMATION: complementarity determining region (CDR) VH-
      CDR3

<400> SEQUENCE: 165 gag gtg cag ctg gtg gag tct ggg gga ggc ttg gtc aag cct gga ggg     48
Glu Val Gln Leu Val Glu Ser Gly Gly Gly Leu Val Lys Pro Gly Gly
1               5                   10                  15 tcc ctg aga ctc tcc tgt gca gcc tct gga ttc acc ttc act aac tac     96
Ser Leu Arg Leu Ser Cys Ala Ala Ser Gly Phe Thr Phe Thr Asn Tyr
            20                  25                  30 tac atg acc tgg gtc cgt cag gct cca gga aag ggg ctg gag tgg gtt    144
Tyr Met Thr Trp Val Arg Gln Ala Pro Gly Lys Gly Leu Glu Trp Val
        35                  40                  45 tca tac att act ggt ggt ggg agt act aca tac tac gca gac tct gtg    192
Ser Tyr Ile Thr Gly Gly Gly Ser Thr Thr Tyr Tyr Ala Asp Ser Val
```

```
acg ggc cga ttc acc atc tcc agg gac aac gcc aag aac tca ctg tat    240
Thr Gly Arg Phe Thr Ile Ser Arg Asp Asn Ala Lys Asn Ser Leu Tyr
 65                  70                  75                  80 ctg caa atg agc agc ctg aga gtc gag gac acg gcc gtc tat tat tgt    288
Leu Gln Met Ser Ser Leu Arg Val Glu Asp Thr Ala Val Tyr Tyr Cys
                 85                  90                  95 gcg aga ggg aga ggc tac ccc gac aac tgg ttc gac ccc tgg ggc cag    336
Ala Arg Gly Arg Gly Tyr Pro Asp Asn Trp Phe Asp Pro Trp Gly Gln
            100                 105                 110 gga acc ctg gtc acc gtc tcc tcg                                    360
Gly Thr Leu Val Thr Val Ser Ser
        115                 120

<210> SEQ ID NO 166
<211> LENGTH: 120
<212> TYPE: PRT
<213> ORGANISM: Homo sapiens

<400> SEQUENCE: 166

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Asn Tyr
            20                  25                  30

Tyr Met Thr Trp Val Arg Gln Ala Pro Gly Lys Gly Leu Glu Trp Val
        35                  40                  45

Ser Tyr Ile Thr Gly Gly Gly Ser Thr Thr Tyr Tyr Ala Asp Ser Val
    50                  55                  60

Thr Gly Arg Phe Thr Ile Ser Arg Asp Asn Ala Lys Asn Ser Leu Tyr
 65                 70                  75                  80

Leu Gln Met Ser Ser Leu Arg Val Glu Asp Thr Ala Val Tyr Tyr Cys
                85                  90                  95

Ala Arg Gly Arg Gly Tyr Pro Asp Asn Trp Phe Asp Pro Trp Gly Gln
            100                 105                 110

Gly Thr Leu Val Thr Val Ser Ser
        115                 120

<210> SEQ ID NO 167
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: NI-307.18F4A variable K-light chain (VK)
      sequence
<220> FEATURE:
<221> NAME/KEY: V_region
<222> LOCATION: (67)..(99)
<223> OTHER INFORMATION: complementarity determining region (CDR) VK-
      CDR1
<220> FEATURE:
<221> NAME/KEY: V_region
<222> LOCATION: (145)..(165)
<223> OTHER INFORMATION: complementarity determining region (CDR) VK-
      CDR2
<220> FEATURE:
<221> NAME/KEY: V_region
<222> LOCATION: (262)..(294)
<223> OTHER INFORMATION: complementarity determining region (CDR) VK-
      CDR3

<400> SEQUENCE: 167 tcc tat gtg ctg act cag cca ccc tcg gtg tca gtg tcc cca gga cag    48
```

```
Ser Tyr Val Leu Thr Gln Pro Pro Ser Val Ser Val Ser Pro Gly Gln
1               5                   10                  15 acg gcc agg atc acc tgc tct gga gat gca ttg cca aaa caa tat gtt       96
Thr Ala Arg Ile Thr Cys Ser Gly Asp Ala Leu Pro Lys Gln Tyr Val
            20                  25                  30 tat tgg tac cag cag aag cca ggc cag gcc cct gtg ttg atg ata tat      144
Tyr Trp Tyr Gln Gln Lys Pro Gly Gln Ala Pro Val Leu Met Ile Tyr
                35                  40                  45 aaa gac gct gag agg ccc tca ggg atc cct gac cga ttc tct ggc tcc      192
Lys Asp Ala Glu Arg Pro Ser Gly Ile Pro Asp Arg Phe Ser Gly Ser
50                  55                  60 agc tca ggg aca aca gtc act ttg acc atc agt gga gtc cag gca gaa      240
Ser Ser Gly Thr Thr Val Thr Leu Thr Ile Ser Gly Val Gln Ala Glu
65                  70                  75                  80 gac gag gct gac tat tac tgt cag tct aca gac atc agt ggt gct gct      288
Asp Glu Ala Asp Tyr Tyr Cys Gln Ser Thr Asp Ile Ser Gly Ala Ala
                85                  90                  95 gtg gtt ttc ggc gga ggg acc aag ctg acc gtc cta                      324
Val Val Phe Gly Gly Gly Thr Lys Leu Thr Val Leu
                100                 105
```

<210> SEQ ID NO 168
<211> LENGTH: 108
<212> TYPE: PRT
<213> ORGANISM: Homo sapiens

<400> SEQUENCE: 168

```
Ser Tyr Val Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Val
            20                  25                  30

Tyr Trp Tyr Gln Gln Lys Pro Gly Gln Ala Pro Val Leu Met Ile Tyr
        35                      40                  45

Lys Asp Ala Glu Arg Pro Ser Gly Ile Pro Asp Arg Phe Ser Gly Ser
 50                 55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Thr Asp Ile Ser Gly Ala Ala
                85                  90                  95

Val Val Phe Gly Gly Gly Thr Lys Leu Thr Val Leu
                100                 105
```

<210> SEQ ID NO 169
<211> LENGTH: 15
<212> TYPE: PRT
<213> ORGANISM: Artificial Sequence
<220> FEATURE:
<223> OTHER INFORMATION: Epitipe recognized by NI-307.11G6 antibody
<220> FEATURE:
<221> NAME/KEY: PEPTIDE
<222> LOCATION: (1)..(15)
<223> OTHER INFORMATION: Epitope of NI-307.11G6 antibody, peptide 82, aa
      325 to aa 339

<400> SEQUENCE: 169

```
Arg Val Phe Glu Gly Thr Glu Glu Leu Pro Gly Asp Pro Asp Met
1               5                   10                  15
```

<210> SEQ ID NO 170
<211> LENGTH: 15
<212> TYPE: PRT
<213> ORGANISM: Artificial Sequence

```
<220> FEATURE:
<223> OTHER INFORMATION: Epitope recognized by NI-307.11G6 antibody
<220> FEATURE:
<221> NAME/KEY: PEPTIDE
<222> LOCATION: (1)..(15)
<223> OTHER INFORMATION: Epitope of NI-307.11G6 antibody, peptide 83, aa
      329 to aa 343

<400> SEQUENCE: 170

Gly Thr Glu Glu Leu Pro Gly Asp Pro Asp Met Met Arg Tyr Val
1               5                   10                  15

<210> SEQ ID NO 171
<211> LENGTH: 15
<212> TYPE: PRT
<213> ORGANISM: Artificial Sequence
<220> FEATURE:
<223> OTHER INFORMATION: Epitope recognized by NI-307.11G6 antibody
<220> FEATURE:
<221> NAME/KEY: PEPTIDE
<222> LOCATION: (1)..(15)
<223> OTHER INFORMATION: Epitope of NI-307.11G6 antibody, peptide 84, aa
      333 to aa 348

<400> SEQUENCE: 171

Leu Pro Gly Asp Pro Asp Met Met Arg Tyr Val Asp Lys Tyr Val
1               5                   10                  15

<210> SEQ ID NO 172
<211> LENGTH: 12
<212> TYPE: PRT
<213> ORGANISM: Artificial Sequence
<220> FEATURE:
<223> OTHER INFORMATION: Epitope recognized by Ab34756
<220> FEATURE:
<221> NAME/KEY: PEPTIDE
<222> LOCATION: (1)..(12)
<223> OTHER INFORMATION: Epitope of Ab34756, aa 340 to aa 351

<400> SEQUENCE: 172

Met Arg Tyr Val Asp Lys Tyr Gly Gln Leu Gln Thr
1               5                   10
```